(12) United States Patent
Crawley et al.

(10) Patent No.: US 12,338,455 B2
(45) Date of Patent: *Jun. 24, 2025

(54) RNA-GUIDED NUCLEASES AND ACTIVE FRAGMENTS AND VARIANTS THEREOF AND METHODS OF USE

(71) Applicant: Life Edit Therapeutics, Inc., Durham, NC (US)

(72) Inventors: Alexandra Briner Crawley, Cary, NC (US); Rodolphe Barrangou, Raleigh, NC (US); Tyson D. Bowen, Morrisville, NC (US); Michael Coyle, Chapel Hill, NC (US); Tedd D. Elich, Durham, NC (US)

(73) Assignee: Life Edit Therapeutics, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/431,662

(22) Filed: Feb. 2, 2024

(65) Prior Publication Data

US 2024/0401084 A1 Dec. 5, 2024

Related U.S. Application Data

(63) Continuation of application No. 17/478,374, filed on Sep. 17, 2021, now Pat. No. 11,926,843, which is a continuation of application No. 16/432,321, filed on Jun. 5, 2019, now Pat. No. 11,162,114.

(60) Provisional application No. 62/805,041, filed on Feb. 13, 2019, provisional application No. 62/805,045, filed on Feb. 13, 2019, provisional application No. 62/686,901, filed on Jun. 19, 2018, provisional application No. 62/680,859, filed on Jun. 5, 2018, provisional application No. 62/680,845, filed on Jun. 5, 2018, provisional application No. 62/680,846, filed on Jun. 5, 2018, provisional application No. 62/680,862, filed on Jun. 5, 2018, provisional application No. 62/680,853, filed on Jun. 5, 2018, provisional application No. 62/680,863, filed on Jun. 5, 2018.

(51) Int. Cl.
| | |
|---|---|
| *C12N 15/90* | (2006.01) |
| *C12N 9/22* | (2006.01) |
| *C12N 15/10* | (2006.01) |
| *C12N 15/11* | (2006.01) |
| *C12N 15/113* | (2010.01) |
| *C12N 15/52* | (2006.01) |
| *C12N 15/63* | (2006.01) |

(52) U.S. Cl.
CPC ............ *C12N 15/907* (2013.01); *C12N 9/22* (2013.01); *C12N 15/11* (2013.01); *C12N 15/902* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 2014/0068797 A1 | 3/2014 | Doudna et al. |
| 2019/0100762 A1 | 4/2019 | Cigan et al. |

FOREIGN PATENT DOCUMENTS

| | | |
|---|---|---|
| CN | 107603976 A | 1/2018 |
| WO | WO 2013/176772 A1 | 11/2013 |
| WO | WO 2015/071474 A2 | 5/2015 |
| WO | WO 2016/186946 A1 | 11/2016 |
| WO | WO 2017/155714 A1 | 9/2017 |
| WO | WO 2017/155717 A1 | 9/2017 |
| WO | WO 2017/222773 A1 | 12/2017 |

OTHER PUBLICATIONS

Jiang. F., et anon., "CRISPR-Cas9 Structures and Mechanisms," *Annu. Rev. Biophys.*, 2017, vol. 46(1), pp. 505-529.
Van Erp, P., et al., "The history and market impact of CRISPR RNA-guided nucleases," *Current Opinion in Virology*, 2015, vol. 12, pp. 85-90.
NCBI Reference Sequence: WP_097814810.1, publication date Oct. 17, 2017, 2 pages.

*Primary Examiner* — Suzanne M Noakes
*Assistant Examiner* — Jae W Lee
(74) *Attorney, Agent, or Firm* — Womble Bond Dickinson (US) LLP

(57) ABSTRACT

Compositions and methods for binding to a target sequence of interest are provided. The compositions find use in cleaving or modifying a target sequence of interest, visualization of a target sequence of interest, and modifying the expression of a sequence of interest. Compositions comprise RNA-guided nuclease polypeptides, CRISPR RNAs, trans-activating CRISPR RNAs, guide RNAs, and nucleic acid molecules encoding the same. Vectors and host cells comprising the nucleic acid molecules are also provided. Further provided are CRISPR systems for binding a target sequence of interest, wherein the CRISPR system comprises an RNA-guided nuclease polypeptide and one or more guide RNAs.

19 Claims, No Drawings
Specification includes a Sequence Listing.

RNA-GUIDED NUCLEASES AND ACTIVE FRAGMENTS AND VARIANTS THEREOF AND METHODS OF USE

CROSS-REFERENCE TO RELATED APPLICATIONS

This application is a continuation of U.S. application Ser. No. 17/478,374, filed Sep. 17, 2021, which is a continuation of U.S. application Ser. No. 16/432,321, filed Jun. 5, 2019, now U.S. Pa. No. 11,162,114, which claims the benefit of U.S. Provisional Application Nos. 62/805,041, filed Feb. 13, 2019, 62/805,045, filed Feb. 13, 2019, 62/686,901, filed Jun. 19, 2018, 62/680,845, filed Jun. 5, 2018, 62/680,846, filed Jun. 5, 2018, 62/680,853, filed Jun. 5, 2018, 62/680,859, filed Jun. 5, 2018, 62/680,862, filed Jun. 5, 2018, and 62/680,863, filed Jun. 5, 2018, each of which is incorporated by reference herein in its entirety.

REFERENCE TO A SEQUENCE LISTING SUBMITTED ELECTRONICALLY AS AN XML FILE

The instant application contains a Sequence Listing which has been submitted in ST.26 XML format via USPTO Patent Center and is hereby incorporated by reference in its entirety. Said ST.26 XML copy, created on Aug. 6, 2024 is named L103438_1160US_C2_SL.XML, and is 1,099,916 bytes in size.

FIELD OF THE INVENTION

The present invention relates to the field of molecular biology and gene editing.

BACKGROUND OF THE INVENTION

Targeted genome editing or modification is rapidly becoming an important tool for basic and applied research. Initial methods involved engineering nucleases such as meganucleases, zinc finger fusion proteins or TALENs, requiring the generation of chimeric nucleases with engineered, programmable, sequence-specific DNA-binding domains specific for each particular target sequence. RNA-guided nucleases, such as the Clustered Regularly Interspaced Short Palindromic Repeats (CRISPR)-associated (cas) proteins of the CRISPR-cas bacterial system, allow for the targeting of specific sequences by complexing the nucleases with guide RNA that specifically hybridizes with a particular target sequence. Producing target-specific guide RNAs is less costly and more efficient than generating chimeric nucleases for each target sequence. Such RNA-guided nucleases can be used to edit genomes through the introduction of a sequence-specific, double-stranded break that is repaired via error-prone non-homologous end-joining (NHEJ) to introduce a mutation at a specific genomic location. Alternatively, heterologous DNA may be introduced into the genomic site via homology-directed repair.

BRIEF SUMMARY OF THE INVENTION

Compositions and methods for binding a target sequence of interest are provided. The compositions find use in cleaving or modifying a target sequence of interest, detection of a target sequence of interest, and modifying the expression of a sequence of interest. Compositions comprise RNA-guided nuclease (RGN) polypeptides, CRISPR RNAs (crRNAs), trans-activating CRISPR RNAs (tracrRNAs), guide RNAs (gRNAs), nucleic acid molecules encoding the same, and vectors and host cells comprising the nucleic acid molecules. Also provided are CRISPR systems for binding a target sequence of interest, wherein the CRISPR system comprises an RNA-guided nuclease polypeptide and one or more guide RNAs. Thus, methods disclosed herein are drawn to binding a target sequence of interest, and in some embodiments, cleaving or modifying the target sequence of interest. The target sequence of interest can be modified, for example, as a result of non-homologous end joining or homology-directed repair with an introduced donor sequence.

DETAILED DESCRIPTION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

I. Overview

RNA-guided nucleases (RGNs) allow for the targeted manipulation of a single site within a genome and are useful in the context of gene targeting for therapeutic and research applications. In a variety of organisms, including mammals, RNA-guided nucleases have been used for genome engineering by stimulating non-homologous end joining and homologous recombination, for example. The compositions and methods described herein are useful for creating single- or double-stranded breaks in polynucleotides, modifying polynucleotides, detecting a particular site within a polynucleotide, or modifying the expression of a particular gene.

The RNA-guided nucleases disclosed herein can alter gene expression by modifying a target sequence. In specific embodiments, the RNA-guided nucleases are directed to the target sequence by a guide RNA (gRNA) as part of a Clustered Regularly Interspaced Short Palindromic Repeats (CRISPR) RNA-guided nuclease system. Guide RNAs form a complex with the RNA-guided nucleases to direct the RNA-guided nuclease to bind to a target sequence and in some embodiments, introduce a single-stranded or double-stranded break at the target sequence. After the target sequence has been cleaved, the break can be repaired such that the DNA sequence of the target sequence is modified during the repair process. Thus, provided herein are methods for using the RNA-guided nucleases to modify a target sequence in the DNA of host cells. For example, RNA-guided nucleases can be used to modify a target sequence at a genomic locus of eukaryotic cells or prokaryotic cells.

II. RNA-Guided Nucleases

Provided herein are RNA-guided nucleases. The term RNA-guided nuclease (RGN) refers to a polypeptide that binds to a particular target nucleotide sequence in a sequence-specific manner and is directed to the target nucleotide sequence by a guide RNA molecule that is complexed with the polypeptide and hybridizes with the target sequence. Although an RNA-guided nuclease can be capable of cleaving the target sequence upon binding, the term RNA-guided nuclease also encompasses nuclease-dead RNA-guided nucleases that are capable of binding to, but not cleaving, a target sequence. Cleavage of a target sequence by an RNA-guided nuclease can result in a single- or double-stranded break. RNA-guided nucleases only capable of cleaving a single strand of a double-stranded nucleic acid molecule are referred to herein as nickases.

The RNA-guided nucleases disclosed herein include the APG05083.1, APG07433.1, APG07513.1, APG08290.1, APG05459.1, APG04583.1, and APG1688.1 RNA-guided nucleases, the amino acid sequences of which are set forth, respectively, as SEQ ID NOs: 1, 11, 19, 27, 36, 45, or 54, and active fragments or variants thereof that retain the ability to bind to a target nucleotide sequence in an RNA-guided sequence-specific manner. In some of these embodiments, the active fragment or variant of the APG05083.1, APG07433.1, APG07513.1, APG08290.1, APG05459.1, APG04583.1, and APG1688.1 RGN is capable of cleaving a single- or double-stranded target sequence. In some embodiments, an active variant of the APG05083.1, APG07433.1, APG07513.1, APG08290.1, APG05459.1, APG04583.1, or APG1688.1 RGN comprises an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth as SEQ ID NOs: 1, 11, 19, 27, 36, 45, or 54. In certain embodiments, an active fragment of the APG05083.1, APG07433.1, APG07513.1, APG08290.1, APG05459.1, APG04583.1, or APG1688.1 RGN comprises at least 50,100,150, 200, 250, 300, 350, 400, 450, 500, 550, 600, 650, 700, 750, 800, 850, 900, 950, 1000, 1050 or more contiguous amino acid residues of the amino acid sequence set forth as SEQ ID NOs: 1, 11, 19, 27, 36, 45, or 54. RNA-guided nucleases provided herein can comprise at least one nuclease domain (e.g., DNase, RNase domain) and at least one RNA recognition and/or RNA binding domain to interact with guide RNAs. Further domains that can be found in RNA-guided nucleases provided herein include, but are not limited to: DNA binding domains, helicase domains, protein-protein interaction domains, and dimerization domains. In specific embodiments, the RNA-guided nucleases provided herein can comprise at least 70%, 75%, 80%, 85%, 90%, 91%, 92%, 93%, 94%, 95%, 96%, 97%, 98%, 99% to one or more of a DNA binding domains, helicase domains, protein-protein interaction domains, and dimerization domains.

A target nucleotide sequence is bound by an RNA-guided nuclease provided herein and hybridizes with the guide RNA associated with the RNA-guided nuclease. The target sequence can then be subsequently cleaved by the RNA-guided nuclease if the polypeptide possesses nuclease activity. The terms "cleave" or "cleavage" refer to the hydrolysis of at least one phosphodiester bond within the backbone of a target nucleotide sequence that can result in either single-stranded or double-stranded breaks within the target sequence. The presently disclosed RGNs can cleave nucleotides within a polynucleotide, functioning as an endonuclease or can be an exonuclease, removing successive nucleotides from the end (the 5' and/or the 3' end) of a polynucleotide. In other embodiments, the disclosed RGNs can cleave nucleotides of a target sequence within any position of a polynucleotide and thus function as both an endonuclease and exonuclease. The cleavage of a target polynucleotide by the presently disclosed RGNs can result in staggered breaks or blunt ends.

The presently disclosed RNA-guided nucleases can be wild-type sequences derived from bacterial or archaeal species. Alternatively, the RNA-guided nucleases can be variants or fragments of wild-type polypeptides. The wild-type RGN can be modified to alter nuclease activity or alter PAM specificity, for example. In some embodiments, the RNA-guided nuclease is not naturally-occurring.

In certain embodiments, the RNA-guided nuclease functions as a nickase, only cleaving a single strand of the target nucleotide sequence. Such RNA-guided nucleases have a single functioning nuclease domain. In some of these embodiments, additional nuclease domains have been mutated such that the nuclease activity is reduced or eliminated.

In other embodiments, the RNA-guided nuclease lacks nuclease activity altogether or exhibits reduced nuclease activity, and is referred to herein as nuclease-dead. Any method known in the art for introducing mutations into an amino acid sequence, such as PCR-mediated mutagenesis and site-directed mutagenesis, can be used for generating nickases or nuclease-dead RGNs. See, e.g., U.S. Publ. No. 2014/0068797 and U.S. Pat. No. 9,790,490; each of which is incorporated by reference in its entirety.

RNA-guided nucleases that lack nuclease activity can be used to deliver a fused polypeptide, polynucleotide, or small molecule payload to a particular genomic location. In some of these embodiments, the RGN polypeptide or guide RNA can be fused to a detectable label to allow for detection of a particular sequence. As a non-limiting example, a nuclease-dead RGN can be fused to a detectable label (e.g., fluorescent protein) and targeted to a particular sequence associated with a disease to allow for detection of the disease-associated sequence.

Alternatively, nuclease-dead RGNs can be targeted to particular genomic locations to alter the expression of a desired sequence. In some embodiments, the binding of a nuclease-dead RNA-guided nuclease to a target sequence results in the repression of expression of the target sequence or a gene under transcriptional control by the target sequence by interfering with the binding of RNA polymerase or transcription factors within the targeted genomic region. In other embodiments, the RGN (e.g., a nuclease-dead RGN) or its complexed guide RNA further comprises an expression modulator that, upon binding to a target sequence, serves to either repress or activate the expression of the target sequence or a gene under transcriptional control by the target sequence. In some of these embodiments, the expression modulator modulates the expression of the target sequence or regulated gene through epigenetic mechanisms.

In other embodiments, the nuclease-dead RGNs or a RGN with only nickase activity can be targeted to particular genomic locations to modify the sequence of a target polynucleotide through fusion to a base-editing polypeptide, for example a deaminase polypeptide or active variant or fragment thereof that deaminates a nucleotide base, resulting in conversion from one nucleotide base to another. The base-editing polypeptide can be fused to the RGN at its N-terminal or C-terminal end. Additionally, the base-editing polypeptide may be fused to the RGN via a peptide linker. A non-limiting example of a deaminase polypeptide that is useful for such compositions and methods include cytidine deaminase or the adenosine deaminase base editor described in Gaudelli et al. (2017) Nature 551:464-471, U.S. Publ. Nos. 2017/0121693 and 2018/0073012, and International Publ. No. WO/2018/027078, each of which is herein incorporated by reference in its entirety.

RNA-guided nucleases that are fused to a polypeptide or domain can be separated or joined by a linker. The term "linker," as used herein, refers to a chemical group or a molecule linking two molecules or moieties, e.g., a binding domain and a cleavage domain of a nuclease. In some embodiments, a linker joins a gRNA binding domain of an RNA guided nuclease and a base-editing polypeptide, such as a deaminase. In some embodiments, a linker joins a nuclease-dead RGN and a deaminase. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The presently disclosed RNA-guided nucleases can comprise at least one nuclear localization signal (NLS) to enhance transport of the RGN to the nucleus of a cell. Nuclear localization signals are known in the art and generally comprise a stretch of basic amino acids (see, e.g., Lange et al., *J. Biol. Chem.* (2007) 282:5101-5105). In particular embodiments, the RGN comprises 2, 3, 4, 5, 6 or more nuclear localization signals. The nuclear localization signal(s) can be a heterologous NLS. Non-limiting examples of nuclear localization signals useful for the presently disclosed RGNs are the nuclear localization signals of SV40 Large T-antigen, nucleopasmin, and c-Myc (see, e.g., Ray et al. (2015) *Bioconjug Chem* 26(6):1004-7). In particular embodiments, the RGN comprises the NLS sequence set forth as SEQ ID NO: 67. The RGN can comprise one or more NLS sequences at its N-terminus, C-terminus, or both the N-terminus and C-terminus. For example, the RGN can comprise two NLS sequences at the N-terminal region and four NLS sequences at the C-terminal region.

Other localization signal sequences known in the art that localize polypeptides to particular subcellular location(s) can also be used to target the RGNs, including, but not limited to, plastid localization sequences, mitochondrial localization sequences, and dual-targeting signal sequences that target to both the plastid and mitochondria (see, e.g., Nassoury and Morse (2005) *Biochim Biophys Acta* 1743:5-19; Kunze and Berger (2015) *Front Physiol* dx.doi.org/10.3389/fphys.2015.00259; Herrmann and Neupert (2003) *JUBMB Life* 55:219-225; Soll (2002) *Curr Opin Plant Biol* 5:529-535; Carrie and Small (2013) *Biochim Biophys Acta* 1833:253-259; Carrie et al. (2009) *FEBS J* 276:1187-1195; Silva-Filho (2003) *Curr Opin Plant Biol* 6:589-595; Peeters and Small (2001) *Biochim Biophys Acta* 1541:54-63; Murcha et al. (2014) *J Exp Bot* 65:6301-6335; Mackenzie (2005) *Trends Cell Biol* 15:548-554; Glaser et al. (1998) *Plant Mol Biol* 38:311-338).

In certain embodiments, the presently disclosed RNA-guided nucleases comprise at least one cell-penetrating domain that facilitates cellular uptake of the RGN. Cell-penetrating domains are known in the art and generally comprise stretches of positively charged amino acid residues (i.e., polycationic cell-penetrating domains), alternating polar amino acid residues and non-polar amino acid residues (i.e., amphipathic cell-penetrating domains), or hydrophobic amino acid residues (i.e., hydrophobic cell-penetrating domains) (see, e.g., Milletti F. (2012) *Drug Discov Today* 17:850-860). A non-limiting example of a cell-penetrating domain is the trans-activating transcriptional activator (TAT) from the human immunodeficiency virus 1.

The nuclear localization signal, plastid localization signal, mitochondrial localization signal, dual-targeting localization signal, and/or cell-penetrating domain can be located at the amino-terminus (N-terminus), the carboxyl-terminus (C-terminus), or in an internal location of the RNA-guided nuclease.

The presently disclosed RGNs can be fused to an effector domain, such as a cleavage domain, a deaminase domain, or an expression modulator domain, either directly or indirectly via a linker peptide. Such a domain can be located at the N-terminus, the C-terminus, or an internal location of the RNA-guided nuclease. In some of these embodiments, the RGN component of the fusion protein is a nuclease-dead RGN.

In some embodiments, the RGN fusion protein comprises a cleavage domain, which is any domain that is capable of cleaving a polynucleotide (i.e., RNA, DNA, or RNA/DNA hybrid) and includes, but is not limited to, restriction endonucleases and homing endonucleases, such as Type IIS endonucleases (e.g., FokI) (see, e.g., Belfort et al. (1997) *Nucleic Acids Res.* 25:3379-3388; Linn et al. (eds.) Nucleases, Cold Spring Harbor Laboratory Press, 1993).

In other embodiments, the RGN fusion protein comprises a deaminase domain that deaminates a nucleotide base, resulting in conversion from one nucleotide base to another, and includes, but is not limited to, a cytidine deaminase or an adenosine deaminase base editor (see, e.g., Gaudelli et al. (2017) Nature 551:464-471, U.S. Publ. Nos. 2017/0121693 and 2018/0073012, U.S. Pat. No. 9,840,699, and International Publ. No. WO/2018/027078).

In some embodiments, the effector domain of the RGN fusion protein can be an expression modulator domain, which is a domain that either serves to upregulate or downregulate transcription. The expression modulator domain can be an epigenetic modification domain, a transcriptional repressor domain or a transcriptional activation domain.

In some of these embodiments, the expression modulator of the RGN fusion protein comprises an epigenetic modification domain that covalently modifies DNA or histone proteins to alter histone structure and/or chromosomal structure without altering the DNA sequence, leading to changes in gene expression (i.e., upregulation or downregulation). Non-limiting examples of epigenetic modifications include acetylation or methylation of lysine residues, arginine methylation, serine and threonine phosphorylation, and lysine ubiquitination and sumoylation of histone proteins, and methylation and hydroxymethylation of cytosine residues in DNA. Non-limiting examples of epigenetic modification domains include histone acetyltransferase domains, histone deacetylase domains, histone methyltransferase domains, histone demethylase domains, DNA methyltransferase domains, and DNA demethylase domains.

In other embodiments, the expression modulator of the fusion protein comprises a transcriptional repressor domain, which interacts with transcriptional control elements and/or transcriptional regulatory proteins, such as RNA polymerases and transcription factors, to reduce or terminate transcription of at least one gene. Transcriptional repressor domains are known in the art and include, but are not limited to, Sp1-like repressors, IκB, and Kruppel associated box (KRAB) domains.

In yet other embodiments, the expression modulator of the fusion protein comprises a transcriptional activation domain, which interacts with transcriptional control elements and/or transcriptional regulatory proteins, such as RNA polymerases and transcription factors, to increase or activate transcription of at least one gene. Transcriptional activation domains are known in the art and include, but are not limited to, a herpes simplex virus VP16 activation domain and an NFAT activation domain.

The presently disclosed RGN polypeptides can comprise a detectable label or a purification tag. The detectable label or purification tag can be located at the N-terminus, the C-terminus, or an internal location of the RNA-guided nuclease, either directly or indirectly via a linker peptide. In some of these embodiments, the RGN component of the fusion protein is a nuclease-dead RGN. In other embodiments, the RGN component of the fusion protein is a RGN with nickase activity.

A detectable label is a molecule that can be visualized or otherwise observed. The detectable label may be fused to the RGN as a fusion protein (e.g., fluorescent protein) or may be a small molecule conjugated to the RGN polypeptide that can be detected visually or by other means. Detectable labels that can be fused to the presently disclosed RGNs as a fusion protein include any detectable protein domain, including but not limited to, a fluorescent protein or a protein domain that can be detected with a specific antibody. Non-limiting examples of fluorescent proteins include green fluorescent proteins (e.g., GFP, EGFP, ZsGreen1) and yellow fluorescent proteins (e.g., YFP, EYFP, ZsYellow1). Non-limiting examples of small molecule detectable labels include radioactive labels, such as $^3$H and $^{35}$S.

RGN polypeptides can also comprise a purification tag, which is any molecule that can be utilized to isolate a protein or fused protein from a mixture (e.g., biological sample, culture medium). Non-limiting examples of purification tags include biotin, myc, maltose binding protein (MBP), and glutathione-S-transferase (GST).

II. Guide RNA

The present disclosure provides guide RNAs and polynucleotides encoding the same. The term "guide RNA" refers to a nucleotide sequence having sufficient complementarity with a target nucleotide sequence to hybridize with the target sequence and direct sequence-specific binding of an associated RNA-guided nuclease to the target nucleotide sequence. Thus, a RGN's respective guide RNA is one or more RNA molecules (generally, one or two), that can bind to the RGN and guide the RGN to bind to a particular target nucleotide sequence, and in those instances wherein the RGN has nickase or nuclease activity, also cleave the target nucleotide sequence. In general, a guide RNA comprises a CRISPR RNA (crRNA) and a transactivating CRISPR RNA (tracrRNA). Native guide RNAs that comprise both a crRNA and a tracrRNA generally comprise two separate RNA molecules that hybridize to each other through the repeat sequence of the crRNA and the anti-repeat sequence of the tracrRNA.

Native direct repeat sequences within a CRISPR array generally range in length from 28 to 37 base pairs, although the length can vary between about 23 bp to about 55 bp. Spacer sequences within a CRISPR array generally range from about 32 to about 38 bp in length, although the length can be between about 21 bp to about 72 bp. Each CRISPR array generally comprises less than 50 units of the CRISPR repeat-spacer sequence. The CRISPRs are transcribed as part of a long transcript termed the primary CRISPR transcript, which comprises much of the CRISPR array. The primary CRISPR transcript is cleaved by Cas proteins to produce crRNAs or in some cases, to produce pre-crRNAs that are further processed by additional Cas proteins into mature crRNAs. Mature crRNAs comprise a spacer sequence and a CRISPR repeat sequence. In some embodiments in which pre-crRNAs are processed into mature (or processed) crRNAs, maturation involves the removal of about one to about six or more 5', 3', or 5' and 3' nucleotides. For the purposes of genome editing or targeting a particular target nucleotide sequence of interest, these nucleotides that are removed during maturation of the pre-crRNA molecule are not necessary for generating or designing a guide RNA.

A CRISPR RNA (crRNA) comprises a spacer sequence and a CRISPR repeat sequence. The "spacer sequence" is the nucleotide sequence that directly hybridizes with the target nucleotide sequence of interest. The spacer sequence is engineered to be fully or partially complementary with the target sequence of interest. In various embodiments, the spacer sequence can comprise from about 8 nucleotides to about 30 nucleotides, or more. For example, the spacer sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the spacer sequence is about 10 to about 26 nucleotides in length, or about 12 to about 30 nucleotides in length. In particular embodiments, the spacer sequence is about 30 nucleotides in length. In some embodiments, the degree of complementarity between a spacer sequence and its corresponding target sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the spacer sequence is free of secondary structure, which can be predicted using any suitable polynucleotide folding algorithm known in the art, including but not limited to mFold (see, e.g., Zuker and Stiegler (1981) *Nucleic Acids Res.* 9:133-148) and RNAfold (see, e.g., Gruber et al. (2008) *Cell* 106(1):23-24).

RGN proteins can have varying sensitivity to mismatches between a spacer sequence in a gRNA and its target sequence that affects the efficiency of cleavage. As discussed in Example 5, APG05459.1 RGN has an unusual sensitivity to mismatches between the spacer sequence and target sequence, extending at least 15 nucleotides 5' of the PAM site. Thus, APG05459.1 has the potential to more finely (i.e., specifically) target particular sequences with greater precision than other RGNs with less sensitivity to mismatches between the spacer sequence and target sequence.

The CRISPR RNA repeat sequence comprises a nucleotide sequence that comprises a region with sufficient complementarity to hybridize to a tracrRNA. In various embodiments, the CRISPR RNA repeat sequence can comprise from about 8 nucleotides to about 30 nucleotides, or more. For example, the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the CRISPR repeat sequence is about 21 nucleotides in length. In some embodiments, the degree of complementarity between a CRISPR repeat sequence and its corresponding tracrRNA sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the CRISPR repeat sequence comprises the nucleotide sequence of SEQ ID NOs: 2, 12, 20, 28, 37, 46, or 55, or an active variant or fragment thereof that when comprised within a guide RNA, is capable of directing the sequence-specific binding of an associated RNA-guided nuclease provided herein to a target sequence of interest. In certain embodiments, an active CRISPR repeat sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth as SEQ ID NOs: 2, 12, 20, 28, 37, 46, or 55. In certain embodiments, an active CRISPR repeat sequence fragment of a wild-type sequence comprises at least 5, 6, 7, 8, 9, 10, 11, 12, 13, 14, 15, 16, 17, 18, 19, or 20 contiguous nucleotides of the nucleotide sequence set forth as SEQ ID NOs: 2, 12, 20, 28, 37, 46, or 55.

In certain embodiments, the crRNA is not naturally-occurring. In some of these embodiments, the specific CRISPR repeat sequence is not linked to the engineered spacer sequence in nature and the CRISPR repeat sequence is considered heterologous to the spacer sequence. In certain embodiments, the spacer sequence is an engineered sequence that is not naturally occurring.

A trans-activating CRISPR RNA or tracrRNA molecule comprises a nucleotide sequence comprising a region that has sufficient complementarity to hybridize to a CRISPR repeat sequence of a crRNA, which is referred to herein as the anti-repeat region. In some embodiments, the tracrRNA molecule further comprises a region with secondary structure (e.g., stem-loop) or forms secondary structure upon hybridizing with its corresponding crRNA. In particular embodiments, the region of the tracrRNA that is fully or partially complementary to a CRISPR repeat sequence is at the 5' end of the molecule and the 3' end of the tracrRNA comprises secondary structure. This region of secondary structure generally comprises several hairpin structures, including the nexus hairpin, which is found adjacent to the anti-repeat sequence. The nexus hairpin often has a conserved nucleotide sequence in the base of the hairpin stem, with the motif UNANNG, UNANNU, or UNANNA (SEQ ID NOs: 68, 557, and 558, respectively) found in many nexus hairpins in tracrRNAs. There are often terminal hairpins at the 3' end of the tracrRNA that can vary in structure and number, but often comprise a GC-rich Rho-independent transcriptional terminator hairpin followed by a string of U's at the 3' end. See, for example, Briner et al. (2014) *Molecular Cell* 56:333-339, Briner and Barrangou (2016) *Cold Spring Harb Protoc*; doi: 10.1101/pdb.top090902, and U.S. Publication No. 2017/0275648, each of which is herein incorporated by reference in its entirety.

In various embodiments, the anti-repeat region of the tracrRNA that is fully or partially complementary to the CRISPR repeat sequence comprises from about 8 nucleotides to about 30 nucleotides, or more. For example, the region of base pairing between the tracrRNA anti-repeat sequence and the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In particular embodiments, the anti-repeat region of the tracrRNA that is fully or partially complementary to a CRISPR repeat sequence is about 20 nucleotides in length.

In some embodiments, the degree of complementarity between a CRISPR repeat sequence and its corresponding tracrRNA anti-repeat sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more.

In various embodiments, the entire tracrRNA can comprise from about 60 nucleotides to more than about 140 nucleotides. For example, the tracrRNA can be about 60, about 65, about 70, about 75, about 80, about 85, about 90, about 95, about 100, about 105, about 110, about 115, about 120, about 125, about 130, about 135, about 140, or more nucleotides in length. In particular embodiments, the tracrRNA is about 80 to about 90 nucleotides in length, including about 80, about 81, about 82, about 83, about 84, about 85, about 86, about 87, about 88, about 89, and about 90 nucleotides in length. In certain embodiments, the tracrRNA is about 85 nucleotides in length.

In particular embodiments, the tracrRNA comprises the nucleotide sequence of SEQ ID NOs: 3, 13, 21, 29, 38, 47, or 56, or an active variant or fragment thereof that when comprised within a guide RNA is capable of directing the sequence-specific binding of an associated RNA-guided nuclease provided herein to a target sequence of interest. In certain embodiments, an active tracrRNA sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth as SEQ ID NOs: 3, 13, 21, 29, 38, 47, or 56. In certain embodiments, an active tracrRNA sequence fragment of a wild-type sequence comprises at least 5, 10, 15, 20, 25, 30, 35, 40, 45, 50, 55, 60, 65, 70, 75, 80, or more contiguous nucleotides of the nucleotide sequence set forth as SEQ ID NOs: 3, 13, 21, 29, 38, 47, or 56.

Two polynucleotide sequences can be considered to be substantially complementary when the two sequences hybridize to each other under stringent conditions. Likewise, an RGN is considered to bind to a particular target sequence within a sequence-specific manner if the guide RNA bound to the RGN binds to the target sequence under stringent conditions. By "stringent conditions" or "stringent hybridization conditions" is intended conditions under which the two polynucleotide sequences will hybridize to each other to a detectably greater degree than to other sequences (e.g., at least 2-fold over background). Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3, and the temperature is at least about 30° C. for short sequences (e.g., 10 to 50 nucleotides) and at least about 60° C. for long sequences (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The Tm is the temperature (under defined ionic strength and pH) at which 50% of a complementary target sequence hybridizes to a perfectly matched sequence. For DNA-DNA hybrids, the Tm can be approximated from the equation of Meinkoth and Wahl (1984) Anal. Biochem. 138:267-284: Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. An extensive guide to the hybridization of nucleic acids is found in Tijssen (1993) Laboratory Techniques in Biochemistry and Molecular Biology-Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, New York).

The guide RNA can be a single guide RNA or a dual-guide RNA system. A single guide RNA comprises the crRNA and tracrRNA on a single molecule of RNA, whereas a dual-guide RNA system comprises a crRNA and a tracrRNA present on two distinct RNA molecules, hybridized to one another through at least a portion of the CRISPR repeat sequence of the crRNA and at least a portion of the tracrRNA, which may be fully or partially complementary to the CRISPR repeat sequence of the crRNA. In some of those embodiments wherein the guide RNA is a single guide RNA, the crRNA and tracrRNA are separated by a linker nucleotide sequence. In general, the linker nucleotide sequence is one that does not include complementary bases in order to avoid the formation of secondary structure within or comprising nucleotides of the linker nucleotide sequence. In some embodiments, the linker nucleotide sequence between the crRNA and tracrRNA is at least 3, at least 4, at least 5, at least 6, at least 7, at least 8, at least 9, at least 10, at least 11, at least 12, or more nucleotides in length. In particular embodiments, the linker nucleotide sequence of a single guide RNA is at least 4 nucleotides in length. In certain embodiments, the linker nucleotide sequence is the nucleotide sequence set forth as SEQ ID NO: 63, 64, or 65. In other embodiments, the linker nucleotide sequence is at least 6 nucleotides in length. In certain embodiments, the linker nucleotide sequence is the nucleotide sequence set forth as SEQ ID NO: 65.

The single guide RNA or dual-guide RNA can be synthesized chemically or via in vitro transcription. Assays for determining sequence-specific binding between a RGN and a guide RNA are known in the art and include, but are not limited to, in vitro binding assays between an expressed RGN and the guide RNA, which can be tagged with a detectable label (e.g., biotin) and used in a pull-down detection assay in which the guide RNA:RGN complex is captured via the detectable label (e.g., with streptavidin beads). A control guide RNA with an unrelated sequence or structure to the guide RNA can be used as a negative control for non-specific binding of the RGN to RNA. In certain embodiments, the guide RNA is SEQ ID NO: 10, 18, 26, 35, 44, 53, or 62, wherein the spacer sequence can be any sequence and is indicated as a poly-N sequence.

As described in Example 8, certain RGNs of the invention can share certain guide RNAs. APG05083.1, APG07433.1, APG07513.1, and APG08290.1 can each function using guide RNAs comprising a crRNA comprising the nucleotide sequence of SEQ ID NOs: 2, 12, 20, or 28, with the corresponding tracrRNA comprising the nucleotide sequence of SEQ ID NOs: 3, 13, 21, or 29, respectively. Further, APG04583.1 and APG01688.1 can each function using guide RNAs comprising a crRNA comprising the nucleotide sequence of SEQ ID NOs: 46 or 55, with the corresponding tracrRNA comprising the nucleotide sequence of SEQ 47 or 56, respectively.

In certain embodiments, the guide RNA can be introduced into a target cell, organelle, or embryo as an RNA molecule. The guide RNA can be transcribed in vitro or chemically synthesized. In other embodiments, a nucleotide sequence encoding the guide RNA is introduced into the cell, organelle, or embryo. In some of these embodiments, the nucleotide sequence encoding the guide RNA is operably linked to a promoter (e.g., an RNA polymerase III promoter). The promoter can be a native promoter or heterologous to the guide RNA-encoding nucleotide sequence.

In various embodiments, the guide RNA can be introduced into a target cell, organelle, or embryo as a ribonucleoprotein complex, as described herein, wherein the guide RNA is bound to an RNA-guided nuclease polypeptide.

The guide RNA directs an associated RNA-guided nuclease to a particular target nucleotide sequence of interest through hybridization of the guide RNA to the target nucleotide sequence. A target nucleotide sequence can comprise DNA, RNA, or a combination of both and can be single-stranded or double-stranded. A target nucleotide sequence can be genomic DNA (i.e., chromosomal DNA), plasmid DNA, or an RNA molecule (e.g., messenger RNA, ribosomal RNA, transfer RNA, micro RNA, small interfering RNA). The target nucleotide sequence can be bound (and in some embodiments, cleaved) by an RNA-guided nuclease in vitro or in a cell. The chromosomal sequence targeted by the RGN can be a nuclear, plastid or mitochondrial chromosomal sequence. In some embodiments, the target nucleotide sequence is unique in the target genome.

The target nucleotide sequence is adjacent to a protospacer adjacent motif (PAM). A protospacer adjacent motif is generally within about 1 to about 10 nucleotides from the target nucleotide sequence, including about 1, about 2, about 3, about 4, about 5, about 6, about 7, about 8, about 9, or about 10 nucleotides from the target nucleotide sequence. The PAM can be 5' or 3' of the target sequence. In some embodiments, the PAM is 3' of the target sequence for the presently disclosed RGNs. Generally, the PAM is a consensus sequence of about 3-4 nucleotides, but in particular embodiments, can be 2, 3, 4, 5, 6, 7, 8, 9, or more nucleotides in length. In various embodiments, the PAM sequence recognized by the presently disclosed RGNs comprises the consensus sequence set forth as SEQ ID NOs: 6, 32, 41, 50, or 59. Non-limiting exemplary PAM sequences are the nucleotide sequences set forth as SEQ ID NO: 7, 69, 70, 71, and 72.

In particular embodiments, an RNA-guided nuclease having SEQ ID NOs: 1, 11, 19, 27, 36, 45, or 54 or an active variant or fragment thereof binds respectively a target nucleotide sequence adjacent to a PAM sequence set forth as SEQ ID NOs: 6, 32, 41, 50, 59, or 7. In some of these embodiments, the RGN binds to a guide sequence comprising a CRISPR repeat sequence set forth in SEQ ID NOs: 2, 12, 20, 28, 37, 46, or 55, respectively, or an active variant or fragment thereof, and a tracrRNA sequence set forth in SEQ ID NOs: 3, 13, 21, 29, 38, 47, or 56, respectively, or an active variant or fragment thereof. The RGN systems are described further in Example 1 and Table 1 of the present specification.

It is well-known in the art that PAM sequence specificity for a given nuclease enzyme is affected by enzyme concentration (see, e.g., Karvelis et al. (2015) *Genome Biol* 16:253), which may be modified by altering the promoter used to express the RGN, or the amount of ribonucleoprotein complex delivered to the cell, organelle, or embryo.

Upon recognizing its corresponding PAM sequence, the RGN can cleave the target nucleotide sequence at a specific cleavage site. As used herein, a cleavage site is made up of the two particular nucleotides within a target nucleotide sequence between which the nucleotide sequence is cleaved by an RGN. The cleavage site can comprise the $1^{st}$ and $2^{nd}$, $2^{nd}$ and $3^{rd}$, $3^{rd}$ and $4^{th}$, $4^{th}$ and $5^{th}$, $5^{th}$ and $6^{th}$, $7^{th}$ and $8^{th}$, or $8^{th}$ and $9^{th}$ nucleotides from the PAM in either the 5' or 3' direction. In some embodiments, the cleavage site may be over 10, 11, 12, 13, 14, 15, 16, 17, 18, 19, or 20 nucleotides from the PAM in either the 5' or 3' direction. In some embodiments, the cleavage site is 4 nucleotides away from the PAM. In other embodiments, the cleavage site is at least 15 nucleotides away from the PAM. As RGNs can cleave a target nucleotide sequence resulting in staggered ends, in some embodiments, the cleavage site is defined based on the distance of the two nucleotides from the PAM on the positive (+) strand of the polynucleotide and the distance of the two nucleotides from the PAM on the negative (−) strand of the polynucleotide.

III. Nucleotides Encoding RNA-Guided Nucleases, Crispr RNA, and or TracrRNA

The present disclosure provides polynucleotides comprising the presently disclosed CRISPR RNAs, tracrRNAs, and/or sgRNAs and polynucleotides comprising a nucleotide sequence encoding the presently disclosed RNA-guided nucleases, CRISPR RNAs, tracrRNAs, and/or sgRNAs. Presently disclosed polynucleotides include those comprising or encoding a CRISPR repeat sequence comprising the nucleotide sequence of SEQ ID NOs: 2, 12, 20, 28, 37, 46, or 55, or an active variant or fragment thereof that when comprised within a guide RNA is capable of directing the sequence-specific binding of an associated RNA-guided nuclease to a target sequence of interest. Also disclosed are polynucleotides comprising or encoding a tracrRNA comprising the nucleotide sequence of SEQ ID NOs: 3, 13, 21, 29, 38, 47, or 56, or an active variant or fragment thereof that when comprised within a guide RNA is capable of directing the sequence-specific binding of an associated RNA-guided nuclease to a target sequence of interest. Polynucleotides are also provided that encode an RNA-guided nuclease comprising the amino acid sequence set forth as SEQ ID NOs: 1, 11, 19, 27, 36, 45, or 54, and active fragments or variants thereof that retain the ability to bind to a target nucleotide sequence in an RNA-guided sequence-specific manner.

The use of the term "polynucleotide" is not intended to limit the present disclosure to polynucleotides comprising DNA. Those of ordinary skill in the art will recognize that polynucleotides can comprise ribonucleotides (RNA) and combinations of ribonucleotides and deoxyribonucleotides. Such deoxyribonucleotides and ribonucleotides include both naturally occurring molecules and synthetic analogues. These include peptide nucleic acids (PNAs), PNA-DNA chimers, locked nucleic acids (LNAs), and phosphothiorate linked sequences. The polynucleotides disclosed herein also encompass all forms of sequences including, but not limited to, single-stranded forms, double-stranded forms, DNA-RNA hybrids, triplex structures, stem-and-loop structures, and the like.

The nucleic acid molecules encoding RGNs can be codon optimized for expression in an organism of interest. A "codon-optimized" coding sequence is a polynucleotide coding sequence having its frequency of codon usage designed to mimic the frequency of preferred codon usage or transcription conditions of a particular host cell. Expression in the particular host cell or organism is enhanced as a result of the alteration of one or more codons at the nucleic acid level such that the translated amino acid sequence is not changed. Nucleic acid molecules can be codon optimized, either wholly or in part. Codon tables and other references providing preference information for a wide range of organisms are available in the art (see, e.g., Campbell and Gowri (1990) *Plant Physiol.* 92:1-11 for a discussion of plant-preferred codon usage). Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Polynucleotides encoding the RGNs, crRNAs, tracrRNAs, and/or sgRNAs provided herein can be provided in expression cassettes for in vitro expression or expression in a cell, organelle, embryo, or organism of interest. The cassette will include 5' and 3' regulatory sequences operably linked to a polynucleotide encoding an RGN, crRNA, tracrRNAs, and/or sgRNAs provided herein that allows for expression of the polynucleotide. The cassette may additionally contain at least one additional gene or genetic element to be cotransformed into the organism. Where additional genes or elements are included, the components are operably linked. The term "operably linked" is intended to mean a functional linkage between two or more elements. For example, an operable linkage between a promoter and a coding region of interest (e.g., region coding for an RGN, crRNA, tracrRNAs, and/or sgRNAs) is a functional link that allows for expression of the coding region of interest. Operably linked elements may be contiguous or non-contiguous. When used to refer to the joining of two protein coding regions, by operably linked is intended that the coding regions are in the same reading frame. Alternatively, the additional gene(s) or element(s) can be provided on multiple expression cassettes. For example, the nucleotide sequence encoding a presently disclosed RGN can be present on one expression cassette, whereas the nucleotide sequence encoding a crRNA, tracrRNA, or complete guide RNA can be on a separate expression cassette. Such an expression cassette is provided with a plurality of restriction sites and/or recombination sites for insertion of the polynucleotides to be under the transcriptional regulation of the regulatory regions. The expression cassette may additionally contain a selectable marker gene.

The expression cassette will include in the 5'-3' direction of transcription, a transcriptional (and, in some embodiments, translational) initiation region (i.e., a promoter), an RGN-, crRNA-, tracrRNA- and/or sgRNA-encoding polynucleotide of the invention, and a transcriptional (and in some embodiments, translational) termination region (i.e., termination region) functional in the organism of interest. The promoters of the invention are capable of directing or driving expression of a coding sequence in a host cell. The regulatory regions (e.g., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. As used herein, a chimeric gene comprises a coding sequence operably linked to a transcription initiation region that is heterologous to the coding sequence.

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional regulatory signals include, but are not limited to, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) Molecular Cloning: A Laboratory Manual, ed. Maniatis et al. (Cold Spring Harbor Laboratory Press, Cold Spring Harbor, N.Y.), hereinafter "Sambrook 11"; Davis et al., eds. (1980) Advanced Bacterial Genetics (Cold Spring Harbor Laboratory Press), Cold Spring Harbor, N.Y., and the references cited therein.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, growth stage-specific, cell type-specific, tissue-preferred, tissue-specific, or other promoters for expression in the organism of interest. See, for example, promoters set forth in WO 99/43838 and in U.S. Pat. Nos. 8,575,425; 7,790,846; 8,147,856; 8,586,832; 7,772,369; 7,534,939; 6,072,050; 5,659,026; 5,608,149; 5,608,144; 5,604,121; 5,569,597; 5,466,785; 5,399,680; 5,268,463; 5,608,142; and 6,177,611; herein incorporated by reference.

For expression in plants, constitutive promoters also include CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); and MAS (Velten et al. (1984) *EMBO J* 3:2723-2730).

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the Axig1 promoter which is auxin induced and tapetum specific but also active in callus (PCT US01/22169), the steroid-responsive promoters (see, for example, the ERE promoter which is estrogen induced, and the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-specific or tissue-preferred promoters can be utilized to target expression of an expression construct within a particular tissue. In certain embodiments, the tissue-specific or tissue-preferred promoters are active in plant tissue. Examples of promoters under developmental control in plants include promoters that initiate transcription preferentially in certain tissues, such as leaves, roots, fruit, seeds, or flowers. A "tissue specific" promoter is a promoter that initiates transcription only in certain tissues. Unlike constitutive expression of genes, tissue-specific expression is the result of several interacting levels of gene regulation. As such, promoters from homologous or closely related plant species can be preferable to use to achieve efficient and reliable expression of transgenes in particular tissues. In some embodiments, the expression comprises a tissue-preferred promoter. A "tissue preferred" promoter is a promoter that initiates transcription preferentially, but not necessarily entirely or solely in certain tissues.

In some embodiments, the nucleic acid molecules encoding a RGN, crRNA, and/or tracrRNA comprise a cell type-specific promoter. A "cell type specific" promoter is a promoter that primarily drives expression in certain cell types in one or more organs. Some examples of plant cells in which cell type specific promoters functional in plants may be primarily active include, for example, BETL cells, vascular cells in roots, leaves, stalk cells, and stem cells. The nucleic acid molecules can also include cell type preferred promoters. A "cell type preferred" promoter is a promoter that primarily drives expression mostly, but not necessarily entirely or solely in certain cell types in one or more organs. Some examples of plant cells in which cell type preferred promoters functional in plants may be preferentially active include, for example, BETL cells, vascular cells in roots, leaves, stalk cells, and stem cells.

The nucleic acid sequences encoding the RGNs, crRNAs, tracrRNAs, and/or sgRNAs can be operably linked to a promoter sequence that is recognized by a phage RNA polymerase for example, for in vitro mRNA synthesis. In such embodiments, the in vitro-transcribed RNA can be purified for use in the methods described herein. For example, the promoter sequence can be a T7, T3, or SP6 promoter sequence or a variation of a T7, T3, or SP6 promoter sequence. In such embodiments, the expressed protein and/or RNAs can be purified for use in the methods of genome modification described herein.

In certain embodiments, the polynucleotide encoding the RGN, crRNA, tracrRNA, and/or sgRNA also can be linked to a polyadenylation signal (e.g., SV40 polyA signal and other signals functional in plants) and/or at least one transcriptional termination sequence. Additionally, the sequence encoding the RGN also can be linked to sequence(s) encoding at least one nuclear localization signal, at least one cell-penetrating domain, and/or at least one signal peptide capable of trafficking proteins to particular subcellular locations, as described elsewhere herein.

The polynucleotide encoding the RGN, crRNA, tracrRNA, and/or sgRNA can be present in a vector or multiple vectors. A "vector" refers to a polynucleotide composition for transferring, delivering, or introducing a nucleic acid into a host cell. Suitable vectors include plasmid vectors, phagemids, cosmids, artificial/mini-chromosomes, transposons, and viral vectors (e.g., lentiviral vectors, adeno-associated viral vectors, baculoviral vector). The vector can comprise additional expression control sequences (e.g., enhancer sequences, Kozak sequences, polyadenylation sequences, transcriptional termination sequences), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001.

The vector can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D).

In some embodiments, the expression cassette or vector comprising the sequence encoding the RGN polypeptide can further comprise a sequence encoding a crRNA and/or a tracrRNA, or the crRNA and tracrRNA combined to create a guide RNA. The sequence(s) encoding the crRNA and/or tracrRNA can be operably linked to at least one transcriptional control sequence for expression of the crRNA and/or tracrRNA in the organism or host cell of interest. For example, the polynucleotide encoding the crRNA and/or tracrRNA can be operably linked to a promoter sequence that is recognized by RNA polymerase III (Pol III). Examples of suitable Pol III promoters include, but are not limited to, mammalian U6, U3, H1, and 7SL RNA promoters and rice U6 and U3 promoters.

As indicated, expression constructs comprising nucleotide sequences encoding the RGNs, crRNA, tracrRNA, and/or sgRNA can be used to transform organisms of interest. Methods for transformation involve introducing a nucleotide construct into an organism of interest. By "introducing" is intended to introduce the nucleotide construct to the host cell in such a manner that the construct gains access to the interior of the host cell. The methods of the invention do not require a particular method for introducing a nucleotide construct to a host organism, only that the nucleotide construct gains access to the interior of at least one cell of the host organism. The host cell can be a eukaryotic or prokaryotic cell. In particular embodiments, the eukaryotic host cell is a plant cell, a mammalian cell, or an insect cell. Methods for introducing nucleotide constructs into plants and other host cells are known in the art including, but not limited to, stable transformation methods, transient transformation methods, and virus-mediated methods.

The methods result in a transformed organism, such as a plant, including whole plants, as well as plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic organisms" or "transformed organisms" or "stably transformed" organisms or cells or tissues refers to organisms that have incorporated or integrated a polynucleotide encoding a RGN, crRNA, and/or tracrRNA of the invention. It is recognized that other exogenous or endogenous nucleic acid sequences or DNA fragments may also be incorporated into the host cell. *Agrobacterium*—and biolistic-mediated transformation remain the two predominantly employed approaches for transformation of plant cells. However, transformation of a host cell may be performed by infection, transfection, microinjection, electroporation, microprojection, biolistics or particle bombardment, electroporation, silica/carbon fibers, ultrasound mediated, PEG mediated, calcium phosphate co-precipitation, polycation DMSO technique, DEAE dextran procedure, and viral mediated, liposome mediated and the like. Viral-mediated introduction of a polynucleotide encoding an RGN, crRNA, and/or tracrRNA includes retroviral, lentiviral, adenoviral, and adeno-associated viral mediated introduction and expression, as well as the use of Cauliviruses, Geminiviruses, and RNA plant viruses.

Transformation protocols as well as protocols for introducing polypeptides or polynucleotide sequences into plants may vary depending on the type of host cell (e.g., monocot or dicot plant cell) targeted for transformation. Methods for transformation are known in the art and include those set forth in U.S. Pat. Nos. 8,575,425; 7,692,068; 8,802,934; 7,541,517; each of which is herein incorporated by reference. See, also, Rakoczy-Trojanowska, M. (2002) *Cell Mol Biol Lett.* 7:849-858; Jones et al. (2005) *Plant Methods* 1:5; Rivera et al. (2012) *Physics of Life Reviews* 9:308-345; Bartlett et al. (2008) *Plant Methods* 4:1-12; Bates, G. W. (1999) *Methods in Molecular Biology* 111:359-366; Binns and Thomashow (1988) *Annual Reviews in Microbiology* 42:575-606; Christou, P. (1992) *The Plant Journal* 2:275-281; Christou, P. (1995) *Euphytica* 85:13-27; Tzfira et al. (2004) *TRENDS in Genetics* 20:375-383; Yao et al. (2006) *Journal of Experimental Botany* 57:3737-3746; Zupan and Zambryski (1995) *Plant Physiology* 107:1041-1047; Jones et al. (2005) *Plant Methods* 1:5;

Transformation may result in stable or transient incorporation of the nucleic acid into the cell. "Stable transformation" is intended to mean that the nucleotide construct introduced into a host cell integrates into the genome of the host cell and is capable of being inherited by the progeny thereof. "Transient transformation" is intended to mean that a polynucleotide is introduced into the host cell and does not integrate into the genome of the host cell.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into a transgenic organism, such as a plant, in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Alternatively, cells that have been transformed may be introduced into an organism. These cells could have originated from the organism, wherein the cells are transformed in an ex vivo approach.

The sequences provided herein may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processed plant product or byproduct that retains the sequences disclosed herein, including for example, soymeal.

The polynucleotides encoding the RGNs, crRNAs, and/or tracrRNAs can also be used to transform any prokaryotic species, including but not limited to, archaea and bacteria (e.g., *Bacillus* sp., *Klebsiella* sp. *Streptomyces* sp., *Rhizobium* sp., *Escherichia* sp., *Pseudomonas* sp., *Salmonella* sp., *Shigella* sp., *Vibrio* sp., *Yersinia* sp., *Mycoplasma* sp., *Agrobacterium, Lactobacillus* sp.).

The polynucleotides encoding the RGNs, crRNAs, and/or tracrRNAs can be used to transform any eukaryotic species, including but not limited to animals (e.g., mammals, insects, fish, birds, and reptiles), fungi, amoeba, algae, and yeast.

Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256: 808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946, 787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Viral. 66:2731-2739 (1992); Johann et al., J. Viral. 66:1635-1640 (1992); Sommnerfelt et al., Viral. 176:58-59 (1990); Wilson et al., J. Viral. 63:2374-2378 (1989); Miller et al., 1. Viral. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Katin, Human Gene Therapy 5:793-801 (1994); Muzyczka, 1. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., 1. Viral. 63:03822-3828 (1989). Packaging cells are typically used to form virus particles that are capable of infecting a host cell. Such cells include 293 cells, which package adenovirus, and ψJ$^2$ cells or PA317 cells, which package retrovirus.

Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences.

The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLaS3, Huh1, Huh4, Huh7, HUVEC, HASMC, HEKn, HEKa, MiaPaCell, Panel, PC-3, TFl, CTLL-2, CIR, Rat6, CVI, RPTE, AlO, T24, 182, A375, ARH-77, Calul, SW480, SW620, SKOV3, SK-UT, CaCo2, P388D1, SEM-K2, WEHI-231, HB56, TIB55, lurkat, 145.01, LRMB, Bcl-1, BC-3, IC21, DLD2, Raw264.7, NRK, NRK-52E, MRC5, MEF, Hep G2, HeLa B, HeLa T4. COS, COS-1, COS-6, COS-M6A, BS-C-1 monkey kidney epithelial, BALB/3T3 mouse embryo fibroblast, 3T3 Swiss, 3T3-Ll, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-I cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr-/-, COR-L23, COR-L23/ CPR, COR-L235010, CORL23/R23, COS-7, COV-434, CML Tl, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, lurkat, IY cells, K562 cells, Ku812, KCL22, KG1, KYOl, LNCap, Ma-Mel 1-48, MC-38, MCF-7, MCF-10A, MDA-MB-231, MDA-MB-468, MDA-MB-435, MDCKII, MDCKII, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THPl cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit.

IV. Variants and Fragments of Polypeptides and Polynucleotides

The present disclosure provides active variants and fragments of a naturally-occurring (i.e., wild-type) RNA-guided nuclease, the amino acid sequence of which is set forth as SEQ ID NOs: 1, 11, 19, 27, 36, 45, or 54, as well as active variants and fragments of naturally-occurring CRISPR repeats, such as the sequence set forth as SEQ ID NOs: 2, 12, 20, 28, 37, 46, or 55, and active variant and fragments of naturally-occurring tracrRNAs, such as the sequence set forth as SEQ ID NOs: 3, 13, 21, 29, 38, 47, or 56, and polynucleotides encoding the same.

While the activity of a variant or fragment may be altered compared to the polynucleotide or polypeptide of interest, the variant and fragment should retain the functionality of the polynucleotide or polypeptide of interest. For example, a variant or fragment may have increased activity, decreased activity, different spectrum of activity or any other alteration in activity when compared to the polynucleotide or polypeptide of interest.

Fragments and variants of naturally-occurring RGN polypeptides, such as those disclosed herein, will retain sequence-specific, RNA-guided DNA-binding activity. In particular embodiments, fragments and variants of naturally-occurring RGN polypeptides, such as those disclosed herein, will retain nuclease activity (single-stranded or double-stranded).

Fragments and variants of naturally-occurring CRISPR repeats, such as those disclosed herein, will retain the ability, when part of a guide RNA (comprising a tracrRNA), to bind to and guide an RNA-guided nuclease (complexed with the guide RNA) to a target nucleotide sequence in a sequence-specific manner.

Fragments and variants of naturally-occurring tracrRNAs, such as those disclosed herein, will retain the ability, when part of a guide RNA (comprising a CRISPR RNA), to guide an RNA-guided nuclease (complexed with the guide RNA) to a target nucleotide sequence in a sequence-specific manner.

The term "fragment" refers to a portion of a polynucleotide or polypeptide sequence of the invention. "Fragments" or "biologically active portions" include polynucleotides comprising a sufficient number of contiguous nucleotides to retain the biological activity (i.e., binding to and directing an RGN in a sequence-specific manner to a target nucleotide sequence when comprised within a guideRNA). "Fragments" or "biologically active portions" include polypeptides comprising a sufficient number of contiguous amino acid residues to retain the biological activity (i.e., binding to a target nucleotide sequence in a sequence-specific manner when complexed with a guide RNA). Fragments of the RGN proteins include those that are shorter than the full-length sequences due to the use of an alternate downstream start site. A biologically active portion of an RGN protein can be a polypeptide that comprises, for example, 10, 25, 50, 100, 150, 200, 250, 300, 350, 400, 450, 500, 550, 600, 650, 700, 750, 800, 850, 900, 950, 1000, 1050 or more contiguous amino acid residues of SEQ ID NOs: 1, 11, 19, 27, 36, 45, or 54. Such biologically active portions can be prepared by recombinant techniques and evaluated for sequence-specific, RNA-guided DNA-binding activity. A biologically active fragment of a CRISPR repeat sequence can comprise at least 8 contiguous amino acids of SEQ ID NOs: 2, 12, 20, 28, 37, 46, or 55. A biologically active portion of a CRISPR repeat sequence can be a polynucleotide that comprises, for example, 8, 9, 10, 11, 12, 13, 14, 15, 16, 17, 18, 19, or 20 contiguous nucleotides of SEQ ID NOs: 2, 12, 20, 28, 37, 46, or 55. A biologically active portion of a tracrRNA can be a polynucleotide that comprises, for example, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80 or more contiguous nucleotides of SEQ ID NOs: 3, 13, 21, 29, 38, 47, or 56.

In general, "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the native amino acid sequence of the gene of interest. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode the polypeptide or the polynucleotide of interest. Generally, variants of a particular polynucleotide disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide disclosed herein (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

In particular embodiments, the presently disclosed polynucleotides encode an RNA-guided nuclease polypeptide comprising an amino acid sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to an amino acid sequence of SEQ ID NOs: 1, 11, 19, 27, 36, 45, or 54.

A biologically active variant of an RGN polypeptide of the invention may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N-terminal or a C-terminal truncation, which can comprise at least a deletion of 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050 amino acids or more from either the N or C terminus of the polypeptide.

In certain embodiments, the presently disclosed polynucleotides comprise or encode a CRISPR repeat comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleotide sequence set forth as SEQ ID NOs: 2, 12, 20, 28, 37, 46, or 55.

The presently disclosed polynucleotides can comprise or encode a tracrRNA comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleotide sequence set forth as SEQ ID NOs: 3, 13, 21, 29, 38, 47, or 56.

Biologically active variants of a CRISPR repeat or tracrRNA of the invention may differ by as few as about 1-15 nucleotides, as few as about 1-10, such as about 6-10, as few as 5, as few as 4, as few as 3, as few as 2, or as few as 1 nucleotides. In specific embodiments, the polynucleotides can comprise a 5' or 3' truncation, which can comprise at least a deletion of 10, 15, 20, 25, 30, 35, 40, 45, 50, 55, 60, 65, 70, 75, 80 nucleotides or more from either the 5' or 3' end of the polynucleotide.

It is recognized that modifications may be made to the RGN polypeptides, CRISPR repeats, and tracrRNAs provided herein creating variant proteins and polynucleotides. Changes designed by man may be introduced through the application of site-directed mutagenesis techniques. Alternatively, native, as yet-unknown or as yet unidentified polynucleotides and/or polypeptides structurally and/or functionally-related to the sequences disclosed herein may also be identified that fall within the scope of the present invention. Conservative amino acid substitutions may be made in nonconserved regions that do not alter the function of the RGN proteins. Alternatively, modifications may be made that improve the activity of the RGN.

Variant polynucleotides and proteins also encompass sequences and proteins derived from a mutagenic and recombinogenic procedure such as DNA shuffling. With such a procedure, one or more different RGN proteins disclosed herein (e.g., SEQ ID NOs: 1, 11, 19, 27, 36, 45, or 54) is manipulated to create a new RGN protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the RGN sequences provided herein and other known RGN genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), for example in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (www.ncbi.nlm.nih.gov). Optimal alignments, including multiple alignments, can be prepared using, e.g., PSI-BLAST, available through www.ncbi.nlm.nih.gov and described by Altschul et al. (1997) *Nucleic Acids Res.* 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

V. Antibodies

Antibodies to the RGN polypeptides or ribonucleoproteins comprising the RGN polypeptides of the present invention, including those having the amino acid sequence set forth as SEQ ID NOs: 1, 11, 19, 27, 36, 45, or 54 or active variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, N.Y.; and U.S. Pat. No. 4,196,265). These antibodies can be used in kits for the detection and isolation of RGN polypeptides or ribonucleoproteins. Thus, this disclosure provides kits comprising antibodies that specifically bind to the polypeptides or ribonucleoproteins described herein, including, for example, polypeptides having the sequence of SEQ ID NOs: 1, 11, 19, 27, 36, 45, or 54.

VI. Systems and Ribonucleoprotein Complexes for Binding a Target Sequence of Interest and Methods of Making the Same The present disclosure provides a system for binding a target sequence of interest, wherein the system comprises at least one guide RNA or a nucleotide sequence encoding the same, and at least one RNA-guided nuclease or a nucleotide sequence encoding the same. The guide RNA hybridizes to the target sequence of interest and also forms a complex with the RGN polypeptide, thereby directing the RGN polypeptide to bind to the target sequence. In some of these embodiments, the RGN comprises an amino acid sequence of SEQ ID NOs: 1, 11, 19, 27, 36, 45, or 54, or an active variant or fragment thereof. In various embodiments, the guide RNA comprises a CRISPR repeat sequence comprising the nucleotide sequence of SEQ ID NOs: 2, 12, 20, 28, 37, 46, or 55, or an active variant or fragment thereof. In particular embodiments, the guide RNA comprises a tracrRNA comprising a nucleotide sequence of SEQ ID NOs: 3, 13, 21, 29, 38, 47, or 56, or an active variant or fragment thereof. The guide RNA of the system can be a single guide RNA or a dual-guide RNA. In particular embodiments, the system comprises a RNA-guided nuclease that is heterologous to the guideRNA, wherein the RGN and guideRNA are not naturally complexed in nature.

The system for binding a target sequence of interest provided herein can be a ribonucleoprotein complex, which is at least one molecule of an RNA bound to at least one protein. The ribonucleoprotein complexes provided herein comprise at least one guide RNA as the RNA component and an RNA-guided nuclease as the protein component. Such ribonucleoprotein complexes can be purified from a cell or organism that naturally expresses an RGN polypeptide and has been engineered to express a particular guide RNA that is specific for a target sequence of interest. Alternatively, the ribonucleoprotein complex can be purified from a cell or organism that has been transformed with polynucleotides that encode an RGN polypeptide and a guide RNA and cultured under conditions to allow for the expression of the RGN polypeptide and guide RNA. Thus, methods are provided for making an RGN polypeptide or an RGN ribonucleoprotein complex. Such methods comprise culturing a cell comprising a nucleotide sequence encoding an RGN polypeptide, and in some embodiments a nucleotide sequence encoding a guide RNA, under conditions in which the RGN polypeptide (and in some embodiments, the guide RNA) is expressed. The RGN polypeptide or RGN ribonucleoprotein can then be purified from a lysate of the cultured cells.

Methods for purifying an RGN polypeptide or RGN ribonucleoprotein complex from a lysate of a biological sample are known in the art (e.g., size exclusion and/or affinity chromatography, 2D-PAGE, HPLC, reversed-phase chromatography, immunoprecipitation). In particular methods, the RGN polypeptide is recombinantly produced and comprises a purification tag to aid in its purification, including but not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, 10×His, biotin carboxyl carrier protein (BCCP), and calmodulin. Generally, the tagged RGN polypeptide or RGN ribonucleoprotein complex is purified using immobilized metal affinity chromatography. It will be appreciated that other similar methods known in the art may be used, including other forms of chromatography or for example immunoprecipitation, either alone or in combination.

An "isolated" or "purified" polypeptide, or biologically active portion thereof, is substantially or essentially free from components that normally accompany or interact with the polypeptide as found in its naturally occurring environment. Thus, an isolated or purified polypeptide is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Particular methods provided herein for binding and/or cleaving a target sequence of interest involve the use of an in vitro assembled RGN ribonucleoprotein complex. In vitro assembly of an RGN ribonucleoprotein complex can be performed using any method known in the art in which an RGN polypeptide is contacted with a guide RNA under conditions to allow for binding of the RGN polypeptide to the guide RNA. As used herein, "contact", contacting", "contacted," refer to placing the components of a desired reaction together under conditions suitable for carrying out the desired reaction. The RGN polypeptide can be purified from a biological sample, cell lysate, or culture medium, produced via in vitro translation, or chemically synthesized. The guide RNA can be purified from a biological sample, cell lysate, or culture medium, transcribed in vitro, or chemically synthesized. The RGN polypeptide and guide RNA can be brought into contact in solution (e.g., buffered saline solution) to allow for in vitro assembly of the RGN ribonucleoprotein complex.

VII. Methods of Binding, Cleaving, or Modifying a Target Sequence

The present disclosure provides methods for binding, cleaving, and/or modifying a target nucleotide sequence of interest. The methods include delivering a system comprising at least one guide RNA or a polynucleotide encoding the same, and at least one RGN polypeptide or a polynucleotide encoding the same to the target sequence or a cell, organelle, or embryo comprising the target sequence. In some of these embodiments, the RGN comprises the amino acid sequence of SEQ ID NOs: 1, 11, 19, 27, 36, 45, or 54, or an active variant or fragment thereof. In various embodiments, the guide RNA comprises a CRISPR repeat sequence comprising the nucleotide sequence of SEQ ID NOs: 2, 12, 20, 28, 37, 46, or 55, or an active variant or fragment thereof. In particular embodiments, the guide RNA comprises a tracrRNA comprising the nucleotide sequence of SEQ ID NOs: 3, 13, 21, 29, 38, 47, or 56, or an active variant or fragment thereof. The guide RNA of the system can be a single guide RNA or a dual-guide RNA. The RGN of the system may be nuclease dead RGN, have nickase activity, or may be a fusion polypeptide. In some embodiments, the fusion polypeptide comprises a base-editing polypeptide, for example a cytidine deaminase or an adenosine deaminase. In particular embodiments, the RGN and/or guide RNA is heterologous to the cell, organelle, or embryo to which the RGN and/or guide RNA (or polynucleotide(s) encoding at least one of the RGN and guide RNA) are introduced.

In those embodiments wherein the method comprises delivering a polynucleotide encoding a guide RNA and/or an RGN polypeptide, the cell or embryo can then be cultured under conditions in which the guide RNA and/or RGN polypeptide are expressed. In various embodiments, the method comprises contacting a target sequence with an RGN ribonucleoprotein complex. The RGN ribonucleoprotein complex may comprise an RGN that is nuclease dead or has nickase activity. In some embodiments, the RGN of the ribonucleoprotein complex is a fusion polypeptide comprising a base-editing polypeptide. In certain embodiments, the method comprises introducing into a cell, organelle, or embryo comprising a target sequence an RGN ribonucleoprotein complex. The RGN ribonucleoprotein complex can be one that has been purified from a biological sample, recombinantly produced and subsequently purified, or in vitro-assembled as described herein. In those embodiments wherein the RGN ribonucleoprotein complex that is contacted with the target sequence or a cell organelle, or embryo has been assembled in vitro, the method can further comprise the in vitro assembly of the complex prior to contact with the target sequence, cell, organelle, or embryo.

A purified or in vitro assembled RGN ribonucleoprotein complex can be introduced into a cell, organelle, or embryo using any method known in the art, including, but not limited to electroporation. Alternatively, an RGN polypeptide and/or polynucleotide encoding or comprising the guide RNA can be introduced into a cell, organelle, or embryo using any method known in the art (e.g., electroporation).

Upon delivery to or contact with the target sequence or cell, organelle, or embryo comprising the target sequence, the guide RNA directs the RGN to bind to the target sequence in a sequence-specific manner. In those embodiments wherein the RGN has nuclease activity, the RGN polypeptide cleaves the target sequence of interest upon binding. The target sequence can subsequently be modified via endogenous repair mechanisms, such as non-homologous end joining, or homology-directed repair with a provided donor polynucleotide.

Methods to measure binding of an RGN polypeptide to a target sequence are known in the art and include chromatin immunoprecipitation assays, gel mobility shift assays, DNA pull-down assays, reporter assays, microplate capture and detection assays. Likewise, methods to measure cleavage or modification of a target sequence are known in the art and include in vitro or in vivo cleavage assays wherein cleavage is confirmed using PCR, sequencing, or gel electrophoresis, with or without the attachment of an appropriate label (e.g., radioisotope, fluorescent substance) to the target sequence to facilitate detection of degradation products. Alternatively, the nicking triggered exponential amplification reaction (NTEXPAR) assay can be used (see, e.g., Zhang et al. (2016) *Chem. Sci.* 7:4951-4957). In vivo cleavage can be evaluated using the Surveyor assay (Guschin et al. (2010) *Methods Mol Biol* 649:247-256).

In some embodiments, the methods involve the use of a single type of RGN complexed with more than one guide RNA. The more than one guide RNA can target different regions of a single gene or can target multiple genes.

In those embodiments wherein a donor polynucleotide is not provided, a double-stranded break introduced by an RGN polypeptide can be repaired by a non-homologous end-joining (NHEJ) repair process. Due to the error-prone nature of NHEJ, repair of the double-stranded break can result in a modification to the target sequence. As used herein, a "modification" in reference to a nucleic acid molecule refers to a change in the nucleotide sequence of the nucleic acid molecule, which can be a deletion, insertion, or substitution of one or more nucleotides, or a combination thereof. Modification of the target sequence can result in the expression of an altered protein product or inactivation of a coding sequence.

In those embodiments wherein a donor polynucleotide is present, the donor sequence in the donor polynucleotide can be integrated into or exchanged with the target nucleotide sequence during the course of repair of the introduced double-stranded break, resulting in the introduction of the exogenous donor sequence. A donor polynucleotide thus comprises a donor sequence that is desired to be introduced into a target sequence of interest. In some embodiments, the donor sequence alters the original target nucleotide sequence such that the newly integrated donor sequence will not be recognized and cleaved by the RGN. Integration of the donor sequence can be enhanced by the inclusion within the donor polynucleotide of flanking sequences that have substantial sequence identity with the sequences flanking the target nucleotide sequence, allowing for a homology-directed repair process. In those embodiments wherein the RGN polypeptide introduces double-stranded staggered breaks, the donor polynucleotide can comprise a donor sequence flanked by compatible overhangs, allowing for direct ligation of the donor sequence to the cleaved target nucleotide sequence comprising overhangs by a non-homologous repair process during repair of the double-stranded break.

In those embodiments wherein the method involves the use of an RGN that is a nickase (i.e., is only able to cleave a single strand of a double-stranded polynucleotide), the method can comprise introducing two RGN nickases that target identical or overlapping target sequences and cleave different strands of the polynucleotide. For example, an RGN nickase that only cleaves the positive (+) strand of a double-stranded polynucleotide can be introduced along with a second RGN nickase that only cleaves the negative (−) strand of a double-stranded polynucleotide.

In various embodiments, a method is provided for binding a target nucleotide sequence and detecting the target sequence, wherein the method comprises introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN and further comprises a detectable label, and the method further comprises detecting the detectable label. The detectable label may be fused to the RGN as a fusion protein (e.g., fluorescent protein) or may be a small molecule conjugated to or incorporated within the RGN polypeptide that can be detected visually or by other means.

Also provided herein are methods for modulating the expression of a target sequence or a gene of interest under the regulation of a target sequence. The methods comprise introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN. In some of these embodiments, the nuclease-dead RGN is a fusion protein comprising an expression modulator domain (i.e., epigenetic modification domain, transcriptional activation domain or a transcriptional repressor domain) as described herein.

The present disclosure also provides methods for binding and/or modifying a target nucleotide sequence of interest. The methods include delivering a system comprising at least one guide RNA or a polynucleotide encoding the same, and at least one fusion polypeptide comprises an RGN of the invention and a base-editing polypeptide, for example a cytidine deaminase or an adenosine deaminase, or a polynucleotide encoding the fusion polypeptide, to the target sequence or a cell, organelle, or embryo comprising the target sequence.

One of ordinary skill in the art will appreciate that any of the presently disclosed methods can be used to target a single target sequence or multiple target sequences. Thus, methods comprise the use of a single RGN polypeptide in combination with multiple, distinct guide RNAs, which can target multiple, distinct sequences within a single gene and/or multiple genes. Also encompassed herein are methods wherein multiple, distinct guide RNAs are introduced in combination with multiple, distinct RGN polypeptides. These guide RNAs and guide RNA/RGN polypeptide systems can target multiple, distinct sequences within a single gene and/or multiple genes.

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a tracr mate sequence and one or more insertion sites for inserting a guide sequence upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme coding sequence encoding said CRISPR enzyme comprising a nuclear localization sequence. Elements may be provided individually or in combinations, and may be provided in any suitable container, such as a vial, a bottle, or a tube.

In some embodiments, the kit includes instructions in one or more languages. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide.

VII. Target Polynucleotides

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including microalgae) and modifying the cell or cells. Culturing may occur at any stage ex vivo. The cell or cells may even be re-introduced into the non-human animal or plant (including micro-algae).

Using natural variability, plant breeders combine most useful genes for desirable qualities, such as yield, quality, uniformity, hardiness, and resistance against pests. These desirable qualities also include growth, day length preferences, temperature requirements, initiation date of floral or reproductive development, fatty acid content, insect resistance, disease resistance, nematode resistance, fungal resistance, herbicide resistance, tolerance to various environmental factors including drought, heat, wet, cold, wind, and adverse soil conditions including high salinity The sources of these useful genes include native or foreign varieties, heirloom varieties, wild plant relatives, and induced mutations, e.g., treating plant material with mutagenic agents. Using the present invention, plant breeders are provided with a new tool to induce mutations. Accordingly, one skilled in the art can analyze the genome for sources of useful genes, and in varieties having desired characteristics or traits employ the present invention to induce the rise of useful genes, with more precision than previous mutagenic agents and hence accelerate and improve plant breeding programs.

The target polynucleotide of an RGN system can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence).

The target polynucleotide of a CRISPR complex may include a number of disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease (e.g., a causal mutation). The transcribed or translated products may be known or unknown, and further may be at a normal or abnormal level. Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Although CRISPR systems are particularly useful for their relative ease in targeting to genomic sequences of interest, there still remains an issue of what the RGN can do to address a causal mutation. One approach is to produce a fusion protein between an RGN (preferably an inactive or nickase variant of the RGN) and a base-editing enzyme or the active domain of a base editing enzyme, such as an cytidine deaminase or an adenosine deaminase base editor (U.S. Pat. No. 9,840,699, herein incorporated by reference). In some embodiments, the methods comprise contacting a DNA molecule with (a) a fusion protein comprising an RGN of the invention and a base-editing polypeptide such as a deaminase; and (b) a gRNA targeting the fusion protein of (a) to a target nucleotide sequence of the DNA strand; wherein the DNA molecule is contacted with the fusion protein and the gRNA in an amount effective and under conditions suitable for the deamination of a nucleotide base. In some embodiments, the target DNA sequence comprises a sequence associated with a disease or disorder, and wherein the deamination of the nucleotide base results in a sequence that is not associated with a disease or disorder. In some embodiments, the target DNA sequence resides in an allele of a crop plant, wherein the particular allele of the trait of interest results in a plant of lesser agronomic value. The deamination of the nucleotide base results in an allele that improves the trait and increases the agronomic value of the plant.

In some embodiments, the DNA sequence comprises a T4C or A4G point mutation associated with a disease or disorder, and wherein the deamination of the mutant C or G base results in a sequence that is not associated with a disease or disorder. In some embodiments, the deamination corrects a point mutation in the sequence associated with the disease or disorder.

In some embodiments, the sequence associated with the disease or disorder encodes a protein, and wherein the deamination introduces a stop codon into the sequence associated with the disease or disorder, resulting in a truncation of the encoded protein. In some embodiments, the contacting is performed in vivo in a subject susceptible to having, having, or diagnosed with the disease or disorder. In some embodiments, the disease or disorder is a disease associated with a point mutation, or a single-base mutation, in the genome. In some embodiments, the disease is a genetic disease, a cancer, a metabolic disease, or a lysosomal storage disease.

Further examples of loci which are causal for certain genetic diseases, particularly loci which can be readily targeted by RGNs or RGN-base editor fusion proteins of the invention, can be found in Example 9 and corresponding Table 12.

Hurler Syndrome

An example of a genetically inherited disease which could be corrected using an approach that relies on an RGN-base editor fusion protein of the invention is Hurler Syndrome. Hurler Syndrome, also known as MPS-1, is the result of a deficiency of α-L-iduronidase (IDUA) resulting in a lysosomal storage disease characterized at the molecular level by the accumulation of dermatan sulfate and heparan sulfate in lysosomes. This disease is generally an inherited genetic disorder caused by mutations in the IDUA gene encoding α-L-iduronidase. Common IDUA mutations are W402X and Q70X, both nonsense mutations resulting in premature termination of translation. Such mutations are well addressed by precise genome editing (PGE) approaches, since reversion of a single nucleotide, for example by a base-editing approach, would restore the wild-type coding sequence and result in protein expression controlled by the endogenous regulatory mechanisms of the genetic locus. Additionally, since heterozygotes are known to be asymptomatic, a PGE therapy that targets one of these mutations would be useful to a large proportion of patients with this disease, as only one of the mutated alleles needs to be corrected (Bunge et al. (1994) Hum. Mol. Genet. 3(6): 861-866, herein incorporated by reference).

Current treatments for Hurler Syndrome include enzyme replacement therapy and bone marrow transplants (Vellodi et al. (1997) Arch. Dis. Child. 76(2): 92-99; Peters et al. (1998) Blood 91(7): 2601-2608, herein incorporated by reference). While enzyme replacement therapy has had a dramatic effect on the survival and quality of life of Hurler Syndrome patients, this approach requires costly and time-consuming weekly infusions. Additional approaches include the delivery of the IDUA gene on an expression vector or the insertion of the gene into a highly expressed locus such as that of serum albumin (U.S. Pat. No. 9,956,247, herein incorporated by reference). However, these approaches do not restore the original IDUA locus to the correct coding sequence. A genome-editing strategy would have a number of advantages, most notably that regulation of gene expression would be controlled by the natural mechanisms present in healthy individuals. Additionally, using base editing does not necessitate causing a double stranded DNA breaks, which could lead to large chromosomal rearrangements, cell death, or oncogenecity by the disruption of tumor suppression mechanisms. An enabling description of a method to correct the causal mutation of this disease is provided in Example 10. The described methods are an example of a general strategy directed toward using RGN-base editor fusion proteins of the invention to target and correct certain disease-causing mutations in the human genome. It will be appreciated that similar approaches to target diseases such as those described in Table 12 may also be pursued. It will be further appreciated that similar approaches to target disease-causing mutations in other species, particularly common household pets or livestock, can also be deployed using the RGNs of the invention. Common household pets and livestock include dogs, cats, horses, pigs, cows, sheep, chickens, donkeys, snakes, ferrets, fish including salmon, and shrimp.

Friedreich's Ataxia

RGNs of the invention could also be useful in human therapeutic approaches where the causal mutation is more complicated. For example, some diseases such as Friedreich's Ataxia and Huntington's Disease are the result of a significant increase in repeats of a three nucleotide motif at a particular region of a gene, which affects the ability of the expressed protein to function or to be expressed. Friedreich's Ataxia (FRDA) is an autosomal recessive disease resulting in progressive degeneration of nervous tissue in the spinal cord. Reduced levels of the frataxin (FXN) protein in the mitochondria cause oxidative damages and iron deficiencies at the cellular level. The reduced FXN expression has been linked to a GAA triplet expansion within the intron 1 of the somatic and germline FXN gene. In FRDA patients, the GAA repeat frequently consists of more than 70, sometimes even more than 1000 (most commonly 600-900) triplets, whereas unaffected individuals have about 40 repeats or less (Pandolfo et al. (2012) Handbook of Clinical Neurology 103: 275-294; Campuzano et al. (1996) Science 271: 1423-1427; Pandolfo (2002) Adv. Exp. Med. Biol. 516: 99-118; all herein incorporated by reference).

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from S. pyogenes (SpCas9), are too large to be packaged into adeno-associated viral (AAV) vectors, especially when considering the length of the SpCas9 gene and the guide RNA in addition to other genetic elements required for functional expression cassettes. This makes an approach using SpCas9 more difficult.

The compact RNA guided nucleases of the invention, particularly APG07433.1 and APG08290.1, are uniquely well suited for the excision of the FRDA instability region. Each RGN has a PAM requirement that is in the vicinity of the FRDA instability region. Additionally, each of these RGNs can be packaged into an AAV vector along with a guide RNA. Packing two guide RNAs would likely require a second vector, but this approach still compares favorably to what would be required of a larger nuclease such as SpCas9, which may require splitting the protein sequence between two vectors. An enabling description of a method to correct the causal mutation of this disease is provided in Example 11. The described methods encompass a strategy using RGNs of the invention in which a region of genomic instability is removed. Such a strategy is applicable to other diseases and disorders which have a similar genetic basis, such as Huntington's Disease. Similar strategies using RGNs of the invention may also be applicable to similar diseases and disorders in non-human animals of agronomic or economic importance, including dogs, cats, horses, pigs, cows, sheep, chickens, donkeys, snakes, ferrets, fish including salmon, and shrimp Hemoglobinopathies RGNs of the invention could also be to introduce disruptive mutations that may result in a beneficial effect. Genetic defects in the genes encoding hemoglobin, particularly the beta globin chain (the HBB gene), can be responsible for a number of diseases known as hemoglobinopathies, including sickle cell anemia and thalassemias.

In adult humans, hemoglobin is a heterotetramer comprising two alpha ($\alpha$)-like globin chains and two beta ($\beta$)-like globin chains and 4 heme groups. In adults the $\alpha2\beta2$ tetramer is referred to as Hemoglobin A (HbA) or adult hemoglobin. Typically, the alpha and beta globin chains are synthesized in an approximate 1:1 ratio and this ratio seems to be critical in terms of hemoglobin and red blood cell (RBC) stabilization. In a developing fetus, a different form of hemoglobin, fetal hemoglobin (HbF), is produced which has a higher binding affinity for oxygen than Hemoglobin A such that oxygen can be delivered to the baby's system via the mother's blood stream. Fetal hemoglobin also contains two $\alpha$ globin chains, but in place of the adult $\beta$-globin chains, it has two fetal gamma ($\gamma$)-globin chains (i.e., fetal hemoglobin is $\alpha2\gamma2$). The regulation of the switch from production of gamma- to beta-globin is quite complex, and primarily involves a down-regulation of gamma globin transcription with a simultaneous up-regulation of beta globin transcription. At approximately 30 weeks of gestation, the synthesis of gamma globin in the fetus starts to drop while the production of beta globin increases. By approximately 10 months of age, the newborn's hemoglobin is nearly all $\alpha2\beta2$ although some HbF persists into adulthood (approximately 1-3% of total hemoglobin). In the majority of patients with hemoglobinopathies, the genes encoding gamma globin remain present, but expression is relatively low due to normal gene repression occurring around parturition as described above.

Sickle cell disease is caused by a V6E mutation in the β globin gene (HBB) (a GAG to GTG at the DNA level), where the resultant hemoglobin is referred to as "hemoglobinS" or "HbS." Under lower oxygen conditions, HbS molecules aggregate and form fibrous precipitates. These aggregates cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of gamma globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thalassemias (alpha thalassemias and beta thalassemia) are also diseases relating to hemoglobin and typically involve a reduced expression of globin chains. This can occur through mutations in the regulatory regions of the genes or from a mutation in a globin coding sequence that results in reduced expression or reduced levels or functional globin protein. Treatment of thalassemias usually involves blood transfusions and iron chelation therapy. Bone marrow transplants are also being used for treatment of people with severe thalassemias if an appropriate donor can be identified, but this procedure can have significant risks.

One approach that has been proposed for the treatment of both SCD and beta thalassemias is to increase the expression of gamma globin so that HbF functionally replaces the aberrant adult hemoglobin As mentioned above, treatment of SCD patients with hydroxyurea is thought to be successful in part due to its effect on increasing gamma globin expression (DeSimone (1982) Proc Nat'l Acad Sci USA 79(14): 4428-31; Ley, et al., (1982) N. Engl. J. Medicine, 307: 1469-1475; Ley, et al., (1983) Blood 62: 370-380; Constantoulakis et al., (1988) Blood 72(6):1961-1967, all herein incorporated by reference). Increasing the expression of HbF involves identification of genes whose products play a role in the regulation of gamma globin expression. One such gene is BCL11A. BCL11A encodes a zinc finger protein that expressed in adult erythroid precursor cells, and down-regulation of its expression leads to an increase in gamma globin expression (Sankaran et at (2008) Science 322: 1839, herein incorporated by reference). Use of an inhibitory RNA targeted to the BCL11A gene has been proposed (e.g., U.S. Patent Publication 2011/0182867, herein incorporated by reference) but this technology has several potential drawbacks, including that complete knock down may not be achieved, delivery of such RNAs may be problematic, and the RNAs must be present continuously, requiring multiple treatments for life.

RGNs of the invention may be used to target the BCL11A enhancer region to disrupt expression of BCL11A, thereby increasing gamma globin expression. This targeted disruption can be achieved by non-homologous end joining (NHEJ), whereby an RGN of the invention targets to a particular sequence within the BCL11A enhancer region, makes a double-stranded break, and the cell's machinery repairs the break, typically simultaneously introducing deleterious mutations. Similar to what is described for other disease targets, the RGNs of the invention have advantages over other known RGNs due to their relatively small size, which enables packaging expression cassettes for the RGN and its guide RNA into a single AAV vector for in vivo delivery. An enabling description of this method is provided in Example 12. Similar strategies using RGNs of the invention may also be applicable to similar diseases and disorders in both humans and in non-human animals of agronomic or economic importance.

IX. Cells Comprising a Polynucleotide Genetic Modification

Provided herein are cells and organisms comprising a target sequence of interest that has been modified using a process mediated by an RGN, crRNA, and/or tracrRNA as described herein. In some of these embodiments, the RGN comprises the amino acid sequence of SEQ ID NOs: 1, 11, 19, 27, 36, 45, or 54, or an active variant or fragment thereof. In various embodiments, the guide RNA comprises a CRISPR repeat sequence comprising the nucleotide sequence of SEQ ID NOs: 2, 12, 20, 28, 37, 46, or 55, or an active variant or fragment thereof. In particular embodiments, the guide RNA comprises a tracrRNA comprising the nucleotide sequence of SEQ ID NOs: 3, 13, 21, 29, 38, 47, or 56, or an active variant or fragment thereof. The guide RNA of the system can be a single guide RNA or a dual-guide RNA.

The modified cells can be eukaryotic (e.g., mammalian, plant, insect cell) or prokaryotic. Also provided are organelles and embryos comprising at least one nucleotide sequence that has been modified by a process utilizing an RGN, crRNA, and/or tracrRNA as described herein. The genetically modified cells, organisms, organelles, and embryos can be heterozygous or homozygous for the modified nucleotide sequence.

The chromosomal modification of the cell, organism, organelle, or embryo can result in altered expression (upregulation or down-regulation), inactivation, or the expression of an altered protein product or an integrated sequence. In those instances wherein the chromosomal modification results in either the inactivation of a gene or the expression of a non-functional protein product, the genetically modified cell, organism, organelle, or embryo is referred to as a "knock out". The knock out phenotype can be the result of a deletion mutation (i.e., deletion of at least one nucleotide), an insertion mutation (i.e., insertion of at least one nucleotide), or a nonsense mutation (i.e., substitution of at least one nucleotide such that a stop codon is introduced).

Alternatively, the chromosomal modification of a cell, organism, organelle, or embryo can produce a "knock in", which results from the chromosomal integration of a nucleotide sequence that encodes a protein. In some of these embodiments, the coding sequence is integrated into the chromosome such that the chromosomal sequence encoding the wild-type protein is inactivated, but the exogenously introduced protein is expressed.

In other embodiments, the chromosomal modification results in the production of a variant protein product. The expressed variant protein product can have at least one amino acid substitution and/or the addition or deletion of at least one amino acid. The variant protein product encoded by the altered chromosomal sequence can exhibit modified characteristics or activities when compared to the wild-type protein, including but not limited to altered enzymatic activity or substrate specificity.

In yet other embodiments, the chromosomal modification can result in an altered expression pattern of a protein. As a non-limiting example, chromosomal alterations in the regulatory regions controlling the expression of a protein product can result in the overexpression or downregulation of the protein product or an altered tissue or temporal expression pattern.

The article "a" and "an" are used herein to refer to one or more than one (i.e., to at least one) of the grammatical object of the article. By way of example, "a polypeptide" means one or more polypeptides.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

Non-limiting embodiments include:

1. A nucleic acid molecule comprising a polynucleotide encoding an RNA-guided nuclease (RGN) polypeptide, wherein said polynucleotide comprises a nucleotide sequence encoding an RGN polypeptide comprising an amino acid sequence having at least 95% sequence identity to SEQ ID NOs: 1, 11, 19, 27, 36, 45, or 54;
   wherein said RGN polypeptide binds a target DNA sequence in an RNA-guided sequence specific manner when bound to a guide RNA (gRNA) capable of hybridizing to said target DNA sequence, and
      wherein said polynucleotide encoding an RGN polypeptide is operably linked to a promoter heterologous to said polynucleotide.
2. The nucleic acid molecule of embodiment 1, wherein said RGN polypeptide is capable of cleaving said target DNA sequence upon binding.
3. The nucleic acid molecule of embodiment 2, wherein cleavage by said RGN polypeptide generates a double-stranded break.
4. The nucleic acid molecule of embodiment 2, wherein cleavage by said RGN polypeptide generates a single-stranded break.
5. The nucleic acid molecule of any one of embodiments 1-4, wherein the RGN polypeptide is operably fused to a base-editing polypeptide.
6. The nucleic acid molecule of any one of embodiments 1-5, wherein the RGN polypeptide comprises one or more nuclear localization signals.
7. The nucleic acid molecule of any one of embodiments 1-6, wherein the RGN polypeptide is codon optimized for expression in a eukaryotic cell.
8. The nucleic acid molecule of any one of embodiments 1-7, wherein said target DNA sequence is located adjacent to a protospacer adjacent motif (PAM).
9. A vector comprising the nucleic acid molecule of any one of embodiments 1-8.
10. The vector of embodiment 9, further comprising at least one nucleotide sequence encoding said gRNA capable of hybridizing to said target DNA sequence.
11. The vector of embodiment 10, where said gRNA is a single guide RNA.
12. The vector of embodiment 10, wherein said gRNA is a dual-guide RNA.
13. The vector of any one of embodiments 10-12, wherein the guide RNA comprises a CRISPR RNA comprising a CRISPR repeat sequence having at least 95% sequence identity to SEQ ID NOs: 2, 12, 20, 28, 37, 46, or 55.
14. The vector of any one of embodiments 10-13, wherein the guide RNA comprises a tracrRNA having at least 95% sequence identity to SEQ ID NOs: 3, 13, 21, 29, 38, 47, or 56.
15. A cell comprising the nucleic acid molecule of any one of embodiments 1-8 or the vector of any one of embodiments 9-14.
16. A method for making an RGN polypeptide comprising culturing the cell of embodiment 15 under conditions in which the RGN polypeptide is expressed.
17. A method for making an RGN polypeptide comprising introducing into a cell a heterologous nucleic acid molecule comprising a nucleotide sequence encoding an RNA-guided nuclease (RGN) polypeptide comprising an amino acid sequence having at least 95% sequence identity to SEQ ID NOs: 1, 11, 19, 27, 36, 45, or 54;
   wherein said RGN polypeptide binds a target DNA sequence in an RNA-guided sequence specific manner when bound to a guide RNA (gRNA) capable of hybridizing to said target DNA sequence;
   and culturing said cell under conditions in which the RGN polypeptide is expressed.
18. The method of embodiment 16 or 17, further comprising purifying said RGN polypeptide.
19. The method of embodiment 16 or 17, wherein said cell further expresses one or more guide RNAs that binds to said RGN polypeptide to form an RGN ribonucleoprotein complex.
20. The method of embodiment 19, further comprising purifying said RGN ribonucleoprotein complex.
21. A nucleic acid molecule comprising a polynucleotide encoding a CRISPR RNA (crRNA), wherein said crRNA comprises a spacer sequence and a CRISPR repeat sequence, wherein said CRISPR repeat sequence comprises a nucleotide sequence having at least 95% sequence identity to SEQ ID NOs: 2, 12, 20, 28, 37, 46, or 55;
   wherein a guide RNA comprising:
      a) said crRNA; and
      b) a trans-activating CRISPR RNA (tracrRNA) hybridized to said CRISPR repeat sequence of said crRNA;
   is capable of hybridizing to a target DNA sequence in a sequence specific manner through the spacer sequence of said crRNA when said guide RNA is bound to an RNA-guided nuclease (RGN) polypeptide, and
      wherein said polynucleotide encoding a crRNA is operably linked to a promoter heterologous to said polynucleotide.
22. A vector comprising the nucleic acid molecule of embodiment 21.
23. The vector of embodiment 22, wherein said vector further comprises a polynucleotide encoding said tracrRNA.
24. The vector of embodiment 23, wherein said tracrRNA comprises a nucleotide sequence having at least 95% sequence identity to SEQ ID NOs: 3, 13, 21, 29, 38, 47, or 56.
25. The vector of embodiment 23 or 24, wherein said polynucleotide encoding said crRNA and said polynucleotide encoding said tracrRNA are operably linked to the same promoter and are encoded as a single guide RNA.

26. The vector of embodiment 23 or 24, wherein said polynucleotide encoding said crRNA and said polynucleotide encoding said tracrRNA are operably linked to separate promoters.

27. The vector of any one of embodiments 22-26, wherein said vector further comprises a polynucleotide encoding said RGN polypeptide, wherein said RGN polypeptide comprises an amino acid sequence having at least 95% sequence identity to SEQ ID NOs: 1, 11, 19, 27, 36, 45, or 54.

28. A nucleic acid molecule comprising a polynucleotide encoding a trans-activating CRISPR RNA (tracrRNA) comprising a nucleotide sequence having at least 95% sequence identity to SEQ ID NOs: 3, 13, 21, 29, 38, 47, or 56;
wherein a guide RNA comprising:
   a) said tracrRNA; and
   b) a crRNA comprising a spacer sequence and a CRISPR repeat sequence, wherein said tracrRNA hybridizes with said CRISPR repeat sequence of said crRNA;
is capable of hybridizing to a target DNA sequence in a sequence specific manner through the spacer sequence of said crRNA when said guide RNA is bound to an RNA-guided nuclease (RGN) polypeptide, and
   wherein said polynucleotide encoding a tracrRNA is operably linked to a promoter heterologous to said polynucleotide.

29. A vector comprising the nucleic acid molecule of embodiment 28.

30. The vector of embodiment 29, wherein said vector further comprises a polynucleotide encoding said crRNA.

31. The vector of embodiment 30, wherein the CRISPR repeat sequence of said crRNA comprises a nucleotide sequence having at least 95% sequence identity to SEQ ID NOs: 2, 12, 20, 28, 37, 46, or 55.

32. The vector of embodiment 30 or 31, wherein said polynucleotide encoding said crRNA and said polynucleotide encoding said tracrRNA are operably linked to the same promoter and are encoded as a single guide RNA.

33. The vector of embodiment 30 or 31, wherein said polynucleotide encoding said crRNA and said polynucleotide encoding said tracrRNA are operably linked to separate promoters.

34. The vector of any one of embodiments 29-33, wherein said vector further comprises a polynucleotide encoding said RGN polypeptide, wherein said RGN polypeptide comprises an amino acid sequence having at least 95% sequence identity to SEQ ID NOs: 1, 11, 19, 27, 36, 45, or 54.

35. A system for binding a target DNA sequence, said system comprising:
   a) one or more guide RNAs capable of hybridizing to said target DNA sequence or one or more nucleotide sequences encoding the one or more guide RNAs (gRNAs); and
   b) an RNA-guided nuclease (RGN) polypeptide comprising an amino acid sequence having at least 95% sequence identity to SEQ ID NOs: 1, 11, 19, 27, 36, 45, or 54 or a nucleotide sequence encoding the RGN polypeptide;
wherein said nucleotide sequences encoding the one or more guide RNAs and encoding the RGN polypeptide are each operably linked to a promoter heterologous to said nucleotide sequence;
wherein the one or more guide RNAs hybridize to the target DNA sequence, and
wherein the one or more guide RNAs form a complex with the RGN polypeptide, thereby directing said RGN polypeptide to bind to said target DNA sequence.

36. The system of embodiment 35, wherein said gRNA is a single guide RNA (sgRNA).

37. The system of embodiment 35, wherein said gRNA is a dual-guide RNA.

38. The system of any one of embodiments 35-37, wherein said gRNA comprises a CRISPR repeat sequence comprising a nucleotide sequence having at least 95% sequence identity to SEQ ID NOs: 2, 12, 20, 28, 37, 46, or 55.

39. The system of any one of embodiments 35-38, wherein said gRNA comprises a tracrRNA comprising a nucleotide sequence having at least 95% sequence identity to SEQ ID NOs: 3, 13, 21, 29, 38, 47, or 56.

40. The system of any one of embodiments 35-39, wherein said target DNA sequence is located adjacent to a protospacer adjacent motif (PAM).

41. The system of any one of embodiments 35-40, wherein the target DNA sequence is within a cell.

42. The system of embodiment 41, wherein the cell is a eukaryotic cell.

43. The system of embodiment 42, wherein the eukaryotic cell is a plant cell.

44. The system of embodiment 42, wherein the eukaryotic cell is a mammalian cell.

45. The system of embodiment 42, wherein the eukaryotic cell is an insect cell.

46. The system of embodiment 41, wherein the cell is a prokaryotic cell.

47. The system of any one of embodiments 35-46, wherein when transcribed the one or more guide RNAs hybridize to the target DNA sequence and the guide RNA forms a complex with the RGN polypeptide which causes cleavage of the target DNA sequence.

48. The system of embodiment 47, wherein the cleavage generates a double-stranded break.

49. The system of embodiment 47, wherein cleavage by said RGN polypeptide generates a single-stranded break.

50. The system of any one of embodiments 35-49, wherein the RGN polypeptide is operably linked to a base-editing polypeptide.

51. The system of any one of embodiments 35-50, wherein the RGN polypeptide comprises one or more nuclear localization signals.

52. The system of any one of embodiments 35-51, wherein the RGN polypeptide is codon optimized for expression in a eukaryotic cell.

53. The system of any one of embodiments 35-52, wherein nucleotide sequences encoding the one or more guide RNAs and the nucleotide sequence encoding an RGN polypeptide are located on one vector.

54. The system of any one of embodiments 35-53, wherein said system further comprises one or more donor polynucleotides or one or more nucleotide sequences encoding the one or more donor polynucleotides.

55. A method for binding a target DNA sequence comprising delivering a system according to any one of embodiments 35-54, to said target DNA sequence or a cell comprising the target DNA sequence.

56. The method of embodiment 55, wherein said RGN polypeptide or said guide RNA further comprises a detectable label, thereby allowing for detection of said target DNA sequence.

57. The method of embodiment 55, wherein said guide RNA or said RGN polypeptide further comprises an expression modulator, thereby modulating expression of said target DNA sequence or a gene under transcriptional control by said target DNA sequence.

58. A method for cleaving or modifying a target DNA sequence comprising delivering a system according to any one of embodiments 35-54, to said target DNA sequence or a cell comprising the target DNA sequence.

59. The method of embodiment 58, wherein said modified target DNA sequence comprises insertion of heterologous DNA into the target DNA sequence.

60. The method of embodiment 58, wherein said modified target DNA sequence comprises deletion of at least one nucleotide from the target DNA sequence.

61. The method of embodiment 58, wherein said modified target DNA sequence comprises mutation of at least one nucleotide in the target DNA sequence.

62. A method for binding a target DNA sequence comprising:
a) assembling a RNA-guided nuclease (RGN) ribonucleotide complex in vitro by combining:
i) one or more guide RNAs capable of hybridizing to the target DNA sequence; and
ii) an RGN polypeptide comprising an amino acid sequence having at least 95% sequence identity to SEQ ID NOs: 1, 11, 19, 27, 36, 45, or 54;
under conditions suitable for formation of the RGN ribonucleotide complex; and
b) contacting said target DNA sequence or a cell comprising said target DNA sequence with the in vitro-assembled RGN ribonucleotide complex;
wherein the one or more guide RNAs hybridize to the target DNA sequence, thereby directing said RGN polypeptide to bind to said target DNA sequence.

63. The method of embodiment 62, wherein said RGN polypeptide or said guide RNA further comprises a detectable label, thereby allowing for detection of said target DNA sequence.

64. The method of embodiment 62, wherein said guide RNA or said RGN polypeptide further comprises an expression modulator, thereby allowing for the modulation of expression of said target DNA sequence.

65. A method for cleaving and/or modifying a target DNA sequence, comprising contacting the DNA molecule with:
a) an RNA-guided nuclease (RGN) polypeptide, wherein said RGN comprises an amino acid sequence having at least 95% sequence identity to SEQ ID NOs: 1, 11, 19, 27, 36, 45 or 54; and
b) one or more guide RNAs capable of targeting the RGN of (a) to the target DNA sequence;
wherein the one or more guide RNAs hybridize to the target DNA sequence, thereby directing said RGN polypeptide to bind to said target DNA sequence and cleavage and/or modification of said target DNA sequence occurs.

66. The method of embodiment 65, wherein said modified target DNA sequence comprises insertion of heterologous DNA into the target DNA sequence.

67. The method of embodiment 65, wherein said modified target DNA sequence comprises deletion of at least one nucleotide from the target DNA sequence.

68. The method of embodiment 65, wherein said modified target DNA sequence comprises mutation of at least one nucleotide in the target DNA sequence.

69. The method of any one of embodiments 62-68, wherein said gRNA is a single guide RNA (sgRNA).

70. The method of any one of embodiments 62-68, wherein said gRNA is a dual-guide RNA.

71. The method of any one of embodiments 62-70, wherein said gRNA comprises a CRISPR repeat sequence comprising a nucleotide sequence having at least 95% sequence identity to SEQ ID NOs: 2, 12, 20, 28, 37, 46, or 55.

72. The method of any one of embodiments 62-71, wherein said gRNA comprises a tracrRNA comprising a nucleotide sequence having at least 95% sequence identity to SEQ ID NOs: 3, 13, 21, 29, 38, 47, or 56.

73. The method of any one of embodiments 62-72, wherein said target DNA sequence is located adjacent to a protospacer adjacent motif (PAM).

74. The method of any one of embodiments 55-73, wherein the target DNA sequence is within a cell.

75. The method of embodiment 74, wherein the cell is a eukaryotic cell.

76. The method of embodiment 75, wherein the eukaryotic cell is a plant cell.

77. The method of embodiment 75, wherein the eukaryotic cell is a mammalian cell.

78. The method of embodiment 75, wherein the eukaryotic cell is an insect cell.

79. The method of embodiment 74, wherein the cell is a prokaryotic cell.

80. The method of any one of embodiments 74-79, further comprising culturing the cell under conditions in which the RGN polypeptide is expressed and cleaves the target DNA sequence to produce a modified DNA sequence; and selecting a cell comprising said modified DNA sequence.

81. A cell comprising a modified target DNA sequence according to the method of embodiment 80.

82. The cell of embodiment 81, wherein the cell is a eukaryotic cell.

83. The cell of embodiment 82, wherein the eukaryotic cell is a plant cell.

84. A plant comprising the cell of embodiment 83.

85. A seed comprising the cell of embodiment 83.

86. The cell of embodiment 82, wherein the eukaryotic cell is a mammalian cell.

87. The cell of embodiment 82, wherein the eukaryotic cell is an insect cell.

88. The cell of embodiment 81, wherein the cell is a prokaryotic cell.

89. A method for producing a genetically modified cell with a correction in a causal mutation for a genetically inherited disease, the method comprising introducing into the cell:
a) an RNA-guided nuclease (RGN) polypeptide, wherein the RGN polypeptide comprises an amino acid sequence having at least 95% sequence identity to SEQ ID NOs: 1, 11, 19, 27, 36, 45, or 54, or a polynucleotide encoding said RGN polypeptide, wherein said polynucleotide encoding the RGN polypeptide is operably linked to a promoter to enable expression of the RGN polypeptide in the cell; and
b) a guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell
whereby the RGN and gRNA target to the genomic location of the causal mutation and modify the genomic sequence to remove the causal mutation.

90. The method of embodiment 89, wherein the RGN is fused to a polypeptide which has base-editing activity.
91. The method of embodiment 90, wherein the polypeptide with base-editing activity is a cytidine deaminase or an adenosine deaminase.
92. The method of embodiment 89, wherein the cell is an animal cell.
93. The method of embodiment 89, wherein the cell is a mammalian cell.
94. The method of embodiment 92, wherein the cell is derived from a dog, cat, mouse, rat, rabbit, horse, cow, pig, or human.
95. The method of embodiment 92, wherein the genetically inherited disease is a disease listed in Table 12.
96. The method of embodiment 92, wherein the genetically inherited disease is Hurler Syndrome.
97. The method of embodiment 96, wherein the gRNA further comprises a spacer sequence that targets SEQ ID NO: 453, 454, or 455.
98. A method for producing a genetically modified cell with a deletion in a disease-causing genomic region of instability, the method comprising introducing into the cell:
a) an RNA-guided nuclease (RGN) polypeptide, wherein the RGN polypeptide comprises an amino acid sequence having at least 95% sequence identity to SEQ ID NOs: 1, 11, 19, 27, 36, 45, or 54, or a polynucleotide encoding said RGN polypeptide, wherein said polynucleotide encoding the RGN polypeptide is operably linked to a promoter to enable expression of the RGN polypeptide in the cell; and
b) a guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell, and further wherein the gRNA comprises a spacer sequence that targets the 5'flank of the genomic region of instability; and
c) a second guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell, and further wherein said second gRNA comprises a spacer sequence that targets the 3'flank of the genomic region of instability;
whereby the RGN and the two gRNAs target to the genomic region of instability and at least a portion of the genomic region of instability is removed.

99. The method of embodiment 98, wherein the cell is an animal cell.
100. The method of embodiment 98, wherein the cell is a mammalian cell.
101. The method of embodiment 100, wherein the cell is derived from a dog, cat, mouse, rat, rabbit, horse, cow, pig, or human.
102. The method of embodiment 99, wherein the genetically inherited disease is Friedrich's Ataxia or Huntington's Disease.
103. The method of embodiment 102, wherein the first gRNA further comprises a spacer sequence that targets SEQ ID NO: 468, 469, or 470.
104. The method of embodiment 103, wherein the second gRNA further comprises a spacer sequence that targets SEQ ID NO: 471.
105. A method for producing a genetically modified mammalian hematopoietic progenitor cell having decreased BCL11A mRNA and protein expression, the method comprising introducing into an isolated human hematopoietic progenitor cell:
a) an RNA-guided nuclease (RGN) polypeptide, wherein the RGN polypeptide comprises an amino acid sequence having at least 95% sequence identity to SEQ ID NOs: 1, 11, 19, 27, 36, 45, or 54, or a polynucleotide encoding said RGN polypeptide, wherein said polynucleotide encoding the RGN polypeptide is operably linked to a promoter to enable expression of the RGN polypeptide in the cell; and
b) a guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell,
whereby the RGN and gRNA are expressed in the cell and cleave at the BCL11A enhancer region, resulting in genetic modification of the human hematopoietic progenitor cell and reducing the mRNA and/or protein expression of BCL11A.
106. The method of embodiment 105, wherein the gRNA further comprises a spacer sequence that targets SEQ ID NO: 473, 474, 475, 476, 477, or 478.
107. A system for binding a target DNA sequence, said system comprising:
a) one or more guide RNAs capable of hybridizing to said target DNA sequence or one or more nucleotide sequences encoding the one or more guide RNAs (gRNAs); and
b) an RNA-guided nuclease (RGN) polypeptide comprising an amino acid sequence having at least 95% sequence identity to SEQ ID NOs: 1, 11, 19, 27, 36, 45, or 54;
wherein the one or more guide RNAs hybridize to the target DNA sequence, and
wherein the one or more guide RNAs forms a complex with the RGN polypeptide, thereby directing said RGN polypeptide to bind to said target DNA sequence.
108. The system of embodiment 107, wherein said RGN polypeptide is nuclease dead or functions as a nickase.
109. The system of embodiment 107 or 108, wherein said RGN polypeptide is operably fused to a base-editing polypeptide.
110. The system of embodiment 109, wherein the base-editing polypeptide is a deaminase.

111. The system of embodiment 110, wherein the deaminase is a cytidine deaminase or an adenosine deaminase.

The following examples are offered by way of illustration and not by way of limitation.

EXPERIMENTAL

Example 1. Identification of RNA-Guided Nuclease

Seven distinct CRISPR-associated RNA-guided nucleases (RGN's) were identified and are described in Table 1 below. Table 1 provides the name of each RGN, its amino acid sequence, the source from which it was derived, and processed crRNA and tracrRNA sequences. Table 1 further provides a generic single guide RNA (sgRNA) sequence, where the poly-N indicates the location of the spacer sequence which determines the nucleic acid target sequence of the sgRNA. RGN systems APG systems APG05083.1, APG07433.1, APG08290.1, and APG08290.1 had a conserved sequence in the base of the hairpin stem of the tracrRNA, UNANNG (SEQ ID NO: 68). For the AP05459.1 system, the sequence in the same location is UNANNU (SEQ ID NO: 557). For APG04583.1 and APG01688.1 systems, the sequence is UNANNA (SEQ ID NO: 558).

TABLE 1

Summary of SEQ IDs and CRISPR associated systems

| RGN ID | SEQ ID NO. | Source | crRNA repeat seq (SEQ ID NO.) | tracrRNA (SEQ ID NO.) | sgRNA (SEQ ID NO) |
|---|---|---|---|---|---|
| APG05083.1 | 1 | Bacillus sp. | 2 | 3 | 10 |
| APG07433.1 | 10 | Bacillus sp. | 12 | 13 | 18 |
| APG07513.1 | 18 | Bacillus sp. | 20 | 21 | 26 |
| APG08290.1 | 26 | Bacillus sp. | 28 | 29 | 35 |
| APG05459.1 | 34 | Enterococcus sp. | 37 | 38 | 44 |
| APG04583.1 | 42 | Enterococcus sp. | 46 | 47 | 53 |
| APG01688.1 | 50 | Empedobacter sp. | 55 | 56 | 62 |

Example 2: Guide RNA Identification and sgRNA Construction

Cultures of bacteria that natively express the RNA-guided nuclease system under investigation were grown to mid-log phase (OD600 of ~0.600), pelleted, and flash frozen. RNA was isolated from the pellets using a mirVANA miRNA Isolation Kit (Life Technologies, Carlsbad, CA), and sequencing libraries were prepared from the isolated RNA using an NEBNext Small RNA Library Prep kit (NEB, Beverly, MA). The library prep was fractionated on a 6% polyacrylamide gel into 2 size fractions corresponding to 18-65 nt and 90-200 nt RNA species to detect crRNAs and tracrRNAs, respectively. Deep sequencing (40 bp paired-end for the smaller fraction and 80 bp paired-end for the larger fraction) was performed on a Next Seq 500 (High Output kit) by a service provider (MoGene, St. Louis, MO). Reads were quality trimmed using Cutadapt and mapped to reference genomes using Bowtie2. A custom RNAseq pipeline was written in python to detect the crRNA and tracrRNA transcripts. Processed crRNA boundaries were determined by sequence coverage of the native repeat spacer array. The anti-repeat portion of the tracrRNA was identified using permissive BLASTn parameters. RNA sequencing depth confirmed the boundaries of the processed tracrRNA by identifying the transcript containing the anti-repeat. Manual curation of RNAs was performed using secondary structure prediction by NUPACK, an RNA folding software. sgRNA cassettes were prepared by DNA synthesis and were generally designed as follows (5'->3'): 20-30 bp spacer sequence—processed repeat portion of the crRNA—4 bp noncomplementary linker (AAAG; SEQ ID NO: 63)—processed tracrRNA. Other 4 bp noncomplementary linkers may also be used, for example GAAA (SEQ ID NO: 64) or ACUU (SEQ ID NO: 65). In some instances, a 6 bp nucleotide linker may be used, for example CAAAGG (SEQ ID NO: 66). For in vitro assays, sgRNAs were synthesized by in vitro transcription of the sgRNA cassettes with a GeneArt™ Precision gRNA Synthesis Kit (ThermoFisher). Processed crRNA and tracrRNA sequences for each of the RGN polypeptides are identified and are set forth in Table 1. See below for the sgRNAs constructed for PAM libraries 1 and 2.

Example 3: Determination of PAM Requirements for Each RGN

PAM requirements for each RGN were determined using a PAM depletion assay essentially adapted from Kleinstiver et al. (2015) Nature 523:481-485 and Zetsche et al. (2015) Cell 163:759-771. Briefly, two plasmid libraries (L1 and L2) were generated in a pUC18 backbone (ampR), with each containing a distinct 30 bp protospacer (target) sequence flanked by 8 random nucleotides (i.e., the PAM region). The target sequence and flanking PAM region of library 1 and library 2 for each RGN are set forth in Table 2.

The libraries were separately electroporated into E. coli BL21(DE3) cells harboring pRSF-1b expression vectors containing an RGN of the invention (codon optimized for E. coli) along with a cognate sgRNA containing a spacer sequence corresponding to the protospacer in L1 or L2. Sufficient library plasmid was used in the transformation reaction to obtain >10^6 cfu. Both the RGN and sgRNA in the pRSF-1b backbone were under the control of T7 promoters. The transformation reaction was allowed to recover for 1 hr after which it was diluted into LB media containing carbenicillin and kanamycin and grown overnight. The following day the mixture was diluted into self-inducing Overnight Express™ Instant TB Medium (Millipore Sigma) to allow expression of the RGN and sgRNA, and grown for an additional 4 h or 20 h after which the cells were spun down and plasmid DNA was isolated with a Mini-prep kit (Qiagen, Germantown, MD). In the presence of the appropriate sgRNA, plasmids containing a PAM that is recognizable by the RGN will be cleaved resulting in their removal from the population. Plasmids containing PAMs that are not recognizable by the RGN, or that are transformed into bacteria not containing an appropriate sgRNA, will survive and replicate. The PAM and protospacer regions of uncleaved plasmids were PCR-amplified and prepared for sequencing following published protocols (16s-metagenomic library prep guide 15044223B, Illumina, San Diego, CA). Deep sequencing (80 bp single end reads) was performed on a MiSeq (Illumina) by a service provider (MoGene, St. Louis, MO). Typically, 1-4M reads were obtained per amplicon. PAM regions were extracted, counted, and normalized to total reads for each sample. PAMs that lead to plasmid cleavage were identified by being underrepresented when compared to controls (i.e., when the library is transformed into E. coli containing the RGN but lacking an appropriate sgRNA). To represent PAM requirements for a novel RGN, the depletion ratios (frequency in sample/ frequency in control) for all sequences in the region in question were converted to enrichment values with a −log base 2 transformation. Sufficient PAMs were defined as those with enrichment values >2.3 (which corresponds to depletion ratios <~−0.2). PAMs above this threshold in both libraries were collected and used to generate web logos, which for example can be generated using a web-based service on the internet known as "weblogo". PAM sequences were identified and reported when there was a consistent pattern in the top enriched PAMs. A PAM (having an enrichment factor (EF)>2.3) for each RGN is provided in Table 2. For some RGNs, non-limiting exemplary PAMs (having an EF>3.3) were also identified. For APG005083.1, the exemplary PAM is NNRNCC (SEQ ID NO: 69). For APG007433.1, the exemplary PAM is NNNNCCR (SEQ ID NO: 70). For APG007513.1, the exemplary PAM is NNRNCC (SEQ ID NO: 71). For APG001688.1, the exemplary PAM is NNRANC (SEQ ID NO: 72).

TABLE 2

PAM determination

| RGN ID | sgRNA L1 (SEQ ID NO.) | sgRNA L2 (SEQ ID NO.) | PAM (SEQ ID NO.) | Target seq and PAM region of plasmid library 1 (SEQ ID NO.) | Target seq and PAM region of plasmid library 2 (SEQ ID NO.) |
|---|---|---|---|---|---|
| APG05083.1 | 4 | 5 | 6 | 8 | 9 |
| APG07433.1 | 13 | 14 | 6 | 16 | 17 |
| APG07513.1 | 21 | 22 | 6 | 24 | 25 |
| APG08290.1 | 29 | 30 | 32 | 33 | 34 |
| APG05459.1 | 37 | 38 | 41 | 42 | 43 |
| APG04583.1 | 45 | 46 | 50 | 51 | 52 |
| APG01688.1 | 53 | 54 | 59 | 60 | 61 | amplified target, referred to as "Sequence 1". Sequence 1 comprised a nucleotide sequence (SEQ ID NO: 73) directly linked at its 3' end to the corresponding PAM sequence for each RGN. Each RGN as a ribonucleoprotein complex was incubated with its respective target polynucleotide at 25° C. (APG04583.1) or 37° C. (all others) for 30 min or 60 min (APG05459.1 and APG01688.1 only). The digestion reaction was heat inactivated and run on an agarose gel. The cleavage product bands were excised from the gel and sequenced using Sanger sequencing. Cleavage sites were identified by aligning the sequencing results with the expected sequence of the PCR product. Results are shown in Table 3. As shown in Table 3, RGN APG007433.1 may also produce a blunt cut with a different target sequence.

The cleavage site for Sequence 2 (SEQ ID NO: 559, operably fused at its 3'end to a PAM sequence for RGN APG0733.1) was determined by the following approach for the nuclease APG07433.1. After digestion, the gel purified DNA products were treated with a DNA end repair kit (Thermo Scientific K0771), ligated into linearized blunt vector, and the resulting circular DNA was transformed into E. coli competent cells. A staggered cut with a 5' overhang would result in detection of overlapping sequences in the clones from both cleavage products. A 3' overhang would result in missing sequence, and a blunt cut would result in all of the original sequence being detected with no overlap. This experiment also verified the finding from the above described method for sequence 1—most of the clones were detected as having originated from a cut with a 5' overlap, so it is not expected that the finding of a blunt cut is an artifact of utilizing this method.

TABLE 3

RGN cleavage sites

| | Sequence 1 | | | Sequence 2 | | |
|---|---|---|---|---|---|---|
| | Distance from PAM | | | Distance from PAM | | |
| Nuclease | NTS cut site | TS cut site | Overhang | NTS cut site | TS cut site | Overhang |
| APG07433.1 | 4 | 3 | 1 nt, 5' | 3 | 3 | None |
| APG08290.1 | 4 | 3 | 1 nt, 5' | Not determined | | |
| APG05459.1 | 3 | 3 | None | Not determined | | |
| APG04583.1 | 3 | 3 | None | Not determined | | |
| APG01688.1 | 3 | 3 | None | Not determined | | |

NTS = non-target strand; TS = target strand

Example 4: Cleavage Determination

Cleavage sites were determined from in vitro cleavage reactions using RNPs (ribonucleoproteins). Expression plasmids containing an RGN fused to a His6 or a His10 tag were constructed and transformed into BL21 (DE3) strains of E. coli. Expression was performed using self-inducing media or with IPTG induction. After lysis and clarification, the proteins were purified by immobilized metal affinity chromatography.

Ribonucleoprotein complexes (comprising nuclease and an sgRNA or a crRNA and tracrRNA duplex) were formed by incubation of nuclease and the RNA in a buffered solution for 20 min at room temperature. The complex was transferred to a tube containing digestion buffer and a PCR Example 5: Mismatch Sensitivity Assay Plasmids were designed and obtained with a target sequence (SEQ ID NO: 73) immediately 5' to a suitable PAM motif for the nuclease being evaluated. Single mismatch sequences were also generated with an altered sequence at the position indicated (Table 4). RNP complexes of purified nuclease (APG08290.1 or APG05459.1) and guide RNA were formed and incubated with PCR amplified linear DNA from the designed plasmids. After incubation for a designated period of time and nuclease inactivation, the samples were analyzed by agarose gel electrophoresis to determine the fraction of the linear PCR product remaining. The percentage of the intact band cleaved is shown in Table 5 for mismatches in each position.

TABLE 4

Sequences tested for the mismatch sensitivity assay for APG08290.1 and APG05459.1

| Protospacer sequence | SEQ ID NO. | Mismatch position |
|---|---|---|
| GAGCGGACAGCAGCTTCCTATATCTCGTAC | 73 | None |
| GAGCGGACAGCAGCTTCCTATATCTCGTAG | 74 | 1 |
| GAGCGGACAGCAGCTTCCTATATCTCGTTC | 75 | 2 |
| GAGCGGACAGCAGCTTCCTATATCTCGAAC | 76 | 3 |
| GAGCGGACAGCAGCTTCCTATATCTCCTAC | 77 | 4 |
| GAGCGGACAGCAGCTTCCTATATCTGGTAC | 78 | 5 |
| GAGCGGACAGCAGCTTCCTATATCACGTAC | 79 | 6 |
| GAGCGGACAGCAGCTTCCTATATGTCGTAC | 80 | 7 |
| GAGCGGACAGCAGCTTCCTATAACTCGTAC | 81 | 8 |
| GAGCGGACAGCAGCTTCCTATTTCTCGTAC | 82 | 9 |
| GAGCGGACAGCAGCTTCCTAAATCTCGTAC | 83 | 10 |
| GAGCGGACAGCAGCTTCCTTTATCTCGTAC | 84 | 11 |
| GAGCGGACAGCAGCTTCCAATATCTCGTAC | 85 | 12 |
| GAGCGGACAGCAGCTTCGTATATCTCGTAC | 86 | 13 |
| GAGCGGACAGCAGCTTGCTATATCTCGTAC | 87 | 14 |
| GAGCGGACAGCAGCTACCTATATCTCGTAC | 88 | 15 |
| GAGCGGACAGCAGCATCCTATATCTCGTAC | 89 | 16 |
| GAGCGGACAGCAGGTTCCTATATCTCGTAC | 90 | 17 |
| GAGCGGACAGCACCTTCCTATATCTCGTAC | 91 | 18 |
| GAGCGGACAGCTGCTTCCTATATCTCGTAC | 92 | 19 |
| GAGCGGACAGGAGCTTCCTATATCTCGTAC | 93 | 20 |
| GAGCGGACACCAGCTTCCTATATCTCGTAC | 94 | 21 |
| GAGCGGACTGCAGCTTCCTATATCTCGTAC | 95 | 22 |
| GAGCGGAGAGCAGCTTCCTATATCTCGTAC | 96 | 23 |
| GAGCGGTCAGCAGCTTCCTATATCTCGTAC | 97 | 24 |
| GAGCGCACAGCAGCTTCCTATATCTCGTAC | 98 | 25 |
| GAGCCGACAGCAGCTTCCTATATCTCGTAC | 99 | 26 |
| GAGGGGACAGCAGCTTCCTATATCTCGTAC | 100 | 27 |
| GACCGGACAGCAGCTTCCTATATCTCGTAC | 101 | 28 |
| GTGCGGACAGCAGCTTCCTATATCTCGTAC | 102 | 29 |
| CAGCGGACAGCAGCTTCCTATATCTCGTAC | 103 | 30 |

TABLE 5

Mismatch sensitivity for RGN APG08290.1 and RGN APG05459.1

| Mismatch position | % cleaved APG08290.1 | % cleaved APG05459.1 |
|---|---|---|
| Incompatible PAM, no mismatch | 0 | 0 |
| No mismatch | 95 | 67 |
| 1 | 0 | 0 |
| 2 | 0 | 74 |
| 3 | 73 | 3 |
| 4 | 0 | 0 |
| 5 | 0 | 0 |
| 6 | 31 | 30 |
| 7 | 0 | 12 |
| 8 | 0 | 51 |
| 9 | 0 | 0 |
| 10 | 75 | 52 |
| 11 | 77 | 5 |
| 12 | 79 | 62 |
| 13 | 28 | 18 |
| 14 | 8 | 5 |
| 15 | 90 | 6 |
| 16 | 85 | 5 |
| 17 | 81 | 4 |
| 18 | 100 | 0 |
| 19 | 100 | 0 |
| 20 | 100 | 2 |
| 21 | 100 | 30 |
| 22 | 100 | 48 |
| 23 | 100 | 40 |
| 24 | 100 | 45 |
| 25 | 100 | 29 |
| 26 | 100 | 33 |
| 27 | 100 | 73 |
| 28 | 100 | 46 |
| 29 | 100 | 59 |
| 30 | 100 | 57 |

A similar mismatch sensitivity experiment was performed for RGN APG07433.1. This experiment was similar to the one described above, except that the alternative base was introduced into the RNA guide rather than the DNA target. DNA sequences for mismatched sgRNA synthesis are shown in Table 6. Results of the mismatch sensitivity assay are shown in Table 7.

TABLE 6

Sequences tested for the mismatch sensitivity assay for RGN APG07433.1

| DNA template for sgRNA synthesis | SEQ ID NO. | Mismatch position |
|---|---|---|
| GAGCGGACAGCAGCTTCCTATATCTCGTAC | 73 | None |
| GAGCGGACAGCAGCTTCCTATATCTCGTAT | 104 | 1 |
| GAGCGGACAGCAGCTTCCTATATCTCGTGC | 105 | 2 |
| GAGCGGACAGCAGCTTCCTATATCTCGCAC | 106 | 3 |
| GAGCGGACAGCAGCTTCCTATATCTCATAC | 107 | 4 |
| GAGCGGACAGCAGCTTCCTATATCTTGTAC | 108 | 5 |
| GAGCGGACAGCAGCTTCCTATATCCCGTAC | 109 | 6 |
| GAGCGGACAGCAGCTTCCTATATTTCGTAC | 110 | 7 |
| GAGCGGACAGCAGCTTCCTATACCTCGTAC | 111 | 8 |
| GAGCGGACAGCAGCTTCCTATGTCTCGTAC | 112 | 9 |

TABLE 6-continued

Sequences tested for the mismatch sensitivity assay for RGN APG07433.1

| DNA template for sgRNA synthesis | SEQ ID NO. | Mismatch position |
|---|---|---|
| GAGCGGACAGCAGCTTCCTACATCTCGTAC | 113 | 10 |
| GAGCGGACAGCAGCTTCCTGTATCTCGTAC | 114 | 11 |
| GAGCGGACAGCAGCTTCCCATATCTCGTAC | 115 | 12 |
| GAGCGGACAGCAGCTTCTTATATCTCGTAC | 116 | 13 |
| GAGCGGACAGCAGCTTTCTATATCTCGTAC | 117 | 14 |
| GAGCGGACAGCAGCTCCCTATATCTCGTAC | 118 | 15 |
| GAGCGGACAGCAGCCTCCTATATCTCGTAC | 119 | 16 |
| GAGCGGACAGCAGTTTCCTATATCTCGTAC | 120 | 17 |
| GAGCGGACAGCAACTTCCTATATCTCGTAC | 121 | 18 |
| GAGCGGACAGCGGCTTCCTATATCTCGTAC | 122 | 19 |
| GAGCGGACAGTAGCTTCCTATATCTCGTAC | 123 | 20 |
| GAGCGGACAACAGCTTCCTATATCTCGTAC | 124 | 21 |
| GAGCGGACGGCAGCTTCCTATATCTCGTAC | 125 | 22 |
| GAGCGGATAGCAGCTTCCTATATCTCGTAC | 126 | 23 |

TABLE 7

Mismatch sensitivity for RGN APG07433.1

| Mismatch position | % cleaved APG07433.1 |
|---|---|
| No mismatch | 86 |
| 1 | 6 |
| 2 | 21 |
| 3 | -2 |
| 4 | 1 |
| 5 | -1 |
| 6 | 0 |
| 7 | 7 |
| 8 | 24 |
| 9 | 14 |
| 10 | -1 |
| 11 | 72 |
| 12 | 44 |
| 13 | 54 |
| 14 | 60 |
| 16 | 65 |
| 17 | 76 |
| 18 | 84 |
| 19 | 86 |
| 20 | 83 |
| 21 | 83 |
| 22 | 93 |
| 23 | 80 |

RGNs APG07433.1 and APG08290.1 show significant sensitivity to mismatches in positions 1-10 5' from the PAM with a few exceptions (Table 5 and Table 7). RGN APG05459.1 is sensitive as well to mismatches in this region, but its ability to cleave dsDNA is also heavily abrogated by mismatches distant from the PAM site (Table 5). The total number of sites with a significant influence on whether or not cleavage occurs is at least 15 positions in the spacer sequence. This compares favorably to other genome editing tools, such as the well-studied Cas9 nuclease from *S. pyogenes*, which is generally sensitive to between 10-13 base pairs (Hsu et al., Nat Biotechnol (2013) 31(9): 827-832). Additionally, many of the critical sites abrogating RGN APG05459.1 mediated cleavage are very far from the PAM sequence, notably in the range of 13-20 bp, where many other nucleases show little if any sensitivity to mismatches. This property could be extraordinarily useful in targeting genetic loci that have close sequence similarity to other sites in the organism of interest.

Example 6: Demonstration of Gene Editing Activity in Mammalian Cells

RGN expression cassettes were produced and introduced into vectors for mammalian expression. Each RGN was codon-optimized for human expression (SEQ ID NOs 127-133), and operably fused at the 5'end to an SV40 nuclear localization sequence (NLS; SEQ ID NO 134) and to 3×FLAG tags (SEQ ID NO: 135), and operably fused at the 3'end to nucleoplasmin NLS sequences (SEQ ID NO: 136). Each expression cassette was under control of a cytomegalovirus (CMV) promoter (SEQ ID NO: 137). It is known in the art that the CMV transcription enhancer (SEQ ID NO: 138) may also be included in constructs comprising the CMV promoter. Guide RNA expression constructs encoding a single gRNA each under the control of a human RNA polymerase III U6 promoter (SEQ ID NO. 139) were produced and introduced into the pTwist High Copy Amp vector. Sequences for the target sequences for each guide are in Table 9.

The constructs described above were introduced into mammalian cells. One day prior to transfection, 1×10⁵ HEK293T cells/well (Sigma) were plated in 24-well dishes in Dulbecco's modified Eagle medium (DMEM) plus 10% (vol/vol) fetal bovine serum (Gibco) and 1% Penicillin-Streptomycin (Gibco). The next day when the cells were at 50-60% confluency, 500 ng of a RGN expression plasmid plus 500 ng of a single gRNA expression plasmid were co-transfected using 1.5 µL of Lipofectamine 3000 (Thermo Scientific) per well, following the manufacturer's instructions. After 48 hours of growth, total genomic DNA was harvested using a genomic DNA isolation kit (Machery-Nagel) according to the manufacturer's instructions.

The total genomic DNA was then analyzed to determine the rate of editing for each RGN for each genomic target. First, oligonucleotides were produced to be used for PCR amplification and subsequent analysis of the amplified genomic target site. Oligonucleotide sequences used are listed in Tables 8.1 to 8.5.

All PCR reactions were performed using 10 µL of 2× Master Mix Phusion High-Fidelity DNA polymerase (Thermo Scientific) in a 20 µL reaction including 0.5 µM of each primer. Large genomic regions encompassing each target gene were first amplified using PCR #1 primers, using a program of: 98° C., 1 min; 30 cycles of [98° C., 10 sec; 62° C., 15 sec; 72° C., 5 min]; 72° C., 5 min; 12° C., forever. One microliter of this PCR reaction was then further amplified using primers specific for each guide (PCR #2 primers), using a program of: 98° C., 1 min; 35 cycles of [98° C., 10 sec; 67° C., 15 sec; 72° C., 30 sec]; 72° C., 5 min; 12° C., forever. Primers for PCR42 include Nextera Read 1 and Read 2 Transposase Adapter overhang sequences for Illumina sequencing.

TABLE 8.1

Oligonucleotides for detection of gene editing activity in mammalian cells, PCR #1

| Description | Sequence | SEQ ID NO |
|---|---|---|
| RelA FWD | 5'-CTT AGT TTC ACC GCA GGT TCT A-3' | 479 |
| RelA REV | 5'-CTG TGC ACT CAA CAC TGA TCT A-3' | 480 |
| AurkB FWD | 5'-CCC AGC CCT AGG TTG TTT ATT-3' | 481 |
| AurkB REV | 5'-CTG GCT ACA TCT TCC TTG ACT AC-3' | 482 |
| HPRT1 FWD | 5'-GTG GCA GAA GCA GTG AGT AA-3' | 483 |
| HPRT1 REV | 5'-TCC CAT CTA GGC ACT AGG TAA A-3' | 484 |

TABLE 8.2

Oligonucleotides for detection of gene editing activity in mammalian cells, PCR#2 for APG05083.1, APG07433.1, APG07513.1, and APG08290.1

| Description | SEQ ID NO. |
|---|---|
| FWD_Guide 134, Guide 135, Guide 136, Guide 137 | 485 |
| REV_Guide 134, Guide 135, Guide 136, Guide 137 | 486 |
| FWD_Guide 138, Guide 139, Guide 140, Guide 141 | 487 |
| REV_Guide 138, Guide 139, Guide 140, Guide 141 | 488 |
| REV_Guide 142, Guide 143, Guide 144, Guide 145 | 489 |
| FWD_Guide 142, Guide 143, Guide 144, Guide 145 | 490 |
| REV_Guide 164, Guide 165, Guide 166, Guide 167 | 491 |
| FWD_Guide 164, Guide 165, Guide 166, Guide 167 | 492 |
| REV_Guide 168, Guide 169, Guide 170, Guide 171 | 493 |
| FWD_Guide 168, Guide 169, Guide 170, Guide 171 | 494 |
| REV_Guide 172, Guide 173, Guide 174, Guide 175 | 495 |
| FWD_Guide 172, Guide 173, Guide 174, Guide 175 | 496 |
| REV_Guide 185, Guide 186, Guide 187, Guide 188 | 497 |
| FWD_Guide 185, Guide 186, Guide 187, Guide 188 | 498 |
| REV_Guide 189, Guide 190, Guide 191, Guide 192 | 499 |
| FWD_Guide 189, Guide 190, Guide 191, Guide 192 | 500 |
| REV_Guide 193, Guide 194, Guide 195, Guide 196 | 501 |
| FWD_Guide 193, Guide 194, Guide 195, Guide 196 | 502 |

TABLE 8.3

Oligonucleotides for detection of gene editing activity in mammalian cells, PCR#2 for APG005459.1

| Description | SEQ ID NO. |
|---|---|
| FWD_Guide 146 | 503 |
| REV_Guide 146 | 504 |
| FWD_Guide 147 | 505 |
| REV_Guide 147 | 506 |
| REV_Guide 148 | 507 |
| FWD_Guide 148 | 508 |
| REV_Guide 176 | 509 |
| FWD_Guide 176 | 510 |
| REV_Guide 177 | 511 |
| FWD_Guide 177 | 512 |
| REV_Guide 209 | 513 |
| FWD_Guide 209 | 514 |
| REV_Guide 197 | 515 |
| FWD_Guide 197 | 516 |
| REV_Guide 198 | 517 |
| FWD_Guide 198 | 518 |
| REV_Guide 199 | 519 |
| FWD_Guide 199 | 520 |

TABLE 8.4

Oligonucleotides for detection of gene editing activity in mammalian cells, PCR#2 for APG004583.1

| Description | SEQ ID NO. |
|---|---|
| FWD_Guide 149 | 521 |
| REV_Guide 149 | 522 |
| FWD_Guide 150 | 523 |
| REV_Guide 150 | 524 |
| REV_Guide 151 | 525 |
| FWD_Guide 151 | 526 |
| REV_Guide 179 | 527 |
| FWD_Guide 179 | 528 |
| REV_Guide 180 | 529 |
| FWD_Guide 180 | 530 |
| REV_Guide 181 | 531 |
| FWD_Guide 181 | 532 |
| REV_Guide 200 | 533 |
| FWD_Guide 200 | 534 |
| REV_Guide 201 | 535 |
| FWD_Guide 201 | 536 |
| REV_Guide 202 | 537 |
| FWD_Guide 202 | 538 |

TABLE 8.5

Oligonucleotides for detection of gene editing activity in mammalian cells, PCR#2 for APG01988.1

| Description | SEQ ID NO. |
|---|---|
| FWD_Guide 152 | 539 |
| REV_Guide 152 | 540 |
| FWD_Guide 153 | 541 |
| REV_Guide 153 | 542 |
| FWD_Guide 154 | 543 |
| REV_Guide 154 | 544 |
| FWD_Guide 182 | 545 |
| REV_Guide 182 | 546 |
| FWD_Guide 183 | 547 |
| REV_Guide 183 | 548 |
| FWD_Guide 184 | 549 |
| REV_Guide 184 | 550 |
| FWD_Guide 203 | 551 |
| REV_Guide 203 | 552 |
| FWD_Guide 204 | 553 |
| REV_Guide 204 | 554 |
| FWD_Guide 205 | 555 |
| REV_Guide 205 | 556 |

Purified genomic DNA was subjected to PCR #1 and PCR #2 as above. Following the second PCR amplification DNA was cleaned using a PCR cleanup kit (Zymo) according to the manufacturer's instructions and eluted in water. 200-500 ng of purified PCR #2 product was combined with 2 μL of 10× NEB Buffer 2 and water in a 20 μL reaction and annealed to form heteroduplex DNA using a program of: 95° C., 5 min; 95-85° C., cooled at a rate of 2° C./sec; 85-25° C., cooled at a rate of 0.1° C./sec.; 12° C., forever. Following annealing 5 μL of DNA was removed as a no enzyme control, and 1 μL of T7 Endonuclease I (NEB) was added and the reaction incubated at 37° C. for 1 hr. After incubation 5× FlashGel loading dye (Lonza) was added and 5 μL of each reaction and controls were analyzed by a 2.2% agarose FlashGel (Lonza) using gel electrophoresis. Following visualization of the gel, the percentage of non-homologous end joining (NHEJ) was determined using the following equation: % NHEJ events=$100 \times [1-(1-\text{fraction cleaved})^{(1/2)}]$, where (fraction cleaved) is defined as: (density of digested products)/(density of digested products+undigested parental band).

For some samples, SURVEYOR® was used to analyze the results following expression in mammalian cells. Cells were incubated at 37° C. for 72 h post-transfection before genomic DNA extraction. Genomic DNA was extracted using the QuickExtract DNA Extraction Solution (Epicentre) following the manufacturer's protocol. The genomic region flanking the RGN target site was PCR amplified, and products were purified using QiaQuick Spin Column (Qiagen) following the manufacturer's protocol. 200-500 ng total of the purified PCR products were mixed with 1 μl 10×Taq DNA Polymerase PCR buffer (Enzymatics) and ultrapure water to a final volume of 10 μl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min.

After reannealing, products were treated with SURVEYOR® nuclease and SURVEYOR® enhancer S (Integrated DNA Technologies) following the manufacturer's recommended protocol and analyzed on 4-20% Novex TBE polyacrylamide gels (Life Technologies). Gels were stained with SYBR Gold DNA stain (Life Technologies) for 10 min and imaged with a Gel Doc gel imaging system (Bio-rad). Quantification was based on relative band intensities. Indel percentage was determined by the formula, $100 \times (1-(1-(b+c)/(a+b+c))^{1/2})$, where a is the integrated intensity of the undigested PCR product, and b and c are the integrated intensities of each cleavage product.

Additionally, products from PCR #2 containing Illumina overhang sequences underwent library preparation following the Illumina 16S Metagenomic Sequencing Library protocol. Deep sequencing was performed on an Illumina Mi-Seq platform by a service provider (MOGene). Typically 200,000 of 250 bp paired-end reads (2×100,000 reads) are generated per amplicon. The reads were analyzed using CRISPResso (Pinello, et al. 2016 Nature Biotech, 34:695-697) to calculate the rates of editing. Output alignments were hand-curated to confirm insertion and deletion sites as well as identify microhomology sites at the recombination sites. The rates of editing are shown in Table 9. All experiments were performed in human cells. The "target sequence" is the targeted sequence within the gene target. For each target sequence, the guide RNA comprised the complementary RNA target sequence and the appropriate sgRNA depending on the RGN used. A selected breakdown of experiments by guide RNA is shown in Tables 10.1-10.9.

TABLE 9

Overall rates of editing

| RGN | Guide RNA ID | Target Sequence (SEQ ID NO.) | Gene Target | Overall Editing Rate in Sample | Deletion Rate in Sample | Insertion Rate in Sample |
|---|---|---|---|---|---|---|
| APG05083.1 | 189 | 140 | RelA | 6.9% | | 100% |
| APG05083.1 | 185 | 141 | RelA | 8.2% | 79.9% | 20.1% |
| APG05083.1 | 168 | 142 | HPRT1 | 11.3% | 36.3% | 72.4% |
| APG07433.1 | 135 | 143 | AurkB | 1.7% | 88.3% | 11.7% |
| APG07433.1 | 139 | 144 | AurkB | 3.32% | 84.3% | 15.6% |
| APG07433.1 | 143 | 145 | AurkB | 2.2% | 35.1% | 64.9% |
| APG07433.1 | 190 | 146 | RelA | 60.5% | 94.8% | 5.2% |
| APG07433.1 | 194 | 147 | RelA | 6.2% | | 100% |
| APG07433.1 | 165 | 148 | HPRT1 | 3.5% | 68.0% | 32.0% |
| APG07433.1 | 169 | 149 | HPRT1 | 18.1% | 30.3% | 69.7% |
| APG07433.1 | 173 | 150 | HPRT1 | 26.6% | 91.9% | 10.0% |
| APG07513.1 | 144 | 151 | AurkB | 2.4% | 59.1% | 40.9% |
| APG07513.1 | 136 | 152 | AurkB | 0.9% | 80.5% | 19.5% |
| APG08290.1 | 145 | 153 | AurkB | 14.18% | 75.85% | 24.15% |
| APG08290.1 | 188 | 154 | RelA | 21.40% | 99.05% | 50.05% |
| APG08290.1 | 192 | 155 | RelA | 28.98% | 42.05% | 57.95% |
| APG08290.1 | 196 | 156 | RelA | 13.27% | 91.80% | 8.20% |
| APG08290.1 | 167 | 157 | HPRT1 | 14.14% | 65.98% | 34.02% |
| APG08290.1 | 171 | 158 | HPRT1 | 48.23% | 58.26% | 41.74% |
| APG08290.1 | 175 | 159 | HPRT1 | 13.60% | 74.18% | 25.82% |
| APG05459.1 | 197 | 160 | RelA | 12.95% | 92.16% | 7.84% |
| APG05459.1 | 199 | 161 | RelA | 5.19% | 100% | |
| APG05459.1 | 146 | 162 | AurkB | 1.12% | 61.50% | 38.50% |
| APG05459.1 | 148 | 163 | AurkB | 0.78% | 49.47% | 50.53% |
| APG05459.1 | 176 | 164 | HPRT1 | 6.20% | 48.91% | 51.09% |
| APG05459.1 | 177 | 165 | HPRT1 | 9.00% | 9.33% | 90.67% |
| APG05459.1 | 209 | 166 | HPRT1 | 2.50% | | 100% |
| APG04583.1 | 151 | 167 | AurkB | 0.0% | | |
| APG01688.1 | 152 | 168 | AurkB | 0.0% | | |

Specific insertions and deletions for respective guides are shown in Tables 10.1-10.7. In these tables, the target sequence is identified by bold upper case letters. The 8mer PAM regions are double underlined, with the main recognized nucleotides in bold. Insertions are identified by lowercase letters. Deletions are indicated with dashes (---). The INDEL location is calculated from the PAM proximal edge of the target sequence, with the edge being location 0. The location is positive (+) if the location is on the target side of the edge; the location is negative (−) if the location is on the PAM side of the edge.

TABLE 10.1

Specific insertions and deletions for Guide 139 using RGN APG07433.1

| Guide 139 (SEQ ID NO: 144) | # Reads | % Reads | % of INDELs | Type | INDEL Location | Size |
|---|---|---|---|---|---|---|
| CCTGGGTGTGAGGCTGGGCCATTAAAACCTCTCC | 82540 | 95.562 | | | | |
| CCTG------------------AAAACCTCTCC | 170 | 0.199 | 23.16 | Deletion | -6 | 19 |
| CCTGGGTGTGA-GCTGGGCCATTAAAACCTCTCC | 132 | 0.155 | 17.98 | Deletion | +1 | 1 |
| C------------CTGGGCCATTAAAACCTCTCC | 107 | 0.125 | 14.57 | Deletion | -9 | 12 |
| CCTGG----------------------CTCTCC | 101 | 0.118 | 13.76 | Deletion | -5 | 23 |
| C----------------GGGCCATTAAAACCTCTCC | 61 | 0.071 | 8.31 | Deletion | -9 | 14 |
| CCTGGGTGTGAGGccagacCTGGGCCATTAAAACCTCTCC | 49 | 0.057 | 6.67 | Insertion | +3 | 6 |
| CCTGGGTGTGAGGgggaagctgacgtcctttccatggctgctcgcctgtgttgccaccGCTGGGCCATTAAAACCTCTCC | 44 | 0.051 | 5.99 | Insertion | +2 | 45 |
| CCTGGGTGTGA-cCTGGGCCATTAAAACCTCTCC | 39 | 0.045 | 5.31 | Deletion & Mutation | +1 | 1 |
| CCTGGGTGTGAGGaCTGGGCCATTAAAACCTCTCC | 31 | 0.036 | 4.22 | Insertion | +3 | 1 |

TABLE 10.2

Specific insertions and deletions for Guide 143 using RGN APG07433.1

| Guide 143 (SEQ ID NO: 145) | # Reads | % Reads | % of INDELs | Type | INDEL Location | Size |
|---|---|---|---|---|---|---|
| AGTTGGCAGATGCTCTAATGTACTGCCATGGGAA | 84043 | 99.646 | | | | |
| AGTTGGCAGATGC---AATGTACTGCCATGGGAA | 126 | 0.149 | 42.281 | Deletion | +3 | 3 |
| AGTTGGCAGATGC----ATGTACTGCCATGGGAA | 81 | 0.096 | 27.181 | Deletion | +3 | 3 |
| AGTTGGCAGATGCT---ATGTACTGCCATGGGAA | 42 | 0.049 | 14.093 | Deletion | +4 | 3 |
| AGTTGGCAGATGC--TAATGTACTGCCATGGGAA | 34 | 0.040 | 11.409 | Deletion | +3 | 2 |
| AGTTGGCAGATGCT---ATGTAaTGCCATGGGAA | 8 | 0.009 | 2.684 | Deletion & Mutation | +4 | 3 |
| AGTTGGCAGATGCTCT-ATGTACTGCCATGGGAA | 7 | 0.008 | 2.348 | Deletion | +6 | 1 |

TABLE 10.3

Specific insertions and deletions for Guide 190 using RGN APG07433.1

| Guide 190 (SEQ ID NO: 146) | # Reads | % Reads | % of INDELs | Type | INDEL Location | Size |
|---|---|---|---|---|---|---|
| CGACCTGAATGCTGTGC-------------------------------------------------------------GGCGCTCTGGCTTCATTCAATC | 64040 | 55.46 | 91.70 | Deletion | -164 | 170 |

TABLE 10.3-continued

Specific insertions and deletions for Guide 190 using RGN APG07433.1

| Guide 190 (SEQ ID NO: 146) | # Reads | % Reads | % of INDELs | Type | INDEL Location | Size |
|---|---|---|---|---|---|---|
| CGACCTGAATGCTGTGCGGCTCTGCTTCCAGGTGA | 45619 | 39.51 | | WT | | |
| CGACCTGAATGCTGTGCGGCaTCTGCTTCCAGGTGA | 3620 | 3.13 | 5.18 | Insertion | +3 | 1 |
| CGACCTGAATG----------CTGCTTCCAGGTGA | 1110 | 0.96 | 1.58 | Deletion | +2 | 10 |
| CGACCTGAATGCT-------TCTGCTTCCAGGTGA | 858 | 0.74 | 1.22 | Deletion | +3 | 7 |
| CGACCTGAA-------------TGCTTCCAGGTGA | 206 | 0.17 | 0.29 | Deletion | +1 | 13 |

TABLE 10.4

Specific insertions and deletions for Guide 194 using RGN APG07433.1

| Guide 194 (SEQ ID NO: 147) | # Reads | % Reads | % of INDELs | Type | INDEL Location | Size |
|---|---|---|---|---|---|---|
| GCGTGGGGACTACGACCTGAATGCTGTGCGGCTCT | 96635 | 97.318 | | | | |
| GCG-----------ACCTGAATGCTGTGCGGCTCT | 1194 | 1.202 | 44.836 | Deletion | -9 | 11 |
| GCGTGGGGACTACGA-------GCTGTGCGGCTCT | 547 | 0.550 | 20.540 | Deletion | +3 | 7 |
| GCGTGGGGA-------CTGAATGCTGTGCGGCTCT | 473 | 0.476 | 17.761 | Deletion | -3 | 7 |
| GCGTGGGGACT----CCTGAATGCTGTGCGGCTCT | 270 | 0.271 | 10.138 | Deletion | -1 | 4 |
| GCGTGGGGACTACGAaCCTGAaTGCTGTGCGGCTCT | 88 | 0.088 | 3.304 | Insertion | +3 | 1 |
| GCGTGGGGACTACGA-----ATGCTGTGCGGCTCT | 41 | 0.041 | 1.539 | Deletion | +3 | 5 |
| GCGTGGGGACTAC---CTGAATGCTGTGCGGCTCT | 31 | 0.031 | 1.164 | Deletion | +2 | 3 |
| GCG--------------TGAATGCTGTGCGGCTCT | 9 | 0.009 | 0.337 | Deletion | -9 | 14 |
| GCG-----------ACCTGAcTGCTGTGCGGCTCT | 5 | 0.005 | 0.187 | Deletion & Mutation | -9 | 11 |
| GCGTGGGGACTACG-CCTGAATGCTGTGCGGCTCT | 5 | 0.005 | 0.187 | Deletion | +2 | 1 |

TABLE 10.5

Specific insertions and deletions for Guide 145 using RGN APG08290.1

| Guide 145 (SEQ ID NO: 153) | # Reads | % Reads | % of INDELs | Type | INDEL Location | Size |
|---|---|---|---|---|---|---|
| ATGGAGGAGTTGGCAGATGCTCTAATGTACTGCCATGGGAAG | 62618 | 95.889 | | | | |
| ATGGAGGAGTTGGCAGATGC-TAATGTACTGCCATGGGAAG | 976 | 1.494 | 36.363 | Deletion | +3 | 2 |
| ATGGAGGAGTTGGCAGATG--------TACTGCCATGGGAAG | 319 | 0.488 | 11.885 | Deletion | +2 | 8 |
| ATG------------------------TACTGCCATGGGAAG | 168 | 0.257 | 6.259 | Deletion | -14 | 24 |
| ATGGAGGAGTTGG------------TGTACTGCCATGGGAAG | 157 | 0.240 | 5.849 | Deletion | -4 | 12 |
| ATGGAGGAGTTGGCAGATGCTCTaAATGTACTGCCATGGGAAG | 147 | 0.225 | 5.476 | Insertion | +6 | 1 |
| ATGGAGGAGTTGGCAGATGCtctTCTAATGTACTGCCATGGGAAG | 123 | 0.188 | 4.582 | Insertion | +2 | 3 |

TABLE 10.5-continued

Specific insertions and deletions for Guide 145 using RGN APG08290.1

| Guide 145 (SEQ ID NO: 153) | # Reads | % Reads | % of INDELs | Type | INDEL Location | Size |
|---|---|---|---|---|---|---|
| ATGGAGGAGTTGGCAGATGccCTCTAATGTACTGCCATGGGAAG | 110 | 0.168 | 4.098 | Insertion | +2 | 2 |
| ATGGAGGAGTTGGCAGAT-----AATGTACTGCCATGGGAAGAAG | 103 | 0.157 | 3.837 | Deletion | +1 | 5 |
| ATGG---------------------cGTACTGCCATGGGAAGAAG | 96 | 0.147 | 3.57 | Deletion & Mutation | -7 | 21 |
| ATGGAGGAGTTGGCAGATGCtTCTAATGTACTGCCATGGGAAGAAG | 85 | 0.130 | 3.166 | Insertion | +3 | 1 |
| ATGGAGGAGTTGGCA-------------TCTGCCATGGGAAGAAG | 84 | 0.128 | 3.129 | Deletion | -2 | 13 |
| ATGGAGGAGTTGGCAGATGC---AATGTACTGCCATGGGAAGAAG | 79 | 0.120 | 2.943 | Deletion | +3 | 3 |
| ATGGAGGAGTTGGCAGATGCcaaactgaaaaacaaatcaaagcactcttattgagtgctggcgatccccgacgccacgggccgaaacccttatcatagaaaCTCTAATGTACTGCCATGGGAAG | 58 | 0.0884 | 2.160 | Insertion | +3 | 81 |
| ATGGAGGAGTTGGCAGATGCtgcttatatagactcccaccgtacacgcctaccgcccatttTCTAATGTACTGCCATGGGAAG | 53 | 0.081 | 1.974 | Insertion | +3 | 42 |
| ATGGAGGAGTTG---------TCTAATGTACTGCCATGGGAAG | 47 | 0.071 | 1.751 | Deletion | -5 | 8 |
| --------------------------CTGCCATGGGAAGAAG | 26 | 0.039 | 0.968 | Deletion | | |
| ATGGAGGAGTTGGCAGATGCgcggctgttcctgtacagaaccgtgggcgagatgtggatcaaggatgcTCTAATGTACTGCCATGGGAAG | 21 | 0.032 | 0.782 | Insertion | +3 | 48 |
| ATGGAGGAGTTGGCAGATGC-CTAATGTACTGCCATGGGAAG | 14 | 0.021 | 0.521 | Deletion | +3 | 1 |
| ATGGAGGAGTTGGCAGATGCtgtcatgatcttttccgctcgtcgtgggacttgctcagttctctggccagctcgTCTAATGTACTGCCATGGGAAG | 10 | 0.015 | 0.372 | Insertion | +3 | 55 |
| ATGGAGGAGTTGGCAGATGCTCT-ATGTACTGCCATGGGAAG | 8 | 0.012 | 0.29 | Deletion | +6 | 1 |

TABLE 10.6

Specific insertions and deletions for Guide 188 using RGN APG08290.1

| Guide 188 (SEQ ID NO: 154) | # Reads | % Reads | % of INDELs | Type | INDEL Location | Size |
|---|---|---|---|---|---|---|
| CAGGGACAGTGCGCATCTCCCTGGTCACCAAG | 59686 | 97.000 | | | | |
| CAGGGACA---------------GTCACCAAG | 1286 | 2.089 | 69.664 | Deletion | 0 | 15 |
| CAGGGACAGTGCGCATCTC-CTGGTCACCAAG | 473 | 0.768 | 25.622 | Deletion | +3 | 1 |
| CAGGGACAGTGCGCATCT--CTGGTCACCAAG | 57 | 0.092 | 3.087 | Deletion | +3 | 2 |
| CAGGGACAGTGCGCATCTCCtCTGGTCACCAAG | 11 | 0.017 | 0.595 | Insertion | +3 | 1 |
| CAGGGACAGTGCGCATC---CTGGTCACCAAG | 7 | 0.011 | 0.379 | Deletion | +3 | 3 |
| CAGGGAC---------------GGTCACCAAG | 7 | 0.011 | 0.379 | Deletion | +2 | 15 |
| CGGGGACAGgGCGCATCTC-CTGGTCACCAAG | 5 | 0.008 | 0.270 | Deletion & Mutation | +3 | 1 |

TABLE 10.7

Specific insertions and deletions for Guide 192 using RGN APG08290.1

| Guide 192 (SEQ ID NO: 155) | # Reads | % Reads | % of INDELs | Type | INDEL Location | Size |
|---|---|---|---|---|---|---|
| CGACCTGAATGCTGTGCGGCTCTGCTTCCAGG | 62352 | 95.658 | | | | |
| CGACCTGAATGCTGTGCGGCaTCTGCTTCCAGG | 1262 | 1.936 | 44.593 | Insertion | +3 | 1 |
| CGACCTGAATGCTGTGCGGCtTCTGCTTCCAGG | 842 | 1.291 | 29.752 | Insertion | +3 | 1 |
| CGACCTGAATGCTGTG----TCTGCTTCCAGG | 686 | 1.052 | 24.240 | Deletion | +3 | 4 |
| CGACCTGcATGCTGTGCGGCaTCTGCTTCCAGG | 18 | 0.027 | 0.636 | Insertion & Mutation | +3 | 1 |
| CGACCTGcATGCTGTGCGGCtTCTGCTTCCAGG | 11 | 0.016 | 0.388 | Insertion & Mutation | +3 | 1 |
| CGACCTGcATGCTGTG----TCTGCTTCCAGG | 6 | 0.009 | 0.212 | Deletion & Mutation | +3 | 4 |
| CGACCTGAATGCTGTGCGaCaTCTGCTTCCAGG | 5 | 0.007 | 0.176 | Insertion & Mutation | +3 | 2 |

TABLE 10.8

Specific insertions and deletions for Guide 196 using RGN APG08290.1

| Guide 196 (SEQ ID NO: 156) | # Reads | % Reads | % of INDELs | Type | INDEL Location | Size |
|---|---|---|---|---|---|---|
| TGGGGACTACGACCTGAATGCTGTGCGGCTCT | 37206 | 93.073 | | | | |
| TGGGGACTACGA-----ATGCTGTGCGGCTCT | 1288 | 3.222 | 46.514 | Deletion | +3 | 5 |
| TGGGGACTACGAgcaggcagaagtatgcaaagcatgcatctcaattCCTGAATGCTGTGCGGCTCT | 881 | 2.203 | 31.816 | Insertion | +3 | 34 |
| TGGGGACTACGAagaaggcgatagaaggccatgcgctgcgaatcgggagcggCCTGAATGCTGTGCGGCTCT | 302 | 0.755 | 10.906 | Insertion | +3 | 40 |
| TGGGGACTACGAtgactcgctgcgctcggtcgttcggctgcggcgagcggtatcagctcactcaaaggcggtaatacggCCTGAATGCTGTGCGGCTCT | 272 | 0.680 | 9.823 | Insertion | +3 | 67 |
| TGGG------------------GTGCGGCTCT | 13 | 0.032 | 0.4694 | Deletion | -5 | 18 |
| TGGGGACTACGAC-----TGCTGTGCGGCTCT | 13 | 0.032 | 0.469 | Deletion | +4 | 5 |

TABLE 10.9

Specific insertions and deletions for Guide 190 using RGN APG07433.1

| Guide 190 (SEQ ID NO: 146) | #Reads | % Reads | % of INDELs | Type | INDEL Location | Size |
|---|---|---|---|---|---|---|
| CGACCTGAATGCTGTGC-----------------------------------------------------------------------------------------------------------------------------GGCGCTCTGGCTTCATTCAATC | 64040 | 55.46 | 91.70 | Deletion | -164 | 170 |
| CGACCTGAATGCTGTGCGGCTCTGCTTCCAGGTGA | 45619 | 39.51 | | WT | | |
| CGACCTGAATGCTGTGCGGCaTCTGCTTCCAGGTGA | 3620 | 3.13 | 5.18 | Insertion | +3 | 1 |

TABLE 10.9-continued

Specific insertions and deletions for Guide 190 using RGN APG07433.1

| Guide 190 (SEQ ID NO: 146) | #Reads | % Reads | % of INDELs | Type | INDEL Location | Size |
|---|---|---|---|---|---|---|
| CGACCTGAATG----------CTGCTTCCAGGTGA | 1110 | 0.96 | 1.58 | Deletion | +2 | 10 |
| CGACCTGAATGCT-------TCTGCTTCCAGGTGA | 858 | 0.74 | 1.22 | Deletion | +3 | 7 |
| CGACCTGAA------------TGCTTCCAGGTGA | 206 | 0.17 | 0.29 | Deletion | +1 | 13 |

Example 7: Demonstration of Gene Editing Activity in Plant Cells

RNA-guided nuclease activity of the RGNs of the invention is demonstrated in plant cells using protocols adapted from Li, et al. (2013) Nat. Biotech. 31:688-691. Briefly, plant codon optimized versions of each RGN (SEQ ID NOs: 169-182) containing an N-terminal SV40 nuclear localization signal are cloned behind the strong constitutive 35S promoter in a transient transformation vector. sgRNAs targeting one or more sites in the plant PDS gene that flank an appropriate PAM sequence are cloned behind a plant U6 promoter in a second transient expression vector. The expression vectors are introduced into *Nicotiana benthamiana* mesophyll protoplasts using PEG-mediated transformation. The transformed protoplasts are incubated in the dark for up to 36 hr. Genomic DNA is isolated from the protoplasts using a DNeasy Plant Mini Kit (Qiagen). The genomic region flanking the RGN target site is PCR amplified, and products are purified using QiaQuick Spin Column (Qiagen) following the manufacturer's protocol. 200-500 ng total of the purified PCR products are mixed with 1 µl 10×Taq DNA Polymerase PCR buffer (Enzymatics) and ultrapure water to a final volume of 10 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min. After reannealing, products are treated with SURVEYOR nuclease and SURVEYOR enhancer S (Integrated DNA Technologies) following the manufacturer's recommended protocol and analyzed on 4-20% Novex TBE polyacrylamide gels (Life Technologies). Gels are stained with SYBR Gold DNA stain (Life Technologies) for 10 min and imaged with a Gel Doc gel imaging system (Bio-rad). Quantification is based on relative band intensities. Indel percentage is determined by the formula, $100 \times (1-(1-(b+c)/(a+b+c))^{1/2})$, where a is the integrated intensity of the undigested PCR product, and b and c are the integrated intensities of each cleavage product.

Alternatively, PCR products derived from the targeted genomic sequence can be subjected to PCR similar to that described in Example 6, so that PCR products contain Illumina overhang sequences and can undergo library preparation and deep sequencing. This method allows determination of the rates of editing as shown in Table 9.

Example 8: Guide Cross-Compatibility

To determine the cross-compatibility of guide RNAs between RGNs, a two-plasmid interference experiment was performed (Esvelt et al (2013), Nat. Methods 10(11): 1116-21). The first plasmid contained the RGN with several targets containing defined PAMs on a kanamycin resistant backbone. These plasmids were transformed into *E. coli* BL21, and the transformed strains were made to be chemically competent. A second plasmid containing a guide RNA on an ampicillin resistance backbone was then introduced. Cells were plated on media containing both antibiotics. If an RGN is able to use the guide on the second plasmid, the kanamycin-resistance plasmid is cleaved and linearized, resulting in little or no colony formation. If an RGN is not able to use the guide on the second plasmid, the kanamycin-resistance plasmid is not be cleaved, resulting in high levels of colony formation. Guide RNAs for *Streptococcus pyogenes* Cas9 (SpyCas9) and *Staphylococcus aureus* Cas9 (SauCas9) were also included to determine cross-compatibility with those guide RNAs.

To calculate the depletion percentage, the number of colonies for each guide transformation is compared to the transformation efficiency using a positive control. Based on this comparison, if an RGN can use a guide, the depletion percentage should be 0, as no colonies are able to survive. If an RGN cannot use a guide, the depletion percentage should be 1 as all plasmids remain intact. Results are shown in Table 11 below. "sg" indicates the guide RNA for the recited RGN.

TABLE 11

Cross-compatibility assay

| | APG05083.1 | APG07513.1 | APG08290.1 | APG05459.1 | APG04583.1 | APG01688.1 |
|---|---|---|---|---|---|---|
| sgAPG05083.1 | 0 | 0 | 0 | 0.21 | 1 | 0.74 |
| sgAPG07433.1 | 0 | 0 | 0 | 0.16 | 0.78 | 0.33 |
| sgAPG07513.1 | 0 | 0.01 | 0 | 0.32 | 0.97 | 0.64 |
| sgAPG05459.1 | 0.24 | 0.53 | 0.26 | 0.09 | 1 | 0.49 |
| sgAPG04583.1 | 0.74 | 0.8 | 0.36 | 0.21 | 0 | 0 |
| sgAPG01688.1 | 0.12 | 0.26 | 0.18 | 0.43 | 0 | 0 |
| sgSauCas9 | 1 | 0.23 | 0.27 | 0.53 | 0.51 | 0.92 |
| sg Spy | 0.16 | 0.27 | 0.32 | 0.06 | 1 | 1 |

As Table 11 indicates, there are four groups of orthogonal systems. RGNs can recognize guides from other systems in their groups, but cannot use guides from other groups. The first group contains APG05083.1, APG07433.1, APG07513.1, and APG08290.1. The second group contains SpyCas9 and APG05459.1. The third group contains APG04583.1 and APG01688.1. The fourth group contains SauCas9.

Example 9: Identification of Disease Targets

A database of clinical variants was obtained from NCBI ClinVar database, which is available through the world wide web at the NCBI ClinVar website. Pathogenic Single Nucleotide Polymorphisms (SNPs) were identified from this list. Using the genomic locus information, CRISPR targets in the region overlapping and surrounding each SNP were identified. A selection of SNPs that can be corrected using base editing in combination with the RGNs of the invention to target the causal mutation is listed in Table 12. In Table 12, only one alias of each disease is listed. The "RS #" corresponds to the RS accession number through the SNP database at the NCBI website. The AlleleID corresponds to a causal allele accession number, and the Chromosome Accession number also provides accession reference information found through the NCBI website. Table 12 also provides genomic target sequence information suitable for the RGN listed for each disease. The target sequence information also provides protospacer sequence for the production of the necessary sgRNA for the corresponding RGN of the invention.

TABLE 12

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Ataxia-telangiectasia syndrome | 1137887 | APG04583.1 | G > A | 18083 | NC_000011.10, NC_000011.9 | ATM | 197 |
| Very long chain acyl-CoA dehydrogenase deficiency | 2309689 | APG05459.1 | G > A | 33868 | NC_000017.10, NC_000017.11 | ACADVL | 198 |
| Abnormality of T cell physiology | 3218716 | APG01688.1 | G > A | 52071 | NC_000014.8, NC_000014.9 | MYH7 | 199 |
| Cardiovascular phenotype | 5742905 | APG05083, APG07433.1, APG07513.1, APG08290.1 | T > C | 15159 | NC_000021.8, NC_000021.9 | CBS | 200 |
| 3-Oxo-5 alpha-steroid delta 4-dehydrogenase deficiency | 9332964 | APG04583.1 | G > A | 18390 | NC_000002.11, NC_000002.12 | SRD5A2 | 201 |
| Acute myeloid leukemia | 11540652 | APG05083, APG07433.1, APG07513.1, APG08290.1 | G > A | 27395 | NC_000017.10, NC_000017.11 | TP53 | 202 |
| Acute myeloid leukemia | 11540652 | APG05459.1 | G > A | 27395 | NC_000017.10, NC_000017.11 | TP53 | 203 |
| Cutaneous malignant melanoma 3 | 11547328 | APG05459.1 | C > T | 31967 | NC_000012.11, NC_000012.12 | CDK4 | 204 |
| Alpha-1-antitrypsin deficiency | 28929474 | APG05459.1 | G > A | 33006 | NC_000014.8, NC_000014.9 | SERPINA1 | 205 |
| Charcot-Marie-Tooth disease, type 2 | 28933093 | APG05459.1 | G > A | 29543 | NC_000001.10, NC_000001.11 | LMNA | 206 |
| Hereditary cancer-predisposing syndrome | 28934578 | APG05083, APG07433.1, APG07513.1, APG08290.1 | G > A | 27413 | NC_000017.10, NC_000017.11 | TP53 | 207 |
| Hereditary cancer-predisposing syndrome | 28934578 | APG01688.1 | G > A | 27413 | NC_000017.10, NC_000017.11 | TP53 | 208 |
| Hereditary cancer-predisposing syndrome | 28934872 | APG05459.1 | G > A | 27436 | NC_000016.9, NC_000016.10 | TSC2 | 209 |
| Brugada syndrome | 28937316 | APG05083, APG07433.1, APG07513.1, APG08290.1 | G > A | 24408 | NC_000003.11, NC_000003.12 | SCN5A | 210 |
| Brugada syndrome | 28937318 | APG05459.1 | G > A | 24429 | NC_000003.11, NC_000003.12 | SCN5A | 211 |
| GRACILE syndrome | 28937590 | APG05459.1 | A > G | 21206 | NC_000002.11, NC_000002.12 | BCS1L | 212 |
| Enhanced s-cone syndrome | 28937873 | APG05459.1 | G > A | 20571 | NC_000015.9, NC_000015.10 | NR2E3 | 213 |
| Charcot-Marie-Tooth disease, type 2 | 28940293 | APG05083, APG07433.1, APG07513.1, APG08290.1 | T > C | 17309 | NC_000001.10, NC_000001.11 | MFN2 | 214 |
| Charcot-Marie-Tooth disease, type 2 | 28940293 | APG05459.1 | T > C | 17309 | NC_000001.10, NC_000001.11 | MFN2 | 215 |
| Arylsulfatase a, allele a | 28940893 | APG05459.1 | C > T | 18091 | NC_000022.10, NC_000022.11 | ARSA | 216 |
| Familial hypercholesterolemia | 28942078 | APG05459.1 | G > A | 18733 | NC_000019.9, NC_000019.10 | LDLR | 217 |
| Familial hypercholesterolemia | 28942079 | APG05459.1 | G > A | 18734 | NC_000019.9, NC_000019.10 | LDLR | 218 |
| HEMOGLOBIN ARLINGTON PARK | 33930165 | APG05083, APG07433.1, APG07513.1, APG08290.1 | G > A | 30165 | NC_000011.9, NC_000011.10 | HBB | 219 |
| Familial hypertrophic cardiomyopathy 1 | 36211715 | APG05459.1 | G > A | 29159 | NC_000014.8, NC_000014.9 | MYH7 | 220 |
| Cardiovascular phenotype | 36211723 | APG05459.1 | G > A | 45266 | NC_000011.9, NC_000011.10 | MYBPC3 | 221 |
| Cardiovascular phenotype | 36211723 | APG01688.1 | G > A | 45266 | NC_000011.9, NC_000011.10 | MYBPC3 | 222 |
| Brugada syndrome | 45546039 | APG05083, | G > A | 48043 | NC_000003.11, NC_000003.12 | SCN5A | 223 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Brugada syndrome | 45546039 | APG07433.1, APG07513.1, APG08290.1 APG01688.1 | G > A | 48043 | NC_000003.11, NC_000003.12 | SCN5A | 224 |
| Hereditary cancer-predisposing syndrome | 55863639 | APG05459.1 | G > A | 176641 | NC_000017.10, NC_000017.11 | TP53 | 225 |
| Deficiency of butyryl-CoA dehydrogenase | 57443665 | APG05459.1 | T > C | 18867 | NC_000012.11, NC_000012.12 | ACADS | 226 |
| Deficiency of butyryl-CoA dehydrogenase | 57443665 | APG01688.1 | T > C | 18867 | NC_000012.11, NC_000012.12 | ACADS | 227 |
| Benign scapuloperoneal muscular dystrophy with cardiomyopathy | 59332535 | APG05459.1 | G > A | 77828 | NC_000001.10, NC_000001.11 | LMNA | 228 |
| Benign scapuloperoneal muscular dystrophy with cardiomyopathy | 60458016 | APG05459.1 | G > A | 29564 | NC_000001.10, NC_000001.11 | LMNA | 229 |
| Cone-rod dystrophy 6 | 61750173 | APG05459.1 | G > A | 24396 | NC_000017.10, NC_000017.11 | GUCY2D | 230 |
| Cone-rod dystrophy 6 | 61750173 | APG01688.1 | G > A | 24396 | NC_000017.10, NC_000017.11 | GUCY2D | 231 |
| Stargardt disease 1 | 61750641 | APG05083, APG07433.1, APG07513.1, APG08290.1 | G > A | 105317 | NC_000001.10, NC_000001.11 | ABCA4 | 232 |
| Leber congenital amaurosis 2 | 61751276 | APG05459.1 | G > A | 104715 | NC_000001.10, NC_000001.11 | RPE65 | 233 |
| Cone-rod dystrophy 3 | 61751407 | APG05459.1 | G > A | 105292 | NC_000001.10, NC_000001.11 | ABCA4 | 234 |
| Nonsyndromic Oculocutaneous Albinism | 61754375 | APG05459.1 | G > A | 18835 | NC_000011.9, NC_000011.10 | TYR | 235 |
| Phenylketonuria | 62508646 | APG05459.1 | T > C | 15654 | NC_000012.11, NC_000012.12 | PAH | 236 |
| Phenylketonuria | 62516101 | APG05083, APG07433.1, APG07513.1, APG08290.1 | G > A | 15658 | NC_000012.11, NC_000012.12 | PAH | 237 |
| Breast-ovarian cancer, familial 1 | 62625303 | APG05459.1 | C > T | 68931 | NC_000017.10, NC_000017.11 | BRCA1 | 238 |
| Hyperphenylalaninemia, non-pku | 62644499 | APG05083, APG07433.1, APG07513.1, APG08290.1 | G > A | 15656 | NC_000012.11, NC_000012.12 | PAH | 239 |
| Hyperphenylalaninemia, non-pku | 62644499 | APG05459.1 | G > A | 15656 | NC_000012.11, NC_000012.12 | PAH | 240 |
| Hereditary cancer-predisposing syndrome | 63750217 | APG05459.1 | G > A | 32138 | NC_000003.11, NC_000003.12 | MLH1 | 241 |
| Hereditary cancer-predisposing syndrome | 63750741 | APG05083, APG07433.1, APG07513.1, APG08290.1 | T > C | 94663 | NC_000002.11, NC_000002.12 | MSH6 | 242 |
| Hereditary cancer-predisposing syndrome | 63750809 | APG05459.1 | T > C | 95480 | NC_000003.11, NC_000003.12 | MLH1 | 243 |
| Hereditary cancer-predisposing syndrome | 63751657 | APG05083, APG07433.1, APG07513.1, APG08290.1 | G > A | 95331 | NC_000003.11, NC_000003.12 | MLH1 | 244 |
| Hereditary cancer-predisposing syndrome | 63751711 | APG05083, APG07433.1, APG07513.1, APG08290.1 | G > A | 95792 | NC_000003.11, NC_000003.12 | MLH1 | 245 |
| Hereditary cancer-predisposing syndrome | 63751711 | APG01688.1 | G > A | 95792 | NC_000003.11, NC_000003.12 | MLH1 | 246 |
| Anterior segment dysgenesis 6 | 72549387 | APG05459.1 | G > A | 22776 | NC_000002.11, NC_000002.12 | CYP1B1 | 247 |
| Brugada syndrome | 72549410 | APG05083, APG07433.1, APG07513.1, APG08290.1 | G > A | 78547 | NC_000003.11, NC_000003.12 | SCN5A | 248 |
| Brugada syndrome | 72549410 | APG05459.1 | G > A | 78547 | NC_000003.11, NC_000003.12 | SCN5A | 249 |
| Ornithine carbamoyltransferase deficiency | 72554308 | APG01688.1 | G > A | 26053 | NC_000023.10, NC_000023.11 | OTC | 250 |
| Osteogenesis imperfecta type I | 72645321 | APG05083, APG07433.1, APG07513.1, APG08290.1 | G > A | 414022 | NC_000017.10, NC_000017.11 | COL1A1 | 251 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Osteogenesis imperfecta type I | 72645321 | APG05083, APG07433.1, APG07513.1, APG08290.1 | G > A | 414022 | NC_000017.10, NC_000017.11 | COL1A1 | 252 |
| Constipation | 74799832 | APG05083, APG07433.1, APG07513.1, APG08290.1 | T > C | 28958 | NC_000010.10, NC_000010.11 | RET | 253 |
| Dopamine beta hydroxylase deficiency | 74853476 | APG05083, APG07433.1, APG07513.1, APG08290.1 | T > C | 16789 | NC_000009.11, NC_000009.12 | DBH | 254 |
| Cystic fibrosis | 75096551 | APG05083, APG07433.1, APG07513.1, APG08290.1 | G > A | 33858 | NC_000007.13, NC_000007.14 | CFTR | 255 |
| Phenylketonuria | 75193786 | APG01688.1 | T > C | 15675 | NC_000012.11, NC_000012.12 | PAH | 256 |
| Deficiency of UDPglucose-hexose-1-phosphate uridylyltransferase | 75391579 | APG05459.1 | A > G | 18653 | NC_000009.11, NC_000009.12 | GALT | 257 |
| Amyloid Cardiomyopathy, Transthyretin-related | 76992529 | APG05459.1 | G > A | 28465 | NC_000018.9, NC_000018.10 | TTR | 258 |
| Carbohydrate-deficient glycoprotein syndrome type I | 80338707 | APG01688.1 | G > A | 22758 | NC_000016.9, NC_000016.10 | PMM2 | 259 |
| Metachromatic leukodystrophy | 80338815 | APG01688.1 | G > A | 18090 | NC_000022.10, NC_000022.11 | ARSA | 260 |
| Smith-Lemli-Opitz syndrome | 80338857 | APG05083, APG07433.1, APG07513.1, APG08290.1 | G > A | 34128 | NC_000011.9, NC_000011.10 | DHCR7 | 261 |
| Deafness, autosomal recessive 1A | 80338940 | APG05459.1 | G > A | 32068 | NC_000013.10, NC_000013.11 | GJB2 | 262 |
| Congenital omphalocele | 80338945 | APG05083, APG07433.1, APG07513.1, APG08290.1 | T > C | 32055 | NC_000013.10, NC_000013.11 | GJB2 | 263 |
| Congenital omphalocele | 80338945 | APG05083, APG07433.1, APG07513.1, APG08290.1 | T > C | 32055 | NC_000013.10, NC_000013.11 | GJB2 | 264 |
| Congenital omphalocele | 80338945 | APG05459.1 | T > C | 32055 | NC_000013.10, NC_000013.11 | GJB2 | 265 |
| Congenital omphalocele | 80338945 | APG05459.1 | T > C | 32055 | NC_000013.10, NC_000013.11 | GJB2 | 266 |
| Congenital myotonia, autosomal dominant form | 80356701 | APG05083, APG07433.1, APG07513.1, APG08290.1 | T > C | 33902 | NC_000007.13, NC_000007.14 | CLCN1 | 267 |
| Breast-ovarian cancer, familial 1 | 80356914 | APG05459.1 | G > A | 70276 | NC_000017.10, NC_000017.11 | BRCA1 | 268 |
| Breast and/or ovarian cancer | 80356962 | APG05459.1 | G > A | 70247 | NC_000017.10, NC_000017.11 | BRCA1 | 269 |
| Breast-ovarian cancer, familial 1 | 80357212 | APG05459.1 | G > A | 70255 | NC_000017.10, NC_000017.11 | BRCA1 | 270 |
| Breast-ovarian cancer, familial 1 | 80357281 | APG05459.1 | T > C | 70177 | NC_000017.10, NC_000017.11 | BRCA1 | 271 |
| Breast-ovarian cancer, familial 1 | 80357307 | APG05459.1 | G > A | 70275 | NC_000017.10, NC_000017.11 | BRCA1 | 272 |
| Breast-ovarian cancer, familial 1 | 80357352 | APG05459.1 | C > T | 69958 | NC_000017.10, NC_000017.11 | BRCA1 | 273 |
| Breast-ovarian cancer, familial 1 | 80358145 | APG05459.1 | G > A | 46229 | NC_000017.10, NC_000017.11 | BRCA1 | 274 |
| Inborn genetic diseases | 80358259 | APG05083, APG07433.1, APG07513.1, APG08290.1 | T > C | 18006 | NC_000018.9, NC_000018.10 | NPC1 | 275 |
| Breast-ovarian cancer, familial 2 | 80358543 | APG05459.1 | G > A | 131539 | NC_000013.10, NC_000013.11 | BRCA2 | 276 |
| Breast-ovarian cancer, familial 2 | 80358544 | APG05459.1 | G > A | 46368 | NC_000013.10, NC_000013.11 | BRCA2 | 277 |
| Breast-ovarian cancer, familial 2 | 80358997 | APG05459.1 | G > A | 67062 | NC_000013.10, NC_000013.11 | BRCA2 | 278 |
| Breast and/or ovarian cancer | 80359003 | APG05083, APG07433.1, APG07513.1, APG08290.1 | G > A | 67069 | NC_000013.10, NC_000013.11 | BRCA2 | 279 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Breast-ovarian cancer, familial 2 | 80359004 | APG05083, APG07433.1, APG07513.1, APG08290.1 | G > A | 46672 | NC_000013.10, NC_000013.11 | BRCA2 | 280 |
| Breast-ovarian cancer, familial 2 | 80359071 | APG05459.1 | G > A | 67203 | NC_000013.10, NC_000013.11 | BRCA2 | 281 |
| Breast-ovarian cancer, familial 2 | 80359112 | APG05459.1 | C > T | 67292 | NC_000013.10, NC_000013.11 | BRCA2 | 282 |
| Breast-ovarian cancer, familial 2 | 80359115 | APG05459.1 | C > T | 67294 | NC_000013.10, NC_000013.11 | BRCA2 | 283 |
| Smith-Lemli-Opitz syndrome | 104886033 | APG05459.1 | A > G | 21833 | NC_000011.9, NC_000011.10 | DHCR7 | 284 |
| Alport syndrome 1, X-linked recessive | 104886142 | APG05083, APG07433.1, APG07513.1, APG08290.1 | G > A | 35796 | NC_000023.10, NC_000023.11 | COL4A5 | 285 |
| Acute neuronopathic Gaucher's disease | 104886460 | APG05459.1 | G > A | 99352 | NC_000001.10, NC_000001.11 | GBA | 286 |
| Gonadotropin deficiency | 104893836 | APG05459.1 | A > G | 31062 | NC_000004.11, NC_000004.12 | GNRHR | 287 |
| Distal arthrogryposis type 1A | 104894129 | APG05459.1 | G > A | 27501 | NC_000009.11, NC_000009.12 | TPM2 | 288 |
| Distal arthrogryposis type 1A | 104894129 | APG05459.1 | G > A | 27501 | NC_000009.11, NC_000009.12 | TPM2 | 289 |
| Hereditary cancer-predisposing syndrome | 104894261 | APG05459.1 | C > T | 31727 | NC_000011.9, NC_000011.10 | MEN1 | 290 |
| Inborn genetic diseases | 104894313 | APG05459.1 | C > T | 18816 | NC_000011.9, NC_000011.10 | TYR | 291 |
| Death in early adulthood | 104894368 | APG05083, APG07433.1, APG07513.1, APG08290.1 | G > A | 29104 | NC_000012.11, NC_000012.12 | MYL2 | 292 |
| Death in early adulthood | 104894368 | APG05459.1 | G > A | 29104 | NC_000012.11, NC_000012.12 | MYL2 | 293 |
| Severe autosomal recessive muscular dystrophy of childhood-North African type | 104894423 | APG05459.1 | G > A | 17048 | NC_000013.10, NC_000013.11, NC_000013.9 | SGCG | 294 |
| Cardiovascular phenotype | 104894503 | APG05459.1 | G > A | 27495 | NC_000015.9, NC_000015.10 | TPM1 | 295 |
| Carbohydrate-deficient glycoprotein syndrome type I | 104894525 | APG01688.1 | G > A | 22747 | NC_000016.9, NC_000016.10 | PMM2 | 296 |
| Charcot-Marie-Tooth disease, type I | 104894621 | APG05459.1 | C > T | 23472 | NC_000017.10, NC_000017.11 | PMP22 | 297 |
| Inborn genetic diseases | 104894635 | APG05083, APG07433.1, APG07513.1, APG08290.1 | G > A | 20146 | NC_000017.10, NC_000017.11 | SGSH | 298 |
| Inborn genetic diseases | 104894635 | APG05459.1 | G > A | 20146 | NC_000017.10, NC_000017.11 | SGSH | 299 |
| Familial Mediterranean fever | 104895097 | APG05083, APG07433.1, APG07513.1, APG08290.1 | G > A | 17588 | NC_000016.9, NC_000016.10 | MEFV | 300 |
| Deafness, autosomal recessive 2 | 111033178 | APG05083, APG07433.1, APG07513.1, APG08290.1 | G > A | 52388 | NC_000011.9, NC_000011.10 | MYO7A | 301 |
| Deafness, autosomal recessive 2 | 111033178 | APG01688.1 | G > A | 52388 | NC_000011.9, NC_000011.10 | MYO7A | 302 |
| Deafness, X-linked 2 | 111033299 | APG05083, APG07433.1, APG07513.1, APG08290.1 | G > A | 53902 | NC_000013.10, NC_000013.11 | GJB2 | 303 |
| Enlarged vestibular aqueduct | 111033305 | APG05083, APG07433.1, APG07513.1, APG08290.1 | G > A | 52666 | NC_000007.13, NC_000007.14 | SLC26A4 | 304 |
| Congenital sensorineural hearing impairment | 111033364 | APG05459.1, APG01688.1 | G > A | 17396 | NC_000001.10, NC_000001.11 | USH2A | 305 |
| Deficiency of UDPglucose-hexose-1-phosphate uridylyltransferase | 111033728 | APG05459.1 | T > C | 36556 | NC_000009.11, NC_000009.12 | GALT | 306 |
| Very long chain acyl-CoA dehydrogenase deficiency | 112406105 | APG05459.1 | G > A | 200333 | NC_000017.10, NC_000017.11 | ACADVL | 307 |
| Cardiovascular phenotype | 112645512 | APG05459.1 | C > T | 178700 | NC_000015.10, NC_000015.9 | FBN1 | 308 |
| Pyruvate kinase deficiency of red cells | 113403872 | APG05459.1 | G > A | 16550 | NC_000001.10, NC_000001.11 | PKLR | 309 |
| Autosomal dominant progressive external ophthalmoplegia with mitochondrial DNA deletions 1 | 113994095 | APG05083, APG07433.1, APG07513.1, APG08290.1 | G > A | 28535 | NC_000015.9, NC_000015.10 | POLG | 310 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Very long chain acyl-CoA dehydrogenase deficiency | 113994167 | APG05459.1 | T > C | 33877 | NC_000017.10, NC_000017.11 | ACADVL | 311 |
| Cystinosis, ocular nonnephropathic | 113994205 | APG05459.1 | G > A | 19482 | NC_000017.10, NC_000017.11 | CTNS | 312 |
| Pyruvate kinase deficiency of red cells | 116100695 | APG05459.1 | C > T | 16552 | NC_000001.10, NC_000001.11 | PKLR | 313 |
| Distal myopathy, Tateyama type | 116840778 | APG01688.1 | G > A | 23322 | NC_000003.11, NC_000003.12 | CAV3; SSUH2 | 314 |
| Malignant hyperthermia, susceptibility to, 1 | 118192122 | APG05083, APG07433.1, APG07513.1, APG08290.1 | G > A | 76888 | NC_000019.9, NC_000019.10 | RYR1 | 315 |
| Malignant hyperthermia, susceptibility to, 1 | 118192122 | APG05083, APG07433.1, APG07513.1, APG08290.1 | G > A | 76888 | NC_000019.9, NC_000019.10 | RYR1 | 316 |
| Myopathy, Central Core | 118192158 | APG05083, APG07433.1, APG07513.1, APG08290.1 | G > A | 76835 | NC_000019.9, NC_000019.10 | RYR1 | 317 |
| Myopathy, Central Core | 118192158 | APG05459.1 | G > A | 76835 | NC_000019.9, NC_000019.10 | RYR1 | 318 |
| Myopathy, Central Core | 118192158 | APG01688.1 | G > A | 76835 | NC_000019.9, NC_000019.10 | RYR1 | 319 |
| Malignant hyperthermia, susceptibility to, 1 | 118192170 | APG05083, APG07433.1, APG07513.1, APG08290.1 | T > C | 28014 | NC_000019.9, NC_000019.10 | RYR1 | 320 |
| Ceroid lipofuscinosis neuronal 2 | 119455954 | APG05459.1 | G > A | 17681 | NC_000011.9, NC_000011.10 | TPP1 | 321 |
| Ceroid lipofuscinosis neuronal 2 | 119455954 | APG01688.1 | G > A | 17681 | NC_000011.9, NC_000011.10 | TPP1 | 322 |
| Niemann-Pick disease type C1 | 120074135 | APG05083, APG07433.1, APG07513.1, APG08290.1 | G > A | 18010 | NC_000018.9, NC_000018.10 | NPC1 | 323 |
| Glutaric aciduria, type 1 | 121434372 | APG05083, APG07433.1, APG07513.1, APG08290.1 | G > A | 17127 | NC_000019.9, NC_000019.10 | GCDH | 324 |
| CAPN3-Related Disorders | 121434548 | APG05083, APG07433.1, APG07513.1, APG08290.1 | G > A | 32661 | NC_000015.9, NC_000015.10 | CAPN3; POMT1 | 325 |
| CAPN3-Related Disorders | 121434548 | APG05459.1 | G > A | 32661 | NC_000015.9, NC_000015.10 | CAPN3; POMT1 | 326 |
| Glycogen storage disease, type II | 121907943 | APG05459.1 | C > T | 19073 | NC_000017.10, NC_000017.11 | GAA | 327 |
| Nonsyndromic Oculocutaneous Albinism | 121908011 | APG05083, APG07433.1, APG07513.1, APG08290.1 | G > A | 18814 | NC_000011.9, NC_000011.10 | TYR | 328 |
| Familial hypercholesterolemia | 121908033 | APG05459.1 | G > A | 18765 | NC_000019.9, NC_000019.10 | LDLR | 329 |
| Familial hypercholesterolemia | 121908039 | APG05459.1 | G > A | 18778 | NC_000019.9, NC_000019.10 | LDLR | 330 |
| Deafness, autosomal recessive 7 | 121908073 | APG05459.1 | C > T | 19142 | NC_000009.11, NC_000009.12 | TMC1 | 331 |
| Chronic infantile neurological, cutaneous and articular syndrome | 121908153 | APG05459.1 | G > A | 19416 | NC_000001.10, NC_000001.11 | NLRP3 | 332 |
| Eichsfeld type congenital muscular dystrophy | 121908185 | APG05459.1 | G > A | 19531 | NC_000001.10, NC_000001.11 | SELENON | 333 |
| Inborn genetic diseases | 121908192 | APG05459.1 | G > A | 23730 | NC_000016.9, NC_000016.10 | GFER | 334 |
| Hyperkalemic Periodic Paralysis Type 1 | 121908557 | APG05459.1 | G > A | 20958 | NC_000017.10, NC_000017.11 | SCN4A | 335 |
| Inclusion body myopathy 2 | 121908627 | APG05459.1 | G > A | 21067 | NC_000009.11, NC_000009.12 | GNE | 336 |
| Severe APG05083.1, APG07433.1, APG07513.1, APG08290.1 immunodeficiency due to ADA deficiency | 121908716 | APG05083, APG07433.1, APG07513.1, APG08290.1 | G > A | 16996 | NC_000020.10, NC_000020.11 | ADA | 337 |
| Severe APG05083.1, APG07433.1, APG07513.1, APG08290.1 immunodeficiency due to ADA deficiency | 121908739 | APG05083, APG07433.1, APG07513.1, APG08290.1 | T > C | 17004 | NC_000020.10, NC_000020.11 | ADA | 338 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Cardiovascular phenotype | 121908987 | APG05459.1 | G > A | 21885 | NC_000007.13, NC_000007.14 | PRKAG2 | 339 |
| Cystic fibrosis | 121909019 | APG05459.1 | G > A | 22197 | NC_000007.13, NC_000007.14 | CFTR | 340 |
| Cystic fibrosis | 121909036 | APG05459.1 | T > C | 22247 | NC_000007.13, NC_000007.14 | CFTR | 341 |
| Adrenocortical carcinoma, pediatric | 121912664 | APG01688.1 | G > A | 27418 | NC_000017.10, NC_000017.11 | TP53 | 342 |
| Fumarase deficiency | 121913123 | APG05459.1 | G > A | 31275 | NC_000001.10, NC_000001.11 | FH | 343 |
| Adenocarcinoma of prostate | 121913272 | APG05459.1 | T > C | 40610 | NC_000003.11, NC_000003.12 | PIK3CA | 344 |
| Familial hypertrophic cardiomyopathy 1 | 121913638 | APG05459.1 | G > A | 29144 | NC_000014.8, NC_000014.9 | MYH7 | 345 |
| Adult hypophosphatasia | 121918007 | APG05083, APG07433.1, APG07513.1, APG08290.1 | G > A | 28709 | NC_000001.10, NC_000001.11 | ALPL | 346 |
| Adult hypophosphatasia | 121918007 | APG01688.1 | G > A | 28709 | NC_000001.10, NC_000001.11 | ALPL | 347 |
| Adult hypophosphatasia | 121918007 | APG01688.1 | G > A | 28709 | NC_000001.10, NC_000001.11 | ALPL | 348 |
| Inborn genetic diseases | 121918166 | APG05083, APG07433.1, APG07513.1, APG08290.1 | G > A | 15994 | NC_000015.9, NC_000015.10 | OCA2 | 349 |
| Inborn genetic diseases | 121918243 | APG05083, APG07433.1, APG07513.1, APG08290.1 | G > A | 16464 | NC_000001.10, NC_000001.11 | MMACHC | 350 |
| Crouzon syndrome | 121918505 | APG05459.1 | T > C | 28329 | NC_000010.10, NC_000010.11 | FGFR2 | 351 |
| Propionyl-CoA carboxylase deficiency | 121964961 | APG05459.1 | A > G | 27057 | NC_000003.11, NC_000003.12 | PCCB | 352 |
| Cardiovascular phenotype | 121964962 | APG05083, APG07433.1, APG07513.1, APG08290.1 | G > A | 15156 | NC_000021.8, NC_000021.9 | CBS | 353 |
| Dysostosis multiplex | 121965019 | APG05083, APG07433.1, APG07513.1, APG08290.1 | G > A | 26947 | NC_000004.11, NC_000004.12 | IDUA | 354 |
| Multiple sulfatase deficiency | 137852850 | APG05459.1 | T > C | 17711 | NC_000003.11, NC_000003.12 | SUMF1 | 355 |
| Bifunctional peroxisomal enzyme deficiency | 137853096 | APG05459.1 | G > A | 22694 | NC_000005.9, NC_000005.10 | HSD17B4 | 356 |
| Bifunctional peroxisomal enzyme deficiency | 137853096 | APG01688.1 | G > A | 22694 | NC_000005.9, NC_000005.10 | HSD17B4 | 357 |
| Hereditary cancer-predisposing syndrome | 137853293 | APG05459.1 | C > T | 28112 | NC_000013.10, NC_000013.11 | RB1 | 358 |
| Cardiovascular phenotype | 137854478 | APG05083, APG07433.1, APG07513.1, APG08290.1 | G > A | 31496 | NC_000015.9, NC_000015.10 | FBN1 | 359 |
| Cardiovascular phenotype | 137854478 | APG05083, APG07433.1, APG07513.1, APG08290.1 | G > A | 31496 | NC_000015.9, NC_000015.10 | FBN1 | 360 |
| Limb-girdle muscular dystrophy, type 2L | 137854529 | APG05459.1 | C > T | 17205 | NC_000011.9, NC_000011.10 | ANO5 | 361 |
| Familial hypercholesterolemia | 137929307 | APG01688.1 | G > A | 171217 | NC_000019.9, NC_000019.10 | LDLR | 362 |
| Spastic Paraplegia, Recessive | 141659620 | APG05459.1 | G > A | 21858 | NC_000016.9, NC_000016.10 | SPG7 | 363 |
| Isovaleryl-CoA dehydrogenase deficiency | 142761835 | APG05459.1 | G > A | 177782 | NC_000015.9, NC_000015.10 | IVD | 364 |
| Familial hypercholesterolemia | 145787161 | APG05459.1 | G > A | 18783 | NC_000019.10, NC_000019.9 | LDLR | 365 |
| Biotinidase deficiency | 146015592 | APG05459.1 | G > A | 46845 | NC_000003.11, NC_000003.12 | BTD | 366 |
| Biotinidase deficiency | 146015592 | APG05459.1 | G > A | 46845 | NC_000003.11, NC_000003.12 | BTD | 367 |
| Leber congenital amaurosis | 150726175 | APG01688.1 | G > A | 45795 | NC_000001.10, NC_000001.11 | NMNAT1 | 368 |
| Familial hyperinsulinism | 151344623 | APG05083, APG07433.1, APG07513.1, APG08290.1 | G > A | 24127 | NC_000011.9, NC_000011.10 | ABCC8 | 369 |
| Familial cancer of breast | 180177122 | APG05083, APG07433.1, APG07513.1, APG08290.1 | G > A | 132185 | NC_000016.10, NC_000016.9 | PALB2 | 370 |
| Cohen syndrome | 180177366 | APG05459.1 | G > A | 71322 | NC_000008.10, NC_000008.11 | VPS13B | 371 |
| Cardiovascular phenotype | 187830361 | APG05083, APG07433.1, APG07513.1, APG08290.1 | T > C | 45267 | NC_000011.9, NC_000011.10 | MYBPC3 | 372 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Wilson disease | 193922103 | APG05459.1 | A > G | 44370 | NC_000013.10, NC_000013.11 | ATP7B | 373 |
| Wilson disease | 193922110 | APG05083, APG07433.1, APG07513.1, APG08290.1 | G > A | 44393 | NC_000013.10, NC_000013.11 | ATP7B | 374 |
| Wilson disease | 193922110 | APG05459.1 | G > A | 44393 | NC_000013.10, NC_000013.11 | ATP7B | 375 |
| Familial hypercholesterolemia | 193922566 | APG05459.1 | G > A | 45113 | NC_000019.9, NC_000019.10 | LDLR | 376 |
| Familial hypercholesterolemia | 193922566 | APG05459.1 | G > A | 45113 | NC_000019.9, NC_000019.10 | LDLR | 377 |
| Floating-Harbor syndrome | 199469464 | APG05459.1 | C > T | 39865 | NC_000016.9, NC_000016.10 | SRCAP | 378 |
| Congenital long QT syndrome | 199472712 | APG05083, APG07433.1, APG07513.1, APG08290.1 | G > A | 67758 | NC_000011.9, NC_000011.10 | KCNQ1 | 379 |
| Congenital long QT syndrome | 199472712 | APG05459.1 | G > A | 67758 | NC_000011.9, NC_000011.10 | KCNQ1 | 380 |
| Andersen Tawil syndrome | 199473384 | APG01688.1 | G > A | 78481 | NC_000017.10, NC_000017.11 | KCNJ2 | 381 |
| Cardiovascular phenotype | 199473460 | APG05083, APG07433.1, APG07513.1, APG08290.1 | T > C | 67776 | NC_000011.9, NC_000011.10 | KCNQ1 | 382 |
| Familial hypercholesterolemia | 200238879 | APG05459.1 | T > C | 18777 | NC_000019.9, NC_000019.10 | LDLR | 383 |
| Cardiovascular phenotype | 200411226 | APG05083, APG07433.1, APG07513.1, APG08290.1 | G > A | 174776 | NC_000011.9, NC_000011.10 | MYBPC3 | 384 |
| Gastrointestinal stroma tumor | 201286421 | APG05459.1 | C > T | 50215 | NC_000001.10, NC_000001.11 | SDHC | 385 |
| Dyskeratosis congenita | 201540674 | APG05459.1 | G > A | 51186 | NC_000020.10, NC_000020.11 | RTEL1 | 386 |
| Dyskeratosis congenita | 201540674 | APG01688.1 | G > A | 51186 | NC_000020.10, NC_000020.11 | RTEL1 | 387 |
| Glycogen storage disease IIIa | 267606640 | APG04583.1 | G > A | 16147 | NC_000001.10, NC_000001.11 | AGL | 388 |
| Dilated cardiomyopathy 1DD | 267607004 | APG05083, APG07433.1, APG07513.1, APG08290.1 | G > A | 15310 | NC_000010.10, NC_000010.11 | RBM20 | 389 |
| Renal carnitine transport defect | 267607054 | APG05459.1 | C > T | 21466 | NC_000005.9, NC_000005.10 | SLC22A5 | 390 |
| Baraitser-Winter syndrome 1 | 281875334 | APG05083, APG07433.1, APG07513.1, APG08290.1 | G > A | 38553 | NC_000007.13, NC_000007.14 | ACTB | 391 |
| Very long chain acyl-CoA dehydrogenase deficiency | 369560930 | APG05083, APG07433.1, APG07513.1, APG08290.1 | G > A | 98197 | NC_000017.10, NC_000017.11 | ACADVL | 392 |
| Familial hypercholesterolemia | 373822756 | APG05459.1 | A > G | 181233 | NC_000019.9, NC_000019.10 | LDLR | 393 |
| Limb-girdle muscular dystrophy, type 2A | 376107921 | APG05459.1 | G > A | 213634 | NC_000015.9, NC_000015.10 | CAPN3 | 394 |
| Familial hypercholesterolemia | 376459828 | APG05083, APG07433.1, APG07513.1, APG08290.1 | G > A | 198012 | NC_000019.10, NC_000019.9 | LDLR | 395 |
| Aortic aneurysm, familial thoracic 6 | 387906592 | APG05459.1 | G > A | 38552 | NC_000010.10, NC_000010.11 | ACTA2 | 396 |
| Acromicric dysplasia | 387906623 | APG05083, APG07433.1, APG07513.1, APG08290.1 | G > A | 38652 | NC_000015.9, NC_000015.10 | FBN1 | 397 |
| Charcot-Marie-Tooth disease type 2C | 387906905 | APG01688.1 | G > A | 39430 | NC_000012.11, NC_000012.12 | TRPV4 | 398 |
| Breast-ovarian cancer, familial 2 | 397507389 | APG01688.1 | G > A | 46666 | NC_000013.10, NC_000013.11 | BRCA2 | 399 |
| Breast-ovarian cancer, familial 1 | 397509284 | APG05459.1 | G > A | 70248 | NC_000017.10, NC_000017.11 | BRCA1 | 400 |
| Charcot-Marie-Tooth disease type 2C | 397514494 | APG05083, APG07433.1, APG07513.1, APG08290.1 | G > A | 48018 | NC_000012.11, NC_000012.12 | TRPV4 | 401 |
| Charcot-Marie-Tooth disease type 2C | 397514494 | APG01688.1 | G > A | 48018 | NC_000012.11, NC_000012.12 | TRPV4 | 402 |
| Hereditary cancer-predisposing syndrome | 397514495 | APG05459.1 | G > A | 152034 | NC_000017.10, NC_000017.11 | TP53 | 403 |
| Early infantile epileptic encephalopathy | 397514581 | APG05083, APG07433.1, APG07513.1, APG08290.1 | G > A | 48359 | NC_000020.10, NC_000020.11 | KCNQ2 | 404 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Early infantile epileptic encephalopathy | 397514581 | APG05459.1 | G > A | 48359 | NC_000020.10, NC_000020.11 | KCNQ2 | 405 |
| Early infantile epileptic encephalopathy | 397514581 | APG01688.1 | G > A | 48359 | NC_000020.10, NC_000020.11 | KCNQ2 | 406 |
| Acromicric dysplasia | 397515757 | APG05459.1 | G > A | 51454 | NC_000015.9, NC_000015.10 | FBN1 | 407 |
| Hypertrophic cardiomyopathy | 397515982 | APG05083, APG07433.1, APG07513.1, APG08290.1 | G > A | 51820 | NC_000011.9, NC_000011.10 | MYBPC3 | 408 |
| Cardiovascular phenotype | 397516031 | APG04583.1 | G > A | 51898 | NC_000011.9, NC_000011.10 | MYBPC3 | 409 |
| Cardiovascular phenotype | 397516074 | APG05083, APG07433.1, APG07513.1, APG08290.1 | G > A | 51962 | NC_000011.9, NC_000011.10 | MYBPC3 | 410 |
| Cardiovascular phenotype | 397516083 | APG01688.1 | G > A | 51977 | NC_000011.9, NC_000011.10 | MYBPC3 | 411 |
| Familial hypertrophic cardiomyopathy 1 | 397516269 | APG05083, APG07433.1, APG07513.1, APG08290.1 | T > C | 52276 | NC_000014.8, NC_000014.9 | MYH7 | 412 |
| Benign scapuloperoneal muscular dystrophy with cardiomyopathy | 397517889 | APG05459.1 | C > T | 57195 | NC_000001.10, NC_000001.11 | LMNA | 413 |
| Glycogen storage disease, type II | 398123172 | APG05083, APG07433.1, APG07513.1, APG08290.1 | G > A | 415590 | NC_000017.10, NC_000017.11 | GAA | 414 |
| Diffuse mesangial sclerosis | 587776576 | APG05083, APG07433.1, APG07513.1, APG08290.1 | G > A | 18532 | NC_000011.10, NC_000011.9 | WT1 | 415 |
| Colobomatous microphthalmia | 587776954 | APG05459.1 | A > G | 51108 | NC_000012.11, NC_000012.12 | C12orf57 | 416 |
| Ataxia-telangiectasia syndrome | 587779826 | APG05459.1 | T > C | 132814 | NC_000011.10, NC_000011.9 | ATM | 417 |
| Familial cancer of breast | 587780226 | APG05459.1 | C > T | 133611 | NC_000017.10, NC_000017.11 | BRIP1 | 418 |
| Limb-girdle muscular dystrophy, type 2A | 587780290 | APG01688.1 | G > A | 134019 | NC_000015.9, NC_000015.10 | CAPN3 | 419 |
| Hereditary cancer-predisposing syndrome | 587781462 | APG05459.1 | C > T | 150772 | NC_000002.11, NC_000002.12 | MSH6 | 420 |
| Asymmetric septal hypertrophy | 587782958 | APG01688.1 | G > A | 165560 | NC_000011.10, NC_000011.9 | MYBPC3 | 421 |
| Hereditary cancer-predisposing syndrome | 587783050 | APG05459.1 | G > A | 166264 | NC_000016.10, NC_000016.9 | CDH1 | 422 |
| Familial hypertrophic cardiomyopathy 2 | 727504247 | APG05083, APG07433.1, APG07513.1, APG08290.1 | G > A | 172354 | NC_000001.10, NC_000001.11 | TNNT2 | 423 |
| Familial hypertrophic cardiomyopathy 2 | 727504247 | APG01688.1 | G > A | 172354 | NC_000001.10, NC_000001.11 | TNNT2 | 424 |
| Familial hypertrophic cardiomyopathy 2 | 727504247 | APG01688.1 | G > A | 172354 | NC_000001.10, NC_000001.11 | TNNT2 | 425 |
| Erythrocytosis, familial, 2 | 730882035 | APG01688.1 | G > A | 180121 | NC_000003.12, NC_000003.11 | VHL | 426 |
| Death in infancy | 730882246 | APG05083, APG07433.1, APG07513.1, APG08290.1 | G > A | 181441 | NC_000014.9, NC_000014.8 | ISCA2 | 427 |
| Muscular Diseases | 751995154 | APG05459.1 | G > A | 200340 | NC_000017.10, NC_000017.11 | ACADVL | 428 |
| Familial hypercholesterolemia | 756039188 | APG04583.1 | G > A | 243266 | NC_000019.9, NC_000019.10 | LDLR | 429 |
| Familial cancer of breast | 761494650 | APG05459.1 | C > T | 185659 | NC_000022.10, NC_000022.11 | CHEK2 | 430 |
| Hereditary cancer-predisposing syndrome | 762307622 | APG01688.1 | G > A | 232266 | NC_000001.10, NC_000001.11 | MUTYH | 431 |
| Familial hypercholesterolemia | 769370816 | APG05083, APG07433.1, APG07513.1, APG08290.1 | G > A | 228176 | NC_000019.10, NC_000019.9 | LDLR | 432 |
| Familial hypercholesterolemia | 775092314 | APG05083, APG07433.1, APG07513.1, APG08290.1 | T > C | 228197 | NC_000019.9, NC_000019.10 | LDLR | 433 |
| Familial hypercholesterolemia | 775924858 | APG05083, APG07433.1, APG07513.1, APG08290.1 | G > A | 246116 | NC_000019.9, NC_000019.10 | LDLR | 434 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Inclusion body myopathy 2 | 779694939 | APG04583.1 | T > C | 214934 | NC_000009.12, NC_000009.11 | GNE | 435 |
| Ataxia-telangiectasia syndrome | 780619951 | APG05459.1 | C > T | 212851 | NC_000011.10, NC_000011.9 | ATM | 436 |
| Benign familial neonatal-infantile seizures | 794727152 | APG04583.1 | G > A | 191718 | NC_000002.11, NC_000002.12 | SCN2A | 437 |
| Marfan Syndronne/Loeys-Dietz Syndrome/Familial Thoracic Aortic Aneurysms and Dissections | 794728228 | APG05459.1 | C > T | 197690 | NC_000015.10, NC_000015.9 | FBN1 | 438 |
| Dilated cardiomyopathy 1G | 869320740 | APG01688.1 | T > C | 136355 | NC_000002.11, NC_000002.12 | TTN | 439 |
| Familial hypercholesterolemia | 875989911 | APG05459.1 | G > A | 228151 | NC_000019.9, NC_000019.10 | LDLR | 440 |
| Breast-ovarian cancer, familial 2 | 876657678 | APG05459.1 | C > T | 230443 | NC_000013.10, NC_000013.11 | BRCA2 | 441 |
| Familial hypercholesterolemia | 879254600 | APG05459.1 | G > A | 245669 | NC_000019.10, NC_000019.9 | LDLR | 442 |
| Familial hypercholesterolemia | 879254803 | APG05083, APG07433.1, APG07513.1, APG08290.1 | T > C | 246008 | NC_000019.10, NC_000019.9 | LDLR | 443 |
| Familial hypercholesterolemia | 879254803 | APG01688.1 | T > C | 246008 | NC_000019.10, NC_000019.9 | LDLR | 444 |
| Familial hypercholesterolemia | 879254849 | APG01688.1 | T > C | 246074 | NC_000019.10, NC_000019.9 | LDLR | 445 |
| Familial cancer of breast | 1057517585 | APG01688.1 | G > A | 358911 | NC_000016.10, NC_000016.9 | PALB2 | 446 |
| Hereditary hemorrhagic telangiectasia type 2 | 1057517944 | APG05459.1 | C > T | 360048 | NC_000012.11, NC_000012.12 | ACVRL1 | 447 |

Example 10: Targeting Mutations Responsible for Hurler Syndrome

The following describes a potential treatment for Hurler Syndrome, also referred to as MPS-1, is described, using an RNA directed base editing system that corrects a mutation responsible for Hurler syndrome in a large proportion of patients with the disease. This approach utilizes a base editing fusion protein that is RNA guided and that can be packaged into a single AAV vector for delivery to a wide range of tissue types. Depending on the exact regulatory elements and base editor domain used, it may also be possible to engineer a single vector that encodes for both the base editing fusion protein and a single guide RNA to target the diseased locus.

Example 10.1: Identifying RGN with Ideal PAM

The genetic disease MPS-1 is a lysosomal storage disease characterized at the molecular level by the accumulation of dermatan sulfate and heparan sulfate in lysosomes. This disease is generally an inherited genetic disorder caused by mutations in the IDUA gene (NCBI Reference sequence NG_008103.1), which encodes α-L-iduronidase. The disease is a result of a deficiency of α-L-iduronidase. The most common IDUA mutations found in studies of individuals of Northern European background are W402X and Q70X, both nonsense mutations resulting in premature termination of translation (Bunge et al. (1994), Hum. Mol. Genet, 3(6): 861-866, herein incorporated by reference). Reversion of a single nucleotide would restore the wild-type coding sequence and result in protein expression controlled by the endogenous regulatory mechanisms of the genetic locus.

The W402X mutation of the human Idua gene accounts for a high proportion of MPS-1H cases. Base editors can target a narrow sequence window relative to the binding site of the protospacer component of the guide RNA and thus the presence of a PAM sequence a specific distance from the target locus is essential for the success of the strategy. Given the constraints that the target mutation must be on the exposed non-target strand (NTS) during the interaction of the base editing protein and that the footprint of the RGN domain will block access to the region near the PAM, an accessible locus is thought to be 10-30 bp from the PAM. To avoid editing and mutagenesis of other nearby adenosine bases in this window, different linkers are screened. The ideal window is 12-16 bp from the PAM.

A PAM sequence compatible with APG07433.1 and APG08290.1 is readily apparent at the genetic locus and within the ideal base editing window as defined above. These nucleases have a PAM sequence of NNNNCC (SEQ ID NO: 6) and NNRNCC (SEQ ID NO: 32), respectively, and are compact in size—potentially allowing delivery via a single AAV vector. This delivery approach bestows multiple advantages relative to others, such as access to a wide range of tissues (liver, muscle, CNS) and well-established safety profile and manufacturing techniques.

Cas9 from *S. pyogenes* (SpyCas9) requires a PAM sequence of NGG (SEQ ID NO: 448), which is present near the W402X locus, but the size of SpyCas9 prevents packaging of a gene encoding a fusion protein of a base editing domain and the SpyCas9 nuclease into a single AAV vector, and thus forgoes the aforementioned advantages of this approach. Including a guide RNA encoding sequence on this vector would be even less feasible, even if there are to be significant technological improvements that reduce the size of gene regulatory elements or increase the packaging limits of AAV vectors. While a dual delivery strategy may be employed (for example, Ryu et al, (2018), Nat. Biotechnol., 36(6): 536-539, herein incorporated by reference), it would add significant manufacturing complexity and cost. Additionally, dual viral vector delivery significantly decreases the efficiency of gene correction, since a successful edit in a given cell requires infection with both vectors and assembly of the fusion protein in the cell.

A commonly used Cas9 ortholog from *S. aureus* (Sau-Cas9) is considerably smaller in size relative to SpyCas9, but has a more complex PAM requirement—NGRRT (SEQ ID NO: 449). This sequence, however, is not within a range expected to be useful for base editing of the causative locus.

Example 10.2: RGN Fusion Constructs and sgRNA Sequences

A DNA sequence encoding a fusion protein with the following domains is produced using standard molecular biology techniques: 1) an RGN domain with mutations that inactivate the DNA cleavage activity ("dead" or "nickase"); 2) an adenosine deaminase useful for base editing. All constructs described in the table below comprise a fusion protein with the base editing active domain, in this example ADAT (SEQ ID NO: 450) operably fused to the N-terminal end of the RGN APG08290.1. It is known in the art that a fusion protein could also be made with the base-editing enzyme at the C-terminal end of the RGN. Additionally, the RGN and the base editor of the fusion protein are typically separated by a linker amino sequence. It is known in the art that lengths of standard linkers range from 15-30 amino acids. Further, it is known in the art that certain fusion proteins between an RGN and a base-editing enzyme, for example a cytidine deaminase, may also comprise at least one uracil glycosylase inhibitor (UGI) domain, which may increase base editing efficiency (U.S. Pat. No. 10,167,457, herein incorporated by reference). Therefore, a fusion protein may comprise APG08290.1, a base-modifying enzyme, and at least one UGI.

TABLE 13

Constructs for RNA-targeted base editing

| Seq ID No. | Construct | RGN | Dead (D) or Nickase (N) | Base editor | Linker |
|---|---|---|---|---|---|
| 451 | Nuc-ADAT-Linker-dAPG08290.1-Linker-SV40 | APG08290.1 | D | ADAT | XTEN1 |
| 452 | Nuc-ADAT-XTEN1-nAPG08290.1-Linker-SV40 | APG08290.1 | N | ADAT | XTEN1 |

The accessible editing sites of an RGN are determined by the PAM sequence. When combining an RGN with a base editing domain, the target residue for editing must reside on the non-target strand (NTS), since the NTS is single stranded while the RGN is associated with the locus. Evaluating a number of nucleases and corresponding guide RNAs enables the selection of the most appropriate gene editing tool for this particular locus. Several potential PAM sequences that can be targeted by the constructs described above in the human Idua gene are in the proximity of the mutant nucleotide responsible for the W402X mutation. A sequence encoding a guide RNA transcript containing 1) a "spacer" that is complementary to the non-coding DNA strand at the disease locus; and 2) RNA sequence required for association of the guide RNA with the RGN is also produced. Useful guide RNA sequences (sgRNA) are shown in Table 14 below. These guide RNA sequences can be evaluated for their efficiency in directing the base editors above to the locus of interest.

TABLE 14

Sequence of guide RNAs

| Sequence of target genomic sequence | SEQ ID NO. | Coding sequence of sgRNA (SEQ ID NO.) |
|---|---|---|
| 5'-GGAGCAGCTCTAGGCCGAAGTGTCG-3' | 453 | 456 |
| 5'-TAGGCCGAAGTGTCGCAGGCCGGGA-3' | 454 | 457 |
| 5'-GCTCTAGGCCGAAGTGTCGCAGGCC-3' | 455 | 458 |

Example 10.3: Assay for Activity in Cells from Hurler Disease Patients

To verify the genotype strategy and evaluate the constructs described above, fibroblasts from Hurler disease patients are used. A vector is designed containing appropriate promoters upstream of the fusion protein coding sequence and the sgRNA encoding sequence for expression of these in human cells, similar to those vectors described in Example 5. It is recognized that promoters and other DNA elements (for example enhancers, or terminators) which either are known for high levels of expression in human cells or may specifically express well in fibroblast cells may also be used. The vector is transfected into the fibroblasts using standard techniques, for example transfection similar to what is described in Example 6. Alternatively, electroporation may be used. The cells are cultured for 1-3 days. Genomic DNA (gDNA) is isolated using standard techniques. The editing efficiency is determined by performing a qPCR genotyping assay and/or next generation sequencing on the purified gDNA, as described further below.

Taqman™ qPCR analysis utilizes probes specific for the wild-type and mutant allele. These probes bear fluorophores which are resolved by their spectral excitation and/or emission properties using a qPCR instrument. A genotyping kit containing PCR primers and probes can be obtained commercially (i.e. Thermo Fisher Taqman™ SNP genotyping assayID C_27862753_10 for SNP ID rs121965019) or designed. An example of a designed primer and probe set is shown in Table 15.

TABLE 15

RT-PCR primers and probes

| Description | Sequence | SEQ ID NO. |
|---|---|---|
| Forward Amplification Primer | 5'-GACTCCTTCACCAAG-3' | 459 |
| Reverse Amplification Primer | 5'-GTAGATCAGCACCG-3' | 460 |
| Wild Type Probe | 5'-CTCTGGGCCGAAGT-3' | 461 |
| W402X Probe | 5'-CTCTAGGCCGAAGT-3' | 462 |

Following the editing experiment, the gDNA is subjected to qPCR analysis using standard methods and the primers and probes described above. Expected results are shown in Table 16. This in vitro system can be used to expediently evaluate constructs and choose one with high editing efficiency for further studies. The systems will be evaluated in comparison with cells with and without the W402X mutation, and preferably with some that are heterozygous for this mutation. The Ct values will be compared to either a reference gene or the total amplification of the locus using a dye such as Sybr green.

TABLE 16

Expected qPCR results

| Genotype | Transfected with base editor | Expected PCR result |
|---|---|---|
| Idua$^{WT/WT}$ | No | Homozygous WT |
| Idua$^{WT/W402X}$ | No | Heterozygous: 50% WT, 50% W402X |
| Idua$^{W402X/W402X}$ | No | Homozygous W402X |
| Idua$^{W402X/W402X}$ | Yes | Variable |

The tissues can also be analyzed by next generation sequencing. Primer binding sites such as the ones shown below (Table 17), or other suitable primer binding sites that can be identified by a person of skill in the art, can be used. Following PCR amplification, products containing Illumina Nextera XT overhang sequences undergo library preparation following the Illumina 16S Metagenomic Sequencing Library protocol. Deep sequencing is performed on an Illumina Mi-Seq platform. Typically, 200,000 of 250 bp paired-end reads (2×100,000 reads) are generated per amplicon. The reads are analyzed using CRISPResso (Pinello et al., 2016) to calculate the rates of editing. Output alignments are hand-curated to confirm insertion and deletion sites as well as identify microhomology sites at the recombination sites.

TABLE 17

NGS primer binding sites

| Direction | Sequence | SEQ ID NO. |
|---|---|---|
| Forward | 5'-ACTTCCTCCAGCC-3' | 463 |
| Reverse | 5'-GAACCCCGGCTTA-3' | 464 |

Western blotting of cell lysate of transfected cells and control cells using an anti-IDUA antibody is performed to verify expression of the full-length protein and an enzyme activity assay on the cell lysate using substrate 4-methyl-umbelliferyl α-L-iduronide verifies that the enzyme is catalytically active (Hopwood et al., Clin. Chim. ACta (1979), 92(2): 257-265, incorporated by reference herein). These experiments are performed in comparison with the original Idua$^{W402X/W402X}$ cell line (without transfection), the Idua$^{W402X/W402X}$ cell line transfected with the base editing construct and a random guide sequence, and a cell line expressing wild-type IDUA.

Example 10.4: Disease Treatment Validation in a Murine Model

To verify the efficacy of this therapeutic approach, a mouse model with a nonsense mutation in the analogous amino acid is used. The mouse strain bears a W392X mutation in its Idua gene (Gene ID: 15932) which corresponds to the homologous mutation in Hurler syndrome patients (Bunge et al., (1994), Hum. Mol. Genet. 3(6): 861-866, incorporated by reference herein). This locus comprises a distinct nucleotide sequence relative to that in humans, which lacks the PAM sequence necessary for correction with the base editors described in the previous examples, and thus necessitates design of a distinct fusion protein to perform the nucleotide correction. Amelioration of the disease in this animal can validate the therapeutic approach of correcting the mutation in tissues accessible by a gene delivery vector.

Mice homozygous for this mutation display a number of phenotypic characteristics similar to Hurler syndrome patients. A base editing-RGN fusion protein as described above (Table 13) along with an RNA guide sequence are incorporated into an expression vector that allows protein expression and RNA transcription in mice. A study design is shown below in Table 18. The study includes groups that are treated with a high dose of the expression vector comprising the base-editing fusion protein and RNA guide sequence, a low dose of same expression vector, control which is the model mouse treated with an expression vector that does not comprise the base editing fusion protein or the guide RNA, and a second control which is a wild type mouse treated with the same empty vector.

TABLE 18

Genome editing experiment in murine model

| Group | Mouse strain | N | Treatment |
|---|---|---|---|
| 1 | Idua-W392X[1] | ≥5 | Low dose of vector |
| 2 | Idua-W392X | ≥5 | High dose of vector |
| 3 | Idua-W392X | ≥5 | Vehicle |
| 4 | 129/Sv (WT) | 5 | Vehicle |

Endpoints to evaluate include body weight, urine GAG excretion, serum IDUA enzymatic activity, IDUA activity in tissues of interest, tissue pathology, genotyping of tissues of interest to verify correction of the SNP, and behavioral and neurological evaluation. Since some endpoints are terminal, additional groups may be added for evaluation of, for example, tissue pathology and tissue IDUA activities before the end of the study. Additional examples of endpoints can be found in published papers establishing Hurler syndrome animal models (Shull et al. (1994), Proc. Natl. Acad. Sci. U.S.A., 91(26): 12937-12941; Wang et al. (2010), Mol. Genet. Metab., 99(1): 62-71; Hartung et al. (2004), Mol. Ther., 9(6): 866-875; Liu et al. (2005), Mol. Ther., 11(1): 35-47; Clarke et al. (1997), Hum. Mol. Genet. 6(4): 503-511; all herein incorporated by reference).

One possible delivery vector utilizes the adeno associated virus (AAV). A vector is produced to include a base editor-dRGN fusion protein coding sequence (for example, SEQ ID NO: 452) preceded by a CMV enhancer (SEQ ID NO: 138) and promoter (SEQ ID NO: 137), or other suitable enhancer and promoter combination), optionally a Kozak sequence, and operably fused at the 3' end to a terminator sequence and a poly adenylation sequence such as the minimal sequence described in Levitt, N.; Briggs, D.; Gil, A.; Proudfoot, N. J. Definition of an Efficient Synthetic Poly(A) Site. Genes Dev. 1989, 3 (7), 1019-1025. The vector may further comprise an expression cassette encoding for a single guide RNA operably linked at its 5' end to a human U6 promoter (SEQ ID NO: 139), or another promoter suitable for production of small non-coding RNAs, and further comprising inverted terminal repeat (ITR) sequences necessary and well-known in the art for packaging into the AAV capsid. Production and viral packaging is performed by standard methods, such as those described in U.S. Pat. No. 9,587,250, herein incorporated by reference.

Other possible viral vectors include adenovirus and lentivirus vectors, which are commonly used and would contain similar elements, with different packaging capabilities and requirements. Non-viral delivery methods also be used, such as mRNA and sgRNA encapsulated by lipid nanoparticles (Cullis, P. R. and Allen, T. M. (2013), Adv. Drug Deliv. Rev. 65(1): 36-48; Finn et al. (2018), Cell Rep. 22(9): 2227-2235, both incorporated by reference) hydrodynamic injection of plasmid DNA (Suda T and Liu D,) 2007) Mol. Ther. 15(12): 2063-2069, herein incorporated by reference), or ribonucleoprotein complexes of sgRNA and associated with gold nanoparticles (Lee, K.; Conboy, M.; Park, H. M.; Jiang, F.; Kim, H. J.; Dewitt, M. A.; Mackley, V. A.; Chang, K.; Rao, A.; Skinner, C.; et al. Nanoparticle Delivery of Cas9 Ribonucleoprotein and Donor DNA in Vivo Induces Homology-Directed DNA Repair. Nat. Biomed. Eng. 2017, 1(11), 889-90).

Example 10.5: Disease Correction in a Murine Model with a Humanized Locus

To evaluate the efficacy of an identical base editor construct as would be used for human therapy, a mouse model in which the nucleotides near W392 are altered to match the sequence in humans around W402 is needed. This can be accomplished by a variety of techniques, including use of an RGN and an HDR template to cut and replace the locus in mouse embryos.

Due to the high degree of amino acid conservation, most nucleotides in the mouse locus can be altered to those of the human sequence with silent mutations as shown in Table 19. The only base changes resulting in altered coding sequence in the resulting engineered mouse genome occur after the introduced stop codon.

TABLE 19

Nucleotide mutations to generate a humanized mouse locus

| Feature | Human (W402X) Nucleotide (SEQ ID NO: 465) | Encoded AA | Mouse (W392X) Nucleotide (SEQ ID NO: 466) | Encoded AA | Humanized Mouse Nucleotide (SEQ ID NO: 467) | Encoded AA |
|---|---|---|---|---|---|---|
| Protospacer | G | E | A | G | G | G |
|  | G | E | G | E | G | E |
|  | A |  | A |  | A |  |
|  | G |  | A |  | G |  |
|  | C | Q | C | Q | C | Q |
|  | A |  | A |  | A |  |
|  | G |  | A |  | G |  |
|  | C | L | C | L | C | L |
|  | T |  | T |  | T |  |
|  | C |  | C |  | C |  |
|  | T | STOP | T | STOP | T | STOP |
|  | A |  | A |  | A |  |
|  | G |  | G |  | G |  |
|  | G | A | G | A | G | A |
|  | C |  | C |  | C |  |
|  | C |  | A |  | C |  |
|  | G | E | G | E | G | E |
|  | A |  | A |  | A |  |
|  | A |  | G |  | A |  |
|  | G | V | G | V | G | V |
|  | T |  | T |  | T |  |
|  | G |  | C |  | G |  |
|  | T | S | T | S | T | S |
|  | C |  | C |  | C |  |
|  | G |  | A |  | G |  |
| PAM, non-critical | C | Q | A | K | C | Q |
|  | A |  | A |  | A |  |
|  | G |  | G |  | G |  |
|  | G | A | G | A | G | A |
| PAM, critical | C |  | C |  | C |  |
|  | C |  | T |  | C |  |

Upon engineering of this mouse strain, similar experiments will be performed as described in Example 10.4.

Example 11: Targeting Mutations Responsible for Friedreich Ataxia

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from *S. pyogenes* (SpCas9), are too large to be packaged into adeno-associated viral (AAV) vectors, especially when considering the length of the SpCas9 gene and the guide RNA in addition to other genetic elements required for functional expression cassettes. This makes a viable approach using SpCas9 unlikely.

The compact RNA guided nucleases of the invention, particularly APG07433.1 and APG08290.1, are uniquely well suited for the excision of the FRDA instability region. Each RGN has a PAM requirement that is in the vicinity of the FRDA instability region. Additionally, each of these RGNs can be packaged into an AAV vector along with a guide RNA. Packing two guide RNAs would likely require a second vector, but this approach still compares favorably to what would be required of a larger nuclease such as SpCas9, which would require splitting the protein sequence between two vectors.

Table 20 shows the location of genomic target sequences suitable for targeting APG07433.1 or APG08290.1 to the 5' and 3' flanks of the FRDA instability region. Once at the locus, the RGN would excise the FA instability region. Excision of the region can be verified with Illumina sequencing of the locus.

TABLE 20

Genomic target sequences for RGN systems

| Guide No. | Location relative to FRDA instability region | Genome target sequence | SEQ ID NO. |
|---|---|---|---|
| 1 | 5' | ATCACCTGAGGTCCGGAGTTCAAGA | 468 |
| 2 | 5' | GTCTTGAACTCCGGACCTCAGGTGA | 469 |
| 3 | 5' | TGAACTCCGGACCTCAGGTGATCCA | 470 |
| 4 | 3' | GAAAAGTTAGCCGGGCGTGGTGTCG | 471 |

Example 12: Targeting Mutations Responsible for Sickle Cell Diseases

Targeting sequences within the BCL11A enhancer region (SEQ ID NO: 472) may provide a mechanism for increasing fetal hemoglobin (HbF) to either cure or alleviate the symptoms of sickle cell diseases. For example, genome wide association studies have identified a set of genetic variations at BCL11A that are associated with increased HbF levels. These variations are a collection of SNPs found in non-coding regions of BCL11A that function as a stage-specific, lineage-restricted enhancer region. Further investigation revealed that this BCL11A enhancer is required in erythroid cells for BCL11A expression (Bauer et al, (2013) Science 343:253-257, incorporated by reference herein). The enhancer region was found within intron 2 of the BCL11A gene, and three areas of DNAseI hypersensitivity (often indicative of a chromatin state that is associated with regulatory potential) in intron 2 were identified. These three areas were identified as "+62", "+58" and "+55" in accordance with the distance in kilobases from the transcription start site of BCL11A. These enhancer regions are roughly 350 (+55); 550 (+58); and 350 (+62) nucleotides in length (Bauer et al., 2013).

Example 12.1: Identifying Preferred RGN Systems

Here we describe a potential treatment for beta-hemoglobinopathies using an RGN system that disrupts BCL11A binding to its binding site within the HBB locus, which is the gene responsible for making beta-globin in adult hemoglobin. This approach uses NHEJ which is more efficient in mammalian cells. In addition, this approach uses a nuclease of sufficiently small size that can be packaged into a single AAV vector for in vivo delivery.

The GATA1 enhancer motif in the human BCL11A enhancer region (SEQ ID NO: 472) is an ideal target for disruption using RNA guided nucleases (RGNs) to reduce BCL11A expression with concurrent re-expression of HbF in adult human erythrocytes (Wu et al. (2019) Nat Med 387:2554). Several PAM sequences compatible with APG07433.1 and APG08290.1 are readily apparent at the genetic locus surrounding this GATA1 site. These nucleases have a PAM sequence of 5'-NNNNCC-3' (SEQ ID NO: 6) and are compact in size, potentially allowing their delivery along with an appropriate guide RNA in a single AAV or adenoviral vector. This delivery approach bestows multiple advantages relative to others, such as access to hematopoietic stem cells and a well-established safety profile and manufacturing techniques.

The commonly used Cas9 nuclease from *S. pyogenes* (SpyCas9) requires a PAM sequence of 5'-NGG-3', (SEQ ID NO: 448) several of which are present near the GATA1 motif. However, the size of SpyCas9 prevents packaging into a single AAV or adenoviral vector and thus forgoes the aforementioned advantages of this approach. While a dual delivery strategy may be employed, it would add significant manufacturing complexity and cost. Additionally, dual viral vector delivery significantly decreases the efficiency of gene correction, since a successful edit in a given cell requires infection with both vectors. An expression cassette encoding a human codon optimized APG07433.1 (SEQ ID NO: 128) or APG08290.1 (SEQ ID NO: 130) is produced, similar to those described in Example 6. Expression cassettes which express guide RNAs for RGNs APG07433.1 and APG08290.1 are also produced. These guide RNAs comprise 1) a protospacer sequence that is complementary to either the non-coding or coding DNA strand within the BCL11A enhancer locus (the target sequence) and 2) an RNA sequence required for association of the guide RNA with the RGN (SEQ ID NO. 18 for APG07433.1 and SEQ ID NO: 35 for APG08290.1). Because several potential PAM sequences for targeting by APG07433.1 or APG08290.1 surround the BCL11A GATA1 enhancer motif, several potential guide RNA constructs are produced to determine the best protospacer sequence that produces robust cleavage and NHEJ mediated disruption of the BCL11A GATA1 enhancer sequence. The target genomic sequences in the table below (Table 21) are evaluated to direct the RGN to this locus.

TABLE 21

Target Sequences for BCL11A GATA1 enhancer locus

| Guide | Nuclease | Target genomic sequence | Target SEQ ID NO. |
|---|---|---|---|
| 1 | APG07433.1 | GCACTAGACTAGCTTCAAAGTTGTAG | 473 |
| 2 | APG07433.1 | CCTAATCAGAGGCCAAACCCTTCCTG | 474 |
| 3 | APG07433.1 | CAAGCTAACAGTTGCTTTTATCACAG | 475 |
| 4 | APG08290.1 | GCACTAGACTAGCTTCAAAGTTGTAG | 476 |
| 5 | APG08290.1 | CCTAATCAGAGGCCAAACCCTTCCTG | 477 |
| 6 | APG08290.1 | CAAGCTAACAGTTGCTTTTATCACAG | 478 |

To evaluate the efficiency with which APG07433.1 or APG08290.1 generates insertions or deletions that disrupt the BCL11A enhancer region, human cell lines such as human embryonic kidney cells (HEK cells) are used. A DNA vector comprising an RGN expression cassette (for example, as described in Example 6) is produced. A separate vector comprising an expression cassette comprising a coding sequence for a guide RNA sequence of Table 21 is also produced. Such an expression cassette may further comprise a human RNA polymerase III U6 promoter (SEQ ID NO: 139), as described in Example 6. Alternatively, a single vector comprising expression cassettes of both the RGN and guide RNA may be used. The vector is introduced into HEK cells using standard techniques such as those described in Example 6, and the cells are cultured for 1-3 days. Following this culture period, genomic DNA is isolated and the frequency of insertions or deletions is determined by using T7 Endonuclease I digestion and/or direct DNA sequencing, as described in Example 6.

A region of DNA encompassing the target BCL11A region is amplified by PCR with primers containing Illumina Nextera XT overhang sequences. These PCR amplicons are either examined for NHEJ formation using T7 Endonuclease I digestion, or undergo library preparation following the Illumina 16S Metagenomic Sequencing Library protocol or a similar Next Generation Sequencing (NGS) library preparation. Following deep sequencing, the reads generated are analyzed by CRISPResso to calculate rates of editing. Output alignments are hand-curated to confirm insertion and deletion sites. This analysis identifies the preferred RGN and the corresponding preferred guide RNA (sgRNA). The analysis may result in both APG07433.1 and APG08290.1 being equally preferred. Additionally, the analysis may determine there is more than one preferred guide RNA, or that all target genomic sequences in Table 21 are equally preferred.

Example 12.2: Assay for Expression of Fetal Hemoglobin

In this example, APG07433.1 or APG08290.1 generated insertions or deletions disrupting the BCL11A enhancer region are assayed for expression of fetal hemoglobin. Healthy human donor $CD34^+$ hematopoietic stem cells (HSCs) are used. These HSCs are cultured and vector(s) comprising expression cassettes comprising the coding regions of the preferred RGN and the preferred sgRNA are introduced using methods similar to those described in Example 11.1. Following electroporation, these cells are differentiated in vitro into erythrocytes using established protocols (for example, Giarratana et al. (2004) Nat Biotechnology 23:69-74, herein incorporated by reference). The expression of HbF is then measured using western blotting with an anti-human HbF antibody, or quantified via High Performance Liquid Chromatography (HPLC). It is expected that successful disruption of the BCL11A enhancer locus will lead to an increase in HbF production when compared to HSCs electroporated with only the RGN but no guide.

Example 12.3: Assay for Decreased Sickle Cell Formation

In this example, APG07433.1 or APG08290.1 generated insertions or deletions disrupting the BCL11A enhancer region are assayed for decreased sickle-cell formation. Donor $CD34^+$ hematopoietic stem cells (HSCs) from patients afflicted with sickle cell disease are used. These HSCs are cultured and vector(s) comprising expression cassettes comprising the coding regions of preferred RGN and the preferred sgRNA are introduced using methods similar to those described in Example 11.1. Following electroporation, these cells are differentiated in vitro into erythrocytes using established protocols (Giarratana et al. (2004) Nat Biotechnology 23:69-74). The expression of HbF is then measured using western blotting with an anti-human HbF antibody, or quantified via High Performance Liquid Chromatography (HPLC). It is expected that successful disruption of the BCL11A enhancer locus will lead to an increase in HbF production when compared to HSCs electroporated with only the RGN but no guide.

Sickle cell formation is induced in these differentiated erythrocytes by the addition of metabisulfite. The numbers of sickled vs normal erythrocytes are counted using a microscope. It is expected that the numbers of sickled cells are less in cells treated with APG07433.1 or APG08290.1 plus sgRNAs than with cells untreated, or treated with RGNs alone.

Example 12.4: Disease Treatment Validation in a Murine Model

To evaluate the efficacy of using APG07433.1 or APG08290.1 disruption of the BCL11A locus, suitable humanized mouse models of sickle cell anemia are used. Expression cassettes encoding for the preferred RGN and for the preferred sgRNA are packaged into AAV vectors or adenovirus vectors. In particular, adenovirus type Ad5/35 is effective at targeting HSCs. A suitable mouse model containing a humanized HBB locus with sickle cell alleles is chosen such as B6; FVB-Tg(LCR-HBA2, LCR-HBB*E26K)53Hhb/J or B6.Cg-Hbatm1Paz Hbbtm1Tow Tg (HBA-HBBs)41Paz/HhbJ. These mice are treated with granulocyte colony-stimulating factor alone or in combination with plerixafor to mobilize HSCs into circulation. AAVs or adenoviruses carrying the RGN and guide plasmid are then injected intravenously, and the mice are allowed to recover for a week. Blood obtained from these mice is tested in an in vitro sickling assay using metabisulfite, and the mice are followed longitudinally to monitor mortality rates and hematopoietic function. It is expected that treatment with AAVs or adenoviruses carrying an RGN and guide RNA will reduce sickling, mortality, and improve hematopoietic function when compared to mice treated with viruses lacking both expression cassettes, or with viruses carrying the RGN expression cassette alone.

SEQUENCE LISTING

```
Sequence total quantity: 651
SEQ ID NO: 1            moltype = AA  length = 1070
FEATURE                 Location/Qualifiers
REGION                  1..1070
                        note = source = /note="APG05083.1"
source                  1..1070
                        mol_type = protein
                        organism = Bacillus sp.
SEQUENCE: 1
MRELDYRIGL DIGTNSIGWG IIELSWNKDR EQYEKARIVD KGVRMFDKAE IPKTGASLAE    60
```

```
PRRIARSSRR RLNRKSQRKK DIRNLLVQHE IISQKELASL YPLTKSSMDI WDIRLDGLDR     120
LLDRFEWTRL LIHLAQRRGF KSNRKSELKD VETGKVLSSI QANEKRLSLY RTVGEMWMKN     180
EDFSKYDKRR NSSNEYVFSV SRADLEKEIV TLFEAQRKFQ SSYASADLQK TYLQIWAHQL     240
PFASGNAIVN KVGYCSLLKG KEKRVPKATY TFQYFSTLDQ INRTRLGPNF QPFTKEQRDV     300
ILDEMFNRTD YYKKKTIPEV TYYDIRKWLA LDETIQFKGL TYDPNEELKK IELKSFINLK     360
PFYEIKKVVT NYAKKTNEAF STLDYDTFAY ALTVYKTDKD IRSYLKKSNN LSKCCYDDQL     420
IEELLTLSYT KFGHLSFKAI NHVLPIMQEG RTYQEAIHQL GYDATNLKKE NRSMFLPLFP     480
DEITNPIVKR ALTQARKVVN AIIRRYGSPN SVHIELAREL SKSHDERTKI MKAHDENYKK     540
NKGAISILIE NGILNPTGYD IVRYKLWKEQ GERCAYSLKQ IPANTFFNEM KKERSGSPVL     600
EIDHILPYSQ SFIDSYHNKV LVYGDENQKK GNRIPYTYFL EGNKDWESFE SYVRLNSFFS     660
KKKRGYLLKK AYLPRESNMI KERHLNDTRY ASSYLKNFIE KNLKFKEVEG STRKKHVQTV     720
NGIITAHLRK RWGLEKDRQE TYLHHAMDAI IVACTDHHMV TKVTEYYQIK ESNKSIRKPY     780
FPLPWVGFRE EILSHLARQP IARKISEELK IGYQSFDYIL VSRMPKRSVT GAAHEQTIMK     840
KGGIDKKGKT IIIKRVYLKD IKFDENGDFK MVGKEQDLAT YEAIKQRYIE YGKESKKAFE     900
TPLYKPSKKG KGNLIKKIKV EVQTKSFVRE VNGGVAQNGD LVRVDLFEKD NRYYMIPIYV     960
MDTVHSELPN KAVTSSKGYE QWLTIDNSFT FKFSLYPYDL VRLVKGNEDR FLYFSTLDIN    1020
SDRLNFKDVN KPSKQAENRY SLKTIENLEK YEVGVLGDLR FVRQEIRKNF              1070

SEQ ID NO: 2          moltype = RNA   length = 19
FEATURE               Location/Qualifiers
misc_feature          1..19
                      note = source = /note="crRNA"
source                1..19
                      mol_type = other RNA
                      organism = Bacillus sp.
SEQUENCE: 2
gtcatagttc cattattgc                                                  19

SEQ ID NO: 3          moltype = RNA   length = 84
FEATURE               Location/Qualifiers
misc_feature          1..84
                      note = source = /note="tracrRNA"
source                1..84
                      mol_type = other RNA
                      organism = Bacillus sp.
SEQUENCE: 3
gctttgatgt ttctatgata aagggcttagg cccgtggcgt tggggatcgc ctgcccattt    60
taatgggctt ctccccatct attt                                            84

SEQ ID NO: 4          moltype = RNA   length = 137
FEATURE               Location/Qualifiers
misc_feature          1..137
                      note = source = /note="Description of Artificial Sequence:
                       Syntheticpolynucleotide"
misc_feature          1..137
                      note = source = /note="sgRNA L1"
source                1..137
                      mol_type = other RNA
                      organism = synthetic construct
SEQUENCE: 4
gagcggacag cagcttccta tatctcgtac gtcatagttc cattattgca aaggctttga     60
tgtttctatg ataagggctt aggcccgtgg cgttggggat cgcctgccca ttttaatggg    120
cttctcccca tctatttt                                                  137

SEQ ID NO: 5          moltype = RNA   length = 137
FEATURE               Location/Qualifiers
misc_feature          1..137
                      note = source = /note="Description of Artificial Sequence:
                       Syntheticpolynucleotide"
misc_feature          1..137
                      note = source = /note="sgRNA L2"
source                1..137
                      mol_type = other RNA
                      organism = synthetic construct
SEQUENCE: 5
ccatgatata gacgttgtgg ctgttgtagt gtcatagttc cattattgca aaggctttga     60
tgtttctatg ataagggctt aggcccgtgg cgttggggat cgcctgccca ttttaatggg    120
cttctcccca tctatttt                                                  137

SEQ ID NO: 6          moltype =    length =
SEQUENCE: 6
000

SEQ ID NO: 7          moltype =    length =
SEQUENCE: 7
000

SEQ ID NO: 8          moltype = DNA   length = 38
FEATURE               Location/Qualifiers
```

```
misc_difference        31..38
                       note = a,c,t,g, unknown, or other
misc_feature           1..38
                       note = source = /note="Description of Artificial Sequence:
                            Syntheticoligonucleotide"
misc_feature           1..38
                       note = source = /note="Target seq and PAM region of plasmid
                            library 1"
source                 1..38
                       mol_type = other DNA
                       organism = synthetic construct
SEQUENCE: 8
gagcggacag cagcttccta tatctcgtac nnnnnnnn                              38

SEQ ID NO: 9           moltype = DNA  length = 38
FEATURE                Location/Qualifiers
misc_difference        31..38
                       note = a,c,t,g, unknown, or other
misc_feature           1..38
                       note = source = /note="Description of Artificial Sequence:
                            Syntheticoligonucleotide"
misc_feature           1..38
                       note = source = /note="Target seq and PAM region of plasmid
                            library 2"
source                 1..38
                       mol_type = other DNA
                       organism = synthetic construct
SEQUENCE: 9
ccatgatata gacgttgtgg ctgttgtagt nnnnnnnn                              38

SEQ ID NO: 10          moltype = RNA  length = 132
FEATURE                Location/Qualifiers
misc_difference        1..25
                       note = a,c,t,g, unknown, or other
misc_feature           1..132
                       note = source = /note="Description of Artificial Sequence:
                            Syntheticpolynucleotide"
misc_feature           1..132
                       note = source = /note="sgRNA with N's"
source                 1..132
                       mol_type = other RNA
                       organism = synthetic construct
SEQUENCE: 10
nnnnnnnnnn nnnnnnnnnn nnnnngtcat agttccatta ttgcaaaggc tttgatgttt      60
ctatgataag ggcttaggcc cgtggcgttg gggatcgcct gcccatttta atgggcttct    120
ccccatctat tt                                                        132

SEQ ID NO: 11          moltype = AA  length = 1071
FEATURE                Location/Qualifiers
REGION                 1..1071
                       note = source = /note="APG07433.1"
source                 1..1071
                       mol_type = protein
                       organism = Bacillus sp.
SEQUENCE: 11
MRELDYRIGL DIGTNSIGWG VIELSWNKDR ERYEKVRIVD QGVRMFDRAE MPKTGASLAE     60
PRRIARSSRR RLNRKSQRKK NIRNLLVQHG VITQEELDSL YPLSKKSMDI WGIRLDGLDR    120
LLNHFEWARL LIHLAQRRGF KSNRKSELKD TETGKVLSSI QLNEKRLSLY RTVGEMWMKD    180
PDFSKYDRKR NSPNEYVFSV SRAELEKEIV TLFAAQRRFQ SPYASKDLQE TYLQIWTHQL    240
PFASGNAILN KVGYCSLLKG KERRIPKATY TFQYFSALDQ VNRTRLGPDF QPFTKEQREI    300
ILNNMFQRTD YYKKKTIPEV TYYDIRKWLE LDETIQFKGL NYDPNEELKK IEKKPFINLK    360
AFYEINKVVA NYSERTNETF STLDYDGIGY ALTVYKTDKD IRSYLKSSHN LPKRCYDDQL    420
IEELLSLSYT KFGHLSLKAI NHVLSIMQKG NTYKEAVDQL GYDTSGLKKE KRSKFLPPIS    480
DEITNPIVKR ALTQARKVVN AIIRRHGSPH SVHIELAREL SKNHDERTKI VSAQDENYKK    540
NKGAISILSE HGILNPTGYD IVRYKLWKEQ GERCAYSLKE IPADTFFNEL KKERNGAPIL    600
EVDHILPYSQ SFIDSYHNKV LVYSDENRKK GNRIPYTYFL ETNKDWEAFE RYVRSNKFFS    660
KKKREYLLKR AYLPRESELI KERHLNDTRY ASTFLKNFIE QNLQFKEAED NPRKRRVQTV    720
NGVITAHFRK RWGLEKDRQE TYLHHAMDAI IVACTDHHEV TRVTEYYQIK ESNKSVKKPY    780
FPMPWEGFRD ELLSHLASQP IAKKISEELK AGYQSLDYIF VSRMPKRSIT GAAHKQTIMR    840
KGGIDKKGKT IIIERLHLKD IKKFDENGDFK MVGKEQDMAT YEAIKQRYLE HGKNSKKAFE    900
TPLYKPSKKG TGNLIKRVKV EGQAKSFVRE VNGGVAQNGD LVRVDLFEKD DKYYMVPIYV    960
PDTVCSELPK KVVASSKGYE QWLTDNSFT KFKFSLYPYDL VRLVKGDEDR FLYFGTLDID   1020
SDRLNFKDVN KPSKKNEYRY SLKTIEDLEK YEVGVLGDLR LVRKETRRNF H            1071

SEQ ID NO: 12          moltype = RNA  length = 21
FEATURE                Location/Qualifiers
misc_feature           1..21
                       note = source = /note="crRNA"
source                 1..21
```

```
                        mol_type = other RNA
                        organism = Bacillus sp.
SEQUENCE: 12
gtcatagttc cattaaagcc a                                              21

SEQ ID NO: 13           moltype = RNA   length = 85
FEATURE                 Location/Qualifiers
misc_feature            1..85
                        note = source = /note="tracrRNA"
source                  1..85
                        mol_type = other RNA
                        organism = Bacillus sp.
SEQUENCE: 13
tggctttgat gtttctatga taagggtttc gacccgtggc gtcgggatc gcctgcccat     60
tgaaatgggc ttctccccat ttatt                                          85

SEQ ID NO: 14           moltype = RNA   length = 140
FEATURE                 Location/Qualifiers
misc_feature            1..140
                        note = source = /note="Description of Artificial Sequence:
                        Syntheticpolynucleotide"
misc_feature            1..140
                        note = source = /note="sgRNA L1"
source                  1..140
                        mol_type = other RNA
                        organism = synthetic construct
SEQUENCE: 14
gagcggacag cagcttccta tatctcgtac gtcatagttc cattaaagcc agaaatggct    60
ttgatgtttc tatgataagg gtttcgaccc gtggcgtcgg ggatcgcctg cccattgaaa   120
tgggcttctc cccatttatt                                               140

SEQ ID NO: 15           moltype = RNA   length = 140
FEATURE                 Location/Qualifiers
misc_feature            1..140
                        note = source = /note="Description of Artificial Sequence:
                        Syntheticpolynucleotide"
misc_feature            1..140
                        note = source = /note="sgRNA L2"
source                  1..140
                        mol_type = other RNA
                        organism = synthetic construct
SEQUENCE: 15
ccatgatata gacgttgtgg ctgttgtagt gtcatagttc cattaaagcc agaaatggct    60
ttgatgtttc tatgataagg gtttcgaccc gtggcgtcgg ggatcgcctg cccattgaaa   120
tgggcttctc cccatttatt                                               140

SEQ ID NO: 16           moltype = DNA   length = 38
FEATURE                 Location/Qualifiers
misc_difference         31..38
                        note = a,c,t,g, unknown, or other
misc_feature            1..38
                        note = source = /note="Description of Artificial Sequence:
                        Syntheticoligonucleotide"
misc_feature            1..38
                        note = source = /note="Target seq and PAM region of plasmid
                        library 1"
source                  1..38
                        mol_type = other DNA
                        organism = synthetic construct
SEQUENCE: 16
gagcggacag cagcttccta tatctcgtac nnnnnnnn                            38

SEQ ID NO: 17           moltype = DNA   length = 38
FEATURE                 Location/Qualifiers
misc_difference         31..38
                        note = a,c,t,g, unknown, or other
misc_feature            1..38
                        note = source = /note="Description of Artificial Sequence:
                        Syntheticoligonucleotide"
misc_feature            1..38
                        note = source = /note="Target seq and PAM region of plasmid
                        library 2"
source                  1..38
                        mol_type = other DNA
                        organism = synthetic construct
SEQUENCE: 17
ccatgatata gacgttgtgg ctgttgtagt nnnnnnnn                            38

SEQ ID NO: 18           moltype = RNA   length = 135
```

```
FEATURE                 Location/Qualifiers
misc_difference         1..25
                        note = a,c,t,g, unknown, or other
misc_feature            1..135
                        note = source = /note="Description of Artificial Sequence:
                          Syntheticpolynucleotide"
misc_feature            1..135
                        note = source = /note="sgRNA with N's"
source                  1..135
                        mol_type = other RNA
                        organism = synthetic construct
SEQUENCE: 18
nnnnnnnnnn nnnnnnnnnn nnnnngtcat agttccatta aagccaaaag tggctttgat    60
gtttctatga taagggtttc gacccgtggc gtcgggatcg cctgcccat  tgaaatgggc   120
ttctccccat ttatt                                                    135

SEQ ID NO: 19           moltype = AA  length = 1071
FEATURE                 Location/Qualifiers
REGION                  1..1071
                        note = source = /note="APG07513.1"
source                  1..1071
                        mol_type = protein
                        organism = Bacillus sp.
SEQUENCE: 19
MRELDYRIGL DIGTNSIGWG VIELSWNKDR EQYEKTRIVD KGVRMFDKAE IPKTGASLAE     60
PRRIARSSRR RLNRKSQRKK DIRNLLVQHE IISQKELTSL YPLSKSSMDI WDIRLDGLDR    120
LLDRFEWARL LIHLAQRRGF KSNRKSELKD VETGKVLSSI QVNEKRLSLY RTVGEMWMKN    180
ADCSKYGKRR NSPNEYVFSV SRADLEKEIV TLFEAQRKFH SSYASVDLQK TYIQIWAHQL    240
PFASGNAIVN KVGYCSLLKG KEKRVPKATY TFQYFNTLDQ INRTRLGPNF QPFTKEQRDI    300
ILDKMFQRTD YYKKKTIPEV TYYDIRKWLA LDETIQFKGL TYDPNEELKK IEMKPFINLK    360
PFYEIKKVVT NYAKKTNEVF SALDYDTVAY ALTVYKTDKD IRSYLKRSNN LSKRCYDDQL    420
IEEELLTLSYT KFGHLSFKAI NHVLPIMQEG RTYQEAIHQL GYDTTNLKKE NRSMFLPIIP    480
DEITNPIVKR ALTQARKVVN AIIRRYGSPN SVHIELAREL SKSHDERKKI MTAHDENYKK    540
NKGAVSILID NGILNPTGYD IVRYKLWKEQ GERCAYSLEK IPANTFFNEL KKERSGPPVL    600
EVDHILPYSQ SFIDSYHNKV LVYGDENQKK GNRIPYTFFS EEDKEWESFE SYVRSNSFFS    660
KKKRGYLLKK AYLPRESNLI KERHLNDTRY ASSYLKNFIE KNLKFKEAVG ITRKKYVQTV    720
NGVITAHLRK RWGLEKDRQE TYLHHAMDAI IVACTDHHMV TKVTEYYQIK EGNKSIKKPY    780
FPLPWMGFRE EILSHLESQP IARKISEELK IGYQSPDYIL VSRMPKRSVT GSAHDQTVMK    840
KGDIDKKGKT IIIKRVHLKD IKFDENGDFK MVGKEQDLAT YEAIKQRYLE YRKESKKAFE    900
TPLYKPSKKG KGNLIKKIKV EVQTKSFVRE INGGVAQNGD LVRVDLFEKD NRYYMVPIYV    960
VDTVRSELPN KAVTSSKGYE QWLSIDNSFT FKFSLYPYDL VRLVKGDEDR FLYFSTLDIN   1020
SDRLNFKDVN KPSKQAEYRY SLKTIENLEK YEIGVLGDLR LVRQETRKIF K            1071

SEQ ID NO: 20           moltype = RNA  length = 27
FEATURE                 Location/Qualifiers
misc_feature            1..27
                        note = source = /note="crRNA"
source                  1..27
                        mol_type = other RNA
                        organism = Bacillus sp.
SEQUENCE: 20
gtcatagttc cattaaagcc attgctg                                        27

SEQ ID NO: 21           moltype = RNA  length = 93
FEATURE                 Location/Qualifiers
misc_feature            1..93
                        note = source = /note="tracrRNA"
source                  1..93
                        mol_type = other RNA
                        organism = Bacillus sp.
SEQUENCE: 21
acagcaatgg ctttgatgtt tctatgataa gggcttcggc ccgtggcgtt ggggatcgcc     60
tgcccatttt aatgggcttc tccccatcta ttt                                 93

SEQ ID NO: 22           moltype = RNA  length = 154
FEATURE                 Location/Qualifiers
misc_feature            1..154
                        note = source = /note="Description of Artificial Sequence:
                          Syntheticpolynucleotide"
misc_feature            1..154
                        note = source = /note="sgRNA L1"
source                  1..154
                        mol_type = other RNA
                        organism = synthetic construct
SEQUENCE: 22
gagcggacag cagcttccta tatctcgtac gtcatagttc cattaaagcc attgctgaaa     60
gacagcaatg gctttgatgt ttctatgata agggcttcgg cccgtggcgt tggggatcgc    120
ctgcccattt taatgggctt ctccccatct attt                                154
```

US 12,338,455 B2
105                                                                                        106
-continued

```
SEQ ID NO: 23            moltype = RNA   length = 154
FEATURE                  Location/Qualifiers
misc_feature             1..154
                         note = source = /note="Description of Artificial Sequence:
                         Syntheticpolynucleotide"
misc_feature             1..154
                         note = source = /note="sgRNA L2"
source                   1..154
                         mol_type = other RNA
                         organism = synthetic construct
SEQUENCE: 23
ccatgatata gacgttgtgg ctgttgtagt gtcatagttc cattaaagcc attgctgaaa    60
gacagcaatg gctttgatgt ttctatgata agggcttcgg cccgtggcgt tggggatcgc   120
ctgcccattt taatgggctt ctccccatct attt                               154

SEQ ID NO: 24            moltype = DNA   length = 38
FEATURE                  Location/Qualifiers
misc_difference          31..38
                         note = a,c,t,g, unknown, or other
misc_feature             1..38
                         note = source = /note="Description of Artificial Sequence:
                         Syntheticoligonucleotide"
misc_feature             1..38
                         note = source = /note="Target seq and PAM region of plasmid
                         library 1"
source                   1..38
                         mol_type = other DNA
                         organism = synthetic construct
SEQUENCE: 24
gagcggacag cagcttccta tatctcgtac nnnnnnnn                             38

SEQ ID NO: 25            moltype = DNA   length = 38
FEATURE                  Location/Qualifiers
misc_difference          31..38
                         note = a,c,t,g, unknown, or other
misc_feature             1..38
                         note = source = /note="Description of Artificial Sequence:
                         Syntheticoligonucleotide"
misc_feature             1..38
                         note = source = /note="Target seq and PAM region of plasmid
                         library 2"
source                   1..38
                         mol_type = other DNA
                         organism = synthetic construct
SEQUENCE: 25
ccatgatata gacgttgtgg ctgttgtagt nnnnnnnn                             38

SEQ ID NO: 26            moltype = RNA   length = 149
FEATURE                  Location/Qualifiers
misc_difference          1..25
                         note = a,c,t,g, unknown, or other
misc_feature             1..149
                         note = source = /note="Description of Artificial Sequence:
                         Syntheticpolynucleotide"
misc_feature             1..149
                         note = source = /note="sgRNA with N's"
source                   1..149
                         mol_type = other RNA
                         organism = synthetic construct
SEQUENCE: 26
nnnnnnnnnn nnnnnnnnnn nnnnngtcat agttccatta aagccattgc tgaaagacag    60
caatggcttt gatgtttcta tgataagggc ttcggcccgt ggcgttgggg atcgcctgcc   120
catttaatg gcttctccc catctattt                                       149

SEQ ID NO: 27            moltype = AA   length = 1072
FEATURE                  Location/Qualifiers
REGION                   1..1072
                         note = source = /note="APG08290.1"
source                   1..1072
                         mol_type = protein
                         organism = Bacillus sp.
SEQUENCE: 27
MSELDYRIGL DIGTNSIGWG VIELFWNKDR ERYEKVRIVD KGVRMFDKAE IPNKGASLAE    60
PRRIARSSRR RLNRKSQRKK EIRNLLVQHG MITQEELDLL YPLSKKSIDI WDIRLDGLDR   120
LLNHLEWARL LIHLAQRRGF KSNRKSELKD AETGKVLSSI QVNEKRLFLY RTVGEMWIKD   180
AEFSKYDRRR NSPNEYVFSV SRADLEKEIV TLFEAQRKFQ SSYASKNLQE TYLQIWAHQL   240
PFASGNAILN KVGYCSLLKG KERRIPKATY TFQYFSALDQ VNRTRLGPDF QPFTQEQKEI   300
ILDKMFQRTD YYKKKTIPEV SYYDIRKWLE LDETIQFKGL NYDPNEELKK IEKKPFINLK   360
AFYEIKKVVA NYAERTNEAF STLDYDAIAY ALTVYKTDKD IRSYLKKSNN LSKRCYDDQL   420
```

```
IEELFTLSYT KFGHLSFKAI NHVLPIMQEG RTYQEAIHQL GYDTTNLKKE NRSMFLPLIP   480
DEITNPIVKR AITQARKVVN AIIRRYGSPN SVHIELAREL SKSHDERKKI MTAHDENYKK   540
NKGAISILIE NGILNPTGYD IVRYKLWKEQ GERCAYSLKE IPPDTFFNEL KKERNGSPIL   600
EVDHILPYSQ SFIDSYHNKV LVYSDENRNK GNRIPYTYFL ETNKDWEAFE RYVRSNKLFS   660
KKKREYLLKK TYLPRESELI KERHLNDTRY ASTFLKNFIE QNLQFKEVEV NLRKKRVQTV   720
NGVITAHLRK RWGLEKNRQE TYLHHAMDAI IVACTDHHMV TRITEYYQIK ESNKSVKKPY   780
FPMPWEGFRD ELLSHLASQP IAKKISEELK AGYQSSDYIF VSRMPKRSVT GAAHDQTIRR   840
KGGIDKKGKT IIIKRVRLKD IKFDENGDFK MVGKEQDLAT YEAIKQRYLE HRKNSKKAFE   900
TPLYKPSKKG TGNLIKRVKI EGQTKAFVRE VNGGVAQNSD LVRVDLFEKD DKYYMVPIYV   960
PDTVCSELPK KVVKSGKGYE QWLTLDNSFT FKSSLYPYDL VRLVKGNEDR FLYFGTLDID  1020
SDRLNFKDVN KPSKQNEYRY SLKTIENLEK YEVGVLGDLR LVKQETRRIF NR          1072

SEQ ID NO: 28           moltype = RNA   length = 21
FEATURE                 Location/Qualifiers
misc_feature            1..21
                        note = source = /note="crRNA"
source                  1..21
                        mol_type = other RNA
                        organism = Bacillus sp.
SEQUENCE: 28
gtcatagttc catgaaagcc a                                             21

SEQ ID NO: 29           moltype = RNA   length = 85
FEATURE                 Location/Qualifiers
misc_feature            1..85
                        note = source = /note="tracrRNA"
source                  1..85
                        mol_type = other RNA
                        organism = Bacillus sp.
SEQUENCE: 29
tggctttgat gtttctatga taagggtttc ggcccgtggc gtcgggatc gcctgcccat    60
tccgatgggc ttctccccat ttatt                                         85

SEQ ID NO: 30           moltype = RNA   length = 140
FEATURE                 Location/Qualifiers
misc_feature            1..140
                        note = source = /note="Description of Artificial Sequence:
                         Syntheticpolynucleotide"
misc_feature            1..140
                        note = source = /note="sgRNA L1"
source                  1..140
                        mol_type = other RNA
                        organism = synthetic construct
SEQUENCE: 30
gagcggacag cagcttccta tatctcgtac gtcatagttc catgaaagcc aaaagtggct   60
ttgatgtttc tatgataagg gtttcggccc gtggcgtcgg ggatcgcctg cccattccga  120
tgggcttctc cccatttatt                                              140

SEQ ID NO: 31           moltype = RNA   length = 140
FEATURE                 Location/Qualifiers
misc_feature            1..140
                        note = source = /note="Description of Artificial Sequence:
                         Syntheticpolynucleotide"
misc_feature            1..140
                        note = source = /note="sgRNA L2"
source                  1..140
                        mol_type = other RNA
                        organism = synthetic construct
SEQUENCE: 31
ccatgatata gacgttgtgg ctgttgtagt gtcatagttc catgaaagcc aaaagtggct   60
ttgatgtttc tatgataagg gtttcggccc gtggcgtcgg ggatcgcctg cccattccga  120
tgggcttctc cccatttatt                                              140

SEQ ID NO: 32           moltype =   length =
SEQUENCE: 32
000

SEQ ID NO: 33           moltype = DNA   length = 38
FEATURE                 Location/Qualifiers
misc_difference         31..38
                        note = a,c,t,g, unknown, or other
misc_feature            1..38
                        note = source = /note="Description of Artificial Sequence:
                         Syntheticoligonucleotide"
misc_feature            1..38
                        note = source = /note="Target seq and PAM region of plasmid
                         library 1"
source                  1..38
                        mol_type = other DNA
```

```
                        organism = synthetic construct
SEQUENCE: 33
gagcggacag cagcttccta tatctcgtac nnnnnnnn                               38

SEQ ID NO: 34           moltype = DNA   length = 38
FEATURE                 Location/Qualifiers
misc_difference         31..38
                        note = a,c,t,g, unknown, or other
misc_feature            1..38
                        note = source = /note="Description of Artificial Sequence:
                           Syntheticoligonucleotide"
misc_feature            1..38
                        note = source = /note="Target seq and PAM region of plasmid
                           library 2"
source                  1..38
                        mol_type = other DNA
                        organism = synthetic construct
SEQUENCE: 34
ccatgatata gacgttgtgg ctgttgtagt nnnnnnnn                               38

SEQ ID NO: 35           moltype = RNA   length = 135
FEATURE                 Location/Qualifiers
misc_difference         1..25
                        note = a,c,t,g, unknown, or other
misc_feature            1..135
                        note = source = /note="Description of Artificial Sequence:
                           Syntheticpolynucleotide"
misc_feature            1..135
                        note = source = /note="sgRNA with N's"
source                  1..135
                        mol_type = other RNA
                        organism = synthetic construct
SEQUENCE: 35
nnnnnnnnnn nnnnnnnnnn nnnnngtcat agttccatga aagccaaaag tggctttgat       60
gtttctatga taagggtttc ggcccgtggc gtcgggatc gcctgcccat tccgatgggc      120
ttctccccat ttatt                                                      135

SEQ ID NO: 36           moltype = AA    length = 1337
FEATURE                 Location/Qualifiers
REGION                  1..1337
                        note = source = /note="APG05459.1"
source                  1..1337
                        mol_type = protein
                        organism = Enterococcus sp.
SEQUENCE: 36
MKKDYVIGLD IGTNSVGWAV MTEDYQLVKK KMPIYGNTEK KKIKKNFWGV RLFEEGHTAE       60
DRRLKRTARR RISRRRNRLR YLQAFFEEAM TALDENFFAR LQESFLVPED KKWHRHPIFA      120
KLEDEVAYHE TYPTIYHLRK KLADSSEQAD LRLIYLALAH IVKYRGHFLI EGKLSTENIS      180
VKEQFQQFMI IYNQTFVNGE SRLVSAPLPE SVLIEEELTE KASRTKKSEK VLQQFPQEKA      240
NGLFGQFLKL MVGNKADFKK VFGLEEEAKI TYASESEYED LEGILAKVGD EYSDVFLAAK      300
NVYDAVELST ILADSDKKSH AKLSSSMIVR FTEHQEDLKK FKRFIRENCP DEYDNLFKNE      360
QKDGYAGYIA HAGKVSQLKF YQYVKKIIQD IAGAEYFLEK IAQENFLRKQ RTFDNGVIPH      420
QIHLAELQAI IHRQAAYYPF LKENQEKIEQ LVTFRIPYYV GPLSKGDAST FAWLKRQSEE      480
PIRPWNLQET VDLDQSATAF IERMTNFDTY LPSEKVLPKH SLLYEKFMVF NELTKISYTD      540
DRGIKANFSG KEKEKIFDYL FKTRRKVKKK DIIQFYRNEY NTEIVTLSGL EEDQFNASFS      600
TYQDLLKCGL TRAELDHPDN AEKLEDIIKI LTIFEDRQRI RTQLSTFKGQ FSAEVLKKLE      660
RKHYTGWGRL SKKLINGIYD KESGKTILDY LIKDDGVSKH YNRNFMQLIN DSQLSFKNAI      720
QKAQSSEHEE TLSETVNELA GSPAIKKGIY QSLKIVDELV AIMGYAPKRI VVEMARENQT      780
TSTGKRRSIQ RLKIVEKAMA EIGSNLLKEQ PTTNEQLRDT RLFLYYMQNG KDMYTGDELS      840
LHRLSHYDID HIIPQSFMKD DSLDNLVLVG STENRGKSDD VPSKEVVKDM KAYWEKLYAA      900
GLISQRKFQR LTKGEQGGLT LEDKAHFIQR QLVETRQITK NVAGILDQRY NANSKEKKVQ      960
IITLKASLTS QFRSIFGLYK VREVNDYHHG QDAYLNCVVA TTLLKVYPNL APEFVYGEYP     1020
KFQAFKENKA TAKTIIYTNL MRFFTEDEPR FMKDGEILWS NSYLKNIKKE LNYHQMNIVK     1080
KVEVQKGGFS KESIKPKGPS NKLIPVKNGL DPQKYGGFDS PVVAYTVLFT HEKGKKPLIK     1140
QEILGITIME KTRFEQNPIL FLEEKGFLRP RVLMKLPKYT LYEFPEGRRR LLASAKEAQK     1200
GNQMVLPEHL LTLLYHAKQC LLPNQSESLA YVEQHQPEFQ EILERVVDFA EVHTLAKSKV     1260
QQIVKLFEAN QTADVKEIAA SFIQLMQFNA MGAPSTFKFF QKDIERARYT SIKEIFDATI     1320
IYQSTTGLYE TRRKVVD                                                   1337

SEQ ID NO: 37           moltype = RNA   length = 16
FEATURE                 Location/Qualifiers
misc_feature            1..16
                        note = source = /note="crRNA"
source                  1..16
                        mol_type = other RNA
                        organism = Enterococcus sp.
SEQUENCE: 37
gttttagagt catgtt                                                      16
```

-continued

| | | |
|---|---|---|
| SEQ ID NO: 38 | moltype = RNA length = 74 | |
| FEATURE | Location/Qualifiers | |
| misc_feature | 1..74 | |
| | note = source = /note="tracrRNA" | |
| source | 1..74 | |
| | mol_type = other RNA | |
| | organism = Enterococcus sp. | |

SEQUENCE: 38
aacatagcaa gttaaaataa ggttttaacc gtaatcaact gtaaagtggc gctgtttcgg 60
cgcttttttt gttt 74

| | | |
|---|---|---|
| SEQ ID NO: 39 | moltype = RNA length = 124 | |
| FEATURE | Location/Qualifiers | |
| misc_feature | 1..124 | |
| | note = source = /note="Description of Artificial Sequence: Syntheticpolynucleotide" | |
| misc_feature | 1..124 | |
| | note = source = /note="sgRNA L1" | |
| source | 1..124 | |
| | mol_type = other RNA | |
| | organism = synthetic construct | |

SEQUENCE: 39
gagcggacag cagcttccta tatctcgtac gttttagagt catgttaaag aacatagcaa 60
gttaaaataa ggttttaacc gtaatcaact gtaaagtggc gctgtttcgg cgcttttttt 120
gttt 124

| | | |
|---|---|---|
| SEQ ID NO: 40 | moltype = RNA length = 124 | |
| FEATURE | Location/Qualifiers | |
| misc_feature | 1..124 | |
| | note = source = /note="Description of Artificial Sequence: Syntheticpolynucleotide" | |
| misc_feature | 1..124 | |
| | note = source = /note="sgRNA L2" | |
| source | 1..124 | |
| | mol_type = other RNA | |
| | organism = synthetic construct | |

SEQUENCE: 40
ccatgatata gacgttgtgg ctgttgtagt gttttagagt catgttaaag aacatagcaa 60
gttaaaataa ggttttaacc gtaatcaact gtaaagtggc gctgtttcgg cgcttttttt 120
gttt 124

| | | |
|---|---|---|
| SEQ ID NO: 41 | moltype = length = | |
| SEQUENCE: 41 | | |
| 000 | | |

| | | |
|---|---|---|
| SEQ ID NO: 42 | moltype = DNA length = 38 | |
| FEATURE | Location/Qualifiers | |
| misc_difference | 31..38 | |
| | note = a,c,t,g, unknown, or other | |
| misc_feature | 1..38 | |
| | note = source = /note="Description of Artificial Sequence: Syntheticoligonucleotide" | |
| misc_feature | 1..38 | |
| | note = source = /note="Target seq and PAM region of plasmid library 1" | |
| source | 1..38 | |
| | mol_type = other DNA | |
| | organism = synthetic construct | |

SEQUENCE: 42
gagcggacag cagcttccta tatctcgtac nnnnnnnn 38

| | | |
|---|---|---|
| SEQ ID NO: 43 | moltype = DNA length = 38 | |
| FEATURE | Location/Qualifiers | |
| misc_difference | 31..38 | |
| | note = a,c,t,g, unknown, or other | |
| misc_feature | 1..38 | |
| | note = source = /note="Description of Artificial Sequence: Syntheticoligonucleotide" | |
| misc_feature | 1..38 | |
| | note = source = /note="Target seq and PAM region of plasmid library 2" | |
| source | 1..38 | |
| | mol_type = other DNA | |
| | organism = synthetic construct | |

SEQUENCE: 43
ccatgatata gacgttgtgg ctgttgtagt nnnnnnnn 38

| | | |
|---|---|---|
| SEQ ID NO: 44 | moltype = RNA length = 119 | |
| FEATURE | Location/Qualifiers | |

| misc_difference | 1..25 |
| --- | --- |
| | note = a,c,t,g, unknown, or other |
| misc_feature | 1..119 |
| | note = source = /note="Description of Artificial Sequence: Syntheticpolynucleotide" |
| misc_feature | 1..119 |
| | note = source = /note="sgRNA with N's" |
| source | 1..119 |
| | mol_type = other RNA |
| | organism = synthetic construct |

SEQUENCE: 44

```
nnnnnnnnnn nnnnnnnnnn nnnnngtttt agagtcatgt taaagaacat agcaagttaa   60
aataaggttt taaccgtaat caactgtaaa gtggcgctgt ttcggcgctt tttttgttt   119
```

| SEQ ID NO: 45 | moltype = AA length = 1436 |
| --- | --- |
| FEATURE | Location/Qualifiers |
| REGION | 1..1436 |
| | note = source = /note="APG04583.1" |
| source | 1..1436 |
| | mol_type = protein |
| | organism = Enterococcus sp. |

SEQUENCE: 45

```
MAKNILGLDL GTNSIGWALV QQDFENKEGN ILGMGSRIIP MSQDILGEFG KGNSISQTAE    60
RTGYRGVRRL RERHLLRRER LHRVLHLLGF LPKHYDEKID FTQRFGKFIN QAEPKLAFDS   120
EFLFKDSFHE MLADFKQNQP EFLKDKNGED CLVPYDWTIY YLRKKALTQK IEKYELAWLI   180
LNFNQKRGYY QLRGEEEKEN PNKLVGFHSL KIVDVIPDAE TNKKGETWYS LHLENGWVYR   240
RSSKISLADW KDKVRDFIVT TDLNDDGSEK LDKDGIVKRS FRAPSADDWT LLKKKTEKDI   300
DNSNKTVGTY IYDNLLLNPK QKIKGKMVRT IERKFYKQEL EQILKTQKEF HSELQSENLL   360
QDCVRELYRN NEQHQQMLEA KDFVHLFLND IIFYQRPLRS QKSSISNCTL EFRKSKNENG   420
EEVIHRLKVI AKSNPYYQEF RLLQWVQNLA IYTKDDDKNV TNEFLKSTQD WEDLLRWLHS   480
KKEIKQDALI KFLIEKKGLK GKALTIEVAK YRWNYVQDKD YPGNETRYLI QSRLDKVEYA   540
PKDFLTYENE MALWHIIYSI NDKIEYEKAL KSFANKKGLD EVTFVEAFKK FPPFKSDYGS   600
FSEKAIKKLL PLMRFGTQWN WDNIDQNSKE RIGKILTGEY DENIKGRVRE KARHLNSETD   660
FQALPLWLAQ YVVYGRHSEA DIAGKWNSVD DLKQFLDDFK QHSLRNPIVE QVITETLRAV   720
KDIWNFYGKG AKDFFSEIHI ELGREMKNTA DERKRITTMV TDNENTNLRI KALLAEMALD   780
QNVDNVRPYS PMQQEILKIY EEGVLNAEEN IDDDILKISK TAQPSATDLK RYKLWLEQKY   840
RSPYTGQMIP LNKLFTPEYE IEHIIPQSRY FDDSMSNKVI CEAAVNKLKD NQIGLVFIKN   900
HHGEVVDFGM GKQVKILEVS DYEDPVKQNY NKNRGKRNKL LLEDIPEKMI ERQLNDTRYI   960
SKYITQVLSN IVRDDKEGSK DDGVNSKNIV PGNGKITTRL KQDWGLNDVW NDLVLPRFER  1020
MNTLTNSNDF TSKNTHGKTI PTVPIELSKG FSKKRIDHRH HAMDALVIAC ATRDHVNLLN  1080
NESSKSDTKR YDLNRKLRKY EKVAYNDPKT GERIEKEVPK DFIKPWETFT EDTRTLLENI  1140
VISFKQNLRV INKATNYYEK IENGKKVKVE QKGINWAVRK ALHKETVSGQ VHLDRIKVAK  1200
GKILTATRKT LDASFNEKTI ESITDTGIQK ILLNYLKSKD NNPEVAFSPE GIEELNKEIR  1260
LYNDGKAHQP ILKVRVFEQG SKFTLGETGN KTTKFVEAAK GTNLFFGIYE DKSGKRSYET  1320
IPLNIVIERQ KQGLQAVPET NEKGKQLLFT LSPNDLVYVP EEGVFDENNI KVDRIYKVVS  1380
FSTYQCFFVR NDVSTSVVNK VEYSALNKME KSIDNIMIKE NCVKLNVDRL GKISKA     1436
```

| SEQ ID NO: 46 | moltype = RNA length = 16 |
| --- | --- |
| FEATURE | Location/Qualifiers |
| misc_feature | 1..16 |
| | note = source = /note="crRNA" |
| source | 1..16 |
| | mol_type = other RNA |
| | organism = Enterococcus sp. |

SEQUENCE: 46

```
gttgtgagtt cctttc                                                   16
```

| SEQ ID NO: 47 | moltype = RNA length = 78 |
| --- | --- |
| FEATURE | Location/Qualifiers |
| misc_feature | 1..78 |
| | note = source = /note="tracrRNA" |
| source | 1..78 |
| | mol_type = other RNA |
| | organism = Enterococcus sp. |

SEQUENCE: 47

```
gaaaggaact cacaataagg attattccgt tgtgaaaaca tttagcgcct cgactatctt   60
cggggctttt ttattttt                                                 78
```

| SEQ ID NO: 48 | moltype = RNA length = 128 |
| --- | --- |
| FEATURE | Location/Qualifiers |
| misc_feature | 1..128 |
| | note = source = /note="Description of Artificial Sequence: Syntheticpolynucleotide" |
| misc_feature | 1..128 |
| | note = source = /note="sgRNA L1" |
| source | 1..128 |
| | mol_type = other RNA |
| | organism = synthetic construct |

SEQUENCE: 48

```
gagcggacag cagcttccta tatctcgtac gttgtgagtt cctttcactt gaaaggaact    60
cacaataagg attattccgt tgtgaaaaca tttagcgcct cgactatctt cggggctttt   120
ttattttt                                                            128

SEQ ID NO: 49           moltype = RNA  length = 128
FEATURE                 Location/Qualifiers
misc_feature            1..128
                        note = source = /note="Description of Artificial Sequence:
                         Syntheticpolynucleotide"
misc_feature            1..128
                        note = source = /note="sgRNA L2"
source                  1..128
                        mol_type = other RNA
                        organism = synthetic construct
SEQUENCE: 49
ccatgatata gacgttgtgg ctgttgtagt gttgtgagtt cctttcactt gaaaggaact    60
cacaataagg attattccgt tgtgaaaaca tttagcgcct cgactatctt cggggctttt   120
ttattttt                                                            128

SEQ ID NO: 50           moltype =   length =
SEQUENCE: 50
000

SEQ ID NO: 51           moltype = DNA  length = 38
FEATURE                 Location/Qualifiers
misc_difference         31..38
                        note = a,c,t,g, unknown, or other
misc_feature            1..38
                        note = source = /note="Description of Artificial Sequence:
                         Syntheticoligonucleotide"
misc_feature            1..38
                        note = source = /note="Target seq and PAM region of plasmid
                         library 1"
source                  1..38
                        mol_type = other DNA
                        organism = synthetic construct
SEQUENCE: 51
gagcggacag cagcttccta tatctcgtac nnnnnnnn                            38

SEQ ID NO: 52           moltype = DNA  length = 38
FEATURE                 Location/Qualifiers
misc_difference         31..38
                        note = a,c,t,g, unknown, or other
misc_feature            1..38
                        note = source = /note="Description of Artificial Sequence:
                         Syntheticoligonucleotide"
misc_feature            1..38
                        note = source = /note="Target seq and PAM region of plasmid
                         library 2"
source                  1..38
                        mol_type = other DNA
                        organism = synthetic construct
SEQUENCE: 52
ccatgatata gacgttgtgg ctgttgtagt nnnnnnnn                            38

SEQ ID NO: 53           moltype = RNA  length = 123
FEATURE                 Location/Qualifiers
misc_difference         1..25
                        note = a,c,t,g, unknown, or other
misc_feature            1..123
                        note = source = /note="Description of Artificial Sequence:
                         Syntheticpolynucleotide"
misc_feature            1..123
                        note = source = /note="sgRNA with N's"
source                  1..123
                        mol_type = other RNA
                        organism = synthetic construct
SEQUENCE: 53
nnnnnnnnnn nnnnnnnnnn nnnnngttgt gagttccttt caaaggaaag gaactcacaa    60
taaggattat tccgttgtga aacatttag cgcctcgact atcttcgggg cttttttatt   120
ttt                                                                 123

SEQ ID NO: 54           moltype = AA  length = 1456
FEATURE                 Location/Qualifiers
REGION                  1..1456
                        note = source = /note="APG01688.1"
source                  1..1456
                        mol_type = protein
                        organism = Empedobacter sp.
```

-continued

```
SEQUENCE: 54
MMIKNILGLD LGTNSIGWAL IKQDFENKHG EILGMGSRII PMSQDILGDF GKGNSISQTA    60
DRTKYRSVRR LRERFLLRRE RLHRVLHLLN FLPQHYASQI DFEKKFGKFK SETEPKLAWE   120
NWGGKFSFLF QNSFNEMLED FKAAGQGLKI PYDWTIYYLR KKALSQKIEK EELAWILLNF   180
NQKRGYYQLR GEEEEENPNK LVEFYSLKIV DVVADEPQKG KSDIWYSLIL ENGWVYRRAS   240
KIPLFDWKDK TRDFIVTTDL NDDRSVKTDK EGNEKRSFRA PSENDWTLVK KKTEQEIDQS   300
HKTVGTYIYE TLLLNPKQKI KGKLVRTIER KFYKDELKQI LEKQKEFHQE LKNDDLYNDC   360
IRELYRNNEA HQLTLSKKDF VHLLMDDLIF YQRPLRSQKS SISNCTLEFR KYKDENGIEH   420
TQYLKAIPKS NPYYQEFRLW QWMYNLNIYR KDDEANVTKE FLNTNKDFES LPEFLNNRKE   480
IEQKPLIKFL LEQKDINKKL LNAEAEKYRW NYVEDKKYPC NETKTMISSR LDKVENISDD   540
FLTRDIEQKI WHIIYSVNDK IEYEKALKSF ATRNDLDENS FIEAFKKFSP FKSEYGSFSE   600
KAIKKLLPLM RLGKYWYEDE IVKHSDIYFK NIENLLGDFS NRDKKISEED KEKWNKSINL   660
KLQEELKDFQ TAEIDLFQGL RLHIAQYLVY GRHSEASMIG KWNSAEDLEE FLKDFKQHSL   720
RNPIVEQVIT ETLRVVKDIW LKYGNGAKDF FNEIHIELGR EMKLPADDRK KLTNQISENE   780
NTNFRIKALL AEMMNDSSVE NVRPFSPMQQ EILKIYEDDV LKSDIEIEDD ILKISKTAQP   840
SPSDLKRYKL WLEQKYKSPY TGQIIPLNKL FTPEYEIEHI IPQSRYFDDS FSNKVICESA   900
VNKLKDNYIG LEFIKQFGGT IIELGFGKSI KVFETKEYED FVKKHYANNQ GKRNKLLMED   960
IPEKMIERQM NDTRYISKYI SGVLSNIVRV EDGSDEGVNS KNIVPGNGKI TTQLKQDWGL  1020
NDVWNDLILP RFERMNQLTN SKVFTAWNEN YQKFLPTVPI EYSKGFSKKR IDHRHHALDA  1080
LVIACATKDH VNLLNNQSAK SDTKRYDLKK KSMKFEKVVY NDAKTGEKIE REVPKQFLKP  1140
WENFTLDVKH NLETIIVSFK QNLRVINKAT NYYEKYVEKD GTKNKERVEQ TGTNWAIRKP  1200
MHKDTVSGKV DLPWVKVPKG KILTATRKSL DSSFDLKSIG SITDTGIQKI LKNYLAFKDG  1260
NPELAFSPEG IDDLNKNIEK YNDGKPHQPI NKVRVFELGS KFQVGQSGNK KDKYVEAAKG  1320
TNLFFAVYED EKGKRNYETI PLNEVIERQK QGLSVVDLKG TNDFYLCPND FVYIPSGDEL  1380
ENINNVDFKD IKKEINERIY KVVSFTGNRL SCIPYMVATT IVNKLEFTQL NKIEFTKEKE  1440
ICIKLNVDRL GNISKA                                                  1456

SEQ ID NO: 55          moltype = RNA   length = 18
FEATURE                Location/Qualifiers
misc_feature           1..18
                       note = source = /note="crRNA"
source                 1..18
                       mol_type = other RNA
                       organism = Empedobacter sp.
SEQUENCE: 55
gttgtgaatt gctttcaa                                                 18

SEQ ID NO: 56          moltype = RNA   length = 75
FEATURE                Location/Qualifiers
misc_feature           1..75
                       note = source = /note="tracrRNA"
source                 1..75
                       mol_type = other RNA
                       organism = Empedobacter sp.
SEQUENCE: 56
ttgaaaagca attcacaata aggattattc cgttgtgaaa acattcaagg cggggcaact   60
cgtcttttt  ctttt                                                   75

SEQ ID NO: 57          moltype = RNA   length = 127
FEATURE                Location/Qualifiers
misc_feature           1..127
                       note = source = /note="Description of Artificial Sequence:
                        Syntheticpolynucleotide"
misc_feature           1..127
                       note = source = /note="sgRNA L1"
source                 1..127
                       mol_type = other RNA
                       organism = synthetic construct
SEQUENCE: 57
gagcggacag cagcttccta tatctcgtac gttgtgaatt gctttcaaaa agttgaaaag   60
caattcacaa taaggattat tccgttgtga aacattcaa ggcggggcaa ctcgtctttt  120
ttcttttt                                                          127

SEQ ID NO: 58          moltype = RNA   length = 127
FEATURE                Location/Qualifiers
misc_feature           1..127
                       note = source = /note="Description of Artificial Sequence:
                        Syntheticpolynucleotide"
misc_feature           1..127
                       note = source = /note="sgRNA L2"
source                 1..127
                       mol_type = other RNA
                       organism = synthetic construct
SEQUENCE: 58
ccatgatata gacgttgtgg ctgttgtagt gttgtgaatt gctttcaaaa agttgaaaag   60
caattcacaa taaggattat tccgttgtga aacattcaa ggcggggcaa ctcgtctttt  120
ttcttttt                                                          127

SEQ ID NO: 59          moltype =       length =
```

```
SEQUENCE: 59
000

SEQ ID NO: 60           moltype = DNA  length = 38
FEATURE                 Location/Qualifiers
misc_difference         31..38
                        note = a,c,t,g, unknown, or other
misc_feature            1..38
                        note = source = /note="Description of Artificial Sequence:
                         Syntheticoligonucleotide"
misc_feature            1..38
                        note = source = /note="Target seq and PAM region of plasmid
                         library 1"
source                  1..38
                        mol_type = other DNA
                        organism = synthetic construct
SEQUENCE: 60
gagcggacag cagcttccta tatctcgtac nnnnnnnn                                    38

SEQ ID NO: 61           moltype = DNA  length = 38
FEATURE                 Location/Qualifiers
misc_difference         31..38
                        note = a,c,t,g, unknown,or other
misc_feature            1..38
                        note = source = /note="Description of Artificial Sequence:
                         Syntheticoligonucleotide"
misc_feature            1..38
                        note = source = /note="Target seq and PAM region of plasmid
                         library 2"
source                  1..38
                        mol_type = other DNA
                        organism = synthetic construct
SEQUENCE: 61
ccatgatata gacgttgtgg ctgttgtagt nnnnnnnn                                    38

SEQ ID NO: 62           moltype = RNA  length = 122
FEATURE                 Location/Qualifiers
misc_difference         1..25
                        note = a,c,t,g, unknown, or other
misc_feature            1..122
                        note = source = /note="Description of Artificial Sequence:
                         Syntheticpolynucleotide"
misc_feature            1..122
                        note = source = /note="sgRNA with N's"
source                  1..122
                        mol_type = other RNA
                        organism = synthetic construct
SEQUENCE: 62
nnnnnnnnnn nnnnnnnnnn nnnnngttgt gaattgcttt caaaaagttg aaaagcaatt       60
cacaataagg attattccgt tgtgaaaaca ttcaaggcgg ggcaactcgt cttttttctt      120
tt                                                                    122

SEQ ID NO: 63           moltype =   length =
SEQUENCE: 63
000

SEQ ID NO: 64           moltype =   length =
SEQUENCE: 64
000

SEQ ID NO: 65           moltype =   length =
SEQUENCE: 65
000

SEQ ID NO: 66           moltype =   length =
SEQUENCE: 66
000

SEQ ID NO: 67           moltype = AA  length = 7
FEATURE                 Location/Qualifiers
REGION                  1..7
                        note = source = /note="Description of Artificial Sequence:
                         Syntheticpeptide"
REGION                  1..7
                        note = source = /note="NLS"
source                  1..7
                        mol_type = protein
                        organism = synthetic construct
SEQUENCE: 67
```

PKKKRKV                                                                        7

SEQ ID NO: 68            moltype =    length =
SEQUENCE: 68
000

SEQ ID NO: 69            moltype =    length =
SEQUENCE: 69
000

SEQ ID NO: 70            moltype =    length =
SEQUENCE: 70
000

SEQ ID NO: 71            moltype =    length =
SEQUENCE: 71
000

SEQ ID NO: 72            moltype =    length =
SEQUENCE: 72
000

SEQ ID NO: 73            moltype = DNA   length = 30
FEATURE                  Location/Qualifiers
misc_feature             1..30
                         note = source = /note="Description of Artificial Sequence:
                            Syntheticoligonucleotide"
misc_feature             1..30
                         note = source = /note="mismatch repair Table 4"
source                   1..30
                         mol_type = other DNA
                         organism = synthetic construct
SEQUENCE: 73
gagcggacag cagcttccta tatctcgtac                                               30

SEQ ID NO: 74            moltype = DNA   length = 30
FEATURE                  Location/Qualifiers
misc_feature             1..30
                         note = source = /note="Description of Artificial Sequence:
                            Syntheticoligonucleotide"
misc_feature             1..30
                         note = source = /note="mismatch repair Table 4"
source                   1..30
                         mol_type = other DNA
                         organism = synthetic construct
SEQUENCE: 74
gagcggacag cagcttccta tatctcgtag                                               30

SEQ ID NO: 75            moltype = DNA   length = 30
FEATURE                  Location/Qualifiers
misc_feature             1..30
                         note = source = /note="Description of Artificial Sequence:
                            Syntheticoligonucleotide"
misc_feature             1..30
                         note = source = /note="mismatch repair Table 4"
source                   1..30
                         mol_type = other DNA
                         organism = synthetic construct
SEQUENCE: 75
gagcggacag cagcttccta tatctcgttc                                               30

SEQ ID NO: 76            moltype = DNA   length = 30
FEATURE                  Location/Qualifiers
misc_feature             1..30
                         note = source = /note="Description of Artificial Sequence:
                            Syntheticoligonucleotide"
misc_feature             1..30
                         note = source = /note="mismatch repair Table 4"
source                   1..30
                         mol_type = other DNA
                         organism = synthetic construct
SEQUENCE: 76
gagcggacag cagcttccta tatctcgaac                                               30

SEQ ID NO: 77            moltype = DNA   length = 30
FEATURE                  Location/Qualifiers
misc_feature             1..30
                         note = source = /note="Description of Artificial Sequence:
                            Syntheticoligonucleotide"

```
misc_feature            1..30
                        note = source = /note="mismatch repair Table 4"
source                  1..30
                        mol_type = other DNA
                        organism = synthetic construct
SEQUENCE: 77
gagcggacag cagcttccta tatctcctac                                              30

SEQ ID NO: 78           moltype = DNA  length = 30
FEATURE                 Location/Qualifiers
misc_feature            1..30
                        note = source = /note="Description of Artificial Sequence:
                         Syntheticoligonucleotide"
misc_feature            1..30
                        note = source = /note="mismatch repair Table 4"
source                  1..30
                        mol_type = other DNA
                        organism = synthetic construct
SEQUENCE: 78
gagcggacag cagcttccta tatctggtac                                              30

SEQ ID NO: 79           moltype = DNA  length = 30
FEATURE                 Location/Qualifiers
misc_feature            1..30
                        note = source = /note="Description of Artificial Sequence:
                         Syntheticoligonucleotide"
misc_feature            1..30
                        note = source = /note="mismatch repair Table 4"
source                  1..30
                        mol_type = other DNA
                        organism = synthetic construct
SEQUENCE: 79
gagcggacag cagcttccta tatcacgtac                                              30

SEQ ID NO: 80           moltype = DNA  length = 30
FEATURE                 Location/Qualifiers
misc_feature            1..30
                        note = source = /note="Description of Artificial Sequence:
                         Syntheticoligonucleotide"
misc_feature            1..30
                        note = source = /note="mismatch repair Table 4"
source                  1..30
                        mol_type = other DNA
                        organism = synthetic construct
SEQUENCE: 80
gagcggacag cagcttccta tatgtcgtac                                              30

SEQ ID NO: 81           moltype = DNA  length = 30
FEATURE                 Location/Qualifiers
misc_feature            1..30
                        note = source = /note="Description of Artificial Sequence:
                         Syntheticoligonucleotide"
misc_feature            1..30
                        note = source = /note="mismatch repair Table 4"
source                  1..30
                        mol_type = other DNA
                        organism = synthetic construct
SEQUENCE: 81
gagcggacag cagcttccta taactcgtac                                              30

SEQ ID NO: 82           moltype = DNA  length = 30
FEATURE                 Location/Qualifiers
misc_feature            1..30
                        note = source = /note="Description of Artificial Sequence:
                         Syntheticoligonucleotide"
misc_feature            1..30
                        note = source = /note="mismatch repair Table 4"
source                  1..30
                        mol_type = other DNA
                        organism = synthetic construct
SEQUENCE: 82
gagcggacag cagcttccta tttctcgtac                                              30

SEQ ID NO: 83           moltype = DNA  length = 30
FEATURE                 Location/Qualifiers
misc_feature            1..30
                        note = source = /note="Description of Artificial Sequence:
                         Syntheticoligonucleotide"
misc_feature            1..30
```

```
                          note = source = /note="mismatch repair Table 4"
source                    1..30
                          mol_type = other DNA
                          organism = synthetic construct
SEQUENCE: 83
gagcggacag cagcttccta aatctcgtac                                            30

SEQ ID NO: 84             moltype = DNA   length = 30
FEATURE                   Location/Qualifiers
misc_feature              1..30
                          note = source = /note="Description of Artificial Sequence:
                            Syntheticoligonucleotide"
misc_feature              1..30
                          note = source = /note="mismatch repair Table 4"
source                    1..30
                          mol_type = other DNA
                          organism = synthetic construct
SEQUENCE: 84
gagcggacag cagcttcctt tatctcgtac                                            30

SEQ ID NO: 85             moltype = DNA   length = 30
FEATURE                   Location/Qualifiers
misc_feature              1..30
                          note = source = /note="Description of Artificial Sequence:
                            Syntheticoligonucleotide"
misc_feature              1..30
                          note = source = /note="mismatch repair Table 4"
source                    1..30
                          mol_type = other DNA
                          organism = synthetic construct
SEQUENCE: 85
gagcggacag cagcttccaa tatctcgtac                                            30

SEQ ID NO: 86             moltype = DNA   length = 30
FEATURE                   Location/Qualifiers
misc_feature              1..30
                          note = source = /note="Description of Artificial Sequence:
                            Syntheticoligonucleotide"
misc_feature              1..30
                          note = source = /note="mismatch repair Table 4"
source                    1..30
                          mol_type = other DNA
                          organism = synthetic construct
SEQUENCE: 86
gagcggacag cagcttcgta tatctcgtac                                            30

SEQ ID NO: 87             moltype = DNA   length = 30
FEATURE                   Location/Qualifiers
misc_feature              1..30
                          note = source = /note="Description of Artificial Sequence:
                            Syntheticoligonucleotide"
misc_feature              1..30
                          note = source = /note="mismatch repair Table 4"
source                    1..30
                          mol_type = other DNA
                          organism = synthetic construct
SEQUENCE: 87
gagcggacag cagcttgcta tatctcgtac                                            30

SEQ ID NO: 88             moltype = DNA   length = 30
FEATURE                   Location/Qualifiers
misc_feature              1..30
                          note = source = /note="Description of Artificial Sequence:
                            Syntheticoligonucleotide"
misc_feature              1..30
                          note = source = /note="mismatch repair Table 4"
source                    1..30
                          mol_type = other DNA
                          organism = synthetic construct
SEQUENCE: 88
gagcggacag cagctaccta tatctcgtac                                            30

SEQ ID NO: 89             moltype = DNA   length = 30
FEATURE                   Location/Qualifiers
misc_feature              1..30
                          note = source = /note="Description of Artificial Sequence:
                            Syntheticoligonucleotide"
misc_feature              1..30
                          note = source = /note="mismatch repair Table 4"
```

```
source              1..30
                    mol_type = other DNA
                    organism = synthetic construct
SEQUENCE: 89
gagcggacag cagcatccta tatctcgtac                                              30

SEQ ID NO: 90       moltype = DNA   length = 30
FEATURE             Location/Qualifiers
misc_feature        1..30
                    note = source = /note="Description of Artificial Sequence:
                      Syntheticoligonucleotide"
misc_feature        1..30
                    note = source = /note="mismatch repair Table 4"
source              1..30
                    mol_type = other DNA
                    organism = synthetic construct
SEQUENCE: 90
gagcggacag caggttccta tatctcgtac                                              30

SEQ ID NO: 91       moltype = DNA   length = 30
FEATURE             Location/Qualifiers
misc_feature        1..30
                    note = source = /note="Description of Artificial Sequence:
                      Syntheticoligonucleotide"
misc_feature        1..30
                    note = source = /note="mismatch repair Table 4"
source              1..30
                    mol_type = other DNA
                    organism = synthetic construct
SEQUENCE: 91
gagcggacag caccttccta tatctcgtac                                              30

SEQ ID NO: 92       moltype = DNA   length = 30
FEATURE             Location/Qualifiers
misc_feature        1..30
                    note = source = /note="Description of Artificial Sequence:
                      Syntheticoligonucleotide"
misc_feature        1..30
                    note = source = /note="mismatch repair Table 4"
source              1..30
                    mol_type = other DNA
                    organism = synthetic construct
SEQUENCE: 92
gagcggacag ctgcttccta tatctcgtac                                              30

SEQ ID NO: 93       moltype = DNA   length = 30
FEATURE             Location/Qualifiers
misc_feature        1..30
                    note = source = /note="Description of Artificial Sequence:
                      Syntheticoligonucleotide"
misc_feature        1..30
                    note = source = /note="mismatch repair Table 4"
source              1..30
                    mol_type = other DNA
                    organism = synthetic construct
SEQUENCE: 93
gagcggacag gagcttccta tatctcgtac                                              30

SEQ ID NO: 94       moltype = DNA   length = 30
FEATURE             Location/Qualifiers
misc_feature        1..30
                    note = source = /note="Description of Artificial Sequence:
                      Syntheticoligonucleotide"
misc_feature        1..30
                    note = source = /note="mismatch repair Table 4"
source              1..30
                    mol_type = other DNA
                    organism = synthetic construct
SEQUENCE: 94
gagcggacac cagcttccta tatctcgtac                                              30

SEQ ID NO: 95       moltype = DNA   length = 30
FEATURE             Location/Qualifiers
misc_feature        1..30
                    note = source = /note="Description of Artificial Sequence:
                      Syntheticoligonucleotide"
misc_feature        1..30
                    note = source = /note="mismatch repair Table 4"
source              1..30
```

```
                        mol_type = other DNA
                        organism = synthetic construct
SEQUENCE: 95
gagcggactg cagcttccta tatctcgtac                                      30

SEQ ID NO: 96           moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 4"
source                  1..30
                        mol_type = other DNA
                        organism = synthetic construct
SEQUENCE: 96
gagcggagag cagcttccta tatctcgtac                                      30

SEQ ID NO: 97           moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 4"
source                  1..30
                        mol_type = other DNA
                        organism = synthetic construct
SEQUENCE: 97
gagcggtcag cagcttccta tatctcgtac                                      30

SEQ ID NO: 98           moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 4"
source                  1..30
                        mol_type = other DNA
                        organism = synthetic construct
SEQUENCE: 98
gagcgcacag cagcttccta tatctcgtac                                      30

SEQ ID NO: 99           moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 4"
source                  1..30
                        mol_type = other DNA
                        organism = synthetic construct
SEQUENCE: 99
gagccgacag cagcttccta tatctcgtac                                      30

SEQ ID NO: 100          moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 4"
source                  1..30
                        mol_type = other DNA
                        organism = synthetic construct
SEQUENCE: 100
gaggggacag cagcttccta tatctcgtac                                      30

SEQ ID NO: 101          moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 4"
source                  1..30
                        mol_type = other DNA
```

```
                        organism = synthetic construct
SEQUENCE: 101
gaccggacag cagcttccta tatctcgtac                                              30

SEQ ID NO: 102          moltype = DNA   length = 30
FEATURE                 Location/Qualifiers
misc_feature            1..30
                        note = source = /note="Description of Artificial Sequence:
                        Syntheticoligonucleotide"
misc_feature            1..30
                        note = source = /note="mismatch repair Table 4"
source                  1..30
                        mol_type = other DNA
                        organism = synthetic construct
SEQUENCE: 102
gtgcggacag cagcttccta tatctcgtac                                              30

SEQ ID NO: 103          moltype = DNA   length = 30
FEATURE                 Location/Qualifiers
misc_feature            1..30
                        note = source = /note="Description of Artificial Sequence:
                        Syntheticoligonucleotide"
misc_feature            1..30
                        note = source = /note="mismatch repair Table 4"
source                  1..30
                        mol_type = other DNA
                        organism = synthetic construct
SEQUENCE: 103
cagcggacag cagcttccta tatctcgtac                                              30

SEQ ID NO: 104          moltype = DNA   length = 30
FEATURE                 Location/Qualifiers
misc_feature            1..30
                        note = source = /note="Description of Artificial Sequence:
                        Syntheticoligonucleotide"
misc_feature            1..30
                        note = source = /note="mismatch repair Table 6"
source                  1..30
                        mol_type = other DNA
                        organism = synthetic construct
SEQUENCE: 104
gagcggacag cagcttccta tatctcgtat                                              30

SEQ ID NO: 105          moltype = DNA   length = 30
FEATURE                 Location/Qualifiers
misc_feature            1..30
                        note = source = /note="Description of Artificial Sequence:
                        Syntheticoligonucleotide"
misc_feature            1..30
                        note = source = /note="mismatch repair Table 6"
source                  1..30
                        mol_type = other DNA
                        organism = synthetic construct
SEQUENCE: 105
gagcggacag cagcttccta tatctcgtgc                                              30

SEQ ID NO: 106          moltype = DNA   length = 30
FEATURE                 Location/Qualifiers
misc_feature            1..30
                        note = source = /note="Description of Artificial Sequence:
                        Syntheticoligonucleotide"
misc_feature            1..30
                        note = source = /note="mismatch repair Table 6"
source                  1..30
                        mol_type = other DNA
                        organism = synthetic construct
SEQUENCE: 106
gagcggacag cagcttccta tatctcgcac                                              30

SEQ ID NO: 107          moltype = DNA   length = 30
FEATURE                 Location/Qualifiers
misc_feature            1..30
                        note = source = /note="Description of Artificial Sequence:
                        Syntheticoligonucleotide"
misc_feature            1..30
                        note = source = /note="mismatch repair Table 6"
source                  1..30
                        mol_type = other DNA
                        organism = synthetic construct
```

```
SEQUENCE: 107
gagcggacag cagcttccta tatctcatac                                              30

SEQ ID NO: 108            moltype = DNA   length = 30
FEATURE                   Location/Qualifiers
misc_feature              1..30
                          note = source = /note="Description of Artificial Sequence:
                          Syntheticoligonucleotide"
misc_feature              1..30
                          note = source = /note="mismatch repair Table 6"
source                    1..30
                          mol_type = other DNA
                          organism = synthetic construct
SEQUENCE: 108
gagcggacag cagcttccta tatcttgtac                                              30

SEQ ID NO: 109            moltype = DNA   length = 30
FEATURE                   Location/Qualifiers
misc_feature              1..30
                          note = source = /note="Description of Artificial Sequence:
                          Syntheticoligonucleotide"
misc_feature              1..30
                          note = source = /note="mismatch repair Table 6"
source                    1..30
                          mol_type = other DNA
                          organism = synthetic construct
SEQUENCE: 109
gagcggacag cagcttccta tatcccgtac                                              30

SEQ ID NO: 110            moltype = DNA   length = 30
FEATURE                   Location/Qualifiers
misc_feature              1..30
                          note = source = /note="Description of Artificial Sequence:
                          Syntheticoligonucleotide"
misc_feature              1..30
                          note = source = /note="mismatch repair Table 6"
source                    1..30
                          mol_type = other DNA
                          organism = synthetic construct
SEQUENCE: 110
gagcggacag cagcttccta tatttcgtac                                              30

SEQ ID NO: 111            moltype = DNA   length = 30
FEATURE                   Location/Qualifiers
misc_feature              1..30
                          note = source = /note="Description of Artificial Sequence:
                          Syntheticoligonucleotide"
misc_feature              1..30
                          note = source = /note="mismatch repair Table 6"
source                    1..30
                          mol_type = other DNA
                          organism = synthetic construct
SEQUENCE: 111
gagcggacag cagcttccta tacctcgtac                                              30

SEQ ID NO: 112            moltype = DNA   length = 30
FEATURE                   Location/Qualifiers
misc_feature              1..30
                          note = source = /note="Description of Artificial Sequence:
                          Syntheticoligonucleotide"
misc_feature              1..30
                          note = source = /note="mismatch repair Table 6"
source                    1..30
                          mol_type = other DNA
                          organism = synthetic construct
SEQUENCE: 112
gagcggacag cagcttccta tgtctcgtac                                              30

SEQ ID NO: 113            moltype = DNA   length = 30
FEATURE                   Location/Qualifiers
misc_feature              1..30
                          note = source = /note="Description of Artificial Sequence:
                          Syntheticoligonucleotide"
misc_feature              1..30
                          note = source = /note="mismatch repair Table 6"
source                    1..30
                          mol_type = other DNA
                          organism = synthetic construct
SEQUENCE: 113
```

```
gagcggacag cagcttccta catctcgtac                                              30

SEQ ID NO: 114          moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 114
gagcggacag cagcttcctg tatctcgtac                                              30

SEQ ID NO: 115          moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 115
gagcggacag cagcttccca tatctcgtac                                              30

SEQ ID NO: 116          moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 116
gagcggacag cagcttctta tatctcgtac                                              30

SEQ ID NO: 117          moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 117
gagcggacag cagctttcta tatctcgtac                                              30

SEQ ID NO: 118          moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 118
gagcggacag cagctcccta tatctcgtac                                              30

SEQ ID NO: 119          moltype = DNA   length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 119
gagcggacag cagcctccta tatctcgtac                                              30
```

```
SEQ ID NO: 120          moltype = DNA  length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 120
gagcggacag cagtttccta tatctcgtac                                          30

SEQ ID NO: 121          moltype = DNA  length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 121
gagcggacag caacttccta tatctcgtac                                          30

SEQ ID NO: 122          moltype = DNA  length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 122
gagcggacag cggcttccta tatctcgtac                                          30

SEQ ID NO: 123          moltype = DNA  length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 123
gagcggacag tagcttccta tatctcgtac                                          30

SEQ ID NO: 124          moltype = DNA  length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 124
gagcggacaa cagcttccta tatctcgtac                                          30

SEQ ID NO: 125          moltype = DNA  length = 30
FEATURE                 Location/Qualifiers
misc_feature            1..30
                        note = source = /note="Description of Artificial Sequence:
                          Syntheticoligonucleotide"
misc_feature            1..30
                        note = source = /note="mismatch repair Table 6"
source                  1..30
                        mol_type = other DNA
                        organism = synthetic construct
SEQUENCE: 125
gagcggacgg cagcttccta tatctcgtac                                          30
```

```
SEQ ID NO: 126            moltype = DNA   length = 30
FEATURE                   Location/Qualifiers
misc_feature              1..30
                          note = source = /note="Description of Artificial Sequence:
                          Syntheticoligonucleotide"
misc_feature              1..30
                          note = source = /note="mismatch repair Table 6"
source                    1..30
                          mol_type = other DNA
                          organism = synthetic construct
SEQUENCE: 126
gagcggatag cagcttccta tatctcgtac                                         30

SEQ ID NO: 127            moltype = DNA   length = 3210
FEATURE                   Location/Qualifiers
misc_feature              1..3210
                          note = source = /note="Description of Artificial Sequence:
                          Syntheticpolynucleotide"
misc_feature              1..3210
                          note = source = /note="APG05083.1 mammalian codon optimized
                          sequence"
source                    1..3210
                          mol_type = other DNA
                          organism = synthetic construct
SEQUENCE: 127
atgagagagc tggattaccg gatcggcctg gatatcggga ccaactccat tggatggggc        60
atcatcgagc tgtcttggaa caaagacaga gaacagtacg agaaggcaag aatcgtggac       120
aagggcgtga aatgttcga caaggccgaa atacccaaga ccggagccag cctggccgag        180
cctagaagaa ttgccagatc aagcagaaga cggctcaaca gaaagtctca gagaaaaaaa       240
gatattcgga acctgctggt ccagcacgag atcatcagcc aaaaggaact cgctagccig       300
tatcctctga ccaagagcag catggacatt tgggacatca gactggacgg cctggacaga       360
ctgctggata gattcgagtg gaccagattg ctgatccacc tggctcagcg gagaggcttc       420
aaaagcaacc ggaagagcga gctgaaggac gtggaaaccg gcaaggtgct ctccagcatc       480
caggctaatg agaagcggct gtccctgtac agaactgtgg gcgagatgtg gatgaagaat       540
gaagattta gcaagtacga caaaagaaga aatagtagca acgaatacgt gttctctgtg        600
tcccgggccg acctggaaaa ggaaatcgtg acactgtttg aagctcagcg gaagttccag        660
agcagctatg ccagcgccga tcttcaaaaa acctacctcc agatctgggc ccatcaactg       720
cctttcgcct ctggcaacgc catcgttaac aaggtgggct actgcagcct actgaaaggc       780
aaggaagaga gagttcctaa ggccacctac accttccaat acttcagcac cctggatcag       840
atcaacagaa ccagactggg cccaacactt cagccctttca ccaaggaaca gagagatgtg       900
atcctggacg agatgtttaa ccggaccgat tattacaaga agaagaccat ccctgaggtg       960
acgtactacg atatcagaaa atggctggcc ctggacgaga caatccagtt caagggcctg      1020
acctacgacc ctaatgaaga actgaagaaa attgagctaa agtcttttat caatctgaag      1080
cctttctacg agataaagaa ggtggtgaca aactacgcca agaagacaaa tgaggccttt      1140
agcacactgg actatgacac cttttgcctac gcccctgacag tgtacaagac cgacaaggac      1200
atccgctcct acctgaaaaa gagtaacaac ctgtccaaat gctgctacga cgaccaactg      1260
atcgaggaat tgctgacact gagctacacc aaattcggcc acctgagctc caaggctatc      1320
aaccacgttc tgcctatcat gcaggagggc agaacctacc aggaggccat tcaccagctc      1380
ggctacgatg ccacaaacct caaaaaagag aaccggtcta tgttcctgcc tctgttccct      1440
gacgagatca ccaaccccat cgtgaagagg gccctgaccc aggccaggaa ggtggtcaac      1500
gccatcatca gacgatacgg gtctccaaac agcgtgcaca tcgagctggc cagagagctg      1560
agcaagagcc acgacgagag aacaaagatc atgaaagctc atgatgaaaa ctacaaaaag      1620
aacaagggcg ctatcagcat cctgatcgag aacggtattc tgaatcctac aggttatgac      1680
atcgtccggt acaagctgtg gaaggaacag ggcgagagat cgcctattc tctgaaacag      1740
atccccgcca acaccttctt caacgaaatg aagaaggagc ggtccggcag ccctgtgctg      1800
gaaatcgatc acatcctgcc ctacagccag agcttcatcg acagctacca caacaaagtg      1860
ctggtgtacg gggatgagaa ccagaaaaag gcaatagaa tcccgtacac ctacttcctg      1920
gaaggcaaca aggactggga gtcttttcgag agctatgtgc cctgaactc cttttttcagc      1980
aagaaaaagc gaggatatct gctgaagaag gcttacctgc caagagagag taacatgatc      2040
aaggaacggc acctcaacga caccccggtac gccagctcct acctgaagaa cttcatcgag      2100
aagaatctga agttcaagga ggtggaaggc tctacccgga agaagcacgt gcaaaccgtg      2160
aacggcataa tcagagccca cctgagaaag agatgggggc tggaaaagga ccgccaggag      2220
acatatcttc atcacgctat ggacgccatc atcgtggcat gcaccgacca ccacatggtg      2280
acaaaggtga ccgagtacta ccagatcaaa gaaagcaata aatctattag aaagccttac      2340
ttccccctgc cttgggtggg ctttagagag gaaattctgt cccacctggc tcggcagcct      2400
atcgccagaa agatctctga agagctgaag atcggatacc agagcttcga ttacatcctc      2460
gtgtctagaa tgcctaaaag atcagtgacc ggcgccgccc acgagcagac cattatgaaa      2520
aagggaggca tcgacaaaaa aggaaaaaacc atcatcatta gcgggtcta cctgaaggat      2580
atcaagttcg acgagaatgg cgatttcaag atggttggaa aggaacagga cctggctacc      2640
tacgaggcca tcaagcagag atacatcgag tacggcaagg aatccaagaa ggccttcgag      2700
accccctctgt ataagcccag caagaaaggc aaggcaacc tgatcaagaa gatcaaagtg      2760
gaagtgcaaa ccaagagctt tgtgagaaa gtcaacggcg gagtggccca gaacggcgat      2820
ctggtgcggg ttgacctgtt cgagaaggat aatagatact acatgatccc catctacgtg      2880
atggatatga tgcacgacga acttcctaac aaggccgtga caggcatgaa aggctatgag      2940
caatggctga ccatcgacaa cagcttcacc ttcaagttca gcctataccc ctacgacctg      3000
gtgcggctgg tcaagggtaa cgaggacaga ttcctgtact tttccaccct ggatattaac      3060
agtgatagac tcaacttcaa agacgtcaac aagcccagca gcaggccgga gaacagatat      3120
agcctgaaga caatcgaaaa cctggaaaaa tacgaggtgg cgtcctggg cgaccctcaga      3180
tttgtgagac aggagatcag aaagaacttc                                        3210
```

| SEQ ID NO: 128 | moltype = DNA length = 3213 |
|---|---|
| FEATURE | Location/Qualifiers |
| misc_feature | 1..3213 |
| | note = source = /note="Description of Artificial Sequence: Syntheticpolynucleotide" |
| misc_feature | 1..3213 |
| | note = source = /note="APG07433.1 mammalian codon optimized sequence" |
| source | 1..3213 |
| | mol_type = other DNA |
| | organism = synthetic construct |

SEQUENCE: 128

```
atgagagagc tggactacag aattggcctg gacatcggca ccaacagcat cggatggggc    60
gtgatcgagc tgtcctggaa caaagaccgg gagagatacg agaaggtcag aatcgtggat   120
caaggcgtga aatgttcga cagagccgag atgcccaaga caggcgccag cttagctgaa   180
cccagaagaa tcgccagatc cagcagacgg agactgaatc gcaagtccca gagaaagaaa   240
aacatccgga acctgctggt gcaacacggc gtgatcacac aggaggaact ggatagcctg   300
taccccctga gcaaaaagag catggacatc tggggcattc ggctcgacgg cctggacaga   360
ctcctcaatc atttcgagtg ggccagactg ctgatccacc tggctcagag acggggcttt   420
aagtccaaca gaaagagtga actgaaagat acagagacag gcaaggtgct gagcagcatc   480
caactgaacg agaaacggct gagcttgtat agaaccgtgc gcgagatgtg gatgaaggac   540
cccgacttct ctaaatacga taggaagaga aatagcccca cgaatacgt gttcagcgtg    600
tctagagccg agctggaaaa ggaaatcgtg accctgttcg ccgcccagcg gagattccag   660
agcccttacg ccagcaaaga tctgcaggag acatatctgc agatctggac ccaccaactg   720
ccttttcgcca gcggcaatgc catcctgaac aaggtcatgc actgctccct gttgaaaggc   780
aaagaaagaa ggattcccaa ggctacatac accttccaat acttctctgc tctggaccag   840
gtgaatcgga ccagactggg acctgatttc cagcccttca ccaaggagca acgggaaatt   900
atcttgaaca acatgttcca gaggacagat tactacaaga gaaaaccat ccccgaggtg   960
acctactatg acatacgaa gtggctggaa ttggacgaa caattcagtt caagggcctg  1020
aactacgacc ctaacgagga actgaagaag atcgagaaga gccttttat caatctgaag  1080
gccttctacg agatcaacaa ggtggtggcc aactacagcg aaagaaccaa cgagaccttc  1140
tccaccctgg actacgacgg catcggctac gccctgaccg tgtacaaaac cgacaaggat  1200
atccgcagct acctgaagag cagtcacaac ctacctaaga gatgctacga cgaccaactg  1260
atcgaggaac tgctgagcct gagctacaca aagttcggcc acctgtccct gaaagccatc  1320
aaccacgtgc tgtctatcat gcagaagggc aatacctaca aggaagcgt ggaccaactg  1380
ggctacgaca ccagcggcct taagaaggag aagaggtcca gttcctgcc acctatttct  1440
gatgaaatca cgaatccaat cgtgaaaagg ccctgaccc aggccagaaa agtggtgaac  1500
gccataatta gaagacacgg atctcctcac tccgtgcaca tcgagctgga cagagagctg  1560
agcaagaacc acgacgagcg gacaaagatc gtcagcgccc aggatgaaaa ctacaagaaa  1620
aacaagggcg ctatcagcat cctgtctgag cacggcatcc tgaacccta caggctacgac  1680
atcgtgagat acaaactgtg gaaggagcag ggcgaacgt gcgcctacag cctgaaggaa  1740
atccctgccg atacatttt caacgagctg aagaaggaac gcaacggcgc ccctatcctt  1800
gaagtggacc acatcctgcc ctacagccca tccttcatcg actcctacca caacaaggtc  1860
ctggtgtaca gcgacgaaaa ccggaaaaag gcaacagaa tccttatac ctacttcctg  1920
gaaaccaaca aggattggga ggcctttgag cggtacgtgc ggagcaacaa attcttctcc  1980
aagaaaaagc gagagtacct tctgaagcgg gcttatctgc ctagagaatc tgagctgatc  2040
aaagaacgcc acctgaacga caccagatac gcctctacct tcctgaagaa cttcatcgag  2100
cagaacctgc agttcaagga agccgaggac aaccccagaa aaagacgggt gcaaaccgtg  2160
aacggcgtta tcaccgccca cttcagaaag cggtggggcc tggagaagga ccggcaggag  2220
acatacctcc atcacgctat ggacgccatc atcgtgacct gtacagacca ccacatgctg  2280
accagagtga ccgagtacta tcagatcaag gaaagcaaca gagcgtgaa gaagccctat  2340
tttcctatgc cttgggaagg cttccggac gagctgctga gccactttgc ttctcagcct  2400
atcgccaaga aaatcagcga ggaactgaag gccggctacc agagcctgga ctacatcttc  2460
gtgtccagaa tgcctaagag aagcattaca ggcgctgctc ataagcagac catcatgcgg  2520
aagggaggaa ttgacaagaa gggcaaaaca atcatcatcg aacgctgca cctgaaggat  2580
atcaagttcg acgagaacgg agatttcaag atggtgggca aggaacagga catgccaca  2640
tacgaagcta ttaaacagag ataccctggag cacggcaaga atagcaagaa ggccttcgag  2700
accctctgt acaagcccag caaaaagggc acggtcaacg tgatcaacg ggtgaaggtg  2760
gaaggacagg ccaagagctt tgtgagggaa gtgaacggcg gagtggccca aatggcagt  2820
ctggttagag ttgatttgtt tgagaaggat gataagtact acatggtccc catctacgtg  2880
ccagacaccg tgtgtagcga gctgcccaaa aaggtggtcg ccagctctaa gggctatgag  2940
cagtggctga cactggataa cagcttcacc tttaagttca gcctgtaccc ttatgatctg  3000
gtgcggctgg tcaagggaga tgaggatcgg ttcctgtact ttggcacct ggacatcgac  3060
agcgacagac ttaacttcaa ggacgtgaac aagccaagca gaagaacga gtaccggtac  3120
agcttgaaaa ccatcgagga cttggagaag tacgaggtgg cgtgctggg cgatctaaga  3180
ctggtccgga aggaaactcg aagaaacttc cac                                 3213
```

| SEQ ID NO: 129 | moltype = DNA length = 3213 |
|---|---|
| FEATURE | Location/Qualifiers |
| misc_feature | 1..3213 |
| | note = source = /note="Description of Artificial Sequence: Syntheticpolynucleotide" |
| misc_feature | 1..3213 |
| | note = source = /note="APG07513.1 mammalian codon optimized sequence" |
| source | 1..3213 |
| | mol_type = other DNA |
| | organism = synthetic construct |

```
SEQUENCE: 129
atgcgggaac tggattacag aattggactg gacatcggga ccaactcaat tggctgggga   60
gtgatcgagc tgagctggaa caaggacaga gagcagtacg agaagaccag aatcgtggac  120
aagggcgtta ggatgttcga caaggccgag atccccaaga ccggagccag cctggccgag  180
cctagacgta tcgccagatc ctccagacgt agactgaaca gaaagtccca gaggaagaag  240
gacattcgga acctgctggt gcaacacgag atcattagcc aaaaagaact gaccagcctg  300
taccctctgt ctaaatccag catgtgacatc tgggacatcc ggctgacgg cctggacaga  360
ctgcttgata gattcgagtg ggcccggctc ctgatccacc tggctcagcg gcggggcttt  420
aaaagcaacc ggaagtctga gcttaaagac gtggaaacag gaaaagttct gtccagcatc  480
caggtgaatg aaaagcggct gagcctgtac agaaccgtgg gcgagatgtg gatgaagaac  540
gccgattgca gcaagtacgg caaacgtaga aatagcccca acgagtacgt gttcagcgtg  600
tctagagccg acttggagaa agaaattgtg acacttttcg aggcccagcg aaaattccac  660
agcagctacg ccagtgtgga cctgcagaag acatacatcc aaatctgggc tcatcaactg  720
ccatttgcct ctggcaatgc cattgtgaac aaggtgggat actgctctct gctgaagggc  780
aaagaaaaga gagtgcctaa ggccacatac accttttcagt attttaacac cctggaccag  840
atcaaccgga caagactggg ccctaacttc caacctttca ccaaggagca gagagatatc  900
atcctagaca aaatgttcca gagaaccgac tactacaaga aaaaaacaat ccctgaggtg  960
acatactacg atatcagaaa gtggctggcc ctggaccaaga ccatccagtt caagggcctg 1020
acctacgatc ctaatgaaga actgaagaag atcgagatga agccattcat caacctgaaa 1080
cctttctacg agatcaagaa ggtggtgacc aactacgcca agaagacaaa cgaggtgttc 1140
tctgccctgg actatgacac cgtggcttat gccctcaccg tgtacaaaac agacaaggat 1200
atcagaagct accttaagcg gtccaacaac ctgagcaaga gatgttacga cgccaactg  1260
atcgaggaac tgctgacact gagctacacc aagttcggcc acctgtcctt caaggccatc 1320
aatcacgtgc tgcccatcat gcaggagggc agaacctacc aagaggctat tcaccaactg 1380
ggctatgaca cgaccaacct gaagaaggaa atagaagca tgttcctgcc catcatccct  1440
gacgagatca ccaaccctat cgtgaagcgg gccctgaacg aggcccggaa agtggtgaat 1500
gccatcatcc gcagatacgg ctctcctaat tctgtccaca tcgagctggc cagagagctg 1560
agcaaaagcc acgacgagcg gaagaagatc atgaccgccc acgacgagaa ctacaagaaa 1620
aacaagggcc ccgtgtccat cctgatcgat aacggcatcc tgaatcctac aggatacgat 1680
atcgtgcggt acaagctgtg gaaggaacag ggcgaaagat gcgcctatag cctgaaaaa  1740
atccccgcca acaccttctt caacgagcta aaaaaggaac ggagcggccc acctgtgctg 1800
gaagtggacc acatcctgcc ctacagccaa agcttcatcg acagctacca caacaaggtg 1860
ctggtgtacg gcgacgagaa ccagaagaag ggcaatagaa tcccttacac atttttcagc 1920
gaagaagata aggaatggga gagcttcgag agctacgttc ggagcaacag cttcttcagc 1980
aagaaaaagc gcggctacct gctgaagaag gcctacctgc ccagagaaag caacctgatc 2040
aaggaacggc acctcaacga cacacggtac gccagcagtt acctgaagaa tttcatcgag 2100
aagaacctga agttcaagga agccgtgggg atcaccggga agaagtacgt gcaaaccgtg 2160
aacggcgtga tcaccgccca cctgcggaag cggtggggcc ttgagaagga ccggcaggag 2220
acctacctgc accacgctat ggacgccatc atcgtggcct gcaccgatca ccacatggtg 2280
acgaaggtgc ccgagtacta ccagatcaaa gaaggcaata agagcatcaa gaagcctta  2340
tttcctctgc cctggatggg cttcagaaa gaaatcctgt ctcacctgga gtctcaacct  2400
atcgccagaa aaattctga agagctgaaa attggatacc agtccccga ttacatcctg  2460
gtcagccgga tgcctaagag aagcgtgacc ggcagcgcc accgatcagc cgtgatgaag 2520
aagggcgata tcgataagaa gggcaagaca atcatcatca agcgggtgca cctgaaggat 2580
atcaagttcg acgaaaatgg cgacttcaaa atggtgggca aggagcagga cctggctaca 2640
tacgaagcta tcaaacagag atacctggag taccggaagg aaagcaagaa ggccttcgag 2700
acccctctgt acaagccatc taaaaaagga aaaggtaacc tgatcaaaaa gatcaaggtg 2760
gaagtgcaaa ccaaatcttt cgtgagagag attaacggcg gagtggccca gaacggcgac 2820
ctggttagag tggatctgtt cgagaaggac aacagatatt acatggtccc catctacgtg 2880
gtggacaccg tgcggtctga actccccaac aaagcagtga caagctccaa aggctatgaa 2940
cagtggcgga gcatcgacaa tagtttcacc ttcaagttta gtctgtaccc ctacgacctc 3000
gtgcggctgg tcaagggcga cgaggatcgc ttcctgtact tctccaccct ggatatcaac 3060
agcgacagac tgaacttcaa ggacgtgaac aagcctagca agcaggctga ataccggtac 3120
agcctgaaga cgatcgagaa cctggaaaaa tacgagatcg tgttctggg agatctgaga 3180
ctcgttagac aggagacaag aaaaatttc aag                                3213

SEQ ID NO: 130      moltype = DNA   length = 3216
FEATURE             Location/Qualifiers
misc_feature        1..3216
                    note = source = /note="Description of Artificial Sequence:
                    Syntheticpolynucleotide"
misc_feature        1..3216
                    note = source = /note="APG08290.1 mammalian codon optimized
                    sequence"
source              1..3216
                    mol_type = other DNA
                    organism = synthetic construct
SEQUENCE: 130
atgagcgagc tggattatag aatcggcctg gatatcggca ccaattctat cggatgggga   60
gtgatcgagc tgttctggaa caaggatcgg gaacggtacg agaaggtccg catcgtggac  120
aaaggggtca gaatgtttga caaggccgag atccccaaca agggcgccag cctggccgag  180
cctcggagaa tcgccggag cagcagaaga cgcctgaaca gaagtccca aggaagaag   240
gagatccgga acctgctggt gcaacacggc atgatcaccc aagaggaact ggacctcctg  300
taccctctga gcaaaaagtc catcgatatc tgggacatca gactagacgg cctggacaga  360
ctgctgaacc acttagagtg ggctagactg ctgattcacc tggcccagcg gcggggcttc  420
aagagcaacc gcaaaagcga gctgaaggac gctgaaacag gcaaggtgtt gtctagcatc  480
caggtgaacg agaagcggct gttcctgtac agaaccgtgg gggaaatgtg gatcaaggac  540
gcagagttca gcaagtacga caggcgtaga aactccccaa cgaatacgt gttcagcgtg  600
tcaagagccg acctggaaaa ggaaatcgtg acactgtttg aggctcagag aaagttccag  660
```

```
agcagctatg cctctaaaaa tctgcaggag acctacctgc agatctgggc ccaccaactg    720
cctttcgcca gcggcaatgc catcctgaac aaagtgggct actgcagcct gctgaaaggg    780
aaggaaaggc ggattcccaa ggccacatac accttccagt acttctccgc cctggatcag    840
gttaaccgga cccggctcgg ccctgacttc caacctttca cccaggaaca aaaggagatc    900
atcctggata agatgttcca gagaacagac tactacaaga agaagaccat ccccgaggtt    960
tcttattatg atatcagaaa gtggctggaa ctcgacgaga caatccagtt taagggactg   1020
aattacgacc ccaacgaaga gctgaagaag atcgaaaaaa aacctttcat caacctgaag   1080
gccttctacg agatcaagaa ggtggttgct aactacgccg aaagaacaaa tgaagccttt   1140
tctaccctgg actacgacgc tatcgcctat gccctgacag tctacaagac cgacaaggac   1200
atccggtcct acctgaagaa atccaacaac ctgtccaagc ggtgctacga tgatcaactg   1260
atcgaggaac tgtttaccct gagctacacc aaattcggcc acctgtcttt caaggccatt   1320
aaccacgtgc tgcctatcat gcaggagggc agaacctacc aggaggccat acaccaactg   1380
ggctacgaca ccaccaacct gaagaaagag aatagaagca tgttcctgcc tctgatccct   1440
gacgagatca caaaccccat tgtgaagcgg gccatcaccc aggccagaaa ggtggtgaac   1500
gccatcatca aagatacggg ctctcctaac agtgtgcaca tcgaactggc cagagagctg   1560
agcaagagcc acgatgagcg gaaaaagatc atgaccgccc acgacgagaa ctacaagaaa   1620
aataagggcc tatttctat cctgatcgag aacggcattc tgaaccctac cggctacgac   1680
atcgtgagat acaagctgtg gaaggaacaa ggcgagagat gcgcctacag cctgaaagaa   1740
attccacctg atactttttt caacgagctg aagaaagaaa gaaacggcag ccccattctg   1800
gaagtggacc acatcctgcc ttacagccag tccttcatcg acagctacca caacaaagtg   1860
ctggtgtact ctgacgagaa cagaaacaag ggcaacagaa tcccttacac ctacttcctg   1920
gaaacaaaca aggactggga ggcctttgaa agatacgtgc ggagtaacaa actgtttctt   1980
aagaaaaaga gagaatatct gctgaagaag acttacctgc ctagagagtc tgaactaatc   2040
aaggaacggc acctgaacga cactcggtat gcttctacat tcctgaagaa tttcatcgag   2100
cagaatctgc agttcaaaga ggtcgaggtc aatctgagaa aaagagagt gcaaaccgtg   2160
aatggcgtga tcaccgccca cctcagaaag cgttgggcc tggaagaaa ccggcaggag   2220
acgtacctgc accacgctat ggacgccatc atcgtggctt gtacagacca ccacatggtg   2280
acccggataa cagagtacta ccagatcaag gaatccaaca agagcgtgaa gaaaccttac   2340
ttccccatgc cttgggaggg ctttagagat gagctgttgt ctcacctcgc tagccagcct   2400
atcgcaaaga agatcagcga ggaactgaag gccggctacc agaagcagca ctacatcttc   2460
gtgtccagaa tgcccaagag aagcgtgacc ggcgccgccc atgatcagac catcagaaga   2520
aagggcggca tcgacaagaa gggcaagaca atcatcatta gcgggtgcg gctgaaagat   2580
atcaagttcg acgaaaacgg cgatttcaag atggtgggca agagcagga cctggcaacc   2640
tacgaggcca tcaagcagaa atacctggag cacagaaca acagtaagaa ggccttcgag   2700
acccctctgt acaaacctag caagaaggga acaggaaacc tgattaagcg ggtgaaaatc   2760
gagggacaga ctaaggcctt cgtgcgggaa gtgaacggag cgtggcccaa aaatagcgac   2820
ctggtcagag tggacctgtt cgagaaggac gacaagtact atatggtgcc tatctacgtg   2880
ccagacaccg tgtgtagcga gctgcctaag aaggtggtta agagcggaaa aggctatgag   2940
cagtgcctga ccctggacaa cagcttcacc ttcaagtcg gcctgtaccc ctacgatctg   3000
gtgcggctcg tgaagggcaa cgaggacaga ttcctgtact tcggcacact ggacattgac   3060
tccgatagac tgaatttcaa ggatgtgaac aagcccagca agcagaacga gtaccggtac   3120
agcctgaaaa caatcgagaa cctggaaaaa tacgaggttg gagtgctggg agatctgcgg   3180
ctggtgaaac aggagaccag gaggatcttt aacaga                              3216

SEQ ID NO: 131       moltype = DNA   length = 4011
FEATURE              Location/Qualifiers
misc_feature         1..4011
                     note = source = /note="Description of Artificial Sequence:
                     Syntheticpolynucleotide"
misc_feature         1..4011
                     note = source = /note="APG05459.1 mammalian codon optimized
                     sequence"
source               1..4011
                     mol_type = other DNA
                     organism = synthetic construct
SEQUENCE: 131
atgaaaaaag attacgtgat cggcctggac attggcacca acagcgtcgg ctgggccgtg     60
atgacagagg actaccaact ggtgaagaag aagatgccaa tctatggcaa tactgagaag    120
aaaaagataa aaaagaattt ctggggcgtg cggctgtttg aggagggcca caccgccgg    180
gatcggcggc tgaaacggac cgctagaaga cggatcctc gccgcagaaa tagactgaga    240
tatctgcagg ccttcttcga ggaagccatg accgcctgg acgagaactt cttcgccaga    300
ctgcaggaga gcttcctggt gcctgaggac aagaaatggc accggcaccc tatcttcgcc    360
aagctggagg atgaggtggc ctatcacgaa acctacccta caatcctacca cctgagaaag    420
aaactggctg attcctctga acaggctgac tcgtgactga tctatctggc cctggcccat    480
atcgtgaagt acagaggcca cttcctgatc gaaggaaagc tgagtaccga gaacatcagc    540
gtcaaggagc agttccagca gttcatgatt atctataacc agatttgt gaacggcgaa    600
agccggctgg tgtctgcccc tctgcctgag agcgtgctga tcgaagaaga gctgaccgaa    660
aaggccagcc ggacaaagaa atctgagaag gtgctgcaac agttcctcca ggagaaagcc    720
aatggactgt tcggccagtt cctgaaactt atggtaggca acaaagccga tttcaagaaa    780
gtctttggcc tggaagaaga ggccaaaata acatacgcca gcgagtccta cgaggaggat    840
ctggaagca ttctgccaa ggtgggcgac gagtacagcg atgttttcct ggccgctaag    900
aacgtctacg acgccgtgga actgtctacc atcctggccg actccgacaa gaagagccac    960
gccaagttgt ctagtagcat gatcgttaga ttcaccgagc caggagga cctgaagaag   1020
ttcaagcgtt ttatcagaga gaattgccc gacgagtacg ataacctgtt caagaacgag   1080
caaaaagacg gctacgccgg ctacatcgcc cacgccgcca aggtgccca actgaagttc   1140
taccagtacg tgaagaagat aatccaggac atcgccggcg ccgaatactt cctggagaaa   1200
atcgcccagg agaacttcct gcgaaaacag aggaccttcg acaacggcgt gatccccac    1260
cagatccacc tggccgagct gcaggccatc atccacagac aggctgctta ctacccttttc   1320
ctgaaggaaa atcaggaaa gattgagcaa ctggtgacat cagaatccc ctactacgtc   1380
```

```
ggccctctga gcaaaggaga tgccagcacc ttcgcctggc tgaaaagaca aagcgaggaa    1440
cctatccggc cttggaacct gcaagagaca gtggacctgg accagtctgc taccgcattc    1500
atcgagagaa tgaccaactt cgatacctac ctgccttctg agaaggtgct gcccaagcac    1560
agcctgctct acgaaaaatt tatggtgttc aacgagctga ccaagatttc ttacactgat    1620
gacagaggca tcaaggccaa cttcagcggc aaggagaagg aaagatatt cgactacctg     1680
tttaagaccc gccggaaggt gaagaaaaag gatatcatcc agttctaccg gaacgagtac    1740
aacaccgaga tcgtcaccct gtctggcctg gaagaggacc agttcaatgc cagcttcagc    1800
acctaccaag atctgctgaa gtgcggccta actagagccg aactggacca ccctgataat    1860
gccgagaaac tggaggacat cattaagatc ctaaccatct tcgaggatag acagcggatc    1920
agaacacagc tcagcacctt caagggacag ttcagcgccg aggtgctgaa gaagctggaa    1980
cggaagcact acaccggctg gggcagactg tccaagaaac tcatcaacgg catctacgac    2040
aaggaatccg gaaagacaat cctggactac ctgatcaaag atgacggcgt tctaagcac     2100
tacaacagaa acttcatgca gctaatcaac gacagcgacc tgagcttcaa gaacgccatc    2160
cagaaggccc agagcagcga gcatgaggaa accctgtctg agaccgtgaa cgagctggcc    2220
ggcagccctg ccatcaagaa aggcatctac cagagcttaa aaatcgttga tgagctggtt    2280
gccatcatgg gctacgcccc taagagaatc gtggtggaga tggctagaga gaaccagaca    2340
acaagcaccg gaaagagaag aagcatccag aggctgaaga tcgtggaaaa agctatggcc    2400
gagattggaa gcaacctgct caaggaacag cctaccacaa acgagcaact gagagataca    2460
agactcttcc tgtattatat gcagaacggt aaggacatgt acaccggcga cgagctgagc    2520
ctgcacagac tgtctcacta cgacatcgac cacatcattc tcagtcctt catgaaggac      2580
gattccctg ataacctggt gctggtgggc agcaccgaga accggggcaa gtctgacgac     2640
gtgcccagca aggaagtggt gaaggacatg aaagcctact ctacgctgct                2700
ggcttgatca gccagcggaa attccagaga ctgacgaagg cgagcaggg cggcctgacc     2760
ctggaggaca aagctcattt catccagaga caactggtgg agacaagaca gatcaccaag    2820
aacgtggctg gaattctgga tcagagatac aacgccaaca gcaaagaaaa aaaggtgcaa    2880
atcataacac tgaaagcctc tctgaccagc cagttccgga gcatcttcag cctgtataag    2940
gtcagagaag tgaacgacta tcaccacggc caggatgcgt acctgaactg cgtggtggcc    3000
actacactcc tgaaagtgta ccccaacctg gctcctgagt tcgtgtacgg cgagtacccc    3060
aagtttcagg cctttaagga aaacaaggct acagccaaga ccatcatcta caccaatctg    3120
atgcggtttt tcaccgagga tgaacccaga ttcatgaagg acggcgagat cctgtgggga    3180
aacagctacc tgaagaacat taagaaagaa ctcaactacc atcagatgaa catagtgaaa    3240
aaggtggaag tgcaaaaggg tggcttctcc aaggaaagca tcaagcctaa gggccccagc    3300
aacaagctga tccctgtgaa gaacggggttg accccccaga aatacggcgg atttgactct    3360
ccagtggtcg cttacacagt gctgtttacc cacgagaagg gcaaaaaacc actgatcaag    3420
caggagatcc tgggaatcac catcatggaa aagaccagat cgagcagaa tcctatcctg    3480
ttcctggaag aaaaaggctt cctgaggcct agagtgctga tgaagctgcc taaatacacc    3540
ctgtacgagt tccctgaggg aagacggcgg ctgctggcca cgccaaaga agcccagaaa    3600
gggaatcaga tggtgctccc cgaacacctg ctgaccctgc tgtaccacgc caaacagtgt    3660
ctgctgccta accagagcga atctctcgct tacgtggaac aacaccaacc ggagttccaa    3720
gagatcctgg agagtggt ggacttcgct gaggtgcaca cactggccaa gagcaaggtg      3780
caacagatcg tgaaactgtt tgaggcaaac cagaccgcag atgtgaagga aatcgccgcc    3840
tccttcatcc aactgatgca gttcaacgca atgggagccc atctaccttt taaattcttc    3900
cagaaggaca tcgagcgggc ccggtacact agcatcaagg aaatcttcga cgccaccatc    3960
atctaccaga gcacaaccgg cctctacgag acacggagaa aggtggtgga c             4011
SEQ ID NO: 132        moltype = DNA  length = 4308
FEATURE               Location/Qualifiers
misc_feature          1..4308
                      note = source = /note="Description of Artificial Sequence:
                      Syntheticpolynucleotide"
misc_feature          1..4308
                      note = source = /note="APG04583.1 mammalian codon optimized
                      sequence"
source                1..4308
                      mol_type = other DNA
                      organism = synthetic construct
SEQUENCE: 132
atggccaaga atatcctggg cctggatctg ggtacaaaca gcatcggctg ggctctggtc     60
cagcaggact tcgagaacaa ggagggaaac atcctgggca tgggatctag aatcatccct    120
atgagccagg acatcctggg cgaattcggt aagggcaaca gcatcagcca gaccgccgag    180
agaacaggat accggggcgt gcgtagactg agagagagac acctcctgag aagagagaga    240
ctgcatagag tgctgcacct gctcggcttt ctgcctaagc actacgatga aaaaatcgac    300
tttacacaaa gattcggcaa gttcatcaac caggctgagc taagctggc tttttgatagc    360
gagttcctgt tcaaggacag cttccacgag atgctgccga gcaatcaacct                420
gaattcctga agacaagaa cggagaggac tgcctggttc cttacgactg gaccatctac    480
tacctgagaa agaaggctct gacccagaag atcgagaaat cgaactagc ttggctgatc    540
ctgaacttca ccaaaagcg gggctactac cagcttagag cgaagaaga gaaggaaaac    600
cctaacaaac tggtgggctt ccactctctg aagattgttg atgtgatccc tgatgccgag    660
accaacaaaa agggcgagac atggtacagc ctgcacctgg aaaacggctg ggtgtacagg    720
cggagcagca agatcagcct ggccgactag aaggacaagg ttcgggactt catcgtcact    780
acagatctga cgacgatgg cagcgagaag ctggacaagg acggcatcgt gaagaggtcc    840
ttcagagccc cttctgccga cgattggaca ctcctgaaaa aaagactga aaggacatc       900
gacaactcca acaagactgt gggcacctac atctacgaca acttgctgct gaaccctaaa    960
cagaagatca aggggaaaat ggtcagaacc atcaaccgaa gcattgttga gcaggagctg    1020
gagcaaatcc tgaaacccca gaagaatttt cactccgagc tgcagtctga aaacctgctg    1080
caggactgcg tgagggagct gtaccggaac aacgagcagc cagcagat gctgaaagcc     1140
aaggattttg tgcacctgtt cctgaacgat atcatcttct accagagacc cctgcgcagc    1200
cagaaaagct ctattagcaa ctgcacctg gaattccgga gagcaagaa cgaatggaa       1260
gaagagtga tccaccggct gaaggtgatc gccaagtcca ccctactc atcaagagtttt     1320
```

```
cggctgctgc agtgggtgca aaacctggct atctcacacta aggacgacga caaaaacgtc 1380
acaaacgaat tcctgaagag cacccaggac tgggaggatc tgctgagatg gctgcacagc 1440
aagaaagaaa tcaagcagga tgccctgatc aaattcctga tcgaaaagaa aggcctgaag 1500
ggtaaggccc tgaccattga agtggctaag tacagatgga attacgtgca agacaaggat 1560
tatccggca acgagacaag atacctgatt cagagccggc tggacaaggt ggaatacgcc 1620
cctaaggact tcctcacgta cgaaaatgag atggccctgt ggcacatcat ctactctatc 1680
aacgataaga tcgaatacga aaaggcccta aagagcttcg ccaacaagaa aggtctcgac 1740
gaggtgacct tcgtggaagc ctttaagaaa ttcccaccct tcaagagcga ttacggcagc 1800
ttcagcgaga aggccatcaa gaagctgctg cctctcatgc ggttcggcac acaatggaac 1860
tgggacaaca tcgaccagaa ctcgaaggaa aggattggaa aaatcctgac cggcgagtac 1920
gacgagaata tcaagggtag agtgcgggaa aaagctagac acctgaacag cgagacggac 1980
tttcaggcgc tccctctgtg gctggcccag tacgtggtgt acggcagaca tagcgaagct 2040
gacatcgccg gcaagtggaa tagtgtggac gacctgaagc agttcttgga cgacttcaag 2100
caacacagcc tgagaaatcc cattgtagaa caggtgatta ctgagacact ggggccgtg 2160
aaggatatct ggaacttcta cggcaagggc gccaaggact ttttctctga gatccacatc 2220
gagctgggaa gagagatgaa aaacaccgcc gacgagagaa aaaggattac cacaatggtg 2280
acagataatg agaataccaa tctgagaatc aaagctctgc tggctgagat ggccctggat 2340
cagaacgtgg acaatgtgcg gccttacagc ccatgcagc aagaaatcct gaaaatctat 2400
gaggaaggcg tgctgaacgc cgaagagaac atcgacgatg acatcctgaa gatctctaaa 2460
actgctcagc ctagcgctac cgatctgaag agatacaagc tgtggctgga acagaagtac 2520
agaagcccct ataccggaca gatgatccct ctgaacaagc tgttcacccc tgagtatgaa 2580
atcgacacac ttatcccca gagcagatac ttcgacgatt ctatgagcaa caaggtgatc 2640
tgcgaggcc ccgtgaacaa gctgaaggat aaccgatcg gcctggtgtt catcaagaac 2700
caccacggcg aagtggtgga cttggcatg ggcaagcagg tgaaaatcct ggaggtgtct 2760
gattacgaag atttcgtgaa gcagaactac aacaaaaaca gaggcaaacg gaacaagctg 2820
ctcctcgaca atatccccga gaaaatgatt gaacggcaac tggctgaatc cagatatatc 2880
agcaagtaca tcactcaggt gctgtctaat atcgtcagaa cgacaaggaa ggctctaag 2940
gatgacggag tgaacagcaa gaacattgtg cccggcaacg gcaagattac aaccagactc 3000
aagcaggatt ggggcctgaa cgatgtgtgg aacgacctgg tgctgcctag attcgagaga 3060
atgaacaccc tcacaaactc caatgatttt acaagcaaga acacacacgg caagaccatt 3120
cctaccgtgc ctatcgagct gagcaagggg ttcagcaaaa agcggatcga tcacagacac 3180
cacgctatgg acgccctggt gatcgcctgc gccaccccggg accacgtgaa cctgctgaat 3240
aacgaatcca gcagtctga cacaaagcgg tacgacctga atagaaaact gagaaaatac 3300
gagaaggtgg cctacaacga cccccaaaacc ggcgagagga ttgaaaaaga agtgccaaaa 3360
gacttcatca gccttggga aacttttacc gaagatacca gaacactgct ggagaatatc 3420
gtgatctcat tcaaacagaa cctgagagtg atcaacaagg ccaccaacta ctacgagaag 3480
atcgagaacg gcaaaaaggt gaaggtggaa caaaagggaa tcaactgggc cgtgagaaag 3540
gctctccata aggagaccgt gtccggccag gtccaccttg acagaatcaa ggtggccaag 3600
ggcaagatcc tgaccgccac aagaaagacc ctggacgctt cttttaacga gaaaaccata 3660
gagagcatca ccgataccgg catccagaag atcctgctga actacctgaa gtcaaaggac 3720
aacaaccctg aggtggcctt ctccccagaa ggaattgagg aactaaacaa gaatatcaga 3780
ctgtacaatg acggcaaggc ccaccagcca atcctaaaag tgcgggtgtt cgagcagggc 3840
agcaagttca cactgggcga gacaggcaac aagacaacca agttcgtgga agctgccaaa 3900
ggcaccaatc ttttcttcgg aatctacgag gacaagagcg gaaaacgtag ctacgagacc 3960
atccccctga atatcgttat tgaaagacag aaacagggcc tccaggccgt gcccgagacc 4020
aacgagaagg gcaagcaact gctgttcacc ctgagccccca acgacctggt ctacgtgcca 4080
gaggaaggcg tattcgacga gaacaacatc aaggtggata gaatctacaa ggtcgtgtct 4140
ttcagcacat accaatgttt tttcgtgcgg aacgacgtat ctaccagcgt ggtcaacaag 4200
gtggagtaca cgcgccctgaa caagatggaa aaatccatcg acaatatcat gatcaaggaa 4260
aactgtgtga agctgaatgt ggaccggctg ggtaagatca gcaaggcc 4308

SEQ ID NO: 133       moltype = DNA   length = 4368
FEATURE              Location/Qualifiers
misc_feature         1..4368
                     note = source = /note="Description of Artificial Sequence:
                     Syntheticpolynucleotide"
misc_feature         1..4368
                     note = source = /note="APG01688.1 mammalian codon optimized
                     sequence"
source               1..4368
                     mol_type = other DNA
                     organism = synthetic construct
SEQUENCE: 133
atgatgatca agaacattct gggactggat ttgggcacaa acagcattgg atgggctctg   60
atcaagcagg acttcgagaa caaacacggc gagatcctgg gcatgggcag cagaatcatc  120
cctatgagcc aggatatcct gggcgatttc ggcaaaggga actcgataag ccagactgct  180
gacagaacca agtacagaag cgtgcggaga ctgagagaaa agattcttgct gcggcgggaa  240
cgcctgcacc gggtgctcca cctgctgaac ttcctccctc aacactacgc ctctcagatc  300
gacttcgaga agaagttcgg caagtttaag tctgagggaa acctaagtc ggcctggaga  360
aactggggag gtaaattctc tttcctcttc cagaacagct tcaacgagat gctggaagac  420
ttcaaggccg ccggccaggg actcaagatt ccctatgact ggaccatcta ctacctacgg  480
aagaaagctc tgtcccagaa gatcgagaaa gaggagcttg cctggattct gctgaacttc  540
aaccagaagc gaggctacta ccagctcaga ggcgaggaag aagaagagaa cccgaacaag  600
ctggtggagt tctactccct gaagatcgtg gatgtgctcg ccgacgagcc tcagaagggg  660
aagagcgaca tctggtattc tctgatcctg aaaacggct gggtctaccg cagagccagt  720
aagatcccac tgtttgattg gaaggataag accagagatt tcatcgtcac cacagacctt  780
aatgacgaca gaagcgtgaa gaccgacaaa gagggcaacg agagcggtc ctttcgggcc  840
cctagcgaaa atgattggac cctggtcaag aagaagacag agcaggagat tgaccagagc  900
cacaagaccg tgggcaccta catctacgag acactgctgc tcaatccaaa gcagaaaatc  960
```

```
aagggcaagc tggtgcgaac aatcgagaga aaatttata aggacgagct gaagcaaatc    1020
ctggaaaagc agaaggaatt tcaccaggag ctgaaaaacg acgatctgta caacgactgc    1080
atcagagagc tgtaccggaa caacgaggcc caccaactga ccctgagcaa gaaagatttc    1140
gtgcacctgc tgatggacga tctgatcttc taccaaagac ccctgcgaag ccagaagtcc    1200
agcatctcta actgcaccct ggaattcaga aaatacaagg acgaaaacgg catcgaaacc    1260
acccagtacc tgaaggccat cccaaagagt aatccgtact accaagagtt tagactgtgg    1320
cagtggatgt acaacctgaa catctacaga aaggacgacg aggctaatgt gaccaaggaa    1380
ttcctgaacc accaataagga cttcgagagc ctgtttgagt tcctgaataa tagaaaggaa    1440
atcgaacaga agcctctgat caagttcctc ctggaacaga aagatattaa caagaagctg    1500
ctgaacgccg aggccgaaaa gtatcggtgg aattacgtgg aagataagaa gtatccttgc    1560
aacgaaacga agaccatgat ctccagcaga ctggacaaag tggagaatat ctctgacgac    1620
ttcctgacca gagacattga gcagaagatc tggcacatca tctacagcgt caacgacaag    1680
atagaatacg agaaggccct gaagtccttc gccaccagaa acgatctcga cgagaacagc    1740
tttatcgaag cctttaagaa gttcagccca ttcaagacgg agtacggatc tttttctgag    1800
aaagccatca agaaactgct gccctgatg agactgggaa agtactggta cgaggacgag    1860
attgtgaagc actctgatat ttactttaag aacatcgaaa atcttctggg cgacttctcc    1920
aacagagata aaaaatatc tgaggaagac aaagagaaat ggaacaagtc tatcaacctg    1980
aaactgcagg aggaactgaa ggactttcag accgccagaa tcgacctgtt ccagggcctt    2040
agactccata tcgcccagta cctggtgtac ggccggcaca gcgaagccag catgatcgga    2100
aagtggaaca gcgccgagga tctggaagaa ttcctgaagg acttcaagca gcacagcctg    2160
agaaacccca tcgtcgagca agtgatcacc gagaccctga gggtggttaa ggatatatgg    2220
ctgaaatacg gcaacggcgc caaggacttc ttcaacgaga ttcacatcga gctgggcaga    2280
gaaatgaagc tgcctgccga cgaccggaaa aagctgacca accagatcag cgagaacgaa    2340
aacacaaatt tcagaatcaa ggccctgctg gctgaaatga tgaacgacag cagtgtggaa    2400
aatgtgcggc ctttcagccc tatgcagcag gagatcctga agatctatga agatgacgtc    2460
ctgaagtctg acattgaaat cgaggatgac atccttaaga tctctaaaac cgcccagcct    2520
tctcctagcg atctcaagcg atacaagctc tggctggagc agaagtacaa gtctccatac    2580
accggccaga tcatacctct gaacaagctg tttaccccctg aatacgagat cgagcacatt    2640
atccctcagt ctagatattt cgacgacagc ttcagcaaca aagtgatctg cgagagcgcc    2700
gtgaacaagc tgaaagacaa ctacattggc ctggaattca tcaagcaatt tggaggcacc    2760
atcatcgaac tgggctttgg caagtccatc aaagtgttcg agaccaaaga gtacgaggac    2820
ttcgtgaaga acactacgc caacaatcag ggcaagagaa acaagctgct catggaagac    2880
atccccgaga aaatgatcga gagacagatg aacgacacca gatacatctc taagtacatc    2940
agcggagtgc tgagcaacat cgtcagagtg gaagatggat ctgatgaggg cgtgaacagc    3000
aagaacatcg tgcccggcaa cggcaagatt acaacacaac tgaagcagga ctgggggcctg    3060
aatgacgtgt ggaacgacct tatcctgccg cggttcgaga gaatgaatca actgaccaac    3120
agcaaggtgt tcacagcctg gaacgaaaac taccagaagt tcctgcctac agtgccaatc    3180
gaatacagca aaggcttcag caagaagcgt atcgatcaca gacaccacgc cctggatgct    3240
ctggttatcg cctgcgccac caaggaccac gtgaacctgc tgaacaacca gtctgccaag    3300
agcgacacca agagatacga cttaaagaaa aaagtatga aattcgagaa agtggtgtac    3360
aatgatgcca agaccggcga aaagatcgag cgggaagtgc ccaagcagtt cctgaagcct    3420
tgggagaact tcacccctgga tgtgaagcac aacctgaaa cgatcatcgt ctcttttaaa    3480
caaaatctgc gggtgatcaa taaagccacg aactactacg agaagtacgt cgagaaggac    3540
ggcaccaaaa acaaagagcg cgtggagcag acagggacaa actgggccat tagaaagccc    3600
atgcacaagg atacagtgtc cggcaaagtg gaccttcctt gggtgaaggt gcctaaggga    3660
aagatcctga ccgccacacg gaagagcttg gatagcagct tcgacctcaa gagcatcggc    3720
tctataacag atacaggcat tcagaagatc taaagaatt acctggcatt caaggacggc    3780
aaccctgagc tggctttcag ccctgagggc atcgacgatc tgaacaagaa catagagaag    3840
tacaacgatg gcaaacctca ccagcctatc aacaaggtgc gagtgtttga gctgggcagc    3900
aagttccagg tgggacaatc tggtaacaag aaggacaagt atgtggaagc tgctaagggc    3960
accaatctct tcttcgccgt gtacgaggat gaaaaagaa agcggaacta cgagaccatc    4020
cctctcaacg aggtgatcga gagacagaag cagggcctga gcgtggtgga cctgaagggt    4080
acaaacgact tctacctgtg ccctaacgac tttgtgtaca tcccaagcgg cgacgagctg    4140
gaaaacatca caacgtgga cttcaaggac atcaagaagg agattaacga gcgcatctac    4200
aaagtggtgt cttttacagg caatagactt tcttgtatcc cttacatggt ggccacaacg    4260
atcgtcaaca aactcgaatt cactcaactg aacaaaatcg agtttaccaa ggaaaaagaa    4320
atttgtatca agctcaacgt ggacagactg ggcaatatct ccaaggcc                4368
```

```
SEQ ID NO: 134         moltype = DNA   length = 21
FEATURE                Location/Qualifiers
misc_feature           1..21
                       note = source = /note="Description of Artificial Sequence:
                       Syntheticoligonucleotide"
misc_feature           1..21
                       note = source = /note="SV40 large T-antigen nuclear
                       localization sequence"
source                 1..21
                       mol_type = other DNA
                       organism = synthetic construct
SEQUENCE: 134
cctaagaaga aagaaaggt g                                                21

SEQ ID NO: 135         moltype = DNA   length = 66
FEATURE                Location/Qualifiers
misc_feature           1..66
                       note = source = /note="Description of Artificial Sequence:
                       Syntheticoligonucleotide"
misc_feature           1..66
                       note = source = /note="Triple FLAG epitope tag"
```

```
source                  1..66
                        mol_type = other DNA
                        organism = synthetic construct
SEQUENCE: 135
gactacaagg accacgacgg cgactacaaa gatcacgata tcgactacaa ggacgacgat   60
gataag                                                              66

SEQ ID NO: 136          moltype = DNA   length = 48
FEATURE                 Location/Qualifiers
misc_feature            1..48
                        note = source = /note="Description of Artificial Sequence:
                         Syntheticoligonucleotide"
misc_feature            1..48
                        note = source = /note="Nucleoplasmin nuclear localization
                         sequence"
source                  1..48
                        mol_type = other DNA
                        organism = synthetic construct
SEQUENCE: 136
aaaagacctg ccgctacaaa gaaggccggc caggccaaga aaagaag                 48

SEQ ID NO: 137          moltype = DNA   length = 203
FEATURE                 Location/Qualifiers
misc_feature            1..203
                        note = source = /note="Description of Artificial Sequence:
                         Syntheticpolynucleotide"
misc_feature            1..203
                        note = source = /note="Cytomegalovirus mammalian
                         transcription promoter"
source                  1..203
                        mol_type = other DNA
                        organism = synthetic construct
SEQUENCE: 137
tgatgcggtt ttggcagtac atcaatgggc gtggatagcg gtttgactca cggggatttc   60
caagtctcca ccccattgac gtcaatggga gtttgttttg gcaccaaaat caacgggact  120
ttccaaaatg tcgtaacaac tccgccccat tgacgcaaat gggcggtagg cgtgtacggt  180
gggaggtcta tataagcaga gct                                          203

SEQ ID NO: 138          moltype = DNA   length = 304
FEATURE                 Location/Qualifiers
misc_feature            1..304
                        note = source = /note="Description of Artificial Sequence:
                         Syntheticpolynucleotide"
misc_feature            1..304
                        note = source = /note="Cytomegalovirus transcription
                         enhancer"
source                  1..304
                        mol_type = other DNA
                        organism = synthetic construct
SEQUENCE: 138
cgttacataa cttacggtaa atggcccgcc tggctgaccg cccaacgacc cccgcccatt   60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catg                                                               304

SEQ ID NO: 139          moltype = DNA   length = 318
FEATURE                 Location/Qualifiers
misc_feature            1..318
                        note = source = /note="Description of Artificial Sequence:
                         Syntheticpolynucleotide"
misc_feature            1..318
                        note = source = /note="Human U6 RNA promoter"
source                  1..318
                        mol_type = other DNA
                        organism = synthetic construct
SEQUENCE: 139
tgtacaaaaa agcaggcttt aaaggaacca attcagtcga ctggatccgg taccaaggtc   60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg tttttaaaatg  240
gactatcata tgcttaccgt aacttgaaag tatttcgatt tcttggcttt atatatcttg  300
tggaaaggac gaaacacc                                                318

SEQ ID NO: 140          moltype = DNA   length = 20
FEATURE                 Location/Qualifiers
misc_feature            1..20
                        note = source = /note="Description of Artificial Sequence:
```

```
                        Syntheticoligonucleotide"
misc_feature            1..20
                        note = source = /note="target for Guide 189"
source                  1..20
                        mol_type = other DNA
                        organism = synthetic construct
SEQUENCE: 140
cctgaatgct gtgcggctct                                                      20

SEQ ID NO: 141          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="target for Guide 185"
source                  1..20
                        mol_type = other DNA
                        organism = synthetic construct
SEQUENCE: 141
ggacagtgcg catctccctg                                                      20

SEQ ID NO: 142          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="target for Guide 168"
source                  1..20
                        mol_type = other DNA
                        organism = synthetic construct
SEQUENCE: 142
cacatctcga gcaagacgtt                                                      20

SEQ ID NO: 143          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="target for Guide 135"
source                  1..20
                        mol_type = other DNA
                        organism = synthetic construct
SEQUENCE: 143
gggccattaa aacctctcca                                                      20

SEQ ID NO: 144          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="target for Guide 139"
source                  1..20
                        mol_type = other DNA
                        organism = synthetic construct
SEQUENCE: 144
aggttttaat ggcccagcct                                                      20

SEQ ID NO: 145          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="target for Guide 143"
source                  1..20
                        mol_type = other DNA
                        organism = synthetic construct
SEQUENCE: 145
catggcagta cattagagca                                                      20

SEQ ID NO: 146          moltype = DNA  length = 20
FEATURE                 Location/Qualifiers
misc_feature            1..20
                        note = source = /note="Description of Artificial Sequence:
                        Syntheticoligonucleotide"
```

```
misc_feature            1..20
                        note = source = /note="target for Guide 190"
source                  1..20
                        mol_type = other DNA
                        organism = synthetic construct
SEQUENCE: 146
cctgaatgct gtgcggctct                                                     20

SEQ ID NO: 147          moltype = DNA  length = 20
FEATURE                 Location/Qualifiers
misc_feature            1..20
                        note = source = /note="Description of Artificial Sequence:
                          Syntheticoligonucleotide"
misc_feature            1..20
                        note = source = /note="target for Guide 194"
source                  1..20
                        mol_type = other DNA
                        organism = synthetic construct
SEQUENCE: 147
gccgcacagc attcaggtcg                                                     20

SEQ ID NO: 148          moltype = DNA  length = 20
FEATURE                 Location/Qualifiers
misc_feature            1..20
                        note = source = /note="Description of Artificial Sequence:
                          Syntheticoligonucleotide"
misc_feature            1..20
                        note = source = /note="target for Guide 165"
source                  1..20
                        mol_type = other DNA
                        organism = synthetic construct
SEQUENCE: 148
atggggaatg tagcaagacc                                                     20

SEQ ID NO: 149          moltype = DNA  length = 20
FEATURE                 Location/Qualifiers
misc_feature            1..20
                        note = source = /note="Description of Artificial Sequence:
                          Syntheticoligonucleotide"
misc_feature            1..20
                        note = source = /note="target for Guide 169"
source                  1..20
                        mol_type = other DNA
                        organism = synthetic construct
SEQUENCE: 149
cacatctcga gcaagacgtt                                                     20

SEQ ID NO: 150          moltype = DNA  length = 20
FEATURE                 Location/Qualifiers
misc_feature            1..20
                        note = source = /note="Description of Artificial Sequence:
                          Syntheticoligonucleotide"
misc_feature            1..20
                        note = source = /note="target for Guide 173"
source                  1..20
                        mol_type = other DNA
                        organism = synthetic construct
SEQUENCE: 150
cttctatagc ctccttcccc                                                     20

SEQ ID NO: 151          moltype = DNA  length = 20
FEATURE                 Location/Qualifiers
misc_feature            1..20
                        note = source = /note="Description of Artificial Sequence:
                          Syntheticoligonucleotide"
misc_feature            1..20
                        note = source = /note="target for Guide 144"
source                  1..20
                        mol_type = other DNA
                        organism = synthetic construct
SEQUENCE: 151
catggcagta cattagagca                                                     20

SEQ ID NO: 152          moltype = DNA  length = 20
FEATURE                 Location/Qualifiers
misc_feature            1..20
                        note = source = /note="Description of Artificial Sequence:
                          Syntheticoligonucleotide"
misc_feature            1..20
```

```
                         note = source = /note="target for Guide 136"
source                   1..20
                         mol_type = other DNA
                         organism = synthetic construct
SEQUENCE: 152
gggccattaa aacctctcca                                                     20

SEQ ID NO: 153           moltype = DNA   length = 20
FEATURE                  Location/Qualifiers
misc_feature             1..20
                         note = source = /note="Description of Artificial Sequence:
                          Syntheticoligonucleotide"
misc_feature             1..20
                         note = source = /note="target for Guide 145"
source                   1..20
                         mol_type = other DNA
                         organism = synthetic construct
SEQUENCE: 153
catggcagta cattagagca                                                     20

SEQ ID NO: 154           moltype = DNA   length = 20
FEATURE                  Location/Qualifiers
misc_feature             1..20
                         note = source = /note="Description of Artificial Sequence:
                          Syntheticoligonucleotide"
misc_feature             1..20
                         note = source = /note="target for Guide 188"
source                   1..20
                         mol_type = other DNA
                         organism = synthetic construct
SEQUENCE: 154
ggacagtgcg catctccctg                                                     20

SEQ ID NO: 155           moltype = DNA   length = 20
FEATURE                  Location/Qualifiers
misc_feature             1..20
                         note = source = /note="Description of Artificial Sequence:
                          Syntheticoligonucleotide"
misc_feature             1..20
                         note = source = /note="target for Guide 192"
source                   1..20
                         mol_type = other DNA
                         organism = synthetic construct
SEQUENCE: 155
cctgaatgct gtgcggctct                                                     20

SEQ ID NO: 156           moltype = DNA   length = 20
FEATURE                  Location/Qualifiers
misc_feature             1..20
                         note = source = /note="Description of Artificial Sequence:
                          Syntheticoligonucleotide"
misc_feature             1..20
                         note = source = /note="target for Guide 196"
source                   1..20
                         mol_type = other DNA
                         organism = synthetic construct
SEQUENCE: 156
gccgcacagc attcaggtcg                                                     20

SEQ ID NO: 157           moltype = DNA   length = 20
FEATURE                  Location/Qualifiers
misc_feature             1..20
                         note = source = /note="Description of Artificial Sequence:
                          Syntheticoligonucleotide"
misc_feature             1..20
                         note = source = /note="target for Guide 167"
source                   1..20
                         mol_type = other DNA
                         organism = synthetic construct
SEQUENCE: 157
atggggaatg tagcaagacc                                                     20

SEQ ID NO: 158           moltype = DNA   length = 20
FEATURE                  Location/Qualifiers
misc_feature             1..20
                         note = source = /note="Description of Artificial Sequence:
                          Syntheticoligonucleotide"
misc_feature             1..20
                         note = source = /note="target for Guide 171"
```

```
source              1..20
                    mol_type = other DNA
                    organism = synthetic construct
SEQUENCE: 158
cacatctcga gcaagacgtt                                               20

SEQ ID NO: 159      moltype = DNA   length = 20
FEATURE             Location/Qualifiers
misc_feature        1..20
                    note = source = /note="Description of Artificial Sequence:
                    Syntheticoligonucleotide"
misc_feature        1..20
                    note = source = /note="target for Guide 175"
source              1..20
                    mol_type = other DNA
                    organism = synthetic construct
SEQUENCE: 159
cttctatagc ctccttcccc                                               20

SEQ ID NO: 160      moltype = DNA   length = 25
FEATURE             Location/Qualifiers
misc_feature        1..25
                    note = source = /note="Description of Artificial Sequence:
                    Syntheticoligonucleotide"
misc_feature        1..25
                    note = source = /note="target for Guide 197"
source              1..25
                    mol_type = other DNA
                    organism = synthetic construct
SEQUENCE: 160
cctcacccc acgagcttgt aggaa                                          25

SEQ ID NO: 161      moltype = DNA   length = 25
FEATURE             Location/Qualifiers
misc_feature        1..25
                    note = source = /note="Description of Artificial Sequence:
                    Syntheticoligonucleotide"
misc_feature        1..25
                    note = source = /note="target for Guide 199"
source              1..25
                    mol_type = other DNA
                    organism = synthetic construct
SEQUENCE: 161
acagtgcgca tctccctggt cacca                                         25

SEQ ID NO: 162      moltype = DNA   length = 25
FEATURE             Location/Qualifiers
misc_feature        1..25
                    note = source = /note="Description of Artificial Sequence:
                    Syntheticoligonucleotide"
misc_feature        1..25
                    note = source = /note="target for Guide 146"
source              1..25
                    mol_type = other DNA
                    organism = synthetic construct
SEQUENCE: 162
ggctgggcca ttaaaacctc tccag                                         25

SEQ ID NO: 163      moltype = DNA   length = 25
FEATURE             Location/Qualifiers
misc_feature        1..25
                    note = source = /note="Description of Artificial Sequence:
                    Syntheticoligonucleotide"
misc_feature        1..25
                    note = source = /note="target for Guide 148"
source              1..25
                    mol_type = other DNA
                    organism = synthetic construct
SEQUENCE: 163
gaggctgggc cattaaaacc tctcc                                         25

SEQ ID NO: 164      moltype = DNA   length = 25
FEATURE             Location/Qualifiers
misc_feature        1..25
                    note = source = /note="Description of Artificial Sequence:
                    Syntheticoligonucleotide"
misc_feature        1..25
                    note = source = /note="target for Guide 176"
source              1..25
```

```
                        mol_type = other DNA
                        organism = synthetic construct
SEQUENCE: 164
gaggctgaga caggagagtt gcttg                                          25

SEQ ID NO: 165          moltype = DNA  length = 25
FEATURE                 Location/Qualifiers
misc_feature            1..25
                        note = source = /note="Description of Artificial Sequence:
                         Syntheticoligonucleotide"
misc_feature            1..25
                        note = source = /note="target for Guide 177"
source                  1..25
                        mol_type = other DNA
                        organism = synthetic construct
SEQUENCE: 165
cccacaaacc gatgtagctc aagag                                          25

SEQ ID NO: 166          moltype = DNA  length = 25
FEATURE                 Location/Qualifiers
misc_feature            1..25
                        note = source = /note="Description of Artificial Sequence:
                         Syntheticoligonucleotide"
misc_feature            1..25
                        note = source = /note="target for Guide 209"
source                  1..25
                        mol_type = other DNA
                        organism = synthetic construct
SEQUENCE: 166
tagggtctta ctctgttgtc cacgc                                          25

SEQ ID NO: 167          moltype = DNA  length = 25
FEATURE                 Location/Qualifiers
misc_feature            1..25
                        note = source = /note="Description of Artificial Sequence:
                         Syntheticoligonucleotide"
misc_feature            1..25
                        note = source = /note="target for Guide 151"
source                  1..25
                        mol_type = other DNA
                        organism = synthetic construct
SEQUENCE: 167
ttctcccgag ccaagtacac gtttc                                          25

SEQ ID NO: 168          moltype = DNA  length = 25
FEATURE                 Location/Qualifiers
misc_feature            1..25
                        note = source = /note="Description of Artificial Sequence:
                         Syntheticoligonucleotide"
misc_feature            1..25
                        note = source = /note="target for Guide 152"
source                  1..25
                        mol_type = other DNA
                        organism = synthetic construct
SEQUENCE: 168
gaaaatctgc tcttagggct caagg                                          25

SEQ ID NO: 169          moltype = DNA  length = 3210
FEATURE                 Location/Qualifiers
misc_feature            1..3210
                        note = source = /note="Description of Artificial Sequence:
                         Syntheticpolynucleotide"
misc_feature            1..3210
                        note = source = /note="APG05083.1 Soy optimized"
source                  1..3210
                        mol_type = other DNA
                        organism = synthetic construct
SEQUENCE: 169
atgagagagc tagattacag gatcggactc gatatcggaa ctaattcaat cgggtgggga    60
ataattgagc tgtcctggaa taaagatcgc gagcaatatg aaaaggctag gattgtggat   120
aagggagtga ggatgttcga taaggctgaa attcctaaga ctggagcttc tcttgctgaa   180
ccaagaagaa ttgctagatc tagcaggagg agattaaaca ggaagtctca gcgcaagaag   240
gatataagga accttctcgt tcagcatgaa atcatttctc agaaggagct tgcttctctc   300
taccctcaa ccaaatcaag catgacatc tgggatataa ggcttgatgg actcgatagg   360
cttcttgata gatttgagtg gaccaggctt ctaatacacc ttgctcaaag aagggggcttc   420
aaatcaaacc gcaagtccga attaaaggat gttgagactg gaaaggtgct ttcaagcatc   480
caagctaatg aaaagaggct ttctttgtac aggactgttg gggagatgtg gatgaaaaac   540
gaggacttct caaaatacga taaaaggagg aactcctcca acgagtacgt gttctctgtt   600
tctagggctg atcttgagaa ggagattgtg actctttttg aggctcaacg caagttccaa   660
```

```
tcaagctacg cttctgctga tcttcaaaag acctaccttc aaatttgggc tcatcagctt    720
ccttttgctt ctggaaacgc cattgtgaat aaagtgggat actgctccct attaaaggga    780
aaggagaaga gagtgcctaa ggctaccttat acattccagt acttctctac cctcgatcaa   840
atcaatagaa ctaggcttgg acctaacttc cagccttttta ctaaggagca gagggatgtg   900
atcctcgatg aaatgttcaa caggaccgac tactataaaa agaagaccat tcccgaggtg    960
acctactacg atataagaaa gtggcttgct ctcgatgaaa ccattcagtt caagggacta   1020
acttatgacc ccaacgagga gctgaagaaa atagaactca agtccttcat aaacctcaag   1080
cccttctacg aaatcaagaa ggtggtaacc aactacgcca agaagaccaa cgaagcattc   1140
tctaccctcg attacgatac attcgcttac gctcttaccg tgtataaaac cgacaaggat   1200
ataaggtcct acctcaagaa atcaaacaac ctctccaagt gctgctacga cgatcaatta   1260
attgaggagc ttctcaccct ctcctatact aagttcggac acctctcttt caaggcaatc   1320
aaccatgtgc ttccaataat gcaagaggga agaacttacc aagaggcaat acaccaactt   1380
ggatacgatg ctaccaacct taagaaggag aacaggtcta tgttccttcc tctcttccct   1440
gatgagatta ctaaccctat tgtgaagaca gctttgactc aagctaggaa ggtggtgaat   1500
gctattatta ggaggtacgg atcacctaac tctgtgcata ttgagcttgc tagggagctt   1560
tctaagtctc atgatgagag gaccaagatt atgaaggctc acgatgagaa ctacaagaag   1620
aacaaggggg ctatttccat tctcattgag aacggaattc ttaaccctac cggatacgat   1680
attgtgaggt acaagttgtg gaaggagcaa ggagagagat gcgcttactc tcttaagcaa   1740
attcctgcta acaccttctt caacgagatg aagaaggaaa gatcaggatc tcctgtgctt   1800
gagattgatc acattctccc ttactcccag tccttcattg attcttacca acaacaaggtg  1860
cttgtttacg gagatgagaa ccaaaagaag gggaacagga ttccttacac ttacttcctt   1920
gagggaaaca aggattggga gtctttcgag tcttacgtga gcttaactc cttcttctct    1980
aagaagaaga gggatacct tcttaagaag gcttatcttc ctagggagtc caatatgatt    2040
aaggagaggc acctaaacga taccaggtac gcttcttctt acctcaagaa cttcatcgag   2100
aagaaccta gttcaagga ggttgaggga tctactagga gaagcatgt tcagaccgtg      2160
aacggaatta ttactgctca tcttagaaag aggtggggac ttgagaagga taggcaagag   2220
acttaccttc atcacgctat ggatgctatt attgtggctt gcactgatca ccatatggtg   2280
actaaggtta ccgagtacta ccagattaag gagtcaaaca agtccatcag gaagccttat   2340
tttcctcttc cttgggttgg attcaggag gagattcttt ctcatcttgc tagacaacct    2400
atcgctagaa agatttccga ggagcttaag attggatacc agtccttcga ttacattctt   2460
gtgtctagga tgcctaagag gtctgttact ggagctgctc atgagcagac tattatgaag   2520
aagggaggaa ttgataagaa ggggaagacc atcatcatta gagggtgta cctaaaggac    2580
atcaagttcg atgagaacgg ggatttcaag atggttggaa aggagcagga tcttgctact   2640
tacgaggcta ttaagcagg gtacattgag tatggaaagg agtctaagaa ggcttttcgag   2700
actcctcttt acaagccttc taagaaggga aaggggaacc tcatcaagaa gattaaggtt   2760
gaggttcaga ctaagtcttt cgttagggag gttaatggag gagttgctca gaatggagat   2820
cttgtgaggg ttgatctatt cgagaaggac aacaggtact acatgatccc tatctacgtg   2880
atggatactg ttcattccga gcttcctaac aaggctgtta cttcttctaa gggatacgag   2940
cagtggcctta ccattgataa ctcttcttcacc ttcaagttct ctctctaccc ttacgatctt   3000
gttaggcttg ttaaggggaaa cgaggatagg ttcctctact tctccaccct cgatattaac   3060
tctgataggc tcaacttcaa ggatgtgaac aagccttcaa agcaagctga gaacaggtac   3120
tctcttaaga ccattgagaa ccttgagaag tacgaagtgg gagttcttgg agatcttagg   3180
ttcgttaggc aagagattag gaagaacttc                                    3210

SEQ ID NO: 170        moltype = DNA    length = 3210
FEATURE               Location/Qualifiers
misc_feature          1..3210
                      note = source = /note="Description of Artificial Sequence:
                      Syntheticpolynucleotide"
misc_feature          1..3210
                      note = source = /note="APG05083.1 Corn optimized"
source                1..3210
                      mol_type = other DNA
                      organism = synthetic construct
SEQUENCE: 170
atgcgcgagc tagattacag gatcggcctg gatatcggca ctaactcaat aggctggggc     60
atcatcgagc tgagctggaa taaagaccgc gagcagtatg aaaaggccag gatcgtggac    120
aagggcgtga ggatgttcga taaggccgag atcccaaaga caggcgcctc tctgccgaa    180
ccaaggagga tcgccaggtc ttctaggagg agattaaaca ggaagtctca gcgcaagaag   240
gatataagga acctgctggt ccagcatgaa atcatctctc agaaggagct ggccagctga   300
tacccgctga ccaagtcaag catggacatc tgggatataa ggctggatgg cctggatagg   360
ctgctggata ggttcgagtg gacaaggct ctgatacatc tggcccagag gaggggcttc    420
aaaatcaaata ggaagagcga attaaggac gtggagacag gcaaggtgct gtcaagcatt    480
caggccaatg aaaagcgcct gagcctgtac aggacggtg atgaaaaac                540
gaggacttct caaaatacga caagcgccgc aacagcagca acgagtacgt gttcagcgtg   600
agcagggccg acctggagaa ggagatcgtg acactgttcg aggcccagag gaagttccaa   660
tcaagctacg cctctgccga tctgcagaag acatacctgc agatctgggc ccaccagctg   720
ccattcgcta gcggcaatgc catcgtgaat aaagtgggct actgctctct attaaagggc   780
aaggagaaga gggtgccaaa ggccacctat acattcagca cttcagcac cctggaccaa    840
atcaatagga cacgcctggg cccaaacttc cagccattca caaggagca gcgcgacgtg    900
atcctgatg aaatgttcaa ccgcaccgac tactataaaa agaagaccat cccggaggtg    960
acatactacg atataaggaa gtggctggcc ctggatgaaa ccatccagtt caagggccta   1020
acctacgacc cgaacgagga gctgaagaaa atagaactga gagcttcat aaacctgaag   1080
ccgttctacg aaatcaagaa ggtggtaacc aactacgcca agaaaccaa cgaagcattc    1140
agcaccctgg actacgatac attcgcctac gccctgaccg tgtataaaac cgacaaggat   1200
ataaggagct acctgaagaa atcaaacaac ctgagcaagt gctgctacga cgaccaatta   1260
atcgaggagc tgctgaccct gagctatact aagttcggcc acctgagctt caaggcaatc   1320
aaccacgtgc tgccaataat gcaggagggc cgcacctacc aggaggcaat acaccagctg   1380
ggctacgacg caaccaacct gaagaaggag aaccgaagca tgttcctgcc gctgttccg    1440
```

```
gacgagatca ccaacccgat cgtgaagcgc gccctgaccc aggcccgcaa ggtggtgaac   1500
gccatcatcc gccgctacgg ctcaccgaac agcgtgcaca ttgagctggc ccgcgagctg   1560
agcaagagcc acgacgagcg cacaaagatc atgaaggccc acgacgagaa ctacaagaag   1620
aacaagggcg ccatcagcat cctgatcgag aacggcatcc tgaacccaac aggctacgac   1680
atcgtgaggt acaagctgtg gaaggagcag ggcgagaggt gcgcctactc tctgaagcag   1740
atcccagcca atacattctt caacgagatg aagaaggaga ggtcaggctc tccagtgctg   1800
gagattgatc acatcctgcc atacagccag agcttcatcg acagctacca caacaaggtg   1860
ctggtgtacg gcgatgagaa ccagaagaag ggcaatcgca tcccatacac atacttcctg   1920
gagggcaaca aggattggga gagcttcgag agctacgtga ggctgaacag cttcttcagc   1980
aagaagagga ggggctacct gctgaagaag gcctacctgc caagggagag caacatgatc   2040
aaggagaggc acctaaacga tacaaggtac gccagcagct acctgaagaa cttcatcgag   2100
aagaacctga agttcaagga ggtggagggc agcacccgta agaagcacgt ccagaccgtg   2160
aacggcatca tcacagccca cctgaggaag aggtggggcc tggagaagga taggcaggag   2220
acatacctgc atcacgccat ggatgccatc atcgtgctgc gcacagatca ccacatggtg   2280
acaaaggtga cagagtacta ccagatcaag gagagcaaca agtcaatccg caagccatac   2340
ttcccactgc catgggtggg cttcaggagg agatcctgtc tcacctggc caggcagcca   2400
atcgccagga agatctctga ggagctgaag atcggctacc agtctttcga ttacatcctg   2460
gtgtctagga tgccaaagag gtctgtgaca ggcgccgccc acgagcagac aatcatgaag   2520
aagggcggca tcgataagaa gggcaagaca atcatcatca agagggtgta cctgaaggat   2580
atcaagttcg atgagaacgg cgatttcaag atggtgggca aggagcagga tctagccaca   2640
tacgaggcca tcaagcagag gtacatcgag tacggcaagg agtctaagaa ggccttcgag   2700
acaccactgt acaagccatc taagaagggc aagggcaact tgatcaagaa gatcaagggtg   2760
gaggttcaga ccaagagctt cgtgagggag gtgaatggcg cgtggcccca gaatggcgat   2820
ctggtgaggg tggatctgtt cgagaaggat aacaggtact acatgatccc gatctacgtg   2880
atggatacag tgcacagcga gctgccaaac aaggccgtga catcttctaa gggctacgag   2940
cagtgcctaa ccatcgacaa cagcttcacc ttcaagttca gcctgtaccc atacgacctg   3000
gtgaggctgg tgaagggcaa tgaggacagg ttcctgtact tcagcaccct ggacatcaac   3060
agcgacaggc tgaacttcaa ggacgtgaac aagccatcta gcaggccgga aacaggtac   3120
agcctgaaga ccatcgagaa cctggagaag tacgaggtgg gcgtgctggg cgatctgagg   3180
ttcgtgaggc aggagatcag gaagaatttc                                    3210

SEQ ID NO: 171       moltype = DNA   length = 3213
FEATURE              Location/Qualifiers
misc_feature         1..3213
                     note = source = /note="Description of Artificial Sequence:
                     Syntheticpolynucleotide"
misc_feature         1..3213
                     note = source = /note="APG07433.1 Soy optimized"
source               1..3213
                     mol_type = other DNA
                     organism = synthetic construct
SEQUENCE: 171
atgagagagc tagattacag gatcggactc gatatcggaa ctaattcaat tggatgggc     60
gtgattgagc tttcctggaa taaagatagg gagcgttatg aaaaggttag gattgtggat   120
cagggagtta ggatgtttga tagagctgag atgcctaaga ctggagcttc attagctgaa   180
ccaagaagga ttgctagatc tagcaggagg agattaaaca ggagtctca gcgcaagaag   240
aatataagga accttcttgt tcagcacgga gttattactc aggaggagct tgattctctc   300
taccctctct ccaagaaatc aatggatatc tggggaatta ggcttgatgg actcgatcgc   360
ctattaaacc attttgagtg ggctaggctt ctaatacacc ttgctcaaag aaggggcttc   420
aaatcaaacc gcaagtccga attaaaggat actgagactg aaaggtgct tcaagcatc   480
cagctcaatg aaaagaggct ttcttttgtat aggactgttg gggagatgtg gatgaaagat   540
cccgacttct caaaatacga taggaagagg aactctccta acgagtacgt gttttctgtt   600
tctagagctg agcttgagaa ggagattgtg actttgtttg ctgctcaaag gaggttccaa   660
tctccttacg cttctaagga tcttcaagag acctaccttc agatttggac tcatcagctt   720
ccttttgctt ccgggaacgc tattctcaat aaagtgggat actgctcctt attaagggaa   780
aaggagagaa ggattcctaa ggccaccctat acattccagt acttctctgc tcttgatcaa   840
gtgaatagaa ctaggcttgg acctgatttc cagcctttta ctaaggagca gcgcgagatc   900
atcctcaata atatgtccta gaggaccgac tactataaa agaagaccat tcccgaggtg   960
acctactacg atataagaaa gtgccttgag cttgatgaa ccattcagtt caagggatta   1020
aactacgacc ccaacgagga gctgaagaaa atagaagaga gcccttcat aaacctcaag   1080
gccttctacg aaatcaacaa ggtggtggct aactactctg agcgaaccaa tgaacccttc   1140
tctaccctcg attacgatgg aattggatac gctcttaccg tgtataaaac cgacaaggat   1200
ataaggtcct acctcaaatc aagccataat ctccctaaga ggtgctacga cgatcaatta   1260
attgaggagc ttctctccct ctcctatact aagttcctga acctctctct taaggcaatc   1320
aaccatgttc taagcattat gcagaagggg aacacatata ggaggctgt tgatcagctt   1380
ggatacgata cttctggact taagaaggag aagggtcta agttcctccc tcctatttct   1440
gatgagatta ccaaccctat tgtgaagaga gctttgactc aagctaggaa ggtggtgaat   1500
gctattatta ggaggcatgg atcttcctcat tctgtgctgcg ttgagcttgc taggagctt   1560
tcaaagaatc acgatgagag gactaagatt gtttctgctc aggacgagaa ctacaagaag   1620
aacaagggga ctatttctat tctctctgag cacggaattc ttaaccctac cggatacgat   1680
attgtgaggt ataagttgtg gaaggagcaa ggagagagat cgcttactc tcttaaggaa   1740
attcctgctg ataccttctt caacgagctt aagaaggaaa ggaacggtgc tcctattcta   1800
gaggtggatc acattcttcc ttactccag tccttcattg attcttacca taacaaggtg   1860
cttgtgtatt ccgatgagaa caggaagaag ggaaacagga ctaaacagg ctacttcctg   1920
gagactaata aggattggga ggcttttgag aggtacgtga ggtctaacaa gttcttctct   1980
aagaagaaga gggagtacct tcttaagagg gcttatcttc ctaggagtc agagcttatt   2040
aaggagaggc atcttaacga taccaggtac gcttctacct tcctcaagaa cttcattgag   2100
cagaaccttc aattcaagga agctgaggat aatcctagaa agaggaggt tcagactgtg   2160
aacggagtta ttactgctca ttttagaaag aggtgggac ttgagaagga taggcaagag   2220
```

```
acttaccttc atcacgctat ggatgctatt attgtggctt gcactgatca tcatatggtg  2280
actagggtta ccgagtacta ccagatcaag gagtcaaaca agtctgtgaa gaagccttat  2340
tttcctatgc cttgggaagg attcaggat  gagcttcttt ctcatcttgc ttctcagcct  2400
atcgctaaga agatttctga agagcttaag gctggatacc agtcccttga ttacattttc  2460
gtgtctagaa tgcctaagag gtctattact ggagctgctc acaagcagac tattatgagg  2520
aagggaggaa ttgataagaa ggggaagacc atcattattg agaggctcca cctcaaggat  2580
atcaagttcg atgagaacgg agatttcaag atggttggaa aggagcagga tatggctact  2640
tacgaggcta ttaagcagag atatctagag cacggaaaga actctaagaa ggctttcgag  2700
actcctcttt acaagccttc taagaaggga accggaaacc ttattaagag agttaaggtt  2760
gagggacagg ctaagtcttt cgttagagag gttaatggag gagttgctca gaatggagat  2820
cttgtgaggg ttgatctttt cgagaaggac gataagtact acatggtgcc tatctacgtt  2880
cctgatactg tttgttccga gcttcctaag aaggttgttg cttcttctaa gggatacgag  2940
caatggctta cccttgataa ctctttcacc ttcaagttct ctctctaccc ttacgatctt  3000
gttaggctag ttaagggaga tgaggatagg ttcctttact tcgggaccct cgatattgat  3060
tctgataggc tcaacttcaa ggatgtgaac aagccttcta agaagaacga gtacaggtac  3120
tctctcaaga ccattgagga tcttgagaag tacgaagtgg gagttcttgg agatcttaga  3180
cttgttagaa aggagactag gaggaacttc cac                               3213

SEQ ID NO: 172       moltype = DNA   length = 3213
FEATURE              Location/Qualifiers
misc_feature         1..3213
                     note = source = /note="Description of Artificial Sequence:
                     Syntheticpolynucleotide"
misc_feature         1..3213
                     note = source = /note="APG07433.1 Corn optimized"
source               1..3213
                     mol_type = other DNA
                     organism = synthetic construct
SEQUENCE: 172
atgcgcgagc tagattacag gatcggcctg gatatcggca ctaactcaat cggctgggc   60
gtgatcgagc tgagctggaa taaagatcgc gagcgctatg aaaaggtgcg catcgtggat  120
cagggcgtta ggatgttcga tagggccgag atgccaaaga caggcgcctc actgccgaa   180
ccaaggagga tagccaggtc ttctaggagg agattaaaca ggaagtctca gcgcaagaaa  240
aatatcagga acctgctggt tcagcacggc gtgatcacaa aggaggagct ggattctctg  300
tacccactga gcaagaaaag catggacatc tggggcatta ggctagatgg cctggaccgc  360
ctattaaacc acttcgagtg ggcccgccta ttaattcacc tggcccagag gaggggcttc  420
aaatcaaata ggaagagcga attaaaggac accgagacag gcaaggtgct gtcaagcatc  480
cagctgaatg aaaagcgcct gagcctgtac aggacagtgg cgagatgtg  gatgaaagac  540
ccggacttct caaaatacga ccgcaagcgc aacagccagg acgtacgt gttctctgtg   600
tctagggccg agctggagaa ggagatcgtg acactgttcg ccgctcagag gaggttccga  660
tctccatacg cctctaagga tctgcaagag acatacctgc agatctggac acaccagctg  720
ccattcgcct ctggcaatgc catcctgaat aaagtgggct actgctctct attaaagggc  780
aaggagagga ggattccaaa ggccacctat acattccgat acttcagcgc cctggaccag  840
gtgaatagga caaggctggg cccagatttc cagccattca caaaggagca gcgcgagatc  900
atcctgaata atatgttcca gcgcaccgac tactataaaa agaagaccat cccggaggtg  960
acatactacg atataaggaa gtggctggag ctggatgaaa ccatccagtt caagggatta 1020
aactacgacc cgaacgagga gctgaagaaa atagagaaga agcgttcat aaacctgaag 1080
gccttctacg aaatcaacaa ggtggtggcc aactacagcg agcgaaccaa cgagaccttc 1140
agcaccctgg actacgacgg catcggctac gccctgaccg tgtataaaac cgacaaggat 1200
ataaggagct acctgaaatc aagccacaac ctgccgaagc gctgctacga cgaccaatta 1260
atcgaggagc tgctgagcct gagctatact aagttcggcc acctgagcct gaaggcaatc 1320
aaccacgtgc taagcatcat gcagaagggc aatacataca aggaggccgt ggaccagctg 1380
ggctacgaca ccagcggcct gaagaaggag aagcgcagca gttcctgcc  gccgatcagc 1440
gacgagatca ccaacccgat cgtgaagcgc gccctgaccc aggccaggaa ggtggtgaac 1500
gccatcatca ggaggcacgg ctctccacat agcgtgcact cgagctggc  cagggagctg 1560
tctaagaatc acgatgagag gacaaagatc gtgtcagccc aggacgagaa ctacaagaag 1620
aataagggcg ccatctctat cctgtctgag cacggcatcc tgaacccaac aggctacgac 1680
atcgtgaggt acaagctgtg gaaggagcag ggcgagaggt gcgcctactc tctgaaggag 1740
atcccagccg atacattctt caatgagctg aagaaggaga ggaatggcgc cccaatcctg 1800
gaggtggatc acatcctgcc atactctcag agcttcatcg attcatacca caacaaggtg 1860
ctggtgtaca gcgacgagaa caggaagaag ggcaatcgca tcccatacac atacttcctg 1920
gagaccaaca aggattggga ggccttcgag aggtacgtgc gcagcaacaa gttcttcagc 1980
aagaagaagc gcgagtacct gctgaagagg gcctacctgc ctaggagtc tgagctgatc 2040
aaggagagga acctgaatga tacaaggtac gccagccct tcctgaagaa cttcatcgag 2100
cagaacctac agttcaagga ggccgaggat aacccaagga gaggaggt  tcagacagtg 2160
aatggcgtga tcagccccca cttcaggaag aggtggggcc tggagaagga taggcaggag 2220
acatacctgc atcacgccat ggatgccatc atcgtggctt gcacagatca ccacatggtg 2280
acaagggtga cagagtacta ccagatcaag gagagcaaca agagcgtgaa gaagcctac  2340
ttcccaatgc catgggaggg cttcaggatg agctactgt ctcacctgcc ctctcagcca 2400
atcgccaaga agatctctga ggagctgaag gccggctacc agtctctgga ttacatcttc 2460
gtgtctagga tgccaaagag gtctatcaca ggcgccgccc acaagcagac aatcatgagg 2520
aagggcggca tcgataagaa gggcaagaca atcatcatcg agaggctgca tctgaaggac 2580
atcaagttcg atgagaacgg cgatttcaag atggtgggaa aggagcagga tatggccaca 2640
tacgaggcca tcaagcagcg ctacctagag cacggaaaga actctaagaa ggccttcgag 2700
acaccactgt acaagccatc taagaagggc accggcaatc tgatcaagag ggtgaaggtg 2760
gagggccagg ccagtctttt cgtgagggag gtgaatggcg gcgtggccca gaatggcgat 2820
ctggtgaggg tggatctgtt cgagaaggat gataagtact acatggtgcc aatctacgtg 2880
ccagatacag tgtgctctga gctgccaaag aaggtggtgg cctcttctaa gggctacgag 2940
cagtggctaa cactggataa cagcttcaca ttcaagttca gcctgtaccc atacgatctg 3000
```

```
gtgaggctgg tgaagggcga tgaggatagg ttcctgtact tcggcacact ggatatcgat    3060
agcgacaggc tgaacttcaa ggacgtgaac aagccgagca agaagaacga gtaccgctac    3120
agcctgaaga caatcgagga cctggagaag tacgaggtgg gcgtgctggg cgatctgagg    3180
ctggtgagga aggagacaag gaggaatttc cac                                 3213
```

| | | |
|---|---|---|
| SEQ ID NO: 173 | moltype = DNA  length = 3213 | |
| FEATURE | Location/Qualifiers | |
| misc_feature | 1..3213 | |
| | note = source = /note="Description of Artificial Sequence: Syntheticpolynucleotide" | |
| misc_feature | 1..3213 | |
| | note = source = /note="APG07513.1 Soy optimized" | |
| source | 1..3213 | |
| | mol_type = other DNA | |
| | organism = synthetic construct | |

```
SEQUENCE: 173
atgagagagc tagattacag gatcggactc gatatcggaa ctaattcaat tggatggggc    60
gtgattgagc tttcctggaa taaagatcgc gagcaatatg aaaagaccag gattgtggat    120
aagggagtga ggatgttcga taaggctgaa attcctaaga ctggagcttc tcttgctgaa    180
ccaagaagaa ttgctagatc tagcaggagg agattaaaca ggaagtctca gcgcaagaag    240
gatataagga acctttctcgt tcagcatgaa atcatttccc agaaggaatt aacctctctc    300
taccctctct ccaaatcaag catggacatc tgggatataa ggcttgatgg actcgatagg    360
cttcttgata gatttgagtg ggctaggctt ctaatacacc ttgctcaaag aaggggcttc    420
aaaatcaaacc gcaagtccga attaaaggat gttgagactg gaaaggtgct ttcaagcatc    480
caggtgaatg aaaagaggct ttctttgtat aggactgttg gggagatgtg gatgaaaaac    540
gccgattgct caaaatatgg aaagaggagg aactctccta acgatacgt gttttctgtt    600
tctagggctg atcttgagaa ggagattgtg actcttttg aggctcagag gaagttccaa    660
tcttcttacg cttctgtgga tctccaaaag acatacattc agatttgggc tcatcagctt    720
ccttttgctt ctggaaacgc cattgtgaat aaagtgggat actgctccct attaaaggga    780
aaggagaaga gagtgcctaa ggctacctat acattccagt acgatacgct acttcaatac cctcgatcaa    840
atcaacagaa ctaggcttgg acctaacttc cagccttta ctaaggagca gaggggatata    900
atcctcgata aaatgttcca gcgcaccgac tactataaaa agaagaccat ccccgaggtg    960
acctactacg atataagaaa gtggcttgct ctcgatgaaa ccattcagtt caagggacta    1020
acttatgacc ccaacgagga gctgaagaaa atagagatga aaccctttcat aaacctcaag    1080
ccctttctacg aaaatcaagga ggtggtaacc aactacgcca agaaaaccaa cgaggtgttc    1140
tctgctcttg attacgatac tgtggcttac gctctttaccg tgtataaaac cgacaaggat    1200
ataaggtctt acctcaagcg ctccaataat ctctctaaga ggtgctacga cgatcaatta    1260
attgaggagc ttctcaccct ctcctatact aagttcggac acctctcttt caaggcaatc    1320
aaccatgtgc ttccaataat gcaagaggga agaacttacc aagaggcaat acaccagctt    1380
ggatacgata caaccaacct caagaaggag aatagaagca tgttcctccc aatcatccct    1440
gatgaaataa ccaaccctat tgtgaagaga gctttgactc aagctaggaa ggtggtgaat    1500
gcaataatta ggaggtacgg atcacctaac tctgtgcata ttgagcttgc cagggaatta    1560
agcaagtctc atgatgagag gaagaagatt atgactgctc acgacgagaa ctacaagaag    1620
aacaagggag ctgtgtccat tctcattgat aacggaattc ttaaccctac cggatacgat    1680
attgtgaggt acaagttgtg gaaggagcaa ggagagagat gcgcttactc tcttaagaag    1740
attcctgcta acaccttctt caacgagctt aagaaggaaa gatctggacc tcctgttctt    1800
gaggtggatc acattctacc ttactcccag tcctcatgg attcttacca taacaaggtg    1860
cttgtttacg gagatgagaa ccaaaagaag gggaacagga ttcctacac tttcttctct    1920
gaagaagata aggagtggga gtctttcgag tcttacgtga ggtccaactc cttcttctct    1980
aagaagaaga ggggatacct tcttaagaag gcttatcttc ctaggagtc taaccttatt    2040
aaggagagcc accttaacga taccaggtac gcttcatctt acctcaagaa cttcatcgag    2100
aagaaccttaa agttcaagga ggctgtggga attactagga agaagtacgt tcagactgtg    2160
aacgagtgaa ttactgctca tcttagaaag agatggggac ttgagaagga taggcaagag    2220
acttacctttc atcacgctat ggatgctatt attgtgggctt gcactgatca ccatatggtg    2280
actaaggtta ccgagtacta ccaaattaag gaggggaaca agtccatcaa gaagccttat    2340
tttcctctac cttggatggg attcaggggag gagattcttt ctcatcttga gtctcaacct    2400
atcgctagaa agatttccga ggagcttaag attggatacc agtccctga ttacattctt    2460
gtgtctagaa tgcctaagag gtctgttact ggatctgctc atgatcagac tgtgatgaag    2520
aaggggggata ttgataagga ggggaagacc atcattatta agaggggtgca cctcaaggac    2580
atcaagttcg atgaaacgg agatttcaag atggttggaa aggagcagga tctagctact    2640
tacgaggcta ttaagcagag gtatcttgag tataggaagg agtctaagaa ggcttttcgag    2700
actcctcttt acaagccttc taagaaggga aaggggaacc tcatcaagaa gattaaggtt    2760
gaggttcaga ctaagtcttt cgtgagggag attaatggag gagttgctca gaatggagat    2820
cttgtgaggg ttgatctttt cgagaaggac aacaggtact acatggtggcc tatctacgtt    2880
gttgatactg ttaggtctga gctacctaac aaggctgtta cttcttctaa gggatacgaa    2940
cagtggctct ctattgataa ctctttcacc ttcaagttct ctctctaccc ttacgatctt    3000
gttaggcttg ttaagggaga tgaggatagg ttcctctact tctccaccct cgatattaac    3060
tctgataggc tcaacttcaa ggatgtgaac aagcttctaa gcaagctga gtacaggtac    3120
tctcttaaga ccattgaaaa cctggagaag tacgagattg gagttcttgg agatctaagg    3180
cttgttaggc aggagaccag gaagatttc aag                                  3213
```

| | | |
|---|---|---|
| SEQ ID NO: 174 | moltype = DNA  length = 3213 | |
| FEATURE | Location/Qualifiers | |
| misc_feature | 1..3213 | |
| | note = source = /note="Description of Artificial Sequence: Syntheticpolynucleotide" | |
| misc_feature | 1..3213 | |
| | note = source = /note="APG07513.1 Corn optimized" | |
| source | 1..3213 | |

```
                    mol_type = other DNA
                    organism = synthetic construct
SEQUENCE: 174
atgcgcgagc tagattacag gatcggcctg gatatcggca ctaactcaat cggctggggc    60
gtgatcggac tgagctggaa taaagatcgc gagcagtatg aaaagaccag gatcgtggac   120
aagggcgtga ggatgttcga taaggccgag atcccaaaga caggcgcctc tctggccgaa   180
ccaaggagga tcgccaggtc ttctaggagg agattaaaca ggaagtctca gcgcaagaag   240
gatataagga acctgctggt ccagcatgaa atcatcagcc agaaggagct gacaagcctg   300
tacccgctga gcaagtcaag catggacatc tgggatataa ggctggatgg cctggatagg   360
ctgctggata ggttcgagtg ggccaggctg ctgatacatc tggcccagag gaggggcttc   420
aaatcaaatc gcaagagcga attaaaggac gtggagacag gcaaggtgct gtcaagcatt   480
caggtgaatg aaaagaggct gagcctgtac aggacagtgg gcgagatgtg gatgaaaaac   540
gccgactgct caaaatacgg caagcgccgc aacagcccaa acgagtacgt gttctctgtg   600
tctagggccg atctggagaa ggagatcgtg cactgttcg aggcccagag gaagttccaa   660
tcttcttacg cctctgtgga cctgcagaag acatacatcc agatctgggc ccaccagctg   720
ccattcgcct ctggcaatgc catcgtgaat aaagtgggct actgctctct attaaagggc   780
aaggagaaga gggtgccaaa ggccacctat acattccagt acttcaatac cctggaccaa   840
atcaacagga cccgcctggg cccaaacttc cagccattca caaggagca gcgcgatata   900
atcctggata aaatgttcca gcgcaccgac tactataaaa agaagaccat cccggaggtg   960
acatactacg atataaggaa gtggctggcc ctggatgaaa ccatccagtt caagggccta  1020
acctacgacc cgaacgagga gctgaagaag atcgagatga aaccgttcat aaacctgaag  1080
ccgttctaca aaatcaagaa ggtggtaacc aactacgcca agaaaaccaa cgaggtgttc  1140
agcgccctgg actacgacac cgtggcctac gccctgaccg tgtataaaac cgacaaggat  1200
ataaggagct acctgaagcg cagcaataat ctgagcaagc gctgctacga cgaccaatta  1260
atcgaggagc tgctgacccct gagctatact aagttcggcc acctgagctt caaggcaatc  1320
aaccacgtgc tgccaataat gcaggagggc cgcacctacc aggaggcaat acaccagctg  1380
ggctacgaca caaccaacct gaagaaggag aaccgaagca tgttcctgcc aataatcccg  1440
gacgagataa ccaacccgat cgtgaagcgc gccctgaccc aggcccgcaa ggtggtgaac  1500
gcaataatcc gccgctacgg ctcaccgaac agcgtgcaca ttgagctggc ccgcgaatta  1560
agcagagccc acgacgagcg caagaagatc atgaccgccc acgatgaaaa ctacaagaaa  1620
aataagggcg ccgtgagcat cctgatcgac aacggcatcc tgaacccgac cggctacgac  1680
atcgtgcgct acaagctgtg gaaggagcag ggcgagaggt gcgcctactc tctgaagaag  1740
atcccagcca caccttctt caacgagctg aagaaggaga ggtctggccc accagtgctg  1800
gaggtggatc acatcctgcc atactcacag agcttcatcg atagctacca caacaaggtg  1860
ctggtgtacg gcgatgagaa ccagaagagg ggcaatcgca tcccatacac attcttcagc  1920
gaggaggata aggagtggga gagcttcgag agctacgtga ggagcaacag cttcttcagc  1980
aagaagaaga ggggctacct gctgaagaag gcctacctgc aagggagtc taacctgatc  2040
aaggagaggc acctgaacga tacaaggtac gccagcagct acctaaagaa cttcatcgag  2100
aagaacctga agttcaagga ggccgtgggc atcacccgca agaagtacgt ccagacagtg  2160
aacggcgtga tcacagccca cctgaggaag aggtgggcc tggaagga taggcaggag  2220
acatacctgc atcacgccat ggatgccatc atcgtggctt gcacagatca ccacatggtg  2280
acaaggtgac cagagtacta ccagatcaag gagggcaaca agagcatcaa gaagccatac  2340
ttcccactac catggatggg cttcagggag gagatcctgt ctcacctgga gtctcagcca  2400
atcgccagga gatctctga ggagctgaag atcggctacc agtctccaga ttacatcctg  2460
gtgtctagga tgccaaagag gtctgtgaca ggctctgccc acgatcagac agtgatgaag  2520
aagggcgata tcgacaagaa gggcaagacc atcatcatca gagggtgca cctgaaggac  2580
atcaagttcg acgagaacgc cgacttcaag atggtgggca aggcaggaa tctagcccaca  2640
tacgaggcca tcaagcagcg ctacctggaga tacaggaagg agtctaagaa ggccttcgag  2700
acaccactgt acaagccatc taagaagggc aagggcaacc tgatcaagaa gatcaaggtg  2760
gaggtccaga ccaagagctt cgtgagggag atcaatggcg gcgtggccca gaatggcgat  2820
ctggtgaggg tggatctgtt cgagaaggat aacaggtact acatggtact aatctactg  2880
gtggatacag tgaggagcga gctaccaaac aaggccgtga catcttctaa gggctacgag  2940
cagtggctga gcatcgacaa cagcttcacc ttcaagttca gcctgtaccc atacgatctg  3000
gtgaggctga tgaagggcga tgaggacagg ttcctgtact tcagcacact ggacatcaac  3060
agcgacaggc tgaacttcaa ggacgtgaac aagccatcta agcaggccga gtacaggtac  3120
agcctgaaga ccatcgagaa cctgagcaag tacgagatcg gcgtgctggg cgatctaagg  3180
ctggtgaggc aggagacaag gaagatcttc aag                                3213

SEQ ID NO: 175        moltype = DNA  length = 3216
FEATURE               Location/Qualifiers
misc_feature          1..3216
                      note = source = /note="Description of Artificial Sequence:
                      Syntheticpolynucleotide"
misc_feature          1..3216
                      note = source = /note="APG08290.1 Soy optimized"
source                1..3216
                      mol_type = other DNA
                      organism = synthetic construct
SEQUENCE: 175
atgtctgagc tagattacag gatcggactc gatatcggaa ctaattcaat tggatgggga    60
gtgattgagc ttttctggaa taaagatcgc gagcgctatg aaaaggttag gattgtggat   120
aagggagtga ggatgttcga taaggccgag attcctaata aggagcttc acttgctgaa   180
ccaagaagga ttgctagatc tagcaggagg agattaaaca ggaagtctca gaggaagaag   240
gagattagga acctcttgt tcagcacgga atgattacca aggaggagct tgatcttctc   300
tacccctctct ccaagaaatc aatcgatatc tgggatataa ggcttgatgg actcgatagg   360
ctattaaaacc atcttgagtg ggctaggctt ctaatacacc ttgctcaaag aaggggcttc   420
aaatcaaacc gcaagtccga attaaaggat gctgagactg aaaggttct ttcaagcatc   480
caggtgaatg aaaagaggct ttttcttgtat aggactgtgg gcgagatgtg gataaaagat   540
gccgagttct caaaatatga taggaggagg aactctccta cgagtacgt gttttctgtt   600
```

```
tctagggctg atcttgagaa ggagattgtg actttgtttg aggctcaacg caagttccaa    660
tcaagctacg cttctaagaa ccttcaagag acctaccttc aaatttgggc tcatcagctt    720
ccttttgctt ccgggaacgc tattctcaat aaagtgggat actgctcctt attaaaggga    780
aaggagagaa ggattcctaa ggccacctat acattccagt acttctctgc tcttgatcaa    840
gtgaatagaa ctaggcttgg acctgatttc caacctttca ctcaggagca gaaggaaata    900
atcctcgata aaatgttcca gcgcaccgac tactataaaa agaagaccat ccccgaggtg    960
tcctactacg atataagaaa gtggcttgag cttgatgaaa ccattcagtt caagggatta   1020
aactacgacc ccaacgagga gctgaagaaa atagagaaga agcccttcat aaacctcaag   1080
gccttctacg aaatcaagaa ggtggttgct aactacgctg aacgaaccaa cgaagcattc   1140
tctaccctcg attacgatgc tattgcttac gctcttaccg tgtataaaac cgacaaggat   1200
ataaggtcct acctcaagaa atcaaacaac ctctccaaga ggtgctacga cgatcaatta   1260
atcgaggagc ttttcaccct ctcctatact aagttcggac acctctcttt caaggcaatc   1320
aaccatgtgc ttcctattat gcaagaggga agaacttacc aagaggctat tcatcagctt   1380
ggatacgata ccaccaacct taagaaggag aacaggtcta tgttcctccc tctcattcct   1440
gatgagatta ctaaccctat tgtgaagagg gctattactc aagctaggaa ggtggtgaat   1500
gctattatta ggaggtacgg atcacctaac tctgtgcata ttgagcttgc tgggagctt    1560
tctaagtctc atgatgagag gaagaagatt atgactgctc acgacgagaa ctacaagaag   1620
aacaaggggg ctatttccat tctcattgag aacggaattc ttaaccctac cggatacgat   1680
attgtgaggt acaagttgtg gaaggagcaa ggagagagat gcgcttactc tcttaaggaa   1740
attcctcctg ataccttctt caacgagctt aagaaggaga ggaacggatc acctattctt   1800
gaggtggatc acattcttcc ttactcccag tccttcattg attcttacca taacaaggtg   1860
cttgtgtatt ccgatgagaa caggaacaag ggaaacagga ttccttacac ctacttcctt   1920
gagactaata aggattggga ggcttttgag aggtatgtga ggtctaacaa gctcttctct   1980
aagaagaaga gggagtacct ccttaagaag acttaccttc ctagggagtc tgagcttatt   2040
aaggagaggc atctaaacga taccaggtac gcttctacct tcctcaagaa cttcattgag   2100
cagaaccttc aattcaagga ggttgaggtt aaccttagga agaagagggt tcagactgtg   2160
aacggagtta ttactgctca tcttagaaag agatggggac ttgagaagaa caggcaagag   2220
acttaccttc atcacgctat ggatgctatt attgtggctt gcactgatca tcacatggtg   2280
actaggatta ccgagtacta ccagattaag gagtcaaaca agtctgtgaa gaagccttat   2340
tttcctatgc cttgggaggg attcaggat gagcttcttt ctcatcttgc ttctcagcct   2400
atcgctaaga agatttctga agagcttaag gctggatacc agtcctctga ttacattttc   2460
gtgtctagaa tgcctaagag gtcgttact ggagctgctc atgatcaaac tattaggagg   2520
aagggaggaa ttgataagaa ggggaagacc atcattatta gagggtgag gctaaaggac   2580
atcaagttcg atgagaacgg ggatttcaag atggttggaa aggagcagga tcttgctact   2640
tacgaggcta ttaagcagag atatcttgag cacaggaaga actctaagaa ggctttcgag   2700
actcctctctt acaagccttc taagaaggga accggaaacc ttatcaagag agttaagatt   2760
gagggacaga ctaaggcttt cgttagagag gttaatggag gagttgctca gaactctgat   2820
cttgtgaggg ttgatctatt cgagaaggac gataagtact acatggtgcc tatctacgtt   2880
cctgatactg tttgttccga gcttcctaag aaggttgtta agtctggaaa gggatacgag   2940
caatggctta cccttgataa ctcttttcacc ttcaagtctt ctctctaccc ttacgatctt   3000
gttaggcttg ttaagggaaa cgaggatagg ttccttact tcgggaccct cgatattgat   3060
tctgataggc tcaacttcaa ggatgtgaac aagccttcaa agcaaacga gtacaggtac   3120
tctctcaaga ccattgagaa ccttgagaag tacgaagtgg gagttcttgg agatcttagg   3180
cttgttaagc aagagaccag gaggattttc aatagg                             3216
SEQ ID NO: 176        moltype = DNA  length = 3216
FEATURE               Location/Qualifiers
misc_feature          1..3216
                      note = source = /note="Description of Artificial Sequence:
                      Syntheticpolynucleotide"
misc_feature          1..3216
                      note = source = /note="APG08290.1 Corn optimized"
source                1..3216
                      mol_type = other DNA
                      organism = synthetic construct
SEQUENCE: 176
atgtcagagc tggactacag gatcggcctg gacataggca ctaattcaat cggctggggc     60
gtgatcgagc tgttctggaa taagaccgc gagcgctatg aaaaggtgcg catcgtggac    120
aagggcgtta ggatgttcga taaggccgag atcccgaata aaggcgcctc actagccgaa    180
ccaaggagga tcgccaggtc ttctaggagg agattaaaca ggaagttctca gaggaagaag    240
gagatcagga acctgctggt ccagcacggc atgatcacac aggaggagct ggatctgctg    300
tacccactga gcaagaaaag cattgacatc tgggacatca ggctagatgg cctggacagg    360
ctgctgaatc acctggagtg ggccaggctg ctgatacatc tggcccagag gaggggcttc    420
aaatcaaatc gcaagtctga attaaaggat gccgagacag gcaaggtgct gtcaagcatc    480
caggtgaatg aaaagaggct gttcctctac cgcacagtgg gcgagatgtg gataaaagac    540
gccgagttca gcaagtacga caggaggagg aacagcccaa acgagtacgt gttctctgtg    600
tcaagggccg atctggagaa ggagatcgtg acactgtttg aggctcagcg caagttccaa    660
tcaagctacg ccagcaagaa cctgcaagag acctacctgc agatctgggc ccaccagctg    720
ccattcgcta gcgccaatgc catcctgaat aaagtgggct actgctctct attaaagggc    780
aaggagagga ggattcccaa ggccacctat acattccagt acttcagcgc cctgaccag    840
gtgaatagga caaggctggg cccagatttc cagccattca cacaggagca gaaggaaata    900
atcctgata aaatgttcca gcgcaccgac tactataaaa agaagaccat cccgaggtg    960
tcatactacg atataaggaa gtggctggag ctggatgaaa ccatccagtt caagggatta   1020
aactacgacc cgaacgagga gctgaagaaa atagagaaga agccgttcat aaacctcaag   1080
gccttctacg aaatcaagaa ggtggtggcc aactacgccg agcgaaccaa cgaagcattc   1140
agcaccctgg actacgacgc catcgcctac gccctgaccg tgtataaaac cgacaaggat   1200
ataaggtcat acctgaagaa atcaaacaac ctgagcaagc gctgctacga cgaccaatta   1260
atcgaggagc tgttcaccct gagctatact aagttcggcc acctgagctt caaggcaatc   1320
aaccacgtgc tgccaataat gcaggagggc cgcacctacc aggaggcaat acaccagctg   1380
```

```
ggctacgaca ccaccaacct gaagaaggag aaccgcagca tgttcctgcc gctaatcccg 1440
gacgagatca ccaacccgat cgtgaagcgc gccatcaccc aggctaggaa ggtggtgaac 1500
gccatcatcc gccgctacgg cagcccgaac agcgtgcaca tcgagctggc ccgcgagctg 1560
agcaagagcc acgacgagcg caagaagatc atgacagccc acgacgagaa ctacaagaag 1620
aacaagggcg ccatctcaat cctgatcgag aacggcatcc tgaacccaac cggctatgac 1680
atcgtgcgct acaagctgtg gaaggagcag ggcgagaggt gcgcctactc tctgaaggag 1740
atcccaccag atacattctt caacgagctg aagaaggaga ggaatggctc tccaatcctg 1800
gaggtggatc acatcctgcc atacagccag tcattcatcg acagctacca caacaaggtg 1860
ctggtgtaca gcgatgagaa caggaacaag ggcaaccgca tcccgtacac atacttcctg 1920
gagaccaaca aggattggga ggccttcgag aggtacgtga ggagcaacaa gctgttcagc 1980
aagaagaagc gcgagtacct gctgaagaag acctacctgc aaggagtc agagctgatc 2040
aaggagaggc acctgaacga tacaaggtac gctagcacct tcctgaagaa cttcatcgag 2100
cagaacctgc agttcaagga ggtggagtg aacctgagga agaagcgcgt tcagacagtg 2160
aacggcgtga tcacagccca cctgaggaag aggtgggcc tggagaagaa taggcaggag 2220
acatacctac accacgccat ggatgccatc atcgtggctt gcacagatca ccacatggtg 2280
acaaggatca cagagtacta ccagatcaag gagagcaaca agagcgtgaa gaagccatac 2340
ttcccaatgc catgggaggg cttcagggat gagctgctgt ctcacctggc ctctcagcca 2400
atcgccaaga agatctcaga ggagctgaag gccggctacc agtcttctga ttacatcttc 2460
gtgtctagga tgccaaagag gtctgtgaca ggcgccgccc acgatcagac aatcaggagg 2520
aagggcggca tcgataagaa gggcaagaca atcatcatca agagggtgag gctgaaggat 2580
atcaagttcg atgagaacgg cgatttcaag atggtgggca aggagcagga tctagccaca 2640
tacgaggcca tcaagcagcg ctacctggag cacaggaaga actctaagaa ggccttcgag 2700
acaccactgt acaagccatc taagaagggc accggcaatc tgatcaagag ggtgaagatc 2760
gagggccaga caaaggcctt cgtgagggag gtgaatggcg cgtggccca gaattctgat 2820
ctggtgaggg tggatctatt cgagaaggac gataagtact acatggtgcc aatctacgtg 2880
ccagatacag tgtgctccga gctgccaaag aaggtggtga gtctggcaa gggctacgag 2940
cagtggctca cactggataa cagcttcaca ttcaagagca gcctgtaccc atacgatctg 3000
gtgaggctgg tgaagggcaa tgaggacagg ttcctgtact tcggcacact agacatcgat 3060
agcgacaggc tgaacttcaa ggacgtgaac aagccaagca agcagaacga gtaccgctac 3120
agcctgaaga ccatcgagaa cctggagaag tacgaggtgg cgcgtgctggg cgatctgagg 3180
ctggtgaagc aggagacaag gaggatcttc aatagg           3216
```

SEQ ID NO: 177          moltype = DNA   length = 4011
FEATURE                 Location/Qualifiers
misc_feature            1..4011
                        note = source = /note="Description of Artificial Sequence:
                        Syntheticpolynucleotide"
misc_feature            1..4011
                        note = source = /note="APG05459.1 Soy optimized"
source                  1..4011
                        mol_type = other DNA
                        organism = synthetic construct
SEQUENCE: 177
```
atgaagaagg actacgtgat cggactagat attggaacta actctgtggg atgggctgtt 60
atgactgagg attaccagct agttaagaag aagatgccca tctacgggaa tacagagaag 120
aagaagatca agaagaactt ctggggagtg agactatttg aagagggtca tactgctgag 180
gataggagat taaagagaac tgctaggaga aggatttgca ggaggagaa caggcttcgt 240
taccttcaag cattctttga agaggctatg accgctctag atgaaaattt cttcgctagg 300
cttcaggagt cttttcttgt gcctgaggat aaaaagtggc acaggcatcc tattttttgct 360
aagttagagg atgaggtggc ttaccatgaa acctacccta ctatctacca ccttaggaag 420
aagttggctg attcttcaga gcaagccgac ttgagattaa tctaccttgc tcttgcccac 480
attgtaaaat ataggggaca cttccttatc gagggaaaac tctccaccga aaatatttca 540
gtgaaggagc agtttcagca gtttcatgatc atctataacc aaaccttcgt gaacggagaa 600
tcaaggcttg tgtctgctcc tcttcctgag tccgttataa ttgaggagga acttactgag 660
aaagcatcca gaaccaagaa gtctgagaag gttcttcaac agttcctca agagaaggct 720
aacggacttt tcggacagtt cctcaaatta atggtgggga ataaagccga cttcaagaag 780
gttttttggac ttgaggagga ggccaaaata acttacgctt ctgagtctta tgaggaggat 840
cttgagggaa tactagctaa ggtgggagat gaatacagcg atgttttcct tgctgctaag 900
aacgtttacg acgctgtgga attaagcacc atactagctg actccgataa aaagtctcac 960
gccaaactct cttcaagcat gattgttagg ttcactgagc atcaggagga tcttaagaag 1020
ttcaagaggt tcattaggga gaactgcccct gatgagtacg ataaccttttt caagaacgag 1080
caaaaggatg ggtacgctgg atacattgct catgctggaa aggtgtcaca attaaagttc 1140
taccagtacg tgaagaaaat aatccaggat atcgctggga ccgagtactt ccttgagaaa 1200
atagctcagg agaacttcct taggaagcag aggacttttcg gattcctcac 1260
caaatacacc ttgctgagct acaggcaata attcataggc aagctgcata ctatcctttc 1320
ctcaaggaga atcaagagaa aatagagcag ctcgtgacct tcagaattcc atactacgtg 1380
ggacctcttt ctaagggaga tgcttctact tttgcttggc ttaagagaca gtcagaggaa 1440
ccaattaggc cttggaatct tcaagagact gtggatcttg atcaatctgc tactgctttc 1500
atagagagga tgaccaactt cgatacatac cttccttctg agaaggtgct ccctaagcat 1560
tctctcctct atgaaaagtt catggtgttc aacgagctaa ccaaaatatc ctacaccgac 1620
gataggggaa tcaaggctaa tttctctgga aaggagaagg agaaaatatt cgactacctc 1680
ttcaagacca ggaggaaggt gaagaagaag gacataaatac agttctaccg caacgaatac 1740
aacaccgaga ttgtgacctt gtcaggactt gaggaggatc aattcaacgc ttcttttctct 1800
acctaccagg atctattaaa gtgcggactt actagggctg agcttgatca tcctgataat 1860
gctgagaagc tggaggacat aatcaagata ctaaccatct tcgaggatag gcaaggatt 1920
aggacccagc tttctacttt caagggacaa ttctctgctg aggttcttaa gaagttggag 1980
aggaagcatt atactggatg gggaaggctc tctaagaagc tcattaacgg aatctacgat 2040
aaggagtcag ggaagaccat cctagattac ctcattaagg atgatggagt gtctaagcac 2100
tacaacagga acttcatgca gctcattaac gattcccagc tctccttcaa gaacgctatt 2160

```
caaaaggctc aatcttctga gcatgaagag actctttctg agactgttaa cgaattagct   2220
gggtccsctg ctattaagaa gggaatctac cagtctctca agattgtgga tgagcttgtg   2280
gctattatgg gatatgctcc taagaggatt gttgttgaga tggctaggga gaaccaaact   2340
acttctactg gaaagaggag gtctattcag aggctaaaga ttgttgaaaa ggctatggct   2400
gagattggat ctaaccttct taaggagcag cctactacta acgagcaact tagggatacc   2460
aggctcttcc tttactacat gcagaacgga aaggatatgt acactggaga tgagcttttc   2520
cttcataggc tctcacacta cgacatagat cacattatcc ctcagtcctt catgaaggat   2580
gattctctcg ataaccttgt gcttgtggga tctactgaga atagggggaaa gtctgatgat   2640
gttccttcta aggaggtggt taaggatatg aaggcttact gggagaaact atacgctgct   2700
ggacttattt ctcaaaggaa gttccagaga cttactaagg gagagcaagg aggacttact   2760
cttgaggata aggctcattt cattcaaagg cagcttgttg agaccaggca gattactaag   2820
aacgtggctg gaattctaga tcaaaggtac aacgctaact ctaaggagaa gaaggttcag   2880
atcattaccc tcaaggcttc tcttacctcc cagttcaggt ctattttcgg actttacaag   2940
gttagggagg tgaacgatta ccatcatgga caagatgctt accttaactg cgtggttgct   3000
actactctac ttaaggttta tcctaacctt gctcctgagt tcgtttacgg agagtatcct   3060
aagttccagg ctttcaagga gaataaggct accgctaaga ccattatcta caccaacctt   3120
atgaggttct ttactgagga tgagcctagg tttatgaagg atggagagat tctctggtca   3180
aactcctacc tcaagaacat caagaaggag cttaactacc accagatgaa cattgtgaag   3240
aaggtggagg ttcaaaaggg aggattctcc aaggagtcta ttaagcctaa gggacccttc   3300
aacaagctca ttcctgtgaa gaacggactt gatcctcaaa agtacggagg attcgattca   3360
cctgttgttg cttacactgt tcttttcact cacgaaaagg ggaagaagcc tctcattaag   3420
caggagattc tcggaattac cattatggag aagactaggt tcgagcagaa ccctattctt   3480
tttctagagg agaagggatt tcttaggcct agggttctta tgaagctccc taagtacact   3540
ctttatgagt ttcctgaggg aagaaggaga cttcttgctt ctgctaagga ggctcaaaag   3600
ggaaaccaaa tggttcttcc tgagcacctt cttactcttc tttaccatgc taagcaatgc   3660
ctacttccta accaatctga gtctcttgct tacgtagaac aacatcaacc tgagttccaa   3720
gagattcttg agagggttgt ggatttcgct gaggttcata cccttgctaa gtctaaggtt   3780
cagcagattg ttaagttgtt cgaggctaac cagactgctg atgttaagga gatcgctgct   3840
tcattcattc agcttatgca attcaatgct atgggtgctc cttctacctt caagttcttc   3900
cagaaggata tagagagggc taggtacacc tccatcaagg agattttcga tgctaccatt   3960
atctaccagt ctactactgg actttatgag actaggagga aggtggttga t           4011
```

SEQ ID NO: 178      moltype = DNA  length = 4011
FEATURE               Location/Qualifiers
misc_feature       1..4011
                       note = source = /note="Description of Artificial Sequence:
                       Syntheticpolynucleotide"
misc_feature       1..4011
                       note = source = /note="APG05459.1 Corn optimized"
source             1..4011
                       mol_type = other DNA
                       organism = synthetic construct
SEQUENCE: 178

```
atgaaaaagg actacgtgat cggcctggac atcggcacta attcagtggg ctgggccgtg   60
atgcagagat actaccagct ggtgaagaag aagatgccta tctacggcaa cactgagaag   120
aagaagatca agaagaactt ctgggcgtg cgcctattcg aggagggcca cacagccgag   180
gaccgcagat taaagaggac agccaggagg aggatctca taggctgcgc   240
tacctgcaag cattcttcga ggaggccatg acagccctgg atgaaaattt cttcgccagg   300
ctgcaggagt ctttcctagt gccggaggat aaaaagtggc acaggcaccc tatcttcgcc   360
aagctggagg atgaggtggc ctaccatgaa acatacccaa caatctacca cctgaggaag   420
aagctggccg attcttctga gcaggccgac ctgagattaa tctacctggc cgtgccccac   480
atcgtcaaat acaggggcca cttcctgatc gagggcaaac tgagcacaga aaatatcagc   540
gtgaaggagc agttccagca gttcatgatc atctataacc aaaccttcgt gaacggcgaa   600
tcaaggctgt gagcgcccc actgccggag agcgttattaa tcgaggagga actgaccgag   660
aaagcatccc gaaccaagaa gagcgagaag gtgctgcagc agtttcccgca agagaaggct   720
aatggcctgt tcggtcagtt cctgaaactg atggtgggca ataaagccga cttcaagaag   780
gtgttcggcc tagaggagga ggccaaaata acctacgcca gcgagagcta cgaggaggac   840
ctggagggca tactagccaa ggtgggcgat gaatacagcg atgtgttcct ggccgccaag   900
aatgtgtacg atgccgtgga gctgtctaca atactagccg acagcgataa aaagagccac   960
gccaagctct cttcaagcat gatcgtgagg ttcacagagc atcaggagga cctgaagaag   1020
ttcaagcgct tcatcaggga gaactgccc gacgagtacg acaacctgtt caagaacgag   1080
cagaaggatg gctacgccgg atacatcgcc cacgccggta agtgtcccca ttaaagttc   1140
taccagtacg tgaagaaaat aatccaggac atcgccggcg ccgagtactt cctggagaaa   1200
atagcccagg agaacttcct gcgcaagcag aggactcg acaaccgcgac catcccgcac   1260
cagatacatc tggccgagct gcaggccatc atacataggc aggccgcata ctacccattc   1320
ctaaaggaga accaagagaa aatagagcag ctggtgacct tccgcatccc atactacgtg   1380
ggcccactgt ctaagggcga tgcctctaca ttcgcctggc tgaagaggca gtctgaggaa   1440
ccaatcaggc catggaatct gcaagagaca gtggatctgg atcagtctgc cacagccttc   1500
atcgagagga tgaccaactt cgatacacat ctaccaaggg agaaggtgct gccaaagcat   1560
agcctgctgt atgaaaagtt catggtgttc aacgagctaa ccaagatcag ctacaccgac   1620
gaccgcggaa tcaaggccaa cttcagcggc aaggagaagg agaaaatatt cgactacctg   1680
ttcaagaccc gccgcaaggt gaagaagaag gacataaatc agttctaccg caacgaatac   1740
aacaccgaga tcgtgaccct gagcggcctt gaggaggacc agttcaacgc cagcttctca   1800
acctaccagg acctattaaa gtgcggcctg accgcgccg agctgaccaa cccgataac   1860
gccgagaagc tggaggacat aatcaagata ctaaccatct tcgaggaccg ccagcgcatc   1920
cgcacccaat taagcacctt caagggccag ttcagcgccg aggtattaaa gaagctggag   1980
cgcaagcatt acacaggctg gggcaggctg agcaagaagc taatcaacgg catctacgac   2040
aaggagagcg gcaagaccat ccttgactac ctgatcaagg acgatggcgt gagcaagcac   2100
tacaaccgca acttcatgca gctgatcaac gacagccagc tgagcttcaa gaacgccatc   2160
```

```
cagaaggccc agtcttctga gcacgaggag acactgtctg agacagtgaa tgagctggcc   2220
ggctcaccag ccatcaagaa gggcatctac cagtctctga agatcgtgga tgagctggtg   2280
gccatcatgg gctacgcccc aaagaggatc gtggtggaga tggccaggga gaatcagaca   2340
acatcaacag gcaagaggag gtctatccag aggctgaaga tcgtggagaa ggccatggcc   2400
gagatcggct ctaatctgct gaaggagcag ccaacaacaa atgagcagct gagggataca   2460
aggctgttcc tgtactacat gcagaatggc aaggatatgt acacaggcga tgagctgtct   2520
ctgcataggc tgagccacta cgacatcgat cacatcatcc cgcagtcatt catgaaggac   2580
gactctctgg ataatctggt gctggtgggc tctacagaga acaggggcaa gagcgatgat   2640
gtgccatcta aggaggtggt gaaggatatg aaggcctact gggagaagct gtacgccgcc   2700
ggcctgatct ctcagaggaa gttccagagg ctgacaaagg gcgagcaggg cggcctgaca   2760
ctggaggata aggcccactt catccagagg cagctagtgg agacaaggca gatcacaaag   2820
aatgtggccg gcatcctgga tcagaggtac aatgccaatt ctaaggagaa gaaggttcag   2880
atcatcacac tgaaggcctc tctgacatct cagttcaggt ctatcttcgg cctgtacaag   2940
gtgcgcgagg tgaatgatta ccaccacggc caggatgcct acctgaattg cgtggtggcc   3000
acaacactac tgaaggtgta cccaaatctg gccccagagt tcgtgtacgg cgagtaccca   3060
aagttccagg ccttcaagga gaataaggcc acagccaaga caatcatcta cacaaacctg   3120
atgaggttct tcagagagga cgagccaagg ttcatgaagg atggcgagat cctgtgggagc  3180
aacagctacc tgaagaacat caaggaggag ctgaactacc accagatgaa catcgtgaag   3240
aaggtggagg tccagaaggg cggcttctca aaggagagca tcaagccgaa gggcccgagc   3300
aacaagctga tcccagtgaa gaatggcctg gacccacaga agtacggcgg ctttgattct   3360
ccagtggtgg cctacacagt gctgttcaca cacgagaagg gcaagaagcc actgatcaag   3420
caggagatcc tgggcatcac aatcatggag aagacaaggt tcgagcagaa cccaatcctg   3480
ttcctggagg agaagggctt cctgaggcca agggtgctga tgaagctacc aaagtacaca   3540
ctgtacgagt tccagagggg caggaggagg ctgctggcct tgccaaggga ggcccagaag   3600
ggcaatcaga tggtgctgcc tgagcacctg ctgacactgc tgtaccacgc caagcagtgc   3660
ctgctgccaa atcagtctga gtctctggcc tacgtgaggc agcaccagcc agagttccag   3720
gagatcctgg agagggtggt ggatttcgcc gaggtgcaca cactggctaa gtctaaggtt   3780
cagcagatcg tgaagctgtt cgaggccaat cagacagccg atgtgaagga gatcgccgcc   3840
tcattcatcc agctgatgca gttcaatgcc atgggcgccc catctacatt caagttcttc   3900
cagaaggata tcgagagggc caggtacaca tctatcaagg agatcttcga tgccacaatc   3960
atctaccagt ctacaacagg cctgtacgag acaaggagga aggtggtgga t           4011
```

SEQ ID NO: 179    moltype = DNA  length = 4308
FEATURE      Location/Qualifiers
misc_feature    1..4308
          note = source = /note="Description of Artificial Sequence:
          Syntheticpolynucleotide"
misc_feature    1..4308
          note = source = /note="APG04583.1 Soy optimized"
source       1..4308
          mol_type = other DNA
          organism = synthetic construct
SEQUENCE: 179

```
atggccaaaa atattctagg actcgatctc ggaaccaact ctattggatg ggctcttgtt   60
cagcaggact ttgaaaataa ggaggggaac atactaggaa tggggtccag aataattcct   120
atgtctcagg atatactagg agagttcggg aagggtaact ctatttctca aactgctgag   180
agaactggat ataggggagt tagaaggtta agggagagac atcttcttag aagggagagg   240
cttcataggg tgcttcatct tcttggattc ctacctaagc attacgacga gaaaatagac   300
ttcactcaga ggttcgggaa gttcatcaat caagctgaac caaagttggc tttcgattca   360
gagttcctct tcaaggactc cttccatgaa atgctagctg acttcaagca gaatcaacct   420
gagttcctca aggataaaaa cggagaggat tgccttgttc cttacgactg gactatatac   480
tacctaagga agaaagcatt gacccagaag atcgaaaaat atgagctggc ctggctcatc   540
ctcaacttca atcaaaagag gggatactat caattaaggg gagaggagga aaggagaac   600
cctaataaac tcgtggggtt ccactctctc aaaatagtgg atgttattcc tgacgctgaa   660
accaataaaa agggagagac ctggtactca cttcatcttg agaacgatg ggtttatagg   720
aggtcctcca aaatatctct cgctgattgg aaggacaaag tgagggattt cattgtgacc   780
accgatctta atgatgatgg atcagagaag ctcgataagg atggaattgt gaagaggtct   840
tttagggctc cttctgctga tgactggacc ctattaaaga agaagaccga gaaggatatc   900
gacaactcta ataaaaccgt ggggacctac atctacgaca acctcctatt aaaccccaag   960
cagaaaatca agggaaagat ggttaggacc attgagagga gttctacaa gcaagactg  1020
gagcagatat taaagactca gaaggagttc attctgagc ttcagtctga aacttgctt  1080
caagattgcg ttagggagct gtacaggaat aatgagcaac atcaacagat gcttgaggct  1140
aaggattcg tgcacctctt cctcaacgat ataattttct accagaggcc tcttaggtcc  1200
cagaaatcaa gcatttctaa ttgcaccctt gagttccgca agtccaagaa tgaaaaccgga  1260
gaggaggtaa tacacagatt aaaggtgatc gccaaatcaa acccatacta ccaggagttc  1320
aggcttcttc aatgggttca gaacctgct atctatacta aggacgacga taagaacgta  1380
accaacgagt tcctcaaatc aactcaggat gggaggatc ttcttaggtg gcttcactct  1440
aagaaggaaa tcaagcagga tgctctaatc aagttcctca ttgaagaa gggactcaag  1500
gggaaagcat tgactattga ggtggcaaaa taaggtaggta actacgttca ggataaggat  1560
taccctggaa atgaaacccg ctacctcatt caatcaaggc ttgataaggt tgagtacgct  1620
cctaaggatt tcctcaccta tgaaaatgaa atggccctct ggcatatcat ctactcaatc  1680
aacgacaaga tcgagtatga aaaggcatta aagtccttcg ccaataaaaa ggggctcgat  1740
gaggtgacct tcgtggaagc attcaagaag ttccctcctt tcagtccgga ttacggatct  1800
ttctctgaga aggcaatcaa gaagctcctt ccattaatga ggttcgaac tcaatggaac  1860
tgggataaca tcgaccaaaa tagcaaggag aggattgaa aaatactaac cggggagtac  1920
gatgaaaata ttaaagggag ggttagggag aaggctaggc accttaactc tgagaccgat  1980
tttcaagcat acctctttg gcttgctcag tacgttgttt atggaaggca ctctgaagct  2040
gatattgctg gaaagtggaa ctctgtggat gatctcaagc agttccttga tgatttcaag  2100
cagcattcct tgaggaaccc tattgtggag caggttatta ctgagactct tagggctgtt  2160
```

```
aaggatatttt ggaacttcta cggaaagggg gctaaggatt tcttctcaga aatacacatt  2220
gagcttggga gggagatgaa aaataccgct gatgaaagga agaggattac caccatggtg  2280
accgacaatg aaaataccaa cctcagaatc aaagcattgc ttgctgagat ggctcttgat  2340
cagaacgttg ataacgttag gccttactct ccctatgcag aggagattct taagatctat  2400
gaggagggag ttctaaacgc tgaggagaac atcgatgatg atatcctcaa gatttctaag  2460
actgctcagc cttctgctac cgatcttaag aggtataagt tgtggcttga gcaaaagtac  2520
aggtctcctt acactggaca gatgattcct cttaacaagt tgttcacccc tgagtacgag  2580
atcgagcaca ttattcctca gtctaggtac ttcgacgatt caatgtccaa caaggttatt  2640
tgcgaggctg ctgtgaacaa gttgaaggat aaccagattg gactcgtgtt cattaagaac  2700
catcatggag aggtggttga tttcggaatg ggaaagcagg tgaagattct tgaggtttct  2760
gattacgagg atttcgtgaa gcagaactat aacaagaaca ggggaaagag gaacaagctc  2820
ctcttagagg atatccctga gaagatgatt gagaggcagc ttaacgatac caggtacatc  2880
tctaagtaca ttacccaggt gctttccaac attgttaggg atgataagga gggatctaag  2940
gatgatggag tgaactccaa gaacattgtt cctggaacag gaaagattac caccaggctt  3000
aaacaggatt ggggacttaa cgatgtgtgg aacgatcttg ttcttcctag gttcgagagg  3060
atgaacactc ttaccaactc taacgatttc acctctaaga acactcacgg aaagactatt  3120
cctactgtgc ctattgagct ttcaaaggga ttctccaaga gaggattga tcacaggcat  3180
catgctatgg atgctcttgt tattgcttgc gctactaggg atcatgtgaa cctttctcaac  3240
aacgagtctt ctaagtctga taccaagagg tacgatctta acaggaagtt gaggaagtac  3300
gagaaggttg cttacaacga tcctaagact ggagagagaa ttgagaagga ggtgcctaag  3360
gatttattta agccttggga gacctttact gaggatacta ggacccttct tgagaacatc  3420
gtgatttctt tcaagcagaa cctcagggtg attaacaagg ctaccaacta ctacgagaag  3480
attgagaacg aaagaaggt gaaggttgag cagaagggaa ttaattggc tgttaggaag  3540
gctctacata aggagactgt ttctggacag gtgcaccttg ataggattaa agtggctaag  3600
ggaaagattc ttaccgctac taggaagact cttgatgctt ctttcaacga gaagaccatt  3660
gagtctatta ccgataccgg gattcagaag atttctcctca actacctcga gtccaaggat  3720
aacaatcctg aggttgcttt ctctcctgaa ggaattgagg agcttaacaa gaacatcagg  3780
ctctataacg atggaaaggc tcaccagcct attcttaagg ttagggtttt cgagcaggga  3840
tctaagttta ctcttggaga gactggaaac aagactacta gtttgttga ggctgctaag  3900
ggaaccaacc ttttcttcgg aatctacgag gataagtcg gaaagaggtc ttacgagacc  3960
atcccttga acattgttat tgagaggcaa aagcaaggac tacaagctgt tcctgagact  4020
aacgagaagg gaaagcagct tcttttcacc ctttctccta acgatcttgt ttatgttcct  4080
gaggagggag ttttcgatga gaacaacatc aaggtggata ggatctacaa ggtggtgtct  4140
ttctctactt accaatgctt cttcgtgagg aacgatgtgt ctacttctgt ggttaacaag  4200
gttgagtact ctgctctcaa caagatggag aagtccatcg acaacatcat gattaaggag  4260
aactgcgtga gttgaacgt tgataggctc ggaaagattt ccaaggct         4308
```

```
SEQ ID NO: 180         moltype = DNA   length = 4308
FEATURE                Location/Qualifiers
misc_feature           1..4308
                       note = source = /note="Description of Artificial Sequence:
                       Syntheticpolynucleotide"
misc_feature           1..4308
                       note = source = /note="APG04583.1 Corn optimized"
source                 1..4308
                       mol_type = other DNA
                       organism = synthetic construct
SEQUENCE: 180
atggccaaga acatactagg cctggacctc ggaaccaatt ctatcggctg ggccctggtt    60
cagcaggact ttgagaacaa ggagggcaac atactaggca tggcagccg aataatccct   120
atgtctcagg acatactggg cgagttcggt aagggcaaca gcatctcaca gacagccgag   180
aggacaggct accgcggcgt gaggaggctc agggagaggc acctgcttag gagggagag   240
ctacacaggg tgctgcatct gctgggcttc ctgccaaagc attacgatga aaagatagat   300
ttcacacaga ggttcggcaa gttcatcaat caagccgaac caaagctagc cttcgattct   360
gagttcctgt tcaaggacag cttccatgaa atgctggccg acttcaagca agaatcaaccg   420
gagttcctga aggataaaaa cggcgaggac tgcctagtgc cgtacgactg gaccatatac   480
tacctgcgca gaaggccct cacccagaag atcgaaaaat acgagctggc ctggctgatc   540
cttaacttca accaaaagcg cggatactac cagctacgcg cgaggagga agggagaac   600
ccgaataaac tggtgggctt ccacagcctg aaaatagtgg acgtagtcgc ggacgccgag   660
actaataaaa agggcgagac ctggtactca cttcacctgg agaacggctg ggtgtaccgc   720
aggagcagca aaatatctct ggccgactgg aaggataaag tgagggactt catcgtgacc   780
acagacctga cgacgatgg ctcagagaag ctggacaagg atggcatcgt gaagaggtca   840
ttcagggccc catctgccga tgactggacc ctataaaga agaagaccga gaaggacatc   900
gacaacagca ataaaaccgt gggcacctac atctacgaca acctgctatt aaaccgaag   960
cagaaaatca agggcaagat ggtgcgcacc atcgagcgca agttctacaa gcaggagctg  1020
gagcagatac taaagaccca gaaggagttc cacagcgagc tgcagagcga acctgctg  1080
caggactgcg tgcgcgagct gtaccgcaat aatgagcagc accagcagat gctggaggcc  1140
aaggacttcg tgcacctgtt cctgaacgat ataatcttct accagaggcc gctcaggagc  1200
cagaagtcaa gcatcagcaa ttgcaccctg gagttccgca agagcaagaa tgaaaacggc  1260
gaggaggtga tacatcgatt aaaggtgatc gccaagagca cccatacta ccaggagttc  1320
cgcctgctgc agtgggtcca gaacctggcc atctatacta aggacgacga caagaacgta  1380
accaacgagt cctgaaatc aacccaggac tgggaggacc tgctgcgctg gctccacagc  1440
aagaaggaaa tcaagcagga cgcccctaatc aagttcctga tcgaagaa gggattaaag  1500
ggcaaagcat tgaccatcga ggtggcaaaa tacaggtgga actacgtcca ggacaaggac  1560
tacccgggca atgaaacccg ctacctaata cagagccgcc tgacaaggt ggagtacgcc  1620
ccgaaggact tcctgaccta cgagaatgaa atggcccgt ggcatatcat ctactcaatc  1680
aacgacaaga tcgagtatga aaaggcatta aagagcttcg ccaataaaa ggggcctggac  1740
gaggtgacct tcgtggaagc attcaagaag ttcccgccgt tcaagagcga ctacggcagc  1800
ttcagcgaga aggcaatcaa gaagctgctg ccattaatgc gcttcggcac ccagtggaac  1860
```

```
tgggacaaca tcgaccaaaa tagcaaggag cgcatcggca aaatactaac cggcgagtac   1920
gacgagaaca taaagggccg cgtgcgcgag aaggcccgcc acctgaacag cgagaccgac   1980
ttccaagcat tgccgctgtg gctggcccag tacgtggtct acggcaggca cagcgaggcc   2040
gatatcgccg gcaagtggaa cagcgtggat gatctcaagc agttcctgga cgatttcaag   2100
cagcacagcc tgaggaatcc aatcgtggag caggtgatca cagagacact aagggccgtg   2160
aaggacatct ggaatttcta cggcaagggc gccaaggact tcttcagcga gatacatatc   2220
gagctgggcc gcgagatgaa aaacaccgcc gatgaaagga agaggatcac aaccatggtg   2280
accgacaatg aaaacaccaa cctgcgaatc aaggccctgc tggccgagat ggccctggat   2340
cagaacgtgg ataacgtgag gccatactct ccaatgcagc aggagatcct gaaaatatac   2400
gaggagggcg tattaaacgc cgaggaaaat atcgacagga acatcctgaa aataagcaag   2460
accgcccaac aagcgccacc gacctgaagc gatataagc tgtggctgga gcaaaaatac   2520
aggagcccgt acaccggcca gatgatcccg ctgaataaac tgttcacccc ggagtatgaa   2580
atcgagcata taatccctca gagccgctac ttcgacgaca gcatgagcaa caaggtgatc   2640
tgcgagggcc ccgtgaacaa gctaaaggac aaccagatcg gcctggtgtt catcaagaac   2700
caccacggcc aggtggtgga cttcggcatg ggcaagcagg tgaagatcct ggaggtgagc   2760
gactacgagg acttcgtgaa gcagaactac aacaagaacc gcggcaagag gaacaagctg   2820
ctgctggagg acatccctga gaagatgatc gagaggcagc tgaacgacac ccgctacatc   2880
agcaagtaca tcacacaggt gctgagcaac atcgtgaggg acgataagga gggctcaaag   2940
gatgatggcg tgaacagcaa gaacatcgtg ccaggcaacg gcaagatcac aacaaggctg   3000
aagcaggatt ggggcctgaa cgatgtgtgg aatgatctgg tgctgccaag gttcgagagg   3060
atgaacaccc tgaccaacag caacgacttc acctctaaga cacccacgg caagacaatc   3120
ccaacagtgc cgatcgagct gagcaagggc ttcagcaaga agaggatcga tcacaggcac   3180
cacgccatgg atgccctggt gatcgcctgc gccacaaggg atcacgtgaa tctactgaat   3240
aacgagtcta gcaagagcga tacaaagagg tacgatctga acaggaagct gcgcaagtac   3300
gagaaggtgg cctacaacga tccaaagaca ggcgagagga tcgagaagga ggtgccgaag   3360
gatttcatca agccatggga gacattcaca gaggacaaca ggaccctgct ggagaacatc   3420
gtgatcagct tcaagcagaa cctgcgcgtg atcaacaagg ccaccaacta ctacagaaag   3480
atcgagaacg gcaagaaggt gaaggtggag cagaagggca tcaattgggc cgtgaggaag   3540
gccctacata aggagacagt gtctggccag gtgcacctgg ataggatcaa ggtggccaag   3600
ggcaagatcc tgacagccac aaggaagaca ctggatgcct ctttcaacga gaagacaatc   3660
gagagcatca cagacaccgg catccagaag atcctgctga actacctgaa gagcaaggac   3720
aacaacccag aggtggcctt ctctccagag ggcatcgagg agctgaacaa gaacatcagg   3780
ctgtacaatg atggcaaggc ccaccagcca atcctgaagg tgcgcgtgtt cgagcagggc   3840
tcaaagttca cactgggcga gacaggcaat aagcaacaa agttcgtgga ggccgccaag   3900
ggcacaaatc tgttcttcgg catctacgag gataagtctg gcaagaggtc ttacgacaga   3960
atcccgctga atatcgtgat cgagaggcag aagcagggac tgcaggccgt gccagagaca   4020
aatgagaagg gcaagcagct gctgttcaca ctgtctccaa atgatctggt gtacgtgcca   4080
gaggagggcg tgttcgatga gaacaatatc aaggtggaca ggatctacaa ggtggtgagc   4140
ttctcaacct accagtgctt cttcgtgagg aacgacgtgg agctgaacaa ggtgaacaag   4200
gtggagtaca gcgccctgaa caagatggag aagagcatcg acaacatcat gatcaaggag   4260
aactgcgtga agctgaacgt ggaccgcctg ggcaagatct ctaaggcc                4308

SEQ ID NO: 181         moltype = DNA   length = 4368
FEATURE                Location/Qualifiers
misc_feature           1..4368
                       note = source = /note="Description of Artificial Sequence:
                       Syntheticpolynucleotide"
misc_feature           1..4368
                       note = source = /note="APG01688.1 Soy optimized"
source                 1..4368
                       mol_type = other DNA
                       organism = synthetic construct
SEQUENCE: 181
atgatgatca gaacatact aggactcgat ctcggaacca actctatcgg atgggctcta   60
atcaagcagg atttcgagaa caagcatgga gaaatactag gcatgggctc cagaataatt   120
cctatgtccc aggatatact aggagatttc ggaaagggta actctatttc tcagaccgct   180
gatagaacca agtataggtc tgttagaagg cttagggaga gatttcttct taggagagag   240
aggcttcata gggtgctcca cctattaaac ttccttcctc aacactacgc ttctcagatc   300
gatttcgaga agaagttcgg aaagtttaag tctgagaccg aaccaaagtt agcttgggaa   360
aattggggag gaaagttctc ttttcctcttc caaaatagct tcaatgaaat gctgaggat   420
ttcaaggctg ctggacaggg gctcaaaata ccttacgact ggaccatata ctatctcagg   480
aagaaagcat tgtcccagaa aatagagaag gaggagctag cttggatact cctcaacttc   540
aatcaaaaga ggggatacta tcaattaaga ggtgaggagg aggaggagaa ccctaataaa   600
ctcgtggagt tctactccct caaaatagtg gatgttgttg ctgatgagcc tcagaaggga   660
aagtccgata tctggtactc attaattctt gagaacggat gggtttatcg cagggcttcc   720
aaaataccct ctttcgactg gaaggataaa accaggcatt tcattgtgac caccgatctt   780
aacgatgata ggtctgtgaa gactgataag gagggaaatg aaaagaggtc ttttaggct   840
ccttcagaga cgattggac tcttgtgaag aagaagacta gcaggagat tgatcagtct   900
cataaaccg tgggaaccta catctatgaa accctcctat taaaccccaa cagaaaatc   960
aagggaaagt tggtgaggac cattgagagg aagttctaca aggacgagct taagcagata   1020
ctagaaaagc aaaaggagtt ccaccaggaa ttaaagaacg acgacctata taacgactgc   1080
attagggagc tgtacaggaa taatgaggct caccaattaa ccctctccaa gaaggatttc   1140
gtgcacctat taatggacga tctcattttc taccagaggc ctcttaggtc ccagaaatca   1200
agcatttcta attgcaccct ggagttcaga aaatacaagg atgaaaacgg gattgagcac   1260
acccagtacc tcaaggctat cccaaaatca aacccatact accaagagtt taggcttgg   1320
cagtggatgt acaacttgaa catctacaga aaggatgatg aggctaacgt aaccaaggag   1380
ttcctcaaca ccaataaaga cttcgagtct ctcttcgagt tcctcaataa tcgcaaggag   1440
attgagcaga agccctaat caagttcctt cttgagcaga aggacataaa caagaagcta   1500
ttaaacgccg aggctgagaa atacaggtgg aactacgtgg aggataaaaa gtaccccgtc   1560
```

```
aatgaaacca agaccatgat ttcctctagg cttgacaagg tggaaaatat ctccgatgat   1620
ttcctcacca gggacatcga gcagaaaata tggcatataa tctactccgt gaacgacaag   1680
atcgagtatg aaaaggcatt aaagtccttc gctaccagga acgacctcga tgaaaatagc   1740
ttcatcgaag cattcaagaa gttctcccct ttcaagtccg agtacggatc tttctctgag   1800
aaggcaatca agaagctcct tccattaatg aggctcgaaa aatactggta cgaggatgaa   1860
atcgtgaagc attccgacat ctacttcaaa aatattgaga acctcctcgg ggatttctcc   1920
aaccgcgaca agaaaatatc tgaggaagac aaggagaagt ggaacaagtc aatcaacctt   1980
aagctccagg aggaattaaa ggatttccag accgctgaga ttgatttgtt ccagggactt   2040
aggcttcaca ttgctcagta ccttgtttat ggaaggcact ccgaagcatc tatgattgga   2100
aagtggaatt ctgctgagga tcttgaggag ttccttaagg atttcaagca gcattccttt   2160
aggaaccccta ttgtggagca ggttattact gagactctta gggtggttaa ggatatttgg   2220
ctaaagtacg aaacggggc taaggatttc ttcaacgaga ttcatattga gcttggaagg   2280
gaaatgaagt tgcctgctga tgataggaag aagctcacca accaaatttc tgagaacgag   2340
aacaccaact tcaggattaa ggctctcctt gctgagatga tgaacgattc ttctgttgag   2400
aacgttaggc cttttctctcc tatgcagcag gagattctaa agatctacga ggatgatgtg   2460
ctcaagtccg atatcgagat cgaggatgat atcctcaaga tttctaagac tgctcaacct   2520
tctccttctg atcttaagag gtacaagttg tggcttgagc agaagtacaa gtctccttac   2580
accggacaga ttattcctct taacaagttg ttcaccccctg agtacgagat cgagcacatt   2640
attcctcagt caaggtactt cgatgattcc ttctccaata aggtgatttg cgagtctgct   2700
gtgaacaagc tcaaggataa ctacatcggg cttgagttca ttaagcagtt cggaggaact   2760
attattgagc ttggattcgg gaagtctatt aaggtgttcg agactaagga gtacgaggat   2820
ttcgtgaaga agcattacgc taacaaccag ggaaagagga acaagctcct tatggaagat   2880
atccctgaga agatgattga gaggcagatg aacgatacca ggtacatctc aaagtacatt   2940
tctggggtgc tttctaacat tgttagggtg gaagatggat ctgatgaggg agtgaactct   3000
aagaacattg ttcctggaaa cggaaagatt accaccccaac ttaagcagga ttgggggactt   3060
aacgatgtgt ggaacgatct cattcttcct aggttcggaa ggatgaatca gcttactaac   3120
tctaaggttt tcactgcttg gaacgagaac taccagaagt tccttcctac tgtgcctatt   3180
gagtactcca agggattctc aaagaagagg attgatcaca ggcatcatgc tcttgatgct   3240
cttgttattg cttgcgctac taaggatcac gtgaaccttc ttaacaacca gtctgctaag   3300
tctgatacca agaggtacga tctcaagaag aagtccatga gttcgagaa ggtggttac   3360
aacgatgcta agactggaga aaagattgag agggaggttc ctaagcaatt tcttaagcct   3420
tgggagaact tcactcttga tgtgaagcac aaccttgaga ccatcattgt gtcattcaag   3480
cagaacctca gggtgattaa caaggctacc aactactacg agaagtacgt tgagaaggat   3540
ggaactaaga ataaggagag ggttgagcaa actggaacta actgggctat taggaagcct   3600
atgcacaagg atactgtgtc tggaaaagtt gatcttcctt gggttaaggt gcctaaggga   3660
aagattctta ctgctaccag gaagtctctc gattcttctt tcgatctcaa gtccattgga   3720
tctattaccg ataccgggat tcagaagatc ctaaagaact acctcgcttt caaggatgga   3780
aatcctgagc ttgctttctc tcctgaggga attgatgacc tcaacaagaa catcgagaag   3840
tataacgatg gaaagcctca ccagcctatt aacaaggtta gggttttcga gcttggatct   3900
aagttccaag ttggacagtc tggaaacaag aaggataagt atgttgaggc tgctaaggga   3960
accaaccttt tcttcgctgt ttatgaggat gagaaggaa agaggaacta cgagactatt   4020
cctctaaacg aggttattga gaggcaaaag cagggactt ctgtggttga tcttaagggg   4080
accaacgatt tctatctttg ccctaacgat ttcgtgtaca ttccttctgg agttgagctg   4140
gagaacatca acaacgtgga cttcaaggat atcaagaagg agattaacga ggatctac   4200
aaggtggtgt ctttcactgg aaacaggctt tcttgcattc cttacatggt ggctaccact   4260
attgtgaaca agttggagtt cacccagcta aacaagattg agttccacca ggagaaggag   4320
atctgcatta agttgaacgt ggataggctc ggaaacattt ctaaggct                4368

SEQ ID NO: 182        moltype = DNA   length = 4368
FEATURE               Location/Qualifiers
misc_feature          1..4368
                      note = source = /note="Description of Artificial Sequence:
                      Syntheticpolynucleotide"
misc_feature          1..4368
                      note = source = /note="APG01688.1 Corn optimized"
source                1..4368
                      mol_type = other DNA
                      organism = synthetic construct
SEQUENCE: 182
atgatgatca agaacatcct aggcctggac ctcggaacca attctatcgg ctgggccctg    60
atcaagcagg acttcgagaa caagcatggc gagatactag gcatgggcag ccgaataatc   120
ccgatgagcc aggacatact aggcgatttc ggcaagggca atagcatctc tcagaccgcc   180
gacagaacca agtacaggtc tgttaggagg ctgagggaga ggttccttct taggaggag   240
aggctgcata gggtgctcca cctattaaac ttcctgccac agcactacgc cagccagatc   300
gacttcgaga agaagttcgg caagttcaag agcgagacag aaccaaagct ggcttgggaa   360
aactggggcg gcaagttcag cttcctgttc caaaatagct tcaatgaaat gctggaggac   420
ttcaaggcc ccgccaggg attaaagatc ccctacgact ggaccatata ctacctgcgc   480
aagaaagcat tgagccagaa aatagagaag gaggagctgg cctgatact gctgaacttc   540
aaccaaaagc gcggatacta ccagctgcgc ggtgaggagg aggaggagaa cccgaataaa   600
ctggtggagt tctactcact gaaaatagtg gactggtgg ccgacgagcc cagaagggc   660
aagagcgaca tctggtacag cctgatacta gagaacggct gggtgtaccg ccgcgctagc   720
aaaataccgc tgttcgactg gaaggataaa acccgcgact tcatcgtgac caccgacctg   780
aacgacgaca ggagcgtgaa gacagataag gagggcaatg aaaagaggag cttcagggcc   840
gagagcgatt ggac cctggtgaag aagaagacag aggagaagat cgatcagagc   900
cataaaccg tgggcacata catctatgaa accctgctat aaacccgaa gcagaaaatc   960
aagggcaagc tggtgcgcac catcgagcgc aagttctaca aggacgagct gaagcagata  1020
ctagagaagc agaaggagtt ccaccaggaa ttaagaacg acgacctata taacgactgc  1080
atccgcgagc tgtaccgcaa taatgaggcc caccaattaa ccctgagcaa gaaggacttc  1140
gtgcacctat taatggacga cctgatcttc taccagcgcc gctgcgcag ccagaagtca  1200
```

```
agcatcagca attgcaccct ggagttccgc aaatacaagg atgaaaacgg catcgagcac   1260
acccagtacc tgaaggccat cccgaagagc aacccatact accaggagtt ccgcctgtgg   1320
cagtggatgt acaacctgaa catctaccgc aaggacgacg aggccaacgt aaccaaggag   1380
ttcctgaata caaataaaga cttcgagagc ctgttcgagt tcctgaataa tcgcaaggag   1440
atcgagcaga agccgctaat caagttcctg ctggagcaga aggacataaa caagaagcta   1500
ttaaacgccg aggccgagaa atacaggtgg aactacgtgg aggataaaaa gtacccgtgc   1560
aacgaaacca agaccatgat cagcagccgc ctggacaagg tggaaaatat cagcgacgac   1620
ttcctgaccc gcgacatcga gcagaaaata tggcatataa tctacagcgt gaacgacaag   1680
atcgagtatg aaaaggcatt aaagagcttc gccacccgca acgacctgga tgaaaacgat   1740
ttcatcgaag cattcaagaa gttcagcccg ttcaagagcg agtacggcag cttcagcgag   1800
aaggcaatca agaagctgct gccattaatg cgcctgggaa aatactggta cgaggacgag   1860
atcgtgaagc atagcgacat ctacttcaaa aatatcgaga acctgctggg cgacttcagc   1920
aaccgcgaca agaaaataag cgaggaggac aaggagaagt ggaacaaaag catcaacctg   1980
aagctgcagg aggaattaaa ggacttccag accgccagga tcgacctgtt ccagggcctg   2040
cgcctccaca tcgcccagta cctggtgtac ggccgccaca gcgaggcaag catgatcggc   2100
aagtggaaca gcgccgagga cctggaggag ttcctgaagg acttcaagca gcatagcctg   2160
cgcaacccga tcgtggagca ggtgatcacc gagaccctgc gcgtggtgaa ggacatctgg   2220
ctaaaatacg gcaacggcgc caaggacttc ttcaatgaaa ttcacatcga gctgagccgc   2280
gagatgaaac tgccgccgga cgaccgcaag aagctgacca accaaatcag cgagaatgaa   2340
aacaccaact tccgaatcaa ggccctgctg gccgagatga tgaacgacag cagcgtggag   2400
aacgtgcgcc cgttcagccc gatgcagcag agatcctgaa aaatatacga ggacgacgtg   2460
ctgaagacga acatcgagat cgaggacgac atcctgaaga tcagcaagac cgcccagccg   2520
agcccgagcg acctgaagcg ctacaagctg tggctggagc agaagtacaa gagcccgtac   2580
accggccaga tcatcccgct aaacaagctg ttcacccggg agtacgagat cgagcacatc   2640
atcccgcaga gccgctactt cgacgacagc ttcagcaaca aggtgatctg cgagagcgcc   2700
gtgaacaagc tgaaggataa ctacatcggc ctggagttca caagcagtt cggcggcacc   2760
atcatcgagc tgggcttcgg caagagcatc aaggtgttcg agaccaagga gtacggagac   2820
ttcgtgaaga agcactacgc caacaaccag ggcaagcgca acaagctgct gatggaggac   2880
atcccggaga agatgatcga gcgccagatg aacgacaccc gctacatcag caagtacatc   2940
agccgccgtg ctgagcaacat cgtcggcgtg gaggatggct cagatgaggg cgtgaacagc   3000
aagaacattg tgccgggcaa cggcaagatc acaacacagc ttaagcagga ctggggcctg   3060
aacgatgtgt ggaacgatct gattctgcca aggttcgaga ggatgaacca gctgaccaac   3120
agcaaggtgt tcaccgcctg gaacgagaac taccagaagt tcctgccaac cgtgccaatc   3180
gagtacagca agggcttcag caagaagagg atcgatcaca ggcatcatgc tctgatgct   3240
ctggtgatcg cctgcgctac aaaggatcac gtgaacctgc tgaacaacca gagcgccaag   3300
agcgacacaa agaggtacga cctgaagaag aagagcatga agttcgagaa ggtggtgtac   3360
aacgacgcca agaccggcga gaagattgag agggaggtgc cgaagcagtt cctaaagcca   3420
tgggagaact tcacactgga cgtgaagcac aacctggaga ccatcatcgt gagcttcaag   3480
cagaacctga gggtgatcaa caaggccacc aactactacg agaagtacgt ggagaaggac   3540
ggcaccaaga acaaggagag ggtggagcag acaggcacaa attgggccat ccgcaagcca   3600
atgcacaagg atacagtgtc tggcaaggtg gatctgccat gggttaaggt gccaaagggc   3660
aagatcctga cagccacaag gaagagcctg gatagcagct tcgatctgaa gagcatcggc   3720
tctatcacag acaccggcat ccagaagatc ctgaagaact acctggcctt caaggatggc   3780
aatccagagc tggctttctc tccagagggc atcgacgacc tgaacaagaa catcgagaag   3840
tacaacgacg gcaagccaca ccagccaatc aataaggtgc gcgtgttcga gctaggctct   3900
aagttccagg ttgccagag cggcaacaag aaggataagt acgttgaggc cgccaagggc   3960
acaaatctgt tcttcgctgt gtacgaggat gagaagggca agcgcaacta cgacaacatc   4020
ccactgaacg aggtgatcga aaggcagaag cagggcctgt ctgttgtgga tctgaagggc   4080
accaacgatt ctacctgtg cccgaacgac ttcgtgtaca ttccatctgg cgacgagctg   4140
gagaacatca caacgtgga cttcaaggac atcaagaagg agatcaacga gcgcatctac   4200
aaggtggtga gcttcaccgg caacaggctg agctgcatcc catacatggt ggccaccacc   4260
atcgtgaaca agctggagtt cacccagctg aacaagatcg agttcaccaa ggagaaggag   4320
atctgcatca agctgaacgt ggacaggctg ggcaacatca gcaaggcc                4368
SEQ ID NO: 183        moltype = DNA   length = 3210
FEATURE               Location/Qualifiers
misc_feature          1..3210
                      note = source = /note="APG05083.1 Native Seq"
source                1..3210
                      mol_type = genomic DNA
                      organism = Bacillus sp.
SEQUENCE: 183
atgagagagt tggattatcg cataggatta gatattggaa cgaattctat tggctggggg     60
atcattgaat tatcttggaa caaagataga gaacaatatg agaaagcaag aattgtcgac    120
aagggtgttc gtatgtttga taaggctgaa atacctaaga ctggtgcttc tcttgctgaa    180
ccgaggcgta tagcacgctc atcacgtaga agattaaatc gcaaaagcca gagaaaaaaa    240
gatatacgta atttactcgt tcaacatgaa attattagtc aaaaggaatt ggcttcgtta    300
tatccctga caaaaagttc aatggatatt tgggatattc gcttggatgg attagatcgc    360
ttgttagacc gttttgaatg gactcgatta ttaattcatt tagcgcaaag acgcggttta    420
aaatcaaatc gaaagtctga actgaaagat gtgggagacag gaaaagtatt atcaagtatt    480
caagcaaatg aaaaacgatt atcactgtac cgtacagtgg gagagatgtg gatgaagaat    540
gaagatttta gtaaatatga caaaggcgt aattcttcta tgagtatgt attttcggtt    600
agccgtgcag atttagaaaa agaaattgtg acactatttg aagcgcaaag aaaatttcag    660
tcatcatatg catcggctac tttacaaaaa acatacttac aaattgggc acaccaactt    720
cctttttgctt ctgggaatgc aattgtaaat aaagtaggat attgttcatt attaaaaggg    780
aaagaaaaga gagttccgaa agcaacatat acttttcaat atttcagtac actagatcaa    840
ataaatcgaa cacgattagg tcctaatttc caaccattta cgaggaaca gagagacgtt    900
attttagatg aaatgtttaa tcgaacagat tattataaaa aaagacaat acccgaagtc    960
acttactatg atattcggaa atggttagca ttagatgaaa caattcaatt taaggactt   1020
```

```
acctatgacc caaatgaaga gctgaaaaaa atagaattga aatcctttat taatttaaag   1080
ccattctatg aaattaaaaa ggtagttact aattacgcca aaaaaacaaa tgaggcattc   1140
tcaacattag actatgatac atttgcatat gctttaacag tttataaaac ggacaaagat   1200
attagatctt atttaaagaa atctaataat ttatcaaaat gttgctacga tgatcaatta   1260
ataaagagc tattaactct ctcctataca aagtttggtc atttatcatt taaagcaatt   1320
aatcatgtac tgccaattat gcaagaggga aggacttatc aggaagcaat acaccaatta   1380
ggatatgatg ccactaatct aaaaaaagaa aacagaagta tgttcttgcc ccttttcc    1440
gatgagataa caaatccaat tgttaaaaga gcactaactc aagcacgtaa agttgtaaat   1500
gctattatta gaagatatgg ttcccccaat tctgttcata ttgaactagc tcgtgagctt   1560
tctaaaagtc atgatgagag aacgaaaata atgaaagctc atgataaaa ttataagaaa   1620
aataaaggag ccatatcaat tttgattgag aatggaattt taaatccgac aggatatgat   1680
attgtacgtt ataagttatg gaaagagcaa ggagaacgat gtgcttattc gctaaaacag   1740
attcctgcta atacgttttt taatgaaatg aaaaaagagc gaagtggctc cccagttcta   1800
gagatagatc acattttacc gtatagtcag agttttattg atagttatca taataaagta   1860
ctagtttatg gagatgagaa tcaaaaaaag ggaaatcgaa ttccatatac ttatttttta   1920
gaaggaaata aggactggga aagctttgaa agctacgtac gattgaatag ttttttttct   1980
aaaaagaagc gcggatattt attgaaaaaa gcttacttgc caagagagag taacatgatt   2040
aaggagcgtc atttaaatga tactcgatat gctagtagct atttgaaaaa cttcattgag   2100
aaaaatttga aatttaaaga agttgaaggt agtacacgaa aaaaacatgt acagacggtt   2160
aacggtataa ttacagccca tcttcgaaaa agatggggat tagaaaaaga taggcaggaa   2220
acatatttgc atcatgcaat ggacgctatt attgttgctt gtacagacca tcatatggtc   2280
actaaagtaa cggagtacta tcaaataaaa gaaagtaata agtcaataag gaaaccatac   2340
tttcctttgc catgggtggg ctttagagag gaaattttat cacatttagc aaggcagcca   2400
attgctagaa aaattagtga ggaacttaaa attggatatc aatcatttga ttatatactt   2460
gtatcgcgaa tgccaaaaag atctgtcact ggagcagctc atgaacagac aatcatgaaa   2520
aaaggtggta tcgacaaaaa aggaaaaact attatcagaa agcgtgtgta cttaaaggat   2580
attaagtttg atgagaatgg cgattttaaa atggttggaa agaacagga tttagcaact   2640
tatgaagcga taaagcaaag atatatagag tatggaaaag aatcgaaaaa agcatttgaa   2700
acaccttat acaagcctag taaaaaagga aaaggaaacc tcattaaaaa gatcaaagta   2760
gaagtgcaaa ccaaatcttt tgttcgagaa gttaatgggg gcgtagctca aaatggtgat   2820
ttagtaagag tagatttgtt tgaaaaggat aatagatatt atatgatacc tatttatgta   2880
atggatactg ttcattccga actaccaaat aaagctgtaa caagcagtaa aggctatgag   2940
caatggttaa caatagataa cagctttacg ttcaaattca gtttatatcc ttatgattta   3000
gtacgacttg taaaaggtaa tgaagatcgt ttcctatatt ttagtaccct tgatattaat   3060
tcggatcgtc ttaatttcaa agatgtaaac aagccatcaa agcaggctga aaatcgttat   3120
agcctttaaaa caattgagaa tttagaaaaa tatgaggttg tgtgtttagg tgatttaagg   3180
tttgtgagac aagaaatacg taaaaatttt                                   3210

SEQ ID NO: 184           moltype = DNA  length = 3210
FEATURE                  Location/Qualifiers
misc_feature             1..3210
                         note = source = /note="Description of Artificial Sequence:
                         Syntheticpolynucleotide"
misc_feature             1..3210
                         note = source = /note="APG05083.1 E. coli optimized"
source                   1..3210
                         mol_type = other DNA
                         organism = synthetic construct
SEQUENCE: 184
atgcgcgagc tagattatcg catcggcctg gatattggca ctaactcaat aggctggggc    60
atcatcgaac tgagctggaa taaagaccgc gagcagtatg aaaaggcgcg catcgtggat   120
aaaggcgtgc gcatgttcga caaagcggaa attccgaaaa ccggtgcaag tctggcggaa   180
ccaagacgta ttgcacgtag tagtcgccgc cgattaaacc gcaaaagtca gcgcaagaag   240
gatataagga acctgctggt ccagcatgaa atcatcagcc agaaggaact ggcgagcctg   300
tacccgctga ccaaatcaag tatggacatc tgggatata ggctggacgg cctggatcgt   360
ctgctggatc gctttgaatg gacccgcta ttaatccatc tggcacacgc cgtggcttc    420
aaatcaaacc gcaagagcga attaaggac gtggagaccg gtaaagtgct gtcaagcatt   480
caggcgaatg aaaagcgcct gagcctgtat cgtaccgtgg cgagatgtg gatgaaaaac   540
gaggacttct caaatacga taaaaggcgc aacagcagca acgagtacgt gttcagcgtg   600
agccgcgcgg acctggagaa agaaatcgtg accctgtttg aggcgcagcg caattccaa   660
tcaagctatg cgagcgcgga tctgcagaaa acctacctgc agatttgggc acatcagctg   720
ccgtttgcaa gcgtaacgc gatcgtgaat aaagtgggct attgcagcct attaaaaggc   780
aaagaaaaac gcgtgccgaa agcgacctat acattccagt acttcagcac cctggaccaa   840
atcaaccgca cccgcctggg cccgaacttc cagccgttca ccaaagaaca gcgcgaagtg   900
atcctggatg aaatgttcaa ccgcaccgac tactataaaa agaaaaccat cccggaggtg   960
acatactacg atataaggaa atggctggcg ctggatgaaa ccatccagtt caaaggctta  1020
acctacgatc cgaacgagga attaaagaag atcgaattaa aatcgttcat taatctgaaa  1080
ccgttctatg aaattaaaaa ggtggtaacc aactacgcga agaaaaccaa cgaagcattc  1140
agcaccctgg actacgatac attcgcgtac gcgctgaccg tgtataaaac cgacaaggat  1200
ataaggagct acctgaagaa atcaaacaac ctgagcaaat gctgctacga cgaccaatta  1260
atcgaagaac tgctgaccct gagctacacc aaattcggcc acctgagctt caaagcgatc  1320
aaccacgtgc tgccgatcat gcaggaaggc cgcacctacc aggaagcgat ccaccagctg  1380
ggctacgatg cgaccaacct gaaaaggaa accgcagca tgttcctgcc gctgttcct    1440
gatgaaatca caacccgat cgtgaaacgc gcgctgaccc agcgcgcaa ggtggtgaac  1500
gcgatcatcc gccgctacgg ctcaccgaac agcgtgcaca tcgaactggc gcgcgaactg  1560
agcaaaagcc acgatgaacg caccaaaatc atgaaagcgc acgatgaaaa ctacaaaaag  1620
aacaaaggcc cgatcagcat cctgatcgaa acggcatcc tgaacccgac cggctacgat  1680
atcgtgcgct acaaactgtg gaagaacag ggcgaacgct gcgcgtacag cctgaaacag  1740
atcccggcga cacccttctt caacgaaatg aaaaaggaac gctcaggcag cccggtgctg  1800
```

```
gaaatcgatc acatcctgcc gtacagccag agcttcatcg atagctacca caacaaagtg   1860
ctggtgtacg gcgatgaaaa ccagaaaaag ggcaaccgca tcccgtacac ctacttcctg   1920
gaaggcaaca aagattggga gagcttcgaa agctacgtgc gcctgaacag cttcttcagc   1980
aaaaagaaac gcggctacct gctgaaaaag gcgtacctgc cgcgcgaaag caacatgatc   2040
aaagaacgcc acttaaacga tacccgctac gcgagcagct acctgaaaaa cttcatcgag   2100
aaaaacctga aattcaaaga agtggaaggc agcaccccgta aaaagcatgt ccagaccgtg   2160
aacggcatca tcaccgcgca tctgcgcaaa cgctggggcc tggaaaaaga tcgccaggaa   2220
acctatctgc atcatgcgat ggatgcgatc atcgtggcgt gcaccgatca tcatatggtg   2280
accaaagtga ccgaatatta tcagatcaaa gaaagcaaca aatcaatccg caaaccgtat   2340
tttccgctgc cgtgggtggg ctttcgcgaa gaaatcctga gccatctggc gcgtcagccg   2400
atcgcgcgta aaatcagcga agaactgaaa atcggctatc agagctttga ttatatcctg   2460
gtgagccgac tgccgaaacg cagcgtgacc ggcgcggcgc atgaacagac catcatgaaa   2520
aagggcggca tcgataaaaa gggcaaaacc atcatcatca aacgcgtgta tctgaaagat   2580
atcaaatttg atgaaaacgg cgatttttaaa atggtgggca aggaacagga cttagcgacc   2640
tacgaagcga tcaaacagcg ctacatcgag tacggcaaag agagcaaaaa ggcgtttgaa   2700
acccccgctgt acaaaccgag caaaaagggc aagggcaacc tgatcaaaaa gatcaaagtg   2760
gaagtccaga ccaaatcgtt tgtgcgcgaa gtgaacggcg gcgtggcgca gaacggcgat   2820
ctggtgcgcg tggatctgtt tgaaaaagat aaccgctact atatgatccc gatctacgtg   2880
atggataccg tgcatagcga gctgccgaac aaagcggtga ccagcagcaa aggctatgaa   2940
cagtggttaa ccatcgataa cagctttacc ttcaaattca gcctgtatcc gtacgacctg   3000
gtgcgcctgg tgaaaggcaa cgaagatcgc ttcctgtatt tcagcaccct ggacatcaac   3060
agcgatcgcc tgaacttcaa ggacgtgaac aaaccgagca aacaggcgga aaaccgtat   3120
agcctgaaga ccatcgagaa cctggagaaa tatgaagtgg gcgtgctggg cgatctgcgc   3180
tttgtgcgcc aggaaattcg caaaaacttc                                    3210

SEQ ID NO: 185          moltype = DNA  length = 3213
FEATURE                 Location/Qualifiers
misc_feature            1..3213
                        note = source = /note="APG07433.1 Native Seq"
source                  1..3213
                        mol_type = genomic DNA
                        organism = Bacillus sp.
SEQUENCE: 185
atgagggagt tggactatcg catagggtta gatattggga cgaattctat tggatggggt     60
gttattgaat tatcctgtaa caaggacaga gaacgatatg aaaaagtaag gattgtcgac   120
cagggtgttc gtatgtttga tagggctgaa atgccaaaaa caggtgcttc tcttgctgaa   180
ccgaggcgta tagcacgttc atcacgtaga aggttaaatc gtaaaagtca gaggaagaaa   240
aatatacgta atttacttgt tcaacatggg gtgattactc aagaagagct ggattcgtta   300
tatcctcttt caaaaaaatc aatggatatt tgggggtattc gattggatgg attagatcgt   360
ctgctaaatc attttgaatg ggctcgatta ttaattcatt tagctcaaag acgtggtttt   420
aaatcgaatc gtaagtctga actgaaagat acggagacgg ggaaggtatt atcgagtatt   480
caattaaatg aaaaacgatt atcactgtac cgtacagtgg gagaaatgtg gatgaaagat   540
cctgattttta gtaagtatga tagaaaacgg aattctccta atgatgatgt attttcggtt   600
agtcgtgcgg aactagaaaa ggaaatagtt acttttatttg cagcacaaag aaggtttcag   660
tcaccatacg catcgaagga tttacaagaa acatatttac aaatttggac acaccaactt   720
cccttttgctt ctgggaatgc aatttttaaat aaagtgggat attgttcatt attgaaaggg   780
aagaaagaa gaattccgaa agcaacatat acttttcagt attttagtgc actagatcaa   840
gtgaatcgaa cacgattagg acctgatttt cagccattta cgaaggaaca aagagaaatt   900
attttaaata acatgtttca acgtacagat tattataaaa aaaagactat acctgaagtt   960
acatactatg atatccggaa atggctagaa ctagatgaaa ctattcaatt taaaggactt   1020
aattatgtc caaacgaaga attgaaaaaa ataagaaaag aaccatttat taatttaaag   1080
gcattctatg aaattaataa ggtagtcgca aattattctg agagaacaaa tgagacattt   1140
tcaacgttag actatgatgg gattggatat gctttaacag tttataaaac ggacaaagat   1200
attggtctt atttgaagag ctctcataat ttacctaaac gttgttacga tgatcaatta   1260
atagaggaac tattaagtct ttcttataca aagtttggtc acttatcact gaaagcaatc   1320
aatcacgtac tatcgattat gcaaaaaggc aatacttata agaagcagt agaccagtta   1380
gggtatgata caagcggttt aaagaaagaa aaaagaagta agttcttgcc tcctatttca   1440
gatgagataa cgaatccaat tgttaaaaga gcgttaacac aagcgcgtaa agttgtgaat   1500
gctataatta gaagacatgg ttctccacat tcagttcata ttgaactggc tcgtgaactt   1560
tctaaaaatc atgacgagag aacaaaaata gtgtcagctc aagataaaa ttataagaag   1620
aataaagggg ctatatcaat tttaagtgag catggaattt tgaatccaac aggctatgat   1680
attgttcgtt ataagttatg gaaagaacaa ggagaacgat gtgcttattc gttaaaggag   1740
attcctgcgg atacgttttt taatgaatta aaaaagaac gaaatggtgc tccaattcta   1800
gaggtagatc acatttacc gtacagtcaa gttttatcg taagttatcg taataaagta   1860
ttagttaca gtgatgaaaa tcgaaaaag gggaatcgaa ttccatatac ctattttta   1920
gagacaaata aggattggga agcttttgaa agatatgtaa gatcaaataa attttttttct   1980
aaaagagc gtgagtattt attgaaaaga gcatatttgc caagagaaag tgaactgata   2040
aaggagcgac atttaaatga tacgcgatat gctagtacct tttgaaaaa cttcattgag   2100
cagaatttgc aattaaaga agctgaagat aatccgcgta aaagacgtgt acaaacgtt   2160
aacggtgtaa ttacagcaca ttttcgaaaa agatggggat tagaaaaaga tagacaagaa   2220
acatacttac atcatgcaat ggacgctatc attgttgctt gtacagacca tcatatggtt   2280
actagagtaa cagagtatta tcaaataaaa gaaagtaata atcagtaaa gaaaccgtat   2340
tttcctatgc catgggaggg ctttagagat gaactcttat cacatttagc gagtcagcca   2400
atagctaaaa aaattagtga agagcttaaa gctgatatca ttattgta ttatatattt   2460
gtgtctcgaa tgccaaaaag atctatcact ggagcagcac ataaacaaac gatcatgaga   2520
aaaggcgta ttgataaaaa aggaaaact attattatag agcgtttgca tttaaggat   2580
attaagtttg atgagaatgg tgattttaaa atggttggca agaacaaga tatggcaact   2640
tacgaggcga taaagcaaag atatttggag catggaaaaa actcgaaaaa agcatttgaa   2700
acacctctat acaaacctag taaaaaagga acaggaaatc ttattaaaag agttaaagtt   2760
```

```
gaaggacaag ctaaatcttt tgttcgagaa gtaaatgggg gcgtagccca aaatggtgat  2820
ttagtgagag ttgatttatt tgaaaaagat gataaatatt acatggtgcc tatttatgta  2880
ccagataccg tttgttcaga attacccaaa aaagttgtgg caagtagtaa gggttatgag  2940
caatggttaa cactagataa cagctttacg tttaaattta gtttatatccc ttatgattta  3000
gtacggcttg taaaagggga cgaagatcgt ttcttatact ttggtactct cgatatcgat  3060
tcagatcgtc ttaattttaa agatgtaaat aagccatcaa aaaagaatga atatcgttat  3120
agccttaaaa caattgagga tttagaaaaa tatgaggtgg gtgtttttagg agatttaagg  3180
ttagtaagaa aagaaacacg tagaaatttt cac                                3213
```

SEQ ID NO: 186          moltype = DNA  length = 3213
FEATURE                 Location/Qualifiers
misc_feature            1..3213
                        note = source = /note="Description of Artificial Sequence:
                        Syntheticpolynucleotide"
misc_feature            1..3213
                        note = source = /note="APG07433.1 E. coli optimized"
source                  1..3213
                        mol_type = other DNA
                        organism = synthetic construct
SEQUENCE: 186

```
atgcgcgagc tagattatcg catcggcctg gatattggca ctaactcaat aggctgggc   60
gtgatcgaac tgagctggaa taaagaccgc gagcgctatg aaaaggtgcg cattgtggat  120
cagggcgtca gaatgtttga tcgtgcggaa atgccgaaaa ccggtgcatc actggcagaa  180
ccaagacgta tagcacgtag tagtcgccgc cgattaaacc gtaaaagcca gcgcaagaaa  240
aatatccgca acctgctggt tcagcatggc gtcatcaccc aggaagaact ggatagcctg  300
tacccgctga gcaagaaatc aatgacatc tgggcgctca gtctggataq tctggaccgc  360
ctattaaacc actttgaatg ggcccgccta ttaattcatc tggcgcagcg ccgcggcttc  420
aaatcaaacc gcaagagcga attaaaggac accgagaccg gtaaagtgct gtcatcgatc  480
cagctgaatg aaaaacgcct gagcctgtat cgcaccgtgg gcgagatgtg gatgaaagac  540
ccggacttct caaaatacga ccgcaaacgc aacagccgca agaatacgt gtttagcgtt  600
agccgtgcgg aactggagaa agaaatcgtg accctgtttg cagctcagcg ccgttttcag  660
agcccgtatg cgagcaaaga tctgcaagaa acctacctgc agatctggac ccatcagctg  720
ccgtttgcaa gcgtaacgc gatattaaac aaagtgggct attgcagcct attaaaaggc  780
aaagaacgcc gcatcccgaa agcgacctat acattccagt acttcagcgc gctggaccag  840
gtgaaccgta cccgtctggg tccggatttt cagccgttca ccaaagaaca gcgcgagatc  900
atattaaaca acatgttcca gcgcaccgac tactataaaa agaaaaccat cccggaggtg  960
acatattacg atataaggaa atggctgaaa ctggatgaaa ccatccagtt caaaggcctg  1020
aactacgatc gaacgagga gctgaaaaaa atcgagaaga aacgcttcat taatctgaaa  1080
gcgttctatg aaatcaacaa agtggtggcg aactacagcg aacgaccaa tgaaacctc   1140
tcaaccctgg attacgatgg catcggctac gcgctgaccg tgtataaaac cgacaaggat  1200
ataaggagct acctgaaatc aagccacaac ctgccgaaac gctgctacga cgaccaatta  1260
atcgaagaac tgctgagcct gagctatact aagttcggcc acctgtcatt aaaagcgatt  1320
aatcacgtgt taagcatcat gcagaaaggc aacacataaa agaagcgct ggatcagctg  1380
ggctacgata ccagcggatt aaaaaaagaa aaacgcagca attcctgcc gcgatcagc   1440
gatgaaatca ccaacccgat cgtgaaacgc gcgctgaccc aggcgcgcaa agtggtgaac  1500
gcgatcatcc gccgccacgg cagcccgcac agcgtgcaca tcgaactggc gcgcgaactg  1560
agcaaaaacc acgatgaacg caccaaaatc gtgagcgcgg aggatgaaaa ctacaaaaag  1620
aacaaaggcg cgatcagcat cctgtcagaa cacggcatcc tgaacccgac cggctacgat  1680
atcgtgcgct acaaactgtg gaaagagcag ggcaacgct gcgcgtacag cctgaaagaa  1740
atcccggcgg ataccttctt caacgagctg aaaaaagaac gcaacggcgc cccgatcctg  1800
gaagtggatc acatcctgcc gtacagccag agcttcatcg atagctacca caacaaagtg  1860
ctggtgtaca gcgatgaaaa ccgcaaaaaa ggcaacgca tcccgtacac ctacttctta  1920
gagaccaaca aagattggga agcgttcgaa cgctacgtgc gcagcaacaa gttcttcagc  1980
aaaaagaagc gcgagtacct gctgaaacgc gcgtacctgc cgcgcgaaag cgaactgatc  2040
aaagaagcgc atctgaacga tacccgctac gcgagccgct tcctgaaaaa cttcatcgaa  2100
cagaacctgc agttcaaaga gcggaagat aacccgcgca aacgccgcgt ccagaccgtg  2160
aacggcgtga tcaccgcgca ttttcgcaaa cgctggggct tagaaaaaga tcgccaggaa  2220
acctatctgc atcatgcgat ggatgcgatc atcgtgcgt gcaccgatca tcatatggtg  2280
acccgcgtga ccgaatatta tcagatcaaa gaaagcaaca aagcgtgaa aaaaccgtat  2340
tttccgatgc cgtgggaagg ctttcgcgat gaactgctga gccatctggc gagccagccg  2400
atcgcgaaaa aaatcagcga agaactgaaa gcgggctatc agagcctgga ttatatctt   2460
gtgagccgca tgccgaaacg ctcaatcacc ggcgcggcgc ataaacgac catcatgcgc  2520
aaaggcggca tcgataaaaa aggcaaaacc atcatcatcg aacgcctgca tctgaaagat  2580
atcaaatttg atgaaaacgg cgattttaaa atggtgggca aagaacagga catggcgacc  2640
tacgaagcga tcaaacagcg ctatctggag catggcaaga acagcaaaaa agcgtttgag  2700
accccgctgt acaaaccgag caaaaaaggc accggcaacc tgatcaaacg cgtgaaagtg  2760
gaaggccagg cgaaatcatt tgtgcgcgaa gtgaacggcg gcgtggcgca aacggcgat   2820
ctggtgcgcg tggatctgtt tgaaaaagat gacaaatatt atatggtgcc gatctatgtg  2880
ccggataccg tgtgtagcga actgccgaaa aaagtggtgg cgagcagcaa aggctatgaa  2940
cagtggctga ccctggataa cagctttacc ttcaaattca gcctgtatcc gtatgatctg  3000
gtgcgcctgt gaaaggcga tgaagatcgc tttctgtatt ttggcaccct ggacatcgat  3060
tcagatcgcc tgaacttcaa ggacgtgaac aaaccgagca aaagaacga atatcgctat  3120
agcctgaaaa ccattgaaga tctggaaaaa tatgaagtgg gcgtgctggg cgatctgcgc  3180
ctggtgcgca aagagacccg ccgcaacttt cat                                3213
```

SEQ ID NO: 187          moltype = DNA  length = 3213
FEATURE                 Location/Qualifiers
misc_feature            1..3213
                        note = source = /note="APG07513.1 Native Seq"

```
source          1..3213
                mol_type = genomic DNA
                organism = Bacillus sp.
SEQUENCE: 187
atgagagagt tggattatcg cataggatta gatattggaa cgaattctat tggctgggt      60
gttattgaat tatcttggaa caaagataga gaacaatatg agaaaacgag aattgtcgac    120
aagggtgttc gtatgtttga taaggctgaa atacctaaga ctggtgcttc tcttgctgaa    180
ccgagacgta tagcgcgctc atcacgtaga aggttaaatc gtaaaagcca gagaaaaaaa    240
gatatacgta atttacttgt tcaacatgaa attattagcc aaaagtaatt gacttcgtta    300
tatccctgt caaaaagttc aatggatatt tgggatattc gcttagatgg attagatcgc     360
ttgttagacc gttttgaatg ggctcgatta ttaattcatt tagcacaaag acgcggtttt    420
aaatcaaatc gaaagtctga actgaaagat gtggagacag gaaaagtatt atcaagtatt    480
caagtaaatg aaaaacgatt atctctgtac cgtacagtgg gagagatgtg gatgaagaat    540
gcggattgta gtaaatatgg caaaaggcgt aattctccta atgagtatgt attttcggtt    600
agccgtgcag atttagaaaa ggaaattgtg actctatttg aggcgcaaag aaaattccat    660
tcatcatatg catcggttga tttacaaaaa acatatatac aaatttgggc acaccaactt    720
ccttttgctt ctgggaatgc aattgtaaat aaagtaggat attgttcatt attaaaaggt    780
aaagaaaaga gagttccaaa agcaacatat acttttcaat atttcaatac actagatcaa    840
ataaaccgaa cacgattagg gcccaatttc caaccattta cgaaggaaca gagagacata    900
attttagata aaatgtttca acggacagat tattataaaa aaaagacaat acccgaagtt    960
acttactatg atattcggaa atggttagca ctagatgaaa caattcaatt taaaggactt   1020
acctatgacc caaacgaaga gctgaaaaaa atagaaatga aacccttat taattttaaag   1080
ccattctatg aaattaaaaa ggtagttact aattacgcaa aaaaaacaaa tgaggtattc    1140
tcagcattag attatgatac agttgcatac gctttaacag tttataaaac ggacaaagat   1200
attagatctt atttgaagag atcaataat ttatcaaaac gttgctacga tgatcaatta    1260
atagaagagc tattaactct ctcctataca aagtttggtc atttatcatt taaagcaatt   1320
aatcatgtac tgccaattat gcaagaggga aggacttatc aggaagcaat acaccaatta   1380
gggtatgata ccactaatct taaaaaagaa aacagaagta tgttcttgcc tattattcca   1440
gatgagataa caaatccaat tgttaaaaga gcgttaactc aagcacgtaa agttgtaaat   1500
gctattatta gaagatatgg ttctccaaat tctgttcata ttgaactgac tcgtgagctt   1560
tcgaaaagtc atgacgagag aaaaaaaata atgacagctc atgatgaaaa ttataagaaa   1620
aataaaggag ctgtatcaat tttgatcgat aatggaattt taaatccgac aggatatgat   1680
attgtacgtt ataagttatg gaaagagcaa ggagaacgat gtgcttattc gttaaaaaag   1740
attcctgcta atacgttttt taatgaattg aaaaaagagc gaagtggccc tccggttcta   1800
gaggtagatc acatttttacc gtatagtcag agttttattg atagttacca taataaagta   1860
ttagtttatg gggatgaaaa tcaaaaaaag ggaaatcgaa ttccatatac tttttttttca   1920
gaagaagata aggagtggga aagctttgaa agctacgtaa gatcgaatag tttttttttct   1980
aaaaagaagc gcggatattt attgaaaaaa gcttacttgc caagagagag taacttgatt   2040
aaggagcgtc atttaaatga tacccgatat gctagtagct atttgaaaaa cttcattgag   2100
aaaaatttaa aatttaaaga agctgtaggt attacacgaa aaaatatgt acagacggtt    2160
aacggtgtaa ttacagcccca tctgcgaaaa aggtgggtt tagaaaaaga taggcaggaa    2220
acatatttgc atcatgcaat ggacgctatt attgttgctt gtacagatca tcatatggtc   2280
actaaagtaa cggagtacta tcaaataaga gaaggtaata agtcaataaa gaaaccgtat   2340
tttcctttgc catggatggg attttagagag gaaattttat cacatttaga aagtcagcca   2400
attgctagaa aaattagtga ggaacttaaa attggatatc aatcacctga ttatatactt   2460
gtatcgcgaa tgccaaaag atctgtcact ggatcagctc atgatcagac agtcatgaaa   2520
aaaggcgtca tcgataaaaa aggaaagact attatcatca agcgtgtgca cttaaaggat   2580
attaagtttg atgagaatgg cgatttttaaa atggttggca aagaacaaga tttagcaact   2640
tacgaagcga taaagcaaag atatttagag tatagaaaag aatcgaaaaa agcatttgaa   2700
acaccttat acaagcctag taaaaaagga aaaggaaacc tcattaaaaa aattaaagta    2760
gaagtgcaaa ccaaatcttt tgttcgagaa attaatgggg gcgtagctca aaatggtgat   2820
ttagtaagag tagatttgtt tgaaaaggat aataggtatt atatggtgcc tatttacgta   2880
gtagatactg ttcgttccga actaccaaat aaagctgtaa caagcagtaa aggctatgag   2940
caatggttat caatagataa cagctttacg ttcaaattca gtttatatcc ttatgattta   3000
gtacgacttg taaaaggcga tgaagatcgt tttctatact ttagtactct tgatattaat   3060
tcggaccgtc ttaattttaa agatgtaaat aagccatcaa agcaagctga atatcgttat   3120
agtcttaaaa caattgagaa tttagaaaaa tatgagattg gtgttttagg tgatttaagg   3180
ttagtgagac aagaaacacg taaaattttt aaa                                3213

SEQ ID NO: 188            moltype = DNA   length = 3213
FEATURE                   Location/Qualifiers
misc_feature              1..3213
                          note = source = /note="Description of Artificial Sequence:
                          Syntheticpolynucleotide"
misc_feature              1..3213
                          note = source = /note="APG07513.1 E. coli optimized"
source                    1..3213
                          mol_type = other DNA
                          organism = synthetic construct
SEQUENCE: 188
atgcgcgagc tagattatcg catcggcctg gatattggca ctaactcaat aggctggggc     60
gtgatcgaac tgagctggaa taagaccgc gagcagtatg aaaagacccg catcgtggat    120
aaaggcgtgc gcatgttcga caaagcgaa attccgaaaa ccggtgcaag tctggcggaa    180
ccaagacgta ttgcacgtag tagtcgccgc cgattaaaac gcaaaagtca gcgcaagaag   240
gatatcagga acctgctggt ccagcatgaa atcatcagcc agaaggaatt aaccagcctg    300
tacccgctga gcaaatcaag tatggacatc tgggatataa ggctgacgg cctgaccgc     360
ctgctggatc gttttgaatg ggcccgccta ttaatccatc tggcacagcg ccgtggcttc    420
aaatcaaacc gcaagagcga attaaaggac gtggagaccg gtaaagtgct gtcaagcatt    480
caggtgaatg aaaagcgcct gagcctgtat cgcaccgtgg gcgagatgtg gatgaaaaac   540
```

```
gcggactgct caaaatatgg caaacgccgc aacagcccga acgaatacgt gtttagcgtt    600
agccgtgcgg acctgaaaaa agaaatcgtg accctgtttg aggcgcagcg caaattccat    660
agcagctatg cgagcgtgga tctgcagaaa acatacatcc agatctgggc acatcagctg    720
ccgtttgcga gcggtaacgc gatcgtgaat aaagtgggct attgcagcct attaaaaggc    780
aaagaaaaac gcgtgccgaa agcgacctat acattccagt acttcaatac actggaccaa    840
atcaaccgca cccgcctggg cccgaacttc cagccgttca ccaaagaaca gcgcgatata    900
atcctggata aaatgttcca gcgcaccgac tactataaaa agaaaaccat cccgagggtg    960
acatactacg atataaggaa atggctggcg ctggatgaaa ccatccagtt caagggctta   1020
acctacgatc cgaacgagga gctgaaaaag atcgagatga aaccgttcat taatctgaaa   1080
ccgttctatg aaattaaaaa ggtggtaacc aactacgcga agaaaaccaa cgaagtgttc   1140
agcgcgctgg attacgatac cgtggcgtac cgcgctgaccg tgtataaaac cgacaaggat   1200
ataaggagct acctgaaacg cagcaataat ctgagcaaac gctgctacga cgaccaatta   1260
atcgaagaac tgctgaccct gagctatact aagttcggcc acctgagctt caaagcgatt   1320
aatcacgtgc tgccaataat gcaggaaggc cgcacctacc aggaagcaat acacagctg   1380
ggctacgata caaccaacct gaaaaaggaa aataggagca tgttcctgcc aataatcccg   1440
gatgaaatca ccaacccgat cgtgaaacgc gcgctgaccc aggcgcgcaa agtggtgaac   1500
gcaataatcc ccgctacgg ctcaccgaac agcgtgcaca tcgaactggc gcgcgaactg   1560
agcaaagcc acgatgaacg caaaaagatc atgaccgcgc acgatgaaaa ctacaaaaag   1620
aacaaaggcg cggtgagcat cctgatcgat aacggcatcc tgaacccgac cggctacgat   1680
atcgtgcgct acaaactgtg gaagaacag ggcgaacgct gcgcgtacag cctgaaaag    1740
atcccggcga acaccttctt caacgaactg aaaaaggaac gctcaggccc gccggtgctg   1800
gaagtggatc acatcctgcc gtacagccag agcttcatcg atagctacca caacaaagtg   1860
ctggtgtacg gcgacgaaaa ccagaaaaag ggcaaccgta tcccgtacac cttcttcagc   1920
gaagaagaca agaatgggga gagcttcgaa agctacgtgc gcagcaacag cttcttcagc   1980
aaaaagaaac gcggctaccct gctgaaaaag gcgtacctgc cgcgcgaaag caacttaatc   2040
aaagaacgcc atctgaacga tacccgctac gcgagcgatc acctgaaaaa cttcattgag   2100
aaaaacctga aattcaagga agcggtgggc atcaccccgca agaagtacgt ccagaccgtg   2160
aacggcgtga tcaccgcgca tctgcgcaaa cgctgggggcc tggaaaaaga tcgccaggaa   2220
acctatctgc atcatgcgat ggatgcgatc atcgtggcgt gcaccgatca tcatatggta   2280
accaaagtga ccgaatatta tcagatcaaa gaaggcaaca aatcaatcaa aaagccgtat   2340
tttccgctgc cgtggatggg cttccgcgaa gaaatcctta gccatctgga aagccagccg   2400
atcgcgcgca aaatcagcga agaactgaaa atcggctatc agagcccgga ttatatcctg   2460
gtgagccgca tgccgaaacg cagcgtgacc ggcagcgcgc atgatcagac cgtgatgaaa   2520
aagggcgata tcgataaaaa gggcaaaacc atcatcatca aacgcgtgca tctgaaagac   2580
atcaaattcg acgaaaacgg cgacttcaaa atggtgggca aggaacagga cttagcgacc   2640
tacgaagcga tcaaacagcg ctacctggaa taccgcaaag agagcaaaaa ggcgtttgaa   2700
accccgctgt acaaaccgag caaaaagggc aagggcaacc tgatcaaaaa gatcaaagtg   2760
gaagtccaga ccaaatcgtt tgtgcgcgag atcaacggcg gcgtggcgca aacggcgat   2820
ctggtgccgcg tggatctgtt tgaaaaagat aaccgctatt atatggtgcc gatctacgtg   2880
gtggatacccg tgcgcagcga actgccgaac aaagcgtgga ccagcagcaa aggctatgaa   2940
cagtggttaa gcatcgataa cagcttcacc ttcaaattca gcctgtaccc gtatgatctg   3000
gtgcgcctgg tgaaagcga tgaagatcgc ttcctgtatt ttagcaccct ggacatcaac   3060
agcgatcgcc tgaacttcaa agacgtgaac aaaccgacga aacaggcgga atatcgctac   3120
agcctgaaga ccatcgagaa cctggagaaa tacgaaattg gcgtgctggg cgatctgcgc   3180
ctggtgcgcc aggaaacccg caaaatcttc aaa                                3213
```

SEQ ID NO: 189          moltype = DNA   length = 3216
FEATURE                 Location/Qualifiers
misc_feature            1..3216
                        note = source = /note="APG08290.1 Native Seq"
source                  1..3216
                        mol_type = genomic DNA
                        organism = Bacillus sp.

SEQUENCE: 189
```
atgagtgagt tggattaccg catagggttg gatattggta cgaattccat tggctgggt     60
gttattgaat tattttgaa caaggacaga gaacgatatg aaaaagtaag gattgtcgac    120
aagggcgttc gtatgtttga taaggctgaa ataccctaata agggtgcttc tcttgctgaa    180
ccgagacgta tagcgcgttc atcacgtaga aggttaaatc gcaaaagtca gaggaagaaa    240
gagatacgta atttacttgt tcaacacgga atgattaccc aagagggaatt ggatttgtta    300
tatcctcttt caaaaaaaatc aatagatatt tgggatattc gtttggatgg attagatcgt    360
ctgttgaatc atcttgaatg ggctcgatta ttaattcatt tagcacaaag acgtggtttt    420
aagtcgaatc gaaagtctga attgaaagat gctgagacgg ggaaggtatt atcgagtatt    480
caagtaaatg aaaaacgact atttctgtac cgtacagtgg gggaaatgtg gataaaagat    540
gctgagttta gtaagtatga tagaagacgt aattctccta gtatgtatgt attttcggtt    600
agtcgtgcgg acttagaaaa ggaaattgtt actctatttg aagcacaaag aaagtttcag    660
tcatcatacg catcgaagaa cttacaagaa acatatttac aaatttgggc acaccaactt    720
cccttttgctt ctgggaatgc aatttaaac aaagtaggct attgttcatt attgaaaggg    780
aaagaaagga gaattccgaa agcaacatat acttttcaat atttcagtgc actagatcag    840
gtgaatcgaa cacgattagg acctgatttt caaccattca cgcaggaaca gaaagagatt    900
attttagata aaatgttttca acgtacagat tattataaaa aaaagactat acctgaagtt    960
agctactatg atatacggaa atggctagag ttagatgaaa ctattcaatt taaggactt    1020
aattatgatc caaacgaaga actgaaaaaa atagaaaaaa accatttat taatttaaag    1080
gcattctatg aaattaaaaa ggtagttgca aattatgctg agagaacaaa tgaggcattt    1140
tcaacgtag acatgatgc gattgcatat gcttaacag tttataaaac ggacaaagat    1200
attagatctt atttgaagaa atctaataat ttatcaaaac gttgctacga cgatcaatta    1260
atagaagagc tatttactct ctcctataca aagtttggtc atttatcatt taagcaatt    1320
aatcatgtac ttccaattat gcaagaggga aggacttatc aagaagcgat acaccaatta    1380
ggatatgata ccactaatct taaaaaagaa acagaagta tgttcttgcc tcttattcca    1440
gatgaaataa caaatccaat tgttaaagga gcgataactc aagcacgtaa agttgtaaac    1500
```

```
gctattatta gaagatatgg ttctccaaat tctgttcata ttgaactagc tcgtgagctt   1560
tctaaaagtc atgacgagag aaagaaaata atgacggctc atgatgaaaa ttataagaaa   1620
aataaaggag ctatatccat tttgatcgag aatggaattt taaatccgac aggatatgat   1680
attgtacgtt ataagttatg gaaagagcaa ggagaacgat gtgcttattc gttaaaggag   1740
attcctccgg atacgttttt taatgaatta aaaaaagaac gaaatggttc tccaattcta   1800
gaggtagatc acattttacc gtatagccaa agttttattg atagttatca taataaagta   1860
ttagtttaca gtgatgaaaa tcgaaacaag ggaaatcgaa ttccatatac ctatttttta   1920
gagacaaata aggattggga agcttttgaa aggtatgtaa gatcaaataa gcttttttct   1980
aaaaagaagc gtgagtattt attgaaaaaa acatatttgc caagagagag tgaactaata   2040
aaggagcgac atttaaatga tacgcgatat gctagtacct tttttgaaaaa cttcattgag   2100
cagaacttgc aatttaaaga agttgaagtt aatctgcgta aaaaacgtgt gcaaacagtt   2160
aatggtgtaa ttacagcgca ccttcgaaaa agatggggat tagaaaaaaa tagacaggaa   2220
acatatctgc atcatgcaat ggacgctatc attgttgctt gtacagacca tcatatggtt   2280
actagaataa cagagtatta tcaaataaaa gaaagtaata aatcagtaaa gaaaccatat   2340
tttccgatgc catgggaggg ttttagagat gaactcttat cacatttagc gagccagcca   2400
attgctaaaa aaattagtga ggagcttaaa gctggatatc aatcatctga ttatatattt   2460
gtgtctcgaa tgccaaaaag atctgtcact ggagcagctc atgatcaaac gattaggaga   2520
aaaggtggta ttgataaaaa aggaaaaact attattataa agcgtgtgcg cttaaaggat   2580
attaagtttg atgagaatgg cgattttaaa atggttggaa aagaacaaga tttagcaact   2640
tatgaggcga taaagcaaag atatttggag catagaaaaa actcgaaaaa agcatttgaa   2700
acacctctat acaagcctag taaaaagggg acaggaaatc tcatcaaaag agttaaaatt   2760
gaaggacaaa ctaaagcttt tgttcgaaaa gtaaatgggg gagtagccca aaatagtgat   2820
ttagtaagag ttgatttatt tgaaaaagat gataaatatt acatggtgcc tatttatgta   2880
ccagataccg tttgttcaga attacccaaa aaagttgtga aaagtggtaa gggttatgag   2940
caatggctaa cactagataa cagctttacg tttaaatcta gtttataccc ttatgattta   3000
gtacgtcttg taaaaggtaa tgaagatcgt tttttatact ttggtactct cgatatcgat   3060
tctgaccgtc ttaatttaaa agatgtaaat aagccatcaa aacagaatga atatcgttat   3120
agtcttaaaa caattgagaa tttagaaaaa tatgaggttg gtgttttagg tgatttaagg   3180
ttagtgaaac aagaaacacg tagaattttt aataga                             3216

SEQ ID NO: 190         moltype = DNA   length = 3216
FEATURE                Location/Qualifiers
misc_feature           1..3216
                       note = source = /note="Description of Artificial Sequence:
                       Syntheticpolynucleotide"
misc_feature           1..3216
                       note = source = /note="APG08290.1 E. coli optimized"
source                 1..3216
                       mol_type = other DNA
                       organism = synthetic construct
SEQUENCE: 190
atgagcgagc tagattatcg catcggcctg gatatcggca ctaactcaat aggctggggc     60
gtgatcgaac tgttctggaa taaagaccgc gagcgctatg aaaaggtgcg catcgtggac    120
aaaggcgtca ggatgttcga caaagcggag atcccgaata aaggtgcatc actggcggaa    180
ccaagacgta tagcacgtag tagtcgccgc cgattaaacc gcaaaagtca gcgcaagaaa    240
gagatccgta acctgctggt tcagcatggc atgatcaccc aggaagaact ggatctgctg    300
tacccgctga gcaagaaatc aatcgacatc tgggatataa gcctggaccg c            360
ctattaaacc atctggaatg ggcccgccta ttaatccatc tggcgcagcg tagaggcttc    420
aaatcaaacc gcaagagcga attaaaggac gcggagaccg gtaaagtgct gtcaagcatt    480
caggtgaatg aaaagcgcct gttcctgtat cgcaccgtgg gcgagatgtg gattaaagac    540
gcggagttct caaaatacga ccgccgtcgc aacagcccga gagtaacgt gtttagcgtt    600
agccgtgcgg acctggagaa agaaatcgtg accctgtttg aagcgcagcg caaattccaa    660
tcaagctacg cgagcaagaa cctgcaagag acctacctgc agatttgggc acatcagctg    720
ccgtttgcaa cgcgcaacgc gatattaaac aaagtgggct attgcagcct attaaaggc    780
aaagaacgcc gcatcccgaa agcgacctat acattccagt cttcagcgc gctggaccag    840
gtgaaccgta cccgtctggg ccctgatttt cagccgttta cccaggaaca gaaagaaata    900
atcctggata aaatgttcca gcgcaccgac tactataaaa agaaaaccat cccggaagtg    960
tcatattacg atataaggaa atggctggag ctggatgaga ccatccagtt caagggcctg   1020
aactacgatc cgaacgagga gctgaaaaaa atcgagaaaa aaacgttcat taatctgaaa   1080
gcgttctatg aaattaaaaa agtggtggcg aactacgcgg aacgaaccaa cgaagcattc   1140
agcaccctgg attacgatgc gatcgcgtac gcgttaaccg tgtataaaac gacaaggat    1200
ataaggagct acctgaaaaa atcaaacaac ctgagcaaac gctgctacga cgaccaatta   1260
atcgaagaac tgttcacact gagctatact aagttcggcc acctgagctt caaagcgatt   1320
aatcacgtgc tgcaataat gcaggaaggc cgcacctacc aggaagcgat caccagctg    1380
ggctacgata ccaccaacct gaaaaaagaa aaccgcagca tgttcctgcc gctgatcccg   1440
gatgaaatca ccaacccgat cgtgaaacgc gcgatcaccc aggcgcgcaa agtggtgaac   1500
gcgatcatcc gccgctacgg ctcaccgaac agcgtgcaca tcgagctggc gcgcgagctg   1560
agcaaaagcc aacgacgagcg caaaaaaatc atgaccgcgc acgacgagaa ctacaagaaa   1620
aacaaaggcg cgatcagcat cctgatcgag acggcctgac cggctacgat                1680
atcgtgcgct acaaactgtg gaagaacagg ggtgaacgct gcgcgtacag cctgaaagaa   1740
atcccgccgg atccttcttc aacgaactga aaaaagaaac gcaacggctc accgatcctg   1800
gaagtggatc acatcctgcc gtacagccag agcttcatcg atagctacca caacaaagtg   1860
ctggtgtaca gcgatgaaaa ccgcaacaaa gcaacgcca tcccgtacac ctacttcctg     1920
gaaaccaaca aagattggga agcgttcgaa gctacgtgcg gaagctataa actgttcagc   1980
aaaaagaaac gcgaatacct gctgaaaaaa acctacctgc gcgcgaaag cgaactgatc   2040
aaagaacgcc acttaaacga tacccgctac gcgagcacct tcctgaaaaa cttcatcgaa   2100
cagaacctgc agttcaaaga agtggagtg aacctgcgta aaaagcgcgt ccagaccgtg    2160
aacggcgtga tcaccgcgca tctgcgcaaa cgctgggggc tggaaaaaaa ccgccaggaa   2220
acctatctgc atcatgcgat ggatgcgatc atcgtggcgt gcaccgatca tcatatggtg   2280
```

```
acccgcatca ccgaatatta tcagatcaaa gaaagcaaca aatcagtgaa aaaaccgtat    2340
tttccgatgc cgtgggaagg ctttcgcgat gaactgctga gccatctggc gagccagccg    2400
atcgcgaaaa aaatcagcga agaactgaaa gcgggctatc agagcagcga ttatatcttt    2460
gtgagccgca tgccgaaacg cagcgtgacc ggcgcggcgc atgatcagac catccgccgc    2520
aaaggcgcga tcgataaaaa aggcaaaacc atcatcatca aacgcgtgcg cctgaaagat    2580
atcaaatttg atgaaaacgg cgattttaaa atggtgggca agaacagga cttagcgacc    2640
tacgaagcga tcaaacagcg ctatctggag catcgcaaga acagcaaaaa agcgtttgag    2700
accccgctgt acaaaccgag caaaaaaggc accggcaacc tgatcaaacg cgtgaaaatc    2760
gagggccaga ccaaagcgtt tgtgcgcgaa gtgaacggcg gcgtggcgca gaacagcgat    2820
ctggtgcgcg tggatctgtt tgaaaaagat gacaaatatt atatggtgcc gatctatgtg    2880
ccggataccg tgtgtagcga actgccgaaa aaagtggtga aaagcggcaa aggctatgaa    2940
cagtggttaa ccctggataa cagcttcacc ttcaagagca gcctgtaccc gtatgatctg    3000
gtgcgcctgg tgaaaggcaa cgaagatcgc tttctgtatt ttggcaccct ggacatcgat    3060
agcgatcgcc tgaacttcaa agacgtgaac aaaccgagca agcagaacga atatccgtac    3120
agcctgaaga ccatcgagaa cctggagaaa tatgaagtgg gcgtgctggg cgatctgcgc    3180
ctggtgaaac aggaaaaccg ccgcattttt aaccgc                              3216

SEQ ID NO: 191        moltype = DNA   length = 4011
FEATURE               Location/Qualifiers
misc_feature          1..4011
                      note = source = /note="APG05459.1 Native Seq"
source                1..4011
                      mol_type = genomic DNA
                      organism = Enterococcus sp.
SEQUENCE: 191
atgaagaaag actacgttat tggtctggat atagggacta attctgtcgg ctgggcagtt    60
atgacagaag actatcagtt ggtgaagaaa aaaatgccta tttatggaaa cactgaaaaa    120
aagaaaatca agaaaatttt tggggtgtg cgtttatttg aagaaggca tacagccgaa    180
gatcgccgat taaaagaac agcacgacga agaattagtc gtcgacgaa tcgtttacgc    240
tacttacaag ctttttttga agaagcgatg acagcttttg ttttgctcgt                 300
ttacaagaga gttttttagt gcctgaagat aagaagtggc acagacatcc gattttgct     360
aagttggaag atgaagtagc ttaccatgaa acgtatccga caatctacca tttacgcaaa    420
aaattagcag attcatctga gcaagcagat ttacgactaa tttatttggc gttggcacat    480
attgtcaaat atcgtggaca ttttttaatt gaaggaaat taagtacaga aaatatttct    540
gttaaagaac aatttcaaca atttatgatc atttataacc aaacctttgt gaatggagag    600
agtcgcttag ttagtgcgcc attacctgaa tctgtcttga ttgaggaaga gttgactgaa    660
aaagcttctc gtactaaaaa atctgaaaaa gtcttacaac aatttcctca agaaaaagct    720
aatggcttat ttggtcagtt cttaaagcta atggtaggga ataaagctga cttttaaaaa    780
gttttttggtt tggaagaaga agccaaaata acctacgcta gtgaaagcta tgaagaagat    840
ttagaaggca ttttagcaaa ggttggggat gaatatagtg acgtgttttt agctgctaaa    900
aatgtgtacg atgcagttga attatcaacg attttagcag attcggataa aaaaagtcac    960
gcgaaattat cttctagcat gattgtccgt tttacagaac atcaagaaga tttaaaaaaa    1020
tcaaacgat ttattcgtga aaattgtcca gacgaatatg ataatctctt taaaaatgaa   1080
cagaaagacg gctatgcagg ctacattgca cacgcaggta aggtttcaca gcttaaattt    1140
taccagtatg ttaagaaaat cattcaagat attgctggag cagaatattt tttagaaaaa    1200
attgctcaag aaaactttt aagaaagcaa cggacctttg ataatgggt gattcctcat     1260
caaattcatt tggctgagtt acaagcaatc attcatcgtc aagcggccta ttatccattt    1320
ttaaagaaa atcaagaaaa aattgaacaa ctggttacat ttcgaattcc ttattatgtc    1380
ggaccattat caaaggaga tgcaagtacc ttcgcttggc taaacgtca aagtgaggaa     1440
ccaattcgac cttggaaccct tcaagaaacc gttgatttgg accaatcagc gacagccttt    1500
attgaacgaa tgaccaattt tgatacgtat ttaccttctg aaagttttt accgaaacat    1560
agtttgttat atgaaaagtt tatggtattt aatgaattga ccaagatttc ttatacggat    1620
gatcgaggaa tcaaagccaa ttttcaggt aaagaaaaag aaaaaatctt tgattatctg    1680
tttaagacgc gtcgaaaagt taagaaaaag gatatcattc aattctatcg aaacgaatat    1740
aatacggaa ttgtcacgct tagtggactt gaagaagacc aatttaatgc tagttttagc     1800
acgtatcagg atttactgaa atgtggttta acaagagctg aattagacca ccctgataat    1860
gccgaaaaat tggaagatat cataaaaatt ttaactattt ttgaagatcg gcaacgaatt    1920
cggacgcaac tttccacatt caaagggcag ttctcagcag aagtactaaa aaaattagaa    1980
cgcaagcact acactggctg gggaagattg tcgaaaaaat taatcaatgg tatctacgat    2040
aaagaatcgg gtaaaacaat tttgactat ttaattaaag atgatggggt ctcaaaacac    2100
tataatcgca attttatgca actgattaat gattcacaat tatctttaa aaatgctatt    2160
caaaagcac agtccagtga acatgaagaa acattaagtg aaactgtcaa tgaattagct    2220
ggtagtccag caataaaaaa aggaattat caaagtttaa aaattgtcga tgaactagtc    2280
gcgattatgg gttatgcgcc caagcggatt gttgtcgaaa tggcacgtga aaatcaaacg    2340
actagcactg gcaagagaag atccatccaa cgcttgaaaa tagttgaaaa agcaatggcc    2400
gaaatcggca gcaattttatt aaaagaacaa ccaacgacta tgaacagtt acgagatacc    2460
cgtctttttcc tttactatat gcaaatggt aaagatatgt acacgggaga tgaattatcg    2520
cttcatcgtt tatctcacta tgatattgat catattatcc cacaaagctt tatgaaagac    2580
gattcattg ataacctagt tttagtgggc tctactgaaa atcgaggaa atccgatgat     2640
gtacctagca aggaagttgt taaggatatg aaagcttatt gggagaaatt atatgctgct    2700
ggcttaatta gtcaacggaa attccaacgt ctgaccaagg gggagcaagg tggcttgact    2760
ctcgaagaca aagcgcattt tatccaacga caattagtag aaactcgtca aattaccaaa    2820
aatgttgcag ggatcttaga tcaacgctac aatgctaatt caaagaggaa aaaagtccaa    2880
atcatcacct tgaaaggcag tttaacgagc caatttcgtt cgatttttgg cttgtataa    2940
gttcgtgaag tgaatgatta tcaccatgga caagatgctt atttaaactg tgtggtcgca    3000
accacgttat taaagttta tcctaattta gcaccagaat tgttacggg agaatatcct    3060
aaattccagg ccctttaaga aaataaagcc acggcgaaga ctataattta tacaaatttg    3120
atgcgctttt tcacgggaaga tgaaccacgg ttcatgaagg atggcgaaat tctttggagt    3180
aacagttatt taaaaaatat caaaaagaa ttaaattacc atcaaatgaa tattgtcaaa     3240
```

```
aaagtagaag tgcaaaaagg cggttttcca aaagagtcga ttaaacccaa aggaccatcg    3300
aataaattga ttcctgtcaa aaatggtttg gatccccaaa aatatggcgg ttttgatagt    3360
cctgtagttg cttatacagt gttattcacg catgaaaaag gtaaaaaacc tcttattaaa    3420
caggagatac tgggcattac gattatgaaa aaacaaggt ttgaacaaaa tcctattctt     3480
tttttagagg agaaaggctt cctacggcct cgtgtattaa tgaaattgcc taagtataca    3540
ctgtatgaat ttccagaggg gcgcaggcgc ttattagcca gcgctaaaga agcgcaaaaa    3600
gggaaccaga tggttttacc tgaacattta cttacgttac tgtaccatgc gaaacaatgt    3660
ttgttaccaa atcaatcaga aagtttggct tatgtagaac aacatcaacc agaatttcaa    3720
gagattttag agagagtggt tgactttgct gaagtgcata cattagccaa gtcaaaagtc    3780
cagcaaattg tgaaactttt tgaagcaaat caaacagcag atgtgaaaga gattgcggca    3840
tcctttatcc aacttatgca gtttaatgcg atgggcgcac caagtacgtt taaattttc    3900
caaaaagaca ttgagcgagc acgctacacg tcaatcaaag aaattttga tgccactatc      3960
atttaccaat cgactacggg actgtatgaa acacgcagaa aggttgtcga c             4011

SEQ ID NO: 192        moltype = DNA   length = 4011
FEATURE               Location/Qualifiers
misc_feature          1..4011
                      note = source = /note="Description of Artificial Sequence:
                      Syntheticpolynucleotide"
misc_feature          1..4011
                      note = source = /note="APG05459.1 E. coli optimized"
source                1..4011
                      mol_type = other DNA
                      organism = synthetic construct
SEQUENCE: 192
atgaaaaagg actacgtgat cggcctagac atcggcacta acagcgttgg ttggcggtg     60
atgaccgaag attaccagct agtgaagaag aagatgccta tctacggtaa tacagagaag    120
aagaagatta aaaagaactt ctggggcgtg aggctattcg aggagggtca caccgcggag    180
gaccgccgcc tgaagcgcac cgctagacgc cgtatttcac gtcgtcgtaa ccgtctgcgt    240
tacctgcaag cattcttcga agaagcaatg accgcgctgg atgaaaactt cttcgctagg    300
ctgcaggagt catttctggt gccggaggat aaaaagtggc accgtcatcc gatcttcgcg    360
aaactagaag acgaggtggc gtaccatgaa acctacccga ctatctacca cctgcgcaaa    420
aagctggcgg atagcagcga acaagcagac ctgcgattaa tctatctggc gctggcgcac    480
atcgtaaaat acagaggcca cttcctcatc gagggcacaa tatcgaccga aaatattagc    540
gtgaaggagc agttccagca gttcatgatc atctacaacc aaaccttcgt gaacggcgaa    600
tcaaggctgg tgagcgcgcc gctgccgag agcgtattaa ttgaggagga ttaaccgag     660
aaagcgagcc gcactaagaa aagcgagaaa gtgcttcagc agttcccgca agaaaaagcg    720
aacggcctgt tcggccagtt cctgaaatta atggtgggca ataaagcgga cttcaaaaag    780
gtgttcggcc tggaagagga ggcgaaaata acctacgcag gcgaaagcta cgaggaagac    840
ctggagggca tactagcgaa agtgggcgac gaatacagtg acgtgttcct ggcggctaaa    900
aacgtgtacg acgcggtgga attaagcacc atactagcgg acagcgataa aaagagtcac    960
gcgaaattaa gctcaagcat gatcgtgcgc ttcaccgaac accaggaaga cctgaaaaag    1020
ttcaaacgct tcatccgcga aaactgcccg gacgaatacg ataacctgtt caaaaacgaa    1080
cagaaagatg gctacgcggg atacatcgcg cacgcgggca aagtgtcaca attaaagttc    1140
taccagtacg tgaagaaaat aatccaggat atcgcgggcg cggaatactt cctggagaaa    1200
atagcgcagg agaacttcct taggaaacag cgcaccttcg acaacggcgt gatcccgcac    1260
caaatacacc tggcggaact acaggcaata attcaccgcc aggcggcata ctaccgttc     1320
ctgaaagaga accaggagaa aatagaacag ctggtgacct tccgcatccc atactacgtg    1380
ggcccgctta gcaaggcga tgcgagcacc ttccgtggc tgaaacgcca gagcgaagaa      1440
ccaatccgcc cgtggaactt acaagaaacc gtggatctgg atcagagcgc gaccgcgttc    1500
atcgaacgca tgaccaactt cgatacatac ctgccgagcg aaaaagtgct gccgaagcat    1560
agcctgctgt atgaaaaatt catggtgttc aacgaactga ccaaaataag ctacaccgat    1620
gatcgcggca ttaaagcgaa cttcagcggc aaagaaaaag agaaaatatt cgattaccta    1680
ttcaaaaccc gccgcaaagt gaaaagaaa gacataatac agttctaccg caacgaatac    1740
aacaccgaaa tcgtgaccct gagcgccctg gaagaagatc agttcaacgc gagcttcagc    1800
acctaccagg acttattaaa atgcggcctg acccgcgcgg agcttgacca cccgacaac    1860
gcggaaaaac tggaagatat cattaaaata ctgaccatct tcgaagatcg ccagcgcatc    1920
cgcacccagc tgagcacctt caagggccag ttcagcgcgg aagtgctgaa aaagctggaa    1980
cgcaaacatt acaccggctg gggccgcctg agcaaaaagc tgatcaacgg catctacgat    2040
aaagaatcag gcaaaaccat cctggactac ctgatcaaag atgcggcgt gagcaaacac     2100
tacaaccgca acttcatgca gctgatcaac gatagccagc tgagcttcaa gaacgcgatc    2160
cagaaagcgc agagcagcga acatgaagaa accctgagcg aaaccgtgaa cgaactggcg    2220
ggcagccgg cgatcaaaaa gggcatctat cagagcctga aatcgtgga tgaattagtg      2280
gcgatcatgg gctatgcgcc gaaacgatc gtggtgaaa tggcgcgca aaaccagacc       2340
accagcaccg gcaaacgccg cagcatccag cgcctgaaaa tcgtggaaaa agcgatggc     2400
gaaatcggca gcaacctgct gaagaacag ccgaccacca cgaacagct gcgcgatacc      2460
cgcctgtttc tgtattatat gcagaacggc aaagatatgt ataccggcga tgaactgtca    2520
ctgcatcgcc tcagcatta tgatatcgat catatcatcc cgcagagctt tatgaaagat    2580
gatagcctgg ataacctggt gctggtgggc agcaccggca accgcggcaa aagcgatgat    2640
gtgccgagca aagaagtggt gaaagatatg aaagcgtatt gggaaaaact gtatgcggcg    2700
ggcctgatca gccagcgcaa atttcagcgc ctgaccaaag gcgaacaggg cggcctgacc    2760
ttagaagata aagcgcattt tatccagcgc cagctggtgg aaaccgcca gatcaccaaa     2820
aacgtggcgg gcatcctgga tcagcgctat aacgcgaaca gcaaagaaaa gaaagtccag    2880
atcatcaccc tggaacgag cctgaccagc cagttcgca gcatctttgg cctgtataaa      2940
gtgcgcgaag tgaacgatta tcatcatggc caggatgcgt atctgaactg cgtggttggca   3000
accaccttac tgaaagtgta tccgaacctg cgccgaat ttgtgatg cgaatatccg        3060
aaatttcagg cgtttaaaga aaacaaagcg accgcgaaaa ccatcatcta taccaacctg    3120
atgcgcttct ttaccgaaga tgaaccgcgc tttatgaaag atgcgaaat tctgtggagc    3180
aacagctatc tgaaaaacat caaaaaggaa ctgaactacc accagatgaa catcgtgaaa    3240
```

```
aaggtggagg tccagaaagg cggcttctca aaggaaagca tcaaaccgaa aggcccgagc    3300
aacaaactga tcccggtgaa aaacggcctg gacccgcaga aatatggcgg ctttgatagc    3360
ccggtggtgg cgtataccgt gctgtttacc catgaaaaag gcaaaagcc gctgatcaaa     3420
caggaaattc tgggcatcac catcatggag aaaacccgct tgaacagaa cccgatcctg     3480
ttcctggaag aaaaaggctt tctgcgcccg cgcgtgctga tgaaactgcc gaaatatacc    3540
ctctatgaat ttccggaagg ccgccgccgc ctgctggcga gcgcgaaaga agcgcagaaa    3600
ggcaaccaga tggtgttacc ggaacatctg ctgaccctgc tgtatcatgc gaaacagtgc    3660
ctgctgccga accagagcga aagcctggcg tatgtggaac agcatcagcc ggaatttcag    3720
gaaattctgg aacgcgtggt ggattttgcg gaagtgcata ccctggcgaa aagcaaagtt    3780
cagcagattg ttaaactgtt tgaagcgaac cagaccgcgg atgtgaaaga aattgcggcg    3840
agctttattc agctgatgca gtttaacgcg atgggcgccc cgagcacctt caaattcttt    3900
cagaaagata ttgaacgcgc gcgctatacc agcattaaag aaattttga tgcgaccatt     3960
atctatcagt caaccaccgg cctgtatgaa acccgccgca agtggtggga t              4011

SEQ ID NO: 193        moltype = DNA  length = 4308
FEATURE               Location/Qualifiers
misc_feature          1..4308
                      note = source = /note="APG04583.1 Native Seq"
source                1..4308
                      mol_type = genomic DNA
                      organism = Enterococcus sp.
SEQUENCE: 193
atggctaaaa atatacttgg attagatttg ggaaccaata gtattggttg ggcgttggta    60
cagcaagact ttgaaaacaa agaaggaaat attcttggaa tgggaagtag gattattccg    120
atgtcgcaag atatttagg agaattcggt aaggggaatt ctatttctca aactgctgaa     180
cgtactcggtt atcgtggtgt ccgtcggtta agagaacgac atttattacg tcgtgagcgt    240
ttgcaccgag ttttgcattt gttgggttc ttgccaaaac attatgatga aaaaatagat     300
tttacacaac gttttgggaa attcattaac caagccgaac ctaaattggc ttttgatagt    360
gaatttcttt ttaaagattc tttccatgaa atgttagctg attttaaaca aaatcaacca    420
gagttttga aagataaaa tggagaagat tgtttagttc ttctatgattg gacgatttat     480
tatttacgta aaaaagcatt aacgcaaaaa attgagaaat atgaattagc ttggttgatt    540
cttaatttta atcaaaaacg tggttattat caattaagag gtgaagaaga gaaagaaaat    600
ccaaatacat tggtgggatt tcattcttg aaaatcgttg atgttattcc cgatgctgaa     660
acaaataaaa aaggagagac ttggtattct ttgcatttga aaaatggttg ggtatatcgc    720
cgttcttcta aaatttcatt agcggattgg aaagataaag ttcgagattt tattgttacg    780
actgatttaa acgatgatgg ttctgaaaaa ttggataaag atggaattgt gaaacgtagc    840
tttcgtgcac caagtgcgga tgattggact tgttgaaaaa agaaacagaa aaagatatt     900
gataactcta acaaaactgt tggaacttat atttacgaca atcttttatt gaacccaaaa    960
caaaaaataa aaggagaaat ggttcgtacc atcgaacgta agttttacaa gcaagaatta    1020
gaacaaattt taaaaactca aaagaatttt cattcagaat tacaaagtga aaatttgcta    1080
caagattgtg ttcgagaatt gtatcgaaat aatgaacaac atcaacaaat gttagaagct    1140
aaagattttg tgcatttgtt cctaaatgat attattttct atcaacgtcc tttgagaagt    1200
caaaaatcca gtatatcgaa ttgtactttg gaatttgaaa atcgaaaaa tgaaaatgt      1260
gaagaagtta ttcatcgttt aaaagtaatt gcaaatcga atccatatta tcaggaattt     1320
agattgttac aatgggtgca aaatttagca atttatacaa aagatgatga taaaaatgta    1380
acaaacgaat ttctaaagtc tactcaagat tgggaggatt tattgagatg gctacattct    1440
aaaaaagaaa ttaaacagga tgctttaatt aagttttga ttgaaaagaa aggtttaaaa      1500
ggcaaagctt taactattga agtagcaaaa tatcgttgga attatgttca ggacaaagat    1560
tacccctggta atgaaacccg atatttaatt caatctcgtt tggataaagt tgaatatgca    1620
cctaaggatt ttttaactta tgaaaatgaa atggcttgt ggcacatcat ttattcgata     1680
aacgataaaa ttgagtacga aaaagcctta aaatcttttg ccaacaaaaa aggttttgga    1740
gaagtaactt tgttgaagc gtttaagaaa ttcccgcctt taaaagtga ttacggaagt      1800
ttttctgaaa aagcaatcaa gaaattattg cctttgatgc gttttggaac tcaatggaat    1860
tgggataata tcgatcaaaa ttctaaagaa agaattggaa aaatattgac aggcaatat     1920
gatgaaaaca tcaaaggtcg tgttcgcgaa aaagcaagac atctcaattc tgaaaccgat    1980
tttcaagctt taccttttgtg gttggcgcaa tacgtagttt acggaagaca ttctgaagct    2040
gatattgcag gtaaatgaa ttcggtggat gatttaaagc aattttaga tgactttaaa      2100
caacattcgc ttcgtaatcc tattgtagag caagtgatta ctgaaacgtt gcgtgcggta    2160
aaagtatttt ggaattttta tggaaaaggt gctaaagatt tcttctctga aattcatatc    2220
gagctgggc gtgaaatgaa aaatacggct gatgaacgaa agcgtattac tacaatggtt    2280
acggataacg aaaacaccaa tttgcgtatc aaagctttgt tggctgaaat ggctttggat    2340
caaaatgtag ataatgttcg tccatattct ccaatgcaac aagaaattt gaaaatctat     2400
gaagaaggtg ttttgaatgc tgaagaaaat atcgatgatg atattctgaa aattagtaaa    2460
acggctcaac cttctgctac agatttaaag cgttacaaat tggtgttaga acaaaatat     2520
cgttcgcctt atacaggtca aatgattcct ttgaataagc tgtttacacc tgaatatgag    2580
attgaacaca taattccgca aagtcgctat tttgatgata gtatgagcaa taaagtgatt    2640
tgcgaagcag cggtgaataa acttaaagac aatcaaattg gtttggtttt cattaagaat    2700
catcacggag aagttgtgga tttcggaatg ggaaacaaag tgaagatttt ggaagtttcc    2760
gattatgagg attttgtaaa acaaaattac aataaaaaca gaggaaaacg taataagttg    2820
ttattggaag atattcctga aaaatgatt gaacgtcaac taaatgatac acgttacatc     2880
agcaaatata ttacgcaagt gttatcgaat attgttcgtg atgataaaga aggtagtaaa    2940
gatgatggtg taaattctaa aatattgtt cctggaaacg aaaaattac cacaagactt      3000
aaacaagatt ggggattgaa tgacgtttgg aatgatttgg ttttacctcg ttttgaacga    3060
atgaatacat tgactaattc aaatgatttt acatcaaaaa tacacatgg aaaaacaatt    3120
ccaacagttc caattgagtt atccaaaggt ttttctaaaa aacgtatcga tcatcgtcat    3180
cacgcaatgg atgcgttggt aattgcctgt gcaacgagag atcacgtgaa tttgttgaat    3240
aacgaaagtt caaaatcgga tacaaaacgt tatgatttga ataggaaatt aagaaaatac    3300
gagaaagtag cttacaatga tcccaaaaca ggcgaacgaa ttgagaaaga gttccaaaa     3360
gacttcatta aaccttggga gacctttacc gaagatacgc gaactttgtt agaaaatatt    3420
```

```
gtaattagtt tcaagcaaaa tctacgagtt atcaataaag caaccaatta ttatgaaaaa  3480
attgagaatg ggaaaaaagt aaaagttgaa caaaagggaa taaattgggc tgtaagaaaa  3540
gctttgcata aagaaaccgt ttctggacaa gtgcatttgg atagaataaa agttgcaaaa  3600
ggtaaaatat taacggctac tcgtaaaact ttggatgcct cttttaatga aaaaacaatt  3660
gagtcaatta cggatacagg gattcaaaag attttattga attatttaaa atcaaaagat  3720
aacaatccag aggttgcatt ttcaccagaa ggaatagaag aattaaataa aaatattagg  3780
ctatataatg atggaaaagc acatcaacca attttgaaag ttcgtgtttt tgagcaagga  3840
agcaaattta ctttaggtga gacgggaaat aaaaccacta gtttgtaga  agcagcaaag  3900
ggtactaatc tatttttcgg aatttatgaa gacaaatgag gtaagagaag ctacgaaacc  3960
attccattaa atattgtcat cgaaagacaa aaacaaggtc tgcaagctgt tcccgaaacc  4020
aatgagaaag ggaaacaatt gttgtttacg ttatctccaa atgatttggt ttacgttcct  4080
gaagaaggag tttttgatga gaataatatc aaggtagata ggatttataa ggtagtgagt  4140
ttttctacct atcaatgttt ttttgtaaga aatgatgttt ctacttctgt agttaataag  4200
gttgaatatt ccgctttaaa taaaatggaa aaatctattg acaacataat gataaaagaa  4260
aactgcgtca aactgaatgt agaccgttta ggaaagattt caaaagct               4308

SEQ ID NO: 194        moltype = DNA  length = 4308
FEATURE               Location/Qualifiers
misc_feature          1..4308
                      note = source = /note="Description of Artificial Sequence:
                      Syntheticpolynucleotide"
misc_feature          1..4308
                      note = source = /note="APG04583.1 E. coli optimized"
source                1..4308
                      mol_type = other DNA
                      organism = synthetic construct
SEQUENCE: 194
atggcgaaga acatactagg cctggatctc ggaaccaaca gcattggttg ggcactggtc  60
cagcaggact tcgagaataa agagggcaac atactaggac tgggcagccg aataatccct  120
atgagtcagg acatactagg cgagttcggc aagggcaacg cattagcca gaccgcagaa  180
cgtactggtt atcgtggtgt gcgccgttta cgtgaacgtc atctgttacg tcgtgaacgt  240
ctgcatcgtg ttctgcatct gttaggcttc ctgccgaagc attacgatga aaagatcgac  300
ttcacccagc gcttcggcaa gttcattaat caagcggaac caaagctggc gttcgacagc  360
gagttcctgt tcaaggacag cttccatgaa atgctagcgg acttcaagca gaatcaaccg  420
gagttcctga aggataaaaa cggcgaggac tgcctggtgc cgtacgactg gaccatatac  480
tacctgcgca agaaagcact gacccagaag atcgaaaaat acgagctagc gtggctcatc  540
ctgaacttca atcaaaagcg cggatactac cagcttaggg gcgaggagga gaaagagaac  600
ccgaataaac tggtgggctt ccacagcctg aaaatagtgg acgtgatccc ggacgcggaa  660
accaataaaa agggcgagac ctggtactca ctgcatcgaa aaaacggctg ggtgtaccgc  720
cgcagcagca aaataagcct ggcggactgg aagacaaag tgcgcgactt catcgtgacc  780
accgacctga acgatgacgg cagcgaaaaa ctggacaaag acggcatcgt gaaacgcagc  840
tttcgtgcac cgagcgcaga tgattggacc ctattaaaga aaagaccga aaagacatc  900
gacaacagca ataaaaccgt gggcacctac atctacgaca acctgttatt aaacccgaag  960
cagaaaatca aggcaaaat ggtgcgcacc atcgaacgca aattctacaa acaggagctg  1020
gagcagatcc tgaaacccca gaaggaattc cacagcgaac tgcagagcga aaacctgctg  1080
caggattgcg tgcgcgaact gtaccgcaat aatgaacagc accagcagat gctggaagcg  1140
aaagatttcg tgcacctgtt cctgaacgat ataatcttct accagcgcc gctgcgcagc  1200
cagaaatcaa gcatcagcaa ttgcaccctg gaattccgca aaagcaagaa tgaaaacggc  1260
gaagaagtga tccaccgcct gaaagtgatc gcgaaaagca cccatacta ccaggaattc  1320
cgcctgctgc agtgggtcca gaacctggcg atctatacta aagacgacga caagaacgta  1380
accaacgagt tcctgaaatc aacccaggac tgggaagatc tgtctgcgg gctgcatagc  1440
aagaaggaga ttaaacagga cgcgctgatc aagttcctga tcgagaaaaa gggcctgaag  1500
ggcaaagcat tgaccatcga ggtggcaaaa taccgctgga actacgtcca ggacaaagat  1560
tacccgggca atgaaaccg ctacctgatc caatcaaggc tggacaaagt ggaatacgcg  1620
ccgaaagatt tcctgaccta cgagaatgaa atggcgctgt ggcacatcat ctacagcatt  1680
aatgataaa tcgaatatga aaagcatta aatcgttcg cgaataaaaa gggcctggat  1740
gaagtgacct tcgtggaagc attcaaaaag ttccgccgt tcaaaagcga ttacggcagc  1800
ttcagcgaaa aagcgattaa aaagctgctg ccattaatgc gcttcggcac ccagtggaac  1860
tgggataaca tcgatcaaaa tagcaaagaa cgcatcggca aaatactaac cggcgaatac  1920
gatgaaaata ttaaaggccg cgtgcgcgaa aagcgcgcc atctgaacag cgaaaccgat  1980
ttccaagcat tgccgctgtg gctggcgcag tacgcggtgt acggccgcca tagcgaagcg  2040
gatatcgcgg gcaaatgaa cagcgtggat gatctgaaac agttcctgga tgatttcaaa  2100
cagcatagcc tgcgcaaccc gatcgtgaaa caggtgatca ccgaaaccct gcgcgcggtg  2160
aaagatatct ggaacttcta tggcaaaggc gcgaaagatt tcttcagcga aatacacatc  2220
gaactgggcc gcgaaatgaa aaataccgcg gatgaaagaa aacgcatcac caccatggtg  2280
accgataatg aaaataccaa cttacgcatt aaagcattgc tggcggaaat ggcgctggat  2340
cagaacgtgg ataacgtgcg cccgtatagc ccgatgcagc aggaaatcct gaaaatatat  2400
gaagaaggcg tattaaacgc ggaagaaaat atcgacgatg atatcctgaa aataagcaaa  2460
accgcgcaac caagcgcgac cgatctgaaa cgctataaac tgtggctgga acagaaatat  2520
cgcagcccgt ataccggcca gatgatcccg ctgaacaaac tgtttacccc ggaatatgaa  2580
atcgaacata tcatcccgca gagccgctat tttgatgata gcatgagcaa caagtgatc  2640
tgcgaagcg cggtgaacaa actgaaagat aaccagatcg gcctggtgtt tatcaaaaac  2700
catcatggcg aagtggtgga ttttggcatg ggcaaacagg tgaaatcct ggaagtgagc  2760
gattatgaag attttgtgaa acagaactat caacaaaaac gccaaatta  2820
ctgctgaaag atatcccgga aaaatgatc gaacgccagc tgaacgatac ccgctatatc  2880
agcaaatata tcacccaggt gctgagcaac atcgtgcgcg atgataaaga aggcagcaaa  2940
gatgatggcg tgaacagcaa aaacatcgtg ccgggcaacg gcaaatcac cacccgcctg  3000
aaacaggatt ggggcctgaa cgatgtgtgg aacgatctgg tgctgccgcg ctttgaacgc  3060
atgaacaccc tgaccaacag caacgatttt accagcaaaa acacccatgg caaaaccatt  3120
```

```
ccgaccgtgc cgattgaact gagcaaaggc tttagcaaaa agcgcattga tcatcgccat   3180
catgcgatgg atgcgctggt gattgcgtgc gcgaccgcg  atcatgtgaa cttactgaac   3240
aacgaaagca gcaaaagcga taccaaacgc tatgatctga accgcaaact gcgcaaatat   3300
gaaaagtgg  cgtataacga tccgaaaacc ggcgaacgca ttgaaaaaga agtgccgaaa   3360
gattttatta aaccgtggga aacctttacc gaagatacccgcaccctgct ggaaaacatt    3420
gtgattagct ttaaacagaa cctgcgcgtg attaacaaag cgaccaacta ttatgagaaa   3480
attgaaaacg gcaaaaaggt gaaagtggaa cagaaaggca ttaactgggc ggtgcgcaaa   3540
gcgctgcata agaaaccgt  gagcggccag gtgcatctgg atcgcattaa agtggcgaaa   3600
ggcaaaattc tgaccgcgac ccgcaaaacc ctggatgcgt cattcaacga gaaaaccatt   3660
gaaagcatta ccgataccgg cattcagaaa attctgctga actatctgaa aagcaaagat   3720
aacaacccgg aagtggcgtt tagcccggaa ggcattgaag aactgaacaa aaacattcgc   3780
ctgtataacg atggcaaagc gcatcagccg attctgaaag tgcgcgtgtt tgaacagggc   3840
agcaaattca ccctgggcga aaccggcaac aaaaccacca aatttgtgga agcggcgaaa   3900
ggcaccaacc tgttcttgg  catctatgaa gataaaacg  gcaaacgcag ctatgaaacc   3960
attccgctga acattgtgat tgaacgccaa aaacagggcc tgcaagcggt gccggaaacc   4020
aacgaaaaag gcaaacagct gctgtttacc ctgtcaccga acgatctggt gtatgtgccg   4080
gaagaaggcg tgtttgatga aaacaacatt aaagtggatc gcatctataa agtggtgagc   4140
tttagcacct atcagtgctt ctttgtgcgc aacgatgtga accagccagt ggtgaacaaa   4200
gtggaatata gcgcgctgaa caaaatggaa aaatcgattg ataacattat gattaaagaa   4260
aactgcgtga aactgaacgt ggatcgcctg ggcaaaatta gcaaagcg                4308
```

SEQ ID NO: 195          moltype = DNA   length = 4368
FEATURE                 Location/Qualifiers
misc_feature            1..4368
                        note = source = /note="APG01688.1 Native Seq"
source                  1..4368
                        mol_type = genomic DNA
                        organism = Empedobacter sp.
SEQUENCE: 195
```
atgatgatta aaaatatact tggattagat ttggggacta actctattgg gtgggcattg   60
ataaaacaag attttgaaaa taagcatggc gaaattcttg gaatgggtag ccggattatt   120
ccgatgtcac aggatattct gggcgatttt gggaaaggaa attctatttc gcaaaccgct   180
gatcgtacca aatacagaag cgtgagaaga ttacgtgaac gattttatt  gaggagagaa   240
cgactacaca gagttttaca tcttttaaat tttcttccac agcattatgc ttcacaaatt   300
gattttgaaa aaaaattcgg gaagtttaaa tctgaaactg aacccaaatt ggcatgggaa   360
aattggggtg gaaagttttc attccttttc caaaactctt tcaatgaaat gcttgaagat   420
tttaaagcag ctggacaggg tttaaaaatt ccttacgact ggacaattta ttatctccgt   480
aaaaaagcac tttcacaaaa aattgaaaag gaggaactgg cctggattct tttaaactt   540
aatcagaaac gaggatatta tcaattgcgt ggtgaggaag aagaagagaa tcctaataag   600
ctggttgaat tttattcttt aaaaattgta gatgttgtag cagatgaacc tcaaaaagga   660
aaatctgata tttggtattc tttgatttta gagaatggat gggtttacag acgagcaagc   720
aaaataccc  tatttgactg gaaagataaa acaagagatt ttattgtaac aactgatttg   780
aatgatgaca gaagtgttaa aacagacaaa gaaggaaatg aaaaaagaag tttcagagca   840
ccaagcgaaa acgattggac attggtaaaa agaaaaccg aacaggaaat cgaccaatct   900
cacaaaaccg ttggaaccta tatctacgaa acacttcttc taaatccgaa acaaaaaatt   960
aaaggaaaat tggttcggac gattgaaaga aaattctata agatgagct  aaaacaaatt   1020
ttagaaaaac aaaaaggaat tcatcaggaa cttaaaaatg atgatttgta taattgattgc   1080
attcgtgagt tgtacagaaa caacgaagca catcagctga ctttgagcaa gaaagatttt   1140
gttcatcttt tgatggatga tcttatttc  taccaaagac ctttgagaag ccagaaatca   1200
tctatttcca actgtacgtt agagtttaga aaatataaag atgaaaatgg aatagagcat   1260
acacaatatt taaagccat  tccaaaatcc aatccgtatt atcaggaatt tcgtcttttga  1320
caatggatgt ataatctgaa tatttacaga aaggacgatg aagcgaatgt taccaaagaa   1380
tttttaaata cgaacaaaga ttttgaaagt ctgtttgaat tttaaataa  tagaaaagaa   1440
attgagcaaa agccattgat taaatttctt ttggaacaaa aagatatcaa taaaaaattg   1500
cttaacgctg aagcagaaaa atatcgctgg aactatgtag aagacaagaa atatccttgc   1560
aatgaaaccaa aaacgatgat ttcttctcgt ttggataaag tcgaaaacat ttctgatgat   1620
ttcctgacaa gggacattga gcagaaaatt tggcacatca tctattccgt caatgataaa   1680
atagaatatg aaaaagcttt gaaatctttt gcaactagaa acgatttgga tgaaaactct   1740
tttatcgaag cgtttaagaa attctcgcct tttaaagtg aaatattggttc ttttccggaa   1800
aaagcaatta aaaagttact gccttaagtg cgattgggta aatattgta tgaagatgaa   1860
attgtaaagc atagtgatat ttatttcaaa aatattgaga atcttttggg tgattttca   1920
aatagagaca aaaaatttc tgaagaagac aaagagaaat ggaataaatc tataaatcta   1980
aagttacagg aagagttaaa agattttcaa acagctgaaa tagattatt  tcaaggatta   2040
cgattgcata ttgctcaata ccttgtttat ggaagacatt cagaagcttc aatgattgga   2100
aaatggaatt ccgccgaaga tttagaagaa ttttaaagg attttaaaca gcattcgctt   2160
cgcaaccga  ttgtagaaca agtgattaca gaaactttgc gtgttgtaaa agatatttgg   2220
ttgaaatacg gaaatggagc aaaggatttc ttcaatgaaa ttcatattga gttaggaaga   2280
gaaatgaaac ttcccgcaga tgatcgaaaa aaactaacga accagatttc tgaaaacgaa   2340
aataccaatt tccgcatcaa agctctattg gctgaaatga tgaatgacag ttccggtagaa   2400
aatgtccgtc cgttttcgcc gatgcagcaa gaaattttaa aaatttatga agacgatgtt   2460
ttaaaatcag atatagaaat tgaagatgat attctgaaaa tcagcaaaac cgctcaacct   2520
tctccttccg atttgaaacg atataaactt tggttggaac agaaatacaa atcgccttac   2580
acgggcaaa  ttattccttt gaataaattg tttacaccag aatacgaaat tgagcacatt   2640
attccgcaga gccgatattt tgatgacagt tttagcaata aagtaattg  tgagtctgcg   2700
gttaataaat tgaaagataa ctacatcgga cttgaatta  ttaagcagtt cggaggaacg   2760
attattgaac ttggttttgg taaaagcata aagttttg  aaacaaaaga atacgaagat   2820
ttcgtcaaaa acattacgc  caacaatcaa ggtaaaagaa acaaacttt  gatgaagat    2880
attcagagaa aaatgattga acgtcaaatg aacgatacac gatatatcag caaatatatt   2940
tcgggcgttt tgtctaatat tgttcgggta gaagatggtt cagatgaagg ggtaaattct   3000

```
aaaaatattg ttcccggaaa cggaaaaatc accacacagc tgaaacaaga ttggggattg   3060
aatgatgttt ggaatgattt gattttacca cgctttgaaa gaatgaacca actcaccaat   3120
tcaaaagttt ttactgcctg gaatgagaat tatcaaaagt ttttaccaac tgttcctatt   3180
gaatattcca aagggttttc aaagaaaaga atagaccacc gccatcacgc tttagatgct   3240
ttggtgattg cctgtgctac aaaagatcac gtgaattat taaataatca atcggcaaaa    3300
tcggatacca aacgatacga tttgaaaaag aaatcgatga agtttgaaaa agtagtttac   3360
aatgatgcca aaacaggaga gaaaatcgaa agggaagtgc caaaacaatt tttaaaacct   3420
tgggaaaatt ttacgctaga tgttaaacat aatttggaaa ctattattgt aagttttaag   3480
caaaatcttc gtgttattaa taaagcgact aattattacg aaaagtatgt tgagaaagac   3540
ggtacaaaaa ataaggaaag agtagagcag accggaacaa actgggcgat taggaaacca   3600
atgcataaag acacggtttc cggtaaagta gatttacctt gggtaaaagt cccaaaaggg   3660
aaaattttaa cagcaacaag gaaaagcctt gatagttcgt ttgacttaaa gtcaataggc   3720
tctattacgg atacaggaat tcagaaaata ctcaaaaatt atttagcatt taaagacgga   3780
aatcctgaac tggctttttc accagaagga attgacgatt tgaataaaaa tattgaaaaa   3840
tacaatgatg gaaaaccgca tcaacccatc aataaagtaa gggttttga attgggaagt    3900
aaatttcagg taggacaaag tggaaataaa aaagataaat atgtagaagc tgcaaaagga   3960
actaatctat tctttgctgt ttatgaagat gaaaaggaa agagaaatta tgaaaccatt     4020
cctttgaatg aagtgattga aaggcaaaag caaggtttat ctgtggttga tttaaaaggt   4080
acaaatgatt tctacttatg tccgaatgat tttgtatata ttccatcagg cgacgaactt   4140
gaaaatataa ataatgttga ttttaaagac attaaaaaag agataaacga aagaatttac   4200
aaagtagtaa gttttacagg taatagactt tcctgtattc catatatggt tgcaacaacg   4260
attgttaata aattagagtt tacgcaactt aataaaattg aattcacaaa agaaaagaa    4320
atttgtataa aactaaatgt cgatcgttta ggtaacattt caaaagcg                4368

SEQ ID NO: 196       moltype = DNA   length = 4368
FEATURE              Location/Qualifiers
misc_feature         1..4368
                     note = source = /note="Description of Artificial Sequence:
                     Syntheticpolynucleotide"
misc_feature         1..4368
                     note = source = /note="APG01688.1 E. coli optimized"
source               1..4368
                     mol_type = other DNA
                     organism = synthetic construct
SEQUENCE: 196
atgatgatta aaaatatcct aggcctggac ctgggaacca acagcatcgg ctgggcgctg    60
attaaacagg acttcgaaaa taagcatggc gagatactag gcatgggcag ccgaataatc   120
ccgatgagtc aggacatact aggcgacttc ggcaagggca acagcatcag ccagaccgcg   180
gaccgcacaa aatatcgcag cgtgcgtaga ctgcgcgaac gctttctgtt acgtcgtgaa   240
cgtctgcatc gtgttcttca cctattaaac ttcctgccgc agcattacgc tagccagatc   300
gacttcgaga gaagttcgg caagttcaag agcgagaccg aaccaaaact ggcgtgggaa    360
aactggggcg gcaattcag cttccctattc caaaatagct tcaacgagat gctagaggac    420
ttcaaggcgg cgggtcaggg attaaaaata ccgtacgact ggaccatata ctacctgccg   480
aagaaagcgc tgagccagaa gatcgagaag gaggagctgg cgtggatact actgaactt    540
aatcaaaagc gcggatacta ccagctgcgc ggcgaggagg aggaggagaa cccgaataaa   600
ctggtggagt ctctacagcct gaaaatagtg acgtggtgg cggacgagcc gcagaaaggc   660
aaaagcgaca tctggtactc actcatacta gaaaacgcgt gggtgtatc ccgcgcgagc    720
aaaataccgc tgttcgactg gaaagataaa accgcgact tcatcgtgac caccgacctg    780
aacgacgacc gcagcgtgaa aaccgacaaa gaaggcaatg aaaaacgcag ctttcgcgcg   840
ccgagcgaaa acgattggac cctggtgaaa agaaaaccg aacaggaaat cgatcagagc    900
cataaaaccg tgggcacata tatctatgaa accctgttat taaacccgaa gcagaagatt   960
aaaggcaaac tggtgcgcac catcgaacgc aaattctaca agacgaatt aaaacagata    1020
ctagaaaaac agaaagaatt ccaccaggaa ttaagaacg acgacttata taacgattgc   1080
atccgcgaac tgtaccgcaa taatgaagcg caccaattaa ccctgagcaa aaaggatttc   1140
gtgcacttat taatgatga tctgatcttc taccagcgcc tgctgcgcaa ccagaaatca   1200
agcatcagca attgcaccct ggaattccgc aaatacaaag atgaaacgg catcgaacac   1260
acccagtacc tgaaagcgat cccgaaatca aacccatact accaggaatt ccgcctgtgg   1320
cagtggatgt acaacctgaa catctaccgc aaagatgatg aagcgaacgt aaccaaagaa   1380
ttcctgaaca ccaataaaga tttcgaaagc ctgttcgaat tcctgaataa tcgcaaagaa   1440
atcgaacaga aaccattaat caaattcctg ctggaacaga aagatattaa taaaaagtta   1500
ttaaacgcgg aagcggaaaa atacagatgg aactacgtgg aagataaaaa gtaccgtgc    1560
aatgaaacca aaccatgat cagcagccgc ctggataaag tggaaaatat cagcgatgat   1620
ttcctgaccc gcgatatcga acagaaaata tggcataaa tctacagcgt gaacgataaa   1680
atcgaatatg aaaaagcatt aaaatcgttc gcgacccgca acgtatctgga tgaaaatagc   1740
ttcatcgaag cattcaaaaa gttcagcccg ttcaaaagcg aatacggcag cttcagcgaa   1800
aaagcgatta aaagctgct gccattaatg cgcctgggaa aatactggta cgaagatgaa   1860
atcgtgaaac acagcgatat ctacttcaaa aacatcgaaa acctgctggg cgatttcagc   1920
aaccgcgata aaagatcag cgaagaagat aaagaaaat ggaacaaaag catcaacctg    1980
aaactgcagg aagaactgaa agatttccag accgcggaa tcgatctgtt ccagggcctg   2040
cgcctgcata tcgcgcagta cctggtgtac ggccgccata cgaagcgag catgatcggc   2100
aaatggaact cagcggaaga tctggaagaa ttcctgaaag atttcaaaca gcatagcctg   2160
cgcaacccga tcgtggaaca ggtgatcacc gaaaccctgc gcgtggtgaa agatatctgg   2220
ctgaaatatg caacggcgc gaaagatttc tttaacgaaa ttcatatcga actgggccgc   2280
gaaatgaac tgccggcga tgatcgcaaa agctgacaa agcaaacgaa                2340
aacaccaact ttcgcatcaa agcgctgctg cgcgaaatga tgaacgatag cagcgtggaa   2400
aacgtgcgcc cgtttagccc gatgcagcag gaaatcctga aatctatga agatgatgtg   2460
ctgaaaagcg atatcgaaat cgaagatgat atcttaaaa tcagcaaaac cgcgcagccg   2520
agcccgagcg atctgaaacg ctataaactg tggctgaac agaaatataa aagcccgtat   2580
accggccaga tcatcccgct gaacaaactg tttacccgg aatatgaaat cgaacatatc   2640
```

```
atcccgcaga gccgctattt tgatgatagc tttagcaaca aagtgatctg cgaaagcgcg   2700
gtgaacaaac tgaaagataa ctatatcggc ctgaaattca tcaaacagtt tggcggcacc   2760
atcatcgaac tgggctttgg caaaagcatc aaagtgtttg aaaccaaaga atatgaagat   2820
tttgtgaaaa agcattatgc gaacaaccag ggcaaacgca acaaactgtt aatgaagat    2880
atcccggaca aaatgatcga acgccagatg aacgataccc gctatatcag caaatatatc   2940
agcggcgtgc tgagcaacat cgtgcgcgtg aagatggca gcgatgaagg cgtgaacagc    3000
aaaaacatcg tgccgggcaa cggcaaaatc accaccagc tgaaacagga ttggggcctg    3060
aacgatgtgt ggaacgatct gatcctgccg cgctttgaac gcatgaacca gctgaccaac   3120
agcaaagtgt ttaccgcgtg gaacgaaaac tatcagaaat ttctgccgac cgtgccgatt   3180
gaatatagca aaggctttag caaaagcgc attgatcatc gccatcatgc gctggatgcg   3240
ttagtgattg cgtgcgcgac caaagatcat gtgaacctgc tgaacaacca gagcgcgaaa   3300
agcgatacca aacgctatga tctgaaaaag aaaagcatga aatttgaaaa agtggtgtat   3360
aacgatgcga aaaccggcga gaaaattgaa cgcgaagtgc cgaaacagtt tctgaaaccg   3420
tgggaaaact ttaccctgga tgtgaaacat aacctggaaa ccattattgt gagctttaaa   3480
cagaacctgc gcgtgattaa caaagcgacc aactattatg aaaaatatgt ggaaaaagat   3540
ggcaccaaaa acaaagaacg cgtggaacag accggcacca ctgggcgat cgcaaaccg    3600
atgcataaag ataccgtgtc aggcaaagtg atctgccgt gggtgaaagt gccgaaaggc   3660
aaaattctga ccgcgacccg caaaagcctg gatagcagct ttgatctgaa aagcattggc   3720
agcattaccg ataccggcat tcagaaaatt ctgaaaaact atctggcgtt taaagatggc   3780
aacccggaac tggcgtttag cccggaaggc attgatgatc tgaacaaaa cattgaaaaa   3840
tataacgatg gcaaaccgca tcagccgatt aacaaagtgc gcgtgtttga actgggcagc   3900
aaatttcagg tgggccagag cggcaacaaa aaggacaaat atgtggaagc ggcgaaaggc   3960
accaacctgt tctttgcggt gtatgaagat gaaaaaggca aacgcaacta tgaaaccatc   4020
ccgttaaacg aagtgattga acgccagaaa cagggcctga gcgtggtgga tctgaaaggc   4080
accaacgatt tttatctgtg cccgaacgat tttgtgtata ttccgagcgg cgatgaactg   4140
gaaaacatta acaacgtgga ttttaaagat attaaaaagg aaattaacga acgcatctat   4200
aaagtggtga gctttaccgg caaccgcctg agctgcattc cgtatatggt ggcgaccacc   4260
attgtgaaca aactggaatt cacccagctg aacaaaattg aattcaccaa agaaaaagaa   4320
atttgcatta aactgaacgt ggatcgcctg ggcaacatta gcaaagcg                4368

SEQ ID NO: 197         moltype = DNA   length = 25
FEATURE                Location/Qualifiers
misc_feature           1..25
                       note = source = /note="target seq for Ataxia-telangiectasia
                         syndrome"
source                 1..25
                       mol_type = genomic DNA
                       organism = Homo sapiens
SEQUENCE: 197
gaattattcc agaaagccaa agtag                                         25

SEQ ID NO: 198         moltype = DNA   length = 20
FEATURE                Location/Qualifiers
misc_feature           1..20
                       note = source = /note="target seq for Very long chain
                         acyl-CoAdehydrogenase deficiency"
source                 1..20
                       mol_type = genomic DNA
                       organism = Homo sapiens
SEQUENCE: 198
ggcttcatga aggtacagga                                               20

SEQ ID NO: 199         moltype = DNA   length = 25
FEATURE                Location/Qualifiers
misc_feature           1..25
                       note = source = /note="target seq for Abnormality of T cell
                         physiology"
source                 1..25
                       mol_type = genomic DNA
                       organism = Homo sapiens
SEQUENCE: 199
ggtgtgctca ccagaatgga gtaca                                         25

SEQ ID NO: 200         moltype = DNA   length = 25
FEATURE                Location/Qualifiers
misc_feature           1..25
                       note = source = /note="target seq for Cardiovascular
                         phenotype"
source                 1..25
                       mol_type = genomic DNA
                       organism = Homo sapiens
SEQUENCE: 200
gcagatcatt ggggtggatc ccgaa                                         25

SEQ ID NO: 201         moltype = DNA   length = 25
FEATURE                Location/Qualifiers
misc_feature           1..25
                       note = source = /note="target seq for 3-Oxo-5 alpha-steroid
                         delta4-dehydrogenase deficiency"
```

-continued

```
source                  1..25
                        mol_type = genomic DNA
                        organism = Homo sapiens
SEQUENCE: 201
ggctgcaagc ttttcaccac cayag                                      25

SEQ ID NO: 202          moltype = DNA  length = 25
FEATURE                 Location/Qualifiers
misc_feature            1..25
                        note = source = /note="target seq for Acute myeloid
                         leukemia"
source                  1..25
                        mol_type = genomic DNA
                        organism = Homo sapiens
SEQUENCE: 202
gggcggcatg aaccggaggc ccatc                                      25

SEQ ID NO: 203          moltype = DNA  length = 20
FEATURE                 Location/Qualifiers
misc_feature            1..20
                        note = source = /note="target seq for Acute myeloid
                         leukemia"
source                  1..20
                        mol_type = genomic DNA
                        organism = Homo sapiens
SEQUENCE: 203
gcatgggcgg catgaaccgg                                            20

SEQ ID NO: 204          moltype = DNA  length = 20
FEATURE                 Location/Qualifiers
misc_feature            1..20
                        note = source = /note="target seq for Cutaneous malignant
                         melanoma 3"
source                  1..20
                        mol_type = genomic DNA
                        organism = Homo sapiens
SEQUENCE: 204
gtggccactg tggggatcac                                            20

SEQ ID NO: 205          moltype = DNA  length = 20
FEATURE                 Location/Qualifiers
misc_feature            1..20
                        note = source = /note="target seq for Alpha-1-antitrypsin
                         deficiency"
source                  1..20
                        mol_type = genomic DNA
                        organism = Homo sapiens
SEQUENCE: 205
gtgctgacca tcgacgagaa                                            20

SEQ ID NO: 206          moltype = DNA  length = 20
FEATURE                 Location/Qualifiers
misc_feature            1..20
                        note = source = /note="target seq for Charcot-Marie-Tooth
                         disease, type 2"
source                  1..20
                        mol_type = genomic DNA
                        organism = Homo sapiens
SEQUENCE: 206
ggcgagctgc atgatctgcg                                            20

SEQ ID NO: 207          moltype = DNA  length = 25
FEATURE                 Location/Qualifiers
misc_feature            1..25
                        note = source = /note="target seq for Hereditary
                         cancer-predisposing syndrome"
source                  1..25
                        mol_type = genomic DNA
                        organism = Homo sapiens
SEQUENCE: 207
gcacatgacg gaggttgtga ggcgc                                      25

SEQ ID NO: 208          moltype = DNA  length = 25
FEATURE                 Location/Qualifiers
misc_feature            1..25
                        note = source = /note="target seq for Hereditary
                         cancer-predisposing syndrome"
source                  1..25
                        mol_type = genomic DNA
```

```
                                 organism = Homo sapiens
SEQUENCE: 208
gaggttgtga ggcactgccc ccacc                                              25

SEQ ID NO: 209          moltype = DNA   length = 20
FEATURE                 Location/Qualifiers
misc_feature            1..20
                        note = source = /note="target seq for Hereditary
                         cancer-predisposing syndrome"
source                  1..20
                        mol_type = genomic DNA
                        organism = Homo sapiens
SEQUENCE: 209
gcagcatccg gctgcaggta                                                    20

SEQ ID NO: 210          moltype = DNA   length = 25
FEATURE                 Location/Qualifiers
misc_feature            1..25
                        note = source = /note="target seq for Brugada syndrome"
source                  1..25
                        mol_type = genomic DNA
                        organism = Homo sapiens
SEQUENCE: 210
ggccaagggg atccgcacgc tgctc                                              25

SEQ ID NO: 211          moltype = DNA   length = 20
FEATURE                 Location/Qualifiers
misc_feature            1..20
                        note = source = /note="target seq for Brugada syndrome"
source                  1..20
                        mol_type = genomic DNA
                        organism = Homo sapiens
SEQUENCE: 211
gcctgatgac gcaggactgc                                                    20

SEQ ID NO: 212          moltype = DNA   length = 20
FEATURE                 Location/Qualifiers
misc_feature            1..20
                        note = source = /note="target seq for GRACILE syndrome"
source                  1..20
                        mol_type = genomic DNA
                        organism = Homo sapiens
SEQUENCE: 212
ggtacgaagt ctcgacactg                                                    20

SEQ ID NO: 213          moltype = DNA   length = 20
FEATURE                 Location/Qualifiers
misc_feature            1..20
                        note = source = /note="target seq for Enhanced s-cone
                         syndrome"
source                  1..20
                        mol_type = genomic DNA
                        organism = Homo sapiens
SEQUENCE: 213
ggcattggcg gtggacccca                                                    20

SEQ ID NO: 214          moltype = DNA   length = 25
FEATURE                 Location/Qualifiers
misc_feature            1..25
                        note = source = /note="target seq for Charcot-Marie-Tooth
                         disease, type 2"
source                  1..25
                        mol_type = genomic DNA
                        organism = Homo sapiens
SEQUENCE: 214
gaagaacagg ttctggacgt caaag                                              25

SEQ ID NO: 215          moltype = DNA   length = 20
FEATURE                 Location/Qualifiers
misc_feature            1..20
                        note = source = /note="target seq for Charcot-Marie-Tooth
                         disease, type 2"
source                  1..20
                        mol_type = genomic DNA
                        organism = Homo sapiens
SEQUENCE: 215
gaacaggttc tggacgtcaa                                                    20

SEQ ID NO: 216          moltype = DNA   length = 20
```

```
FEATURE              Location/Qualifiers
misc_feature         1..20
                     note = source = /note="target seq for Arylsulfatase a,
                      allele a"
source               1..20
                     mol_type = genomic DNA
                     organism = Homo sapiens
SEQUENCE: 216
gacaggtcat agagcagcgg                                                     20

SEQ ID NO: 217       moltype = DNA   length = 20
FEATURE              Location/Qualifiers
misc_feature         1..20
                     note = source = /note="target seq for Familial
                      hypercholesterolemia"
source               1..20
                     mol_type = genomic DNA
                     organism = Homo sapiens
SEQUENCE: 217
gaacgtggtc gctctggaca                                                     20

SEQ ID NO: 218       moltype = DNA   length = 20
FEATURE              Location/Qualifiers
misc_feature         1..20
                     note = source = /note="target seq for Familial
                      hypercholesterolemia"
source               1..20
                     mol_type = genomic DNA
                     organism = Homo sapiens
SEQUENCE: 218
gaacgtggtc gctctggaca                                                     20

SEQ ID NO: 219       moltype = DNA   length = 25
FEATURE              Location/Qualifiers
misc_feature         1..25
                     note = source = /note="target seq for HEMOGLOBIN ARLINGTON
                      PARK"
source               1..25
                     mol_type = genomic DNA
                     organism = Homo sapiens
SEQUENCE: 219
ggtgcatctg actcctgagg agaag                                               25

SEQ ID NO: 220       moltype = DNA   length = 20
FEATURE              Location/Qualifiers
misc_feature         1..20
                     note = source = /note="target seq for Familial hypertrophic
                      cardiomyopathy 1"
source               1..20
                     mol_type = genomic DNA
                     organism = Homo sapiens
SEQUENCE: 220
gaagtccgag gctcgccgca                                                     20

SEQ ID NO: 221       moltype = DNA   length = 20
FEATURE              Location/Qualifiers
misc_feature         1..20
                     note = source = /note="target seq for Cardiovascular
                      phenotype"
source               1..20
                     mol_type = genomic DNA
                     organism = Homo sapiens
SEQUENCE: 221
gtcaaggtca tcggtgaggc                                                     20

SEQ ID NO: 222       moltype = DNA   length = 25
FEATURE              Location/Qualifiers
misc_feature         1..25
                     note = source = /note="target seq for Cardiovascular
                      phenotype"
source               1..25
                     mol_type = genomic DNA
                     organism = Homo sapiens
SEQUENCE: 222
ggtcatcagt gaggccggcc ggggt                                               25

SEQ ID NO: 223       moltype = DNA   length = 25
FEATURE              Location/Qualifiers
misc_feature         1..25
```

```
                            note = source = /note="target seq for Brugada syndrome"
source                      1..25
                            mol_type = genomic DNA
                            organism = Homo sapiens
SEQUENCE: 223
gtctcagcct tacgcacctt ccgag                                              25

SEQ ID NO: 224              moltype = DNA  length = 25
FEATURE                     Location/Qualifiers
misc_feature                1..25
                            note = source = /note="target seq for Brugada syndrome"
source                      1..25
                            mol_type = genomic DNA
                            organism = Homo sapiens
SEQUENCE: 224
gcaccttcca agtcctccgg gccct                                              25

SEQ ID NO: 225              moltype = DNA  length = 26
FEATURE                     Location/Qualifiers
misc_feature                1..26
                            note = source = /note="target seq for Hereditary
                             cancer-predisposing syndrome"
source                      1..26
                            mol_type = genomic DNA
                            organism = Homo sapiens
SEQUENCE: 225
gaagccagcc cctcagggca actgac                                             26

SEQ ID NO: 226              moltype = DNA  length = 20
FEATURE                     Location/Qualifiers
misc_feature                1..20
                            note = source = /note="target seq for Deficiency of
                             butyryl-CoA dehydrogenase"
source                      1..20
                            mol_type = genomic DNA
                            organism = Homo sapiens
SEQUENCE: 226
ggcgactcat gggttctgaa                                                    20

SEQ ID NO: 227              moltype = DNA  length = 25
FEATURE                     Location/Qualifiers
misc_feature                1..25
                            note = source = /note="target seq for Deficiency of
                             butyryl-CoA dehydrogenase"
source                      1..25
                            mol_type = genomic DNA
                            organism = Homo sapiens
SEQUENCE: 227
gcgactcacg ggttctgaat ggaac                                              25

SEQ ID NO: 228              moltype = DNA  length = 20
FEATURE                     Location/Qualifiers
misc_feature                1..20
                            note = source = /note="target seq for Benign
                             scapuloperoneal musculardystrophy with cardiomyopathy"
source                      1..20
                            mol_type = genomic DNA
                            organism = Homo sapiens
SEQUENCE: 228
ggaactgcgg gcccagcatg                                                    20

SEQ ID NO: 229              moltype = DNA  length = 20
FEATURE                     Location/Qualifiers
misc_feature                1..20
                            note = source = /note="target seq for Benign
                             scapuloperoneal musculardystrophy with cardiomyopathy"
source                      1..20
                            mol_type = genomic DNA
                            organism = Homo sapiens
SEQUENCE: 229
ggacgagtac caggagcttc                                                    20

SEQ ID NO: 230              moltype = DNA  length = 20
FEATURE                     Location/Qualifiers
misc_feature                1..20
                            note = source = /note="target seq for Cone-rod dystrophy 6"
source                      1..20
                            mol_type = genomic DNA
                            organism = Homo sapiens
```

```
SEQUENCE: 230
ggatctgatc cgggagcgca                                              20

SEQ ID NO: 231         moltype = DNA  length = 25
FEATURE                Location/Qualifiers
misc_feature           1..25
                       note = source = /note="target seq for Cone-rod dystrophy 6"
source                 1..25
                       mol_type = genomic DNA
                       organism = Homo sapiens
SEQUENCE: 231
gaatgcacta tgttctattc catcc                                        25

SEQ ID NO: 232         moltype = DNA  length = 25
FEATURE                Location/Qualifiers
misc_feature           1..25
                       note = source = /note="target seq for Stargardt disease 1"
source                 1..25
                       mol_type = genomic DNA
                       organism = Homo sapiens
SEQUENCE: 232
gagctgctca caggacgaga acatc                                        25

SEQ ID NO: 233         moltype = DNA  length = 20
FEATURE                Location/Qualifiers
misc_feature           1..20
                       note = source = /note="target seq for Leber congenital
                        amaurosis 2"
source                 1..20
                       mol_type = genomic DNA
                       organism = Homo sapiens
SEQUENCE: 233
gtctatccag taagtatctc                                              20

SEQ ID NO: 234         moltype = DNA  length = 20
FEATURE                Location/Qualifiers
misc_feature           1..20
                       note = source = /note="target seq for Cone-rod dystrophy 3"
source                 1..20
                       mol_type = genomic DNA
                       organism = Homo sapiens
SEQUENCE: 234
ggtacgtcca tgccacaccc                                              20

SEQ ID NO: 235         moltype = DNA  length = 20
FEATURE                Location/Qualifiers
misc_feature           1..20
                       note = source = /note="target seq for Nonsyndromic
                        Oculocutaneous Albinism"
source                 1..20
                       mol_type = genomic DNA
                       organism = Homo sapiens
SEQUENCE: 235
ggacctttac ggcgtaatcc                                              20

SEQ ID NO: 236         moltype = DNA  length = 20
FEATURE                Location/Qualifiers
misc_feature           1..20
                       note = source = /note="target seq for Phenylketonuria"
source                 1..20
                       mol_type = genomic DNA
                       organism = Homo sapiens
SEQUENCE: 236
gtcatccttt ggtgaattac                                              20

SEQ ID NO: 237         moltype = DNA  length = 25
FEATURE                Location/Qualifiers
misc_feature           1..25
                       note = source = /note="target seq for Phenylketonuria"
source                 1..25
                       mol_type = genomic DNA
                       organism = Homo sapiens
SEQUENCE: 237
gtattacgtg gcagagagtt ttaat                                        25

SEQ ID NO: 238         moltype = DNA  length = 20
FEATURE                Location/Qualifiers
misc_feature           1..20
                       note = source = /note="target seq for Breast-ovarian
```

```
                        cancer, familial 1"
source                  1..20
                        mol_type = genomic DNA
                        organism = Homo sapiens
SEQUENCE: 238
ggacgctctt gtattatctg                                              20

SEQ ID NO: 239          moltype = DNA  length = 25
FEATURE                 Location/Qualifiers
misc_feature            1..25
                        note = source = /note="target seq for
                        Hyperphenylalaninemia, non-pku"
source                  1..25
                        mol_type = genomic DNA
                        organism = Homo sapiens
SEQUENCE: 239
gcccttctca gttcgctacg accca                                        25

SEQ ID NO: 240          moltype = DNA  length = 20
FEATURE                 Location/Qualifiers
misc_feature            1..20
                        note = source = /note="target seq for
                        Hyperphenylalaninemia, non-pku"
source                  1..20
                        mol_type = genomic DNA
                        organism = Homo sapiens
SEQUENCE: 240
gctacgaccc atacacccaa                                              20

SEQ ID NO: 241          moltype = DNA  length = 20
FEATURE                 Location/Qualifiers
misc_feature            1..20
                        note = source = /note="target seq for Hereditary
                        cancer-predisposing syndrome"
source                  1..20
                        mol_type = genomic DNA
                        organism = Homo sapiens
SEQUENCE: 241
gcgctatgtt ctattccatc                                              20

SEQ ID NO: 242          moltype = DNA  length = 25
FEATURE                 Location/Qualifiers
misc_feature            1..25
                        note = source = /note="target seq for Hereditary
                        cancer-predisposing syndrome"
source                  1..25
                        mol_type = genomic DNA
                        organism = Homo sapiens
SEQUENCE: 242
ggggctggta ttcatgaaag gcaac                                        25

SEQ ID NO: 243          moltype = DNA  length = 20
FEATURE                 Location/Qualifiers
misc_feature            1..20
                        note = source = /note="target seq for Hereditary
                        cancer-predisposing syndrome"
source                  1..20
                        mol_type = genomic DNA
                        organism = Homo sapiens
SEQUENCE: 243
gcgctatgtt ctattccatc                                              20

SEQ ID NO: 244          moltype = DNA  length = 25
FEATURE                 Location/Qualifiers
misc_feature            1..25
                        note = source = /note="target seq for Hereditary
                        cancer-predisposing syndrome"
source                  1..25
                        mol_type = genomic DNA
                        organism = Homo sapiens
SEQUENCE: 244
gtgttctcag gttatcggta agttt                                        25

SEQ ID NO: 245          moltype = DNA  length = 25
FEATURE                 Location/Qualifiers
misc_feature            1..25
                        note = source = /note="target seq for Hereditary
                        cancer-predisposing syndrome"
source                  1..25
```

```
                            mol_type = genomic DNA
                            organism = Homo sapiens
SEQUENCE: 245
ggaaatgctg ttagtcggta tgtcg                                       25

SEQ ID NO: 246         moltype = DNA  length = 25
FEATURE                Location/Qualifiers
misc_feature           1..25
                       note = source = /note="target seq for Hereditary
                         cancer-predisposing syndrome"
source                 1..25
                       mol_type = genomic DNA
                       organism = Homo sapiens
SEQUENCE: 246
ggaaatgctg ttagtcagta tgtcg                                       25

SEQ ID NO: 247         moltype = DNA  length = 20
FEATURE                Location/Qualifiers
misc_feature           1..20
                       note = source = /note="target seq for Anterior segment
                         dysgenesis 6"
source                 1..20
                       mol_type = genomic DNA
                       organism = Homo sapiens
SEQUENCE: 247
gtggccactg atcggaaacg                                             20

SEQ ID NO: 248         moltype = DNA  length = 25
FEATURE                Location/Qualifiers
misc_feature           1..25
                       note = source = /note="target seq for Brugada syndrome"
source                 1..25
                       mol_type = genomic DNA
                       organism = Homo sapiens
SEQUENCE: 248
gaacctgatc ctggccgtgg tcgca                                       25

SEQ ID NO: 249         moltype = DNA  length = 20
FEATURE                Location/Qualifiers
misc_feature           1..20
                       note = source = /note="target seq for Brugada syndrome"
source                 1..20
                       mol_type = genomic DNA
                       organism = Homo sapiens
SEQUENCE: 249
gatcctggcc gtggtcgcaa                                             20

SEQ ID NO: 250         moltype = DNA  length = 25
FEATURE                Location/Qualifiers
misc_feature           1..25
                       note = source = /note="target seq for Ornithine
                         carbamoyltransferasedeficiency"
source                 1..25
                       mol_type = genomic DNA
                       organism = Homo sapiens
SEQUENCE: 250
gaagggccat gaccttctca ctcta                                       25

SEQ ID NO: 251         moltype = DNA  length = 25
FEATURE                Location/Qualifiers
misc_feature           1..25
                       note = source = /note="target seq for Osteogenesis
                         imperfecta type I"
source                 1..25
                       mol_type = genomic DNA
                       organism = Homo sapiens
SEQUENCE: 251
ggtgctcgag gattgcccgg aacag                                       25

SEQ ID NO: 252         moltype = DNA  length = 25
FEATURE                Location/Qualifiers
misc_feature           1..25
                       note = source = /note="target seq for Osteogenesis
                         imperfecta type I"
source                 1..25
                       mol_type = genomic DNA
                       organism = Homo sapiens
SEQUENCE: 252
gctcgaggat tgcccggaac agctg                                       25
```

```
SEQ ID NO: 253          moltype = DNA  length = 25
FEATURE                 Location/Qualifiers
misc_feature            1..25
                        note = source = /note="target seq for Constipation"
source                  1..25
                        mol_type = genomic DNA
                        organism = Homo sapiens
SEQUENCE: 253
gattccagtt aaatggatgg caatt                                              25

SEQ ID NO: 254          moltype = DNA  length = 25
FEATURE                 Location/Qualifiers
misc_feature            1..25
                        note = source = /note="target seq for Dopamine beta
                         hydroxylase deficiency"
source                  1..25
                        mol_type = genomic DNA
                        organism = Homo sapiens
SEQUENCE: 254
ggacactgcc tattttgcgg tgagt                                              25

SEQ ID NO: 255          moltype = DNA  length = 25
FEATURE                 Location/Qualifiers
misc_feature            1..25
                        note = source = /note="target seq for Cystic fibrosis"
source                  1..25
                        mol_type = genomic DNA
                        organism = Homo sapiens
SEQUENCE: 255
gacttcatcc aggtatgtaa aaata                                              25

SEQ ID NO: 256          moltype = DNA  length = 25
FEATURE                 Location/Qualifiers
misc_feature            1..25
                        note = source = /note="target seq for Phenylketonuria"
source                  1..25
                        mol_type = genomic DNA
                        organism = Homo sapiens
SEQUENCE: 256
gatgtaaacc tgacccacac tgaat                                              25

SEQ ID NO: 257          moltype = DNA  length = 20
FEATURE                 Location/Qualifiers
misc_feature            1..20
                        note = source = /note="target seq for Deficiency
                         ofUDPglucose-hexose-1-phosphate uridylyltransferase"
source                  1..20
                        mol_type = genomic DNA
                        organism = Homo sapiens
SEQUENCE: 257
gagcccctga caccctttacc                                                   20

SEQ ID NO: 258          moltype = DNA  length = 20
FEATURE                 Location/Qualifiers
misc_feature            1..20
                        note = source = /note="target seq for Amyloid
                         Cardiomyopathy,Transthyretin-related"
source                  1..20
                        mol_type = genomic DNA
                        organism = Homo sapiens
SEQUENCE: 258
gtcaccaatc ccaaggaatg                                                    20

SEQ ID NO: 259          moltype = DNA  length = 25
FEATURE                 Location/Qualifiers
misc_feature            1..25
                        note = source = /note="target seq for
                         Carbohydrate-deficientglycoprotein syndrome type I"
source                  1..25
                        mol_type = genomic DNA
                        organism = Homo sapiens
SEQUENCE: 259
ggctactcca tgacagcgcc tgagg                                              25

SEQ ID NO: 260          moltype = DNA  length = 25
FEATURE                 Location/Qualifiers
misc_feature            1..25
                        note = source = /note="target seq for Metachromatic
```

```
                            leukodystrophy"
source                      1..25
                            mol_type = genomic DNA
                            organism = Homo sapiens
SEQUENCE: 260
gcatcccgta ctcccacgac cagat                                               25

SEQ ID NO: 261              moltype = DNA   length = 25
FEATURE                     Location/Qualifiers
misc_feature                1..25
                            note = source = /note="target seq for Smith-Lemli-Opitz
                             syndrome"
source                      1..25
                            mol_type = genomic DNA
                            organism = Homo sapiens
SEQUENCE: 261
gttcttcaat gggcgccccg ggatc                                               25

SEQ ID NO: 262              moltype = DNA   length = 20
FEATURE                     Location/Qualifiers
misc_feature                1..20
                            note = source = /note="target seq for Deafness, autosomal
                             recessive 1A"
source                      1..20
                            mol_type = genomic DNA
                            organism = Homo sapiens
SEQUENCE: 262
gcaggtgagc ccgccggccc                                                     20

SEQ ID NO: 263              moltype = DNA   length = 25
FEATURE                     Location/Qualifiers
misc_feature                1..25
                            note = source = /note="target seq for Congenital
                             omphalocele"
source                      1..25
                            mol_type = genomic DNA
                            organism = Homo sapiens
SEQUENCE: 263
gccagcgctc ctagtggcca tgcac                                               25

SEQ ID NO: 264              moltype = DNA   length = 25
FEATURE                     Location/Qualifiers
misc_feature                1..25
                            note = source = /note="target seq for Congenital
                             omphalocele"
source                      1..25
                            mol_type = genomic DNA
                            organism = Homo sapiens
SEQUENCE: 264
gcgctcctag tggccatgca cgtgg                                               25

SEQ ID NO: 265              moltype = DNA   length = 20
FEATURE                     Location/Qualifiers
misc_feature                1..20
                            note = source = /note="target seq for Congenital
                             omphalocele"
source                      1..20
                            mol_type = genomic DNA
                            organism = Homo sapiens
SEQUENCE: 265
gtccacgcca gcgctcctag                                                     20

SEQ ID NO: 266              moltype = DNA   length = 20
FEATURE                     Location/Qualifiers
misc_feature                1..20
                            note = source = /note="target seq for Congenital
                             omphalocele"
source                      1..20
                            mol_type = genomic DNA
                            organism = Homo sapiens
SEQUENCE: 266
gctcctagtg gccatgcacg                                                     20

SEQ ID NO: 267              moltype = DNA   length = 25
FEATURE                     Location/Qualifiers
misc_feature                1..25
                            note = source = /note="target seq for Congenital myotonia,
                             autosomaldominant form"
source                      1..25
```

```
                            mol_type = genomic DNA
                            organism = Homo sapiens
SEQUENCE: 267
gagaggattc tttgcagcca cgttc                                      25

SEQ ID NO: 268          moltype = DNA   length = 20
FEATURE                 Location/Qualifiers
misc_feature            1..20
                        note = source = /note="target seq for Breast-ovarian
                            cancer, familial 1"
source                  1..20
                        mol_type = genomic DNA
                        organism = Homo sapiens
SEQUENCE: 268
ggtgacccga gagtgggtgt                                            20

SEQ ID NO: 269          moltype = DNA   length = 20
FEATURE                 Location/Qualifiers
misc_feature            1..20
                        note = source = /note="target seq for Breast and/or ovarian
                            cancer"
source                  1..20
                        mol_type = genomic DNA
                        organism = Homo sapiens
SEQUENCE: 269
gatgcctgga cagaggacaa                                            20

SEQ ID NO: 270          moltype = DNA   length = 20
FEATURE                 Location/Qualifiers
misc_feature            1..20
                        note = source = /note="target seq for Breast-ovarian
                            cancer, familial 1"
source                  1..20
                        mol_type = genomic DNA
                        organism = Homo sapiens
SEQUENCE: 270
ggacaatggc ttccatggta                                            20

SEQ ID NO: 271          moltype = DNA   length = 20
FEATURE                 Location/Qualifiers
misc_feature            1..20
                        note = source = /note="target seq for Breast-ovarian
                            cancer, familial 1"
source                  1..20
                        mol_type = genomic DNA
                        organism = Homo sapiens
SEQUENCE: 271
gggctagaaa tctgttgcta                                            20

SEQ ID NO: 272          moltype = DNA   length = 20
FEATURE                 Location/Qualifiers
misc_feature            1..20
                        note = source = /note="target seq for Breast-ovarian
                            cancer, familial 1"
source                  1..20
                        mol_type = genomic DNA
                        organism = Homo sapiens
SEQUENCE: 272
ggtgacccga gagtgggtgt                                            20

SEQ ID NO: 273          moltype = DNA   length = 20
FEATURE                 Location/Qualifiers
misc_feature            1..20
                        note = source = /note="target seq for Breast-ovarian
                            cancer, familial 1"
source                  1..20
                        mol_type = genomic DNA
                        organism = Homo sapiens
SEQUENCE: 273
gattctgcaa ctttcaattg                                            20

SEQ ID NO: 274          moltype = DNA   length = 20
FEATURE                 Location/Qualifiers
misc_feature            1..20
                        note = source = /note="target seq for Breast-ovarian
                            cancer, familial 1"
source                  1..20
                        mol_type = genomic DNA
                        organism = Homo sapiens
```

```
SEQUENCE: 274
ggacaatggc ttccatggta                                                     20

SEQ ID NO: 275           moltype = DNA  length = 25
FEATURE                  Location/Qualifiers
misc_feature             1..25
                         note = source = /note="target seq for Inborn genetic
                          diseases"
source                   1..25
                         mol_type = genomic DNA
                         organism = Homo sapiens
SEQUENCE: 275
gaaagcccga cttatagcca gtaat                                               25

SEQ ID NO: 276           moltype = DNA  length = 20
FEATURE                  Location/Qualifiers
misc_feature             1..20
                         note = source = /note="target seq for Breast-ovarian
                          cancer, familial 2"
source                   1..20
                         mol_type = genomic DNA
                         organism = Homo sapiens
SEQUENCE: 276
gattacatga acaaatgggc                                                     20

SEQ ID NO: 277           moltype = DNA  length = 20
FEATURE                  Location/Qualifiers
misc_feature             1..20
                         note = source = /note="target seq for Breast-ovarian
                          cancer, familial 2"
source                   1..20
                         mol_type = genomic DNA
                         organism = Homo sapiens
SEQUENCE: 277
gattacatga acaaatgggc                                                     20

SEQ ID NO: 278           moltype = DNA  length = 20
FEATURE                  Location/Qualifiers
misc_feature             1..20
                         note = source = /note="target seq for Breast-ovarian
                          cancer, familial 2"
source                   1..20
                         mol_type = genomic DNA
                         organism = Homo sapiens
SEQUENCE: 278
gactggaaaa ggaatacagt                                                     20

SEQ ID NO: 279           moltype = DNA  length = 25
FEATURE                  Location/Qualifiers
misc_feature             1..25
                         note = source = /note="target seq for Breast and/or ovarian
                          cancer"
source                   1..25
                         mol_type = genomic DNA
                         organism = Homo sapiens
SEQUENCE: 279
gttggctgat ggtggatggc tcata                                               25

SEQ ID NO: 280           moltype = DNA  length = 25
FEATURE                  Location/Qualifiers
misc_feature             1..25
                         note = source = /note="target seq for Breast-ovarian
                          cancer, familial 2"
source                   1..25
                         mol_type = genomic DNA
                         organism = Homo sapiens
SEQUENCE: 280
gttggctgat ggtggatggc tcata                                               25

SEQ ID NO: 281           moltype = DNA  length = 20
FEATURE                  Location/Qualifiers
misc_feature             1..20
                         note = source = /note="target seq for Breast-ovarian
                          cancer, familial 2"
source                   1..20
                         mol_type = genomic DNA
                         organism = Homo sapiens
SEQUENCE: 281
ggtcagaaga ttattcttca                                                     20
```

```
SEQ ID NO: 282          moltype = DNA  length = 20
FEATURE                 Location/Qualifiers
misc_feature            1..20
                        note = source = /note="target seq for Breast-ovarian
                         cancer, familial 2"
source                  1..20
                        mol_type = genomic DNA
                        organism = Homo sapiens
SEQUENCE: 282
ggcttctagt ctcttttgtt                                                   20

SEQ ID NO: 283          moltype = DNA  length = 20
FEATURE                 Location/Qualifiers
misc_feature            1..20
                        note = source = /note="target seq for Breast-ovarian
                         cancer, familial 2"
source                  1..20
                        mol_type = genomic DNA
                        organism = Homo sapiens
SEQUENCE: 283
ggcttctagt ctcttttgtt                                                   20

SEQ ID NO: 284          moltype = DNA  length = 20
FEATURE                 Location/Qualifiers
misc_feature            1..20
                        note = source = /note="target seq for Smith-Lemli-Opitz
                         syndrome"
source                  1..20
                        mol_type = genomic DNA
                        organism = Homo sapiens
SEQUENCE: 284
gttgcgattt tgcagccatt                                                   20

SEQ ID NO: 285          moltype = DNA  length = 25
FEATURE                 Location/Qualifiers
misc_feature            1..25
                        note = source = /note="target seq for Alport syndrome 1,
                         X-linked recessive"
source                  1..25
                        mol_type = genomic DNA
                        organism = Homo sapiens
SEQUENCE: 285
ggcctatggg tccccctggt ttcgg                                             25

SEQ ID NO: 286          moltype = DNA  length = 20
FEATURE                 Location/Qualifiers
misc_feature            1..20
                        note = source = /note="target seq for Acute neuronopathic
                         Gaucher's disease"
source                  1..20
                        mol_type = genomic DNA
                        organism = Homo sapiens
SEQUENCE: 286
ggcatcaggt gagtgagtca                                                   20

SEQ ID NO: 287          moltype = DNA  length = 20
FEATURE                 Location/Qualifiers
misc_feature            1..20
                        note = source = /note="target seq for Gonadotropin
                         deficiency"
source                  1..20
                        mol_type = genomic DNA
                        organism = Homo sapiens
SEQUENCE: 287
gtaactctcc agcataccat                                                   20

SEQ ID NO: 288          moltype = DNA  length = 20
FEATURE                 Location/Qualifiers
misc_feature            1..20
                        note = source = /note="target seq for Distal arthrogryposis
                         type 1A"
source                  1..20
                        mol_type = genomic DNA
                        organism = Homo sapiens
SEQUENCE: 288
gaagctggag gaggccgaga                                                   20

SEQ ID NO: 289          moltype = DNA  length = 20
```

```
FEATURE                 Location/Qualifiers
misc_feature            1..20
                        note = source = /note="target seq for Distal arthrogryposis
                         type 1A"
source                  1..20
                        mol_type = genomic DNA
                        organism = Homo sapiens
SEQUENCE: 289
gctggaggag gccgagaagg                                                   20

SEQ ID NO: 290          moltype = DNA  length = 20
FEATURE                 Location/Qualifiers
misc_feature            1..20
                        note = source = /note="target seq for Hereditary
                         cancer-predisposing syndrome"
source                  1..20
                        mol_type = genomic DNA
                        organism = Homo sapiens
SEQUENCE: 290
gctgccacct tcagggcctc                                                   20

SEQ ID NO: 291          moltype = DNA  length = 20
FEATURE                 Location/Qualifiers
misc_feature            1..20
                        note = source = /note="target seq for Inborn genetic
                         diseases"
source                  1..20
                        mol_type = genomic DNA
                        organism = Homo sapiens
SEQUENCE: 291
gataaacttc ttgaagagga                                                   20

SEQ ID NO: 292          moltype = DNA  length = 25
FEATURE                 Location/Qualifiers
misc_feature            1..25
                        note = source = /note="target seq for Death in early
                         adulthood"
source                  1..25
                        mol_type = genomic DNA
                        organism = Homo sapiens
SEQUENCE: 292
gtgttctcca tgttcgaaca gaccc                                             25

SEQ ID NO: 293          moltype = DNA  length = 20
FEATURE                 Location/Qualifiers
misc_feature            1..20
                        note = source = /note="target seq for Death in early
                         adulthood"
source                  1..20
                        mol_type = genomic DNA
                        organism = Homo sapiens
SEQUENCE: 293
gttcgaacag acccaaatcc                                                   20

SEQ ID NO: 294          moltype = DNA  length = 20
FEATURE                 Location/Qualifiers
misc_feature            1..20
                        note = source = /note="target seq for Severe autosomal
                         recessive musculardystrophy of childhood - North African
                         type"
source                  1..20
                        mol_type = genomic DNA
                        organism = Homo sapiens
SEQUENCE: 294
gaaatctgtg tgtgtccaga                                                   20

SEQ ID NO: 295          moltype = DNA  length = 20
FEATURE                 Location/Qualifiers
misc_feature            1..20
                        note = source = /note="target seq for Cardiovascular
                         phenotype"
source                  1..20
                        mol_type = genomic DNA
                        organism = Homo sapiens
SEQUENCE: 295
ggtcatcatt gagagcgacc                                                   20

SEQ ID NO: 296          moltype = DNA  length = 20
FEATURE                 Location/Qualifiers
```

```
misc_feature         1..20
                     note = source = /note="target seq for
                      Carbohydrate-deficient glycoproteinsyndrome type I"
source               1..20
                     mol_type = genomic DNA
                     organism = Homo sapiens
SEQUENCE: 296
gaatgctgaa gatgatcgac                                                    20

SEQ ID NO: 297       moltype = DNA  length = 20
FEATURE              Location/Qualifiers
misc_feature         1..20
                     note = source = /note="target seq for Charcot-Marie-Tooth
                      disease, type I"
source               1..20
                     mol_type = genomic DNA
                     organism = Homo sapiens
SEQUENCE: 297
gaatgctgaa gatgatcgac                                                    20

SEQ ID NO: 298       moltype = DNA  length = 25
FEATURE              Location/Qualifiers
misc_feature         1..25
                     note = source = /note="target seq for Inborn genetic
                      diseases"
source               1..25
                     mol_type = genomic DNA
                     organism = Homo sapiens
SEQUENCE: 298
gctcagtaca ccaccgtcgg ccgca                                              25

SEQ ID NO: 299       moltype = DNA  length = 20
FEATURE              Location/Qualifiers
misc_feature         1..20
                     note = source = /note="target seq for Inborn genetic
                      diseases"
source               1..20
                     mol_type = genomic DNA
                     organism = Homo sapiens
SEQUENCE: 299
gtacaccacc gtcggccgca                                                    20

SEQ ID NO: 300       moltype = DNA  length = 25
FEATURE              Location/Qualifiers
misc_feature         1..25
                     note = source = /note="target seq for Familial
                      Mediterranean fever"
source               1..25
                     mol_type = genomic DNA
                     organism = Homo sapiens
SEQUENCE: 300
ggacacgtga tggagggaag aacac                                              25

SEQ ID NO: 301       moltype = DNA  length = 25
FEATURE              Location/Qualifiers
misc_feature         1..25
                     note = source = /note="target seq for Deafness, autosomal
                      recessive 2"
source               1..25
                     mol_type = genomic DNA
                     organism = Homo sapiens
SEQUENCE: 301
ggacctttgt caatgggaca cggac                                              25

SEQ ID NO: 302       moltype = DNA  length = 25
FEATURE              Location/Qualifiers
misc_feature         1..25
                     note = source = /note="target seq for Deafness, autosomal
                      recessive 2"
source               1..25
                     mol_type = genomic DNA
                     organism = Homo sapiens
SEQUENCE: 302
ggacctttgt caatgggaca cagac                                              25

SEQ ID NO: 303       moltype = DNA  length = 25
FEATURE              Location/Qualifiers
misc_feature         1..25
                     note = source = /note="target seq for Deafness, X-linked 2"
```

```
source                  1..25
                        mol_type = genomic DNA
                        organism = Homo sapiens
SEQUENCE: 303
gcgctcctag tggccatgca cgtgg                                              25

SEQ ID NO: 304          moltype = DNA   length = 25
FEATURE                 Location/Qualifiers
misc_feature            1..25
                        note = source = /note="target seq for Enlarged vestibular
                         aqueduct"
source                  1..25
                        mol_type = genomic DNA
                        organism = Homo sapiens
SEQUENCE: 304
gccaccactg ctctttcccg cacgg                                              25

SEQ ID NO: 305          moltype = DNA   length = 20
FEATURE                 Location/Qualifiers
misc_feature            1..20
                        note = source = /note="target seq for Congenital
                         sensorineuralhearing impairment"
source                  1..20
                        mol_type = genomic DNA
                        organism = Homo sapiens
SEQUENCE: 305
gtggtcatta acacaaactc                                                    20

SEQ ID NO: 306          moltype = DNA   length = 20
FEATURE                 Location/Qualifiers
misc_feature            1..20
                        note = source = /note="target seq for Deficiency
                         ofUDPglucose-hexose-1-phosphate uridylyltransferase"
source                  1..20
                        mol_type = genomic DNA
                        organism = Homo sapiens
SEQUENCE: 306
gccagatatt gcccagcgtg                                                    20

SEQ ID NO: 307          moltype = DNA   length = 20
FEATURE                 Location/Qualifiers
misc_feature            1..20
                        note = source = /note="target seq for Very long chain
                         acyl-CoAdehydrogenase deficiency"
source                  1..20
                        mol_type = genomic DNA
                        organism = Homo sapiens
SEQUENCE: 307
gccactaatc gtacccagtt                                                    20

SEQ ID NO: 308          moltype = DNA   length = 20
FEATURE                 Location/Qualifiers
misc_feature            1..20
                        note = source = /note="target seq for Cardiovascular
                         phenotype"
source                  1..20
                        mol_type = genomic DNA
                        organism = Homo sapiens
SEQUENCE: 308
gatattccac tggtggtcga                                                    20

SEQ ID NO: 309          moltype = DNA   length = 20
FEATURE                 Location/Qualifiers
misc_feature            1..20
                        note = source = /note="target seq for Pyruvate kinase
                         deficiency of red cells"
source                  1..20
                        mol_type = genomic DNA
                        organism = Homo sapiens
SEQUENCE: 309
ggaagactcc tgggcataag                                                    20

SEQ ID NO: 310          moltype = DNA   length = 25
FEATURE                 Location/Qualifiers
misc_feature            1..25
                        note = source = /note="target seq for Autosomal dominant
                         progressiveexternal ophthalmoplegia with mitochondrial
                         DNAdeletions 1"
source                  1..25
```

```
                                   mol_type = genomic DNA
                                   organism = Homo sapiens
SEQUENCE: 310
gaagtcgttg atggatctgg ccaat                                         25

SEQ ID NO: 311             moltype = DNA   length = 20
FEATURE                    Location/Qualifiers
misc_feature               1..20
                           note = source = /note="target seq for Very long chain
                            acyl-CoAdehydrogenase deficiency"
source                     1..20
                           mol_type = genomic DNA
                           organism = Homo sapiens
SEQUENCE: 311
gaagatcaca gcttttgtgg                                               20

SEQ ID NO: 312             moltype = DNA   length = 20
FEATURE                    Location/Qualifiers
misc_feature               1..20
                           note = source = /note="target seq for Cystinosis, ocular
                            nonnephropathic"
source                     1..20
                           mol_type = genomic DNA
                           organism = Homo sapiens
SEQUENCE: 312
gtccatctcc ttctaccctc                                               20

SEQ ID NO: 313             moltype = DNA   length = 20
FEATURE                    Location/Qualifiers
misc_feature               1..20
                           note = source = /note="target seq for Pyruvate kinase
                            deficiency of redcells"
source                     1..20
                           mol_type = genomic DNA
                           organism = Homo sapiens
SEQUENCE: 313
gctcagccca gcttctgtct                                               20

SEQ ID NO: 314             moltype = DNA   length = 25
FEATURE                    Location/Qualifiers
misc_feature               1..25
                           note = source = /note="target seq for Distal myopathy,
                            Tateyama type"
source                     1..25
                           mol_type = genomic DNA
                           organism = Homo sapiens
SEQUENCE: 314
gattgacctg gtgaaccaag acccc                                         25

SEQ ID NO: 315             moltype = DNA   length = 25
FEATURE                    Location/Qualifiers
misc_feature               1..25
                           note = source = /note="target seq for Malignant
                            hyperthermia,susceptibility to, 1"
source                     1..25
                           mol_type = genomic DNA
                           organism = Homo sapiens
SEQUENCE: 315
ggccctgcgg atccgcgcca tcctc                                         25

SEQ ID NO: 316             moltype = DNA   length = 25
FEATURE                    Location/Qualifiers
misc_feature               1..25
                           note = source = /note="target seq for Malignant
                            hyperthermia,susceptibility to, 1"
source                     1..25
                           mol_type = genomic DNA
                           organism = Homo sapiens
SEQUENCE: 316
ggatccgcgc catcctccgc tccct                                         25

SEQ ID NO: 317             moltype = DNA   length = 25
FEATURE                    Location/Qualifiers
misc_feature               1..25
                           note = source = /note="target seq for Myopathy, Central
                            Core"
source                     1..25
                           mol_type = genomic DNA
                           organism = Homo sapiens
```

```
SEQUENCE: 317
ggtctgatca tcgacgcttt tggtg                                              25

SEQ ID NO: 318          moltype = DNA  length = 20
FEATURE                 Location/Qualifiers
misc_feature            1..20
                        note = source = /note="target seq for Myopathy, Central
                         Core"
source                  1..20
                        mol_type = genomic DNA
                        organism = Homo sapiens
SEQUENCE: 318
ggtctgatca tcgacgcttt                                                    20

SEQ ID NO: 319          moltype = DNA  length = 25
FEATURE                 Location/Qualifiers
misc_feature            1..25
                        note = source = /note="target seq for Myopathy, Central
                         Core"
source                  1..25
                        mol_type = genomic DNA
                        organism = Homo sapiens
SEQUENCE: 319
gatcatcgac acttttggtg agctc                                              25

SEQ ID NO: 320          moltype = DNA  length = 25
FEATURE                 Location/Qualifiers
misc_feature            1..25
                        note = source = /note="target seq for Malignant
                         hyperthermia,susceptibility to, 1"
source                  1..25
                        mol_type = genomic DNA
                        organism = Homo sapiens
SEQUENCE: 320
ggcggaggca ttggggacga gatcg                                              25

SEQ ID NO: 321          moltype = DNA  length = 20
FEATURE                 Location/Qualifiers
misc_feature            1..20
                        note = source = /note="target seq for Ceroid lipofuscinosis
                         neuronal 2"
source                  1..20
                        mol_type = genomic DNA
                        organism = Homo sapiens
SEQUENCE: 321
gtgacagtgg ggccgggtgt                                                    20

SEQ ID NO: 322          moltype = DNA  length = 25
FEATURE                 Location/Qualifiers
misc_feature            1..25
                        note = source = /note="target seq for Ceroid lipofuscinosis
                         neuronal 2"
source                  1..25
                        mol_type = genomic DNA
                        organism = Homo sapiens
SEQUENCE: 322
ggggccgggt attggtctgt ctctg                                              25

SEQ ID NO: 323          moltype = DNA  length = 25
FEATURE                 Location/Qualifiers
misc_feature            1..25
                        note = source = /note="target seq for Niemann-Pick disease
                         type C1"
source                  1..25
                        mol_type = genomic DNA
                        organism = Homo sapiens
SEQUENCE: 323
ggatcgacga ttatttcgac tgggt                                              25

SEQ ID NO: 324          moltype = DNA  length = 25
FEATURE                 Location/Qualifiers
misc_feature            1..25
                        note = source = /note="target seq for Glutaric aciduria,
                         type 1"
source                  1..25
                        mol_type = genomic DNA
                        organism = Homo sapiens
SEQUENCE: 324
gagtatcacg tgatccggca cgcca                                              25
```

-continued

```
SEQ ID NO: 325          moltype = DNA   length = 25
FEATURE                 Location/Qualifiers
misc_feature            1..25
                        note = source = /note="target seq for CAPN3-Related
                         Disorders"
source                  1..25
                        mol_type = genomic DNA
                        organism = Homo sapiens
SEQUENCE: 325
gccctgatgc agaagaaccg gcgga                                                25

SEQ ID NO: 326          moltype = DNA   length = 20
FEATURE                 Location/Qualifiers
misc_feature            1..20
                        note = source = /note="target seq for CAPN3-Related
                         Disorders"
source                  1..20
                        mol_type = genomic DNA
                        organism = Homo sapiens
SEQUENCE: 326
gatgcagaag aaccggcgga                                                      20

SEQ ID NO: 327          moltype = DNA   length = 20
FEATURE                 Location/Qualifiers
misc_feature            1..20
                        note = source = /note="target seq for Glycogen storage
                         disease, type II"
source                  1..20
                        mol_type = genomic DNA
                        organism = Homo sapiens
SEQUENCE: 327
gtcccagaac agctcccctc                                                      20

SEQ ID NO: 328          moltype = DNA   length = 25
FEATURE                 Location/Qualifiers
misc_feature            1..25
                        note = source = /note="target seq for Nonsyndromic
                         Oculocutaneous Albinism"
source                  1..25
                        mol_type = genomic DNA
                        organism = Homo sapiens
SEQUENCE: 328
gtacagggat ctgccaacga tccta                                                25

SEQ ID NO: 329          moltype = DNA   length = 20
FEATURE                 Location/Qualifiers
misc_feature            1..20
                        note = source = /note="target seq for Familial
                         hypercholesterolemia"
source                  1..20
                        mol_type = genomic DNA
                        organism = Homo sapiens
SEQUENCE: 329
gcgaagatgg ctcggatgag                                                      20

SEQ ID NO: 330          moltype = DNA   length = 20
FEATURE                 Location/Qualifiers
misc_feature            1..20
                        note = source = /note="target seq for Familial
                         hypercholesterolemia"
source                  1..20
                        mol_type = genomic DNA
                        organism = Homo sapiens
SEQUENCE: 330
gagtggccgc agcgctgtag                                                      20

SEQ ID NO: 331          moltype = DNA   length = 20
FEATURE                 Location/Qualifiers
misc_feature            1..20
                        note = source = /note="target seq for Deafness, autosomal
                         recessive 7"
source                  1..20
                        mol_type = genomic DNA
                        organism = Homo sapiens
SEQUENCE: 331
ggtctcaagc tctctcttcg                                                      20

SEQ ID NO: 332          moltype = DNA   length = 20
```

```
FEATURE                 Location/Qualifiers
misc_feature            1..20
                        note = source = /note="target seq for Chronic infantile
                         neurological,cutaneous and articular syndrome"
source                  1..20
                        mol_type = genomic DNA
                        organism = Homo sapiens
SEQUENCE: 332
gacggcttcg atgagctgca                                                      20

SEQ ID NO: 333          moltype = DNA   length = 20
FEATURE                 Location/Qualifiers
misc_feature            1..20
                        note = source = /note="target seq for Eichsfeld type
                         congenitalmuscular dystrophy"
source                  1..20
                        mol_type = genomic DNA
                        organism = Homo sapiens
SEQUENCE: 333
gactctccgg gagactgtcc                                                      20

SEQ ID NO: 334          moltype = DNA   length = 20
FEATURE                 Location/Qualifiers
misc_feature            1..20
                        note = source = /note="target seq for Inborn genetic
                         diseases"
source                  1..20
                        mol_type = genomic DNA
                        organism = Homo sapiens
SEQUENCE: 334
gctcaaaagt ggatgagcgc                                                      20

SEQ ID NO: 335          moltype = DNA   length = 20
FEATURE                 Location/Qualifiers
misc_feature            1..20
                        note = source = /note="target seq for Hyperkalemic Periodic
                         ParalysisType 1"
source                  1..20
                        mol_type = genomic DNA
                        organism = Homo sapiens
SEQUENCE: 335
gcagctgcgg gtcttcaagc                                                      20

SEQ ID NO: 336          moltype = DNA   length = 20
FEATURE                 Location/Qualifiers
misc_feature            1..20
                        note = source = /note="target seq for Inclusion body
                         myopathy 2"
source                  1..20
                        mol_type = genomic DNA
                        organism = Homo sapiens
SEQUENCE: 336
ggacgtggat gtggtggttt                                                      20

SEQ ID NO: 337          moltype = DNA   length = 25
FEATURE                 Location/Qualifiers
misc_feature            1..25
                        note = source = /note="target seq for Severe APG05083.1,
                         APG07433.1,APG07513.1, APG08290.1 immunodeficiency due to
                         ADADeficiency"
source                  1..25
                        mol_type = genomic DNA
                        organism = Homo sapiens
SEQUENCE: 337
gaagagcggc attcaccgta ctgtc                                                25

SEQ ID NO: 338          moltype = DNA   length = 25
FEATURE                 Location/Qualifiers
misc_feature            1..25
                        note = source = /note="target seq for Severe APG05083.1,
                         APG07433.1,APG07513.1, APG08290.1 immunodeficiency due to
                         ADADeficiency"
source                  1..25
                        mol_type = genomic DNA
                        organism = Homo sapiens
SEQUENCE: 338
gcggtacagt ccgcacctgc tggcc                                                25

SEQ ID NO: 339          moltype = DNA   length = 20
```

```
FEATURE              Location/Qualifiers
misc_feature         1..20
                     note = source = /note="target seq for Cardiovascular
                      phenotype"
source               1..20
                     mol_type = genomic DNA
                     organism = Homo sapiens
SEQUENCE: 339
gtgtccgagc agcgccactg                                                   20

SEQ ID NO: 340       moltype = DNA  length = 20
FEATURE              Location/Qualifiers
misc_feature         1..20
                     note = source = /note="target seq for Cystic fibrosis"
source               1..20
                     mol_type = genomic DNA
                     organism = Homo sapiens
SEQUENCE: 340
ggacacttcg tgccttcgga                                                   20

SEQ ID NO: 341       moltype = DNA  length = 20
FEATURE              Location/Qualifiers
misc_feature         1..20
                     note = source = /note="target seq for Cystic fibrosis"
source               1..20
                     mol_type = genomic DNA
                     organism = Homo sapiens
SEQUENCE: 341
ggacacttcg tgccttcgga                                                   20

SEQ ID NO: 342       moltype = DNA  length = 25
FEATURE              Location/Qualifiers
misc_feature         1..25
                     note = source = /note="target seq for Adrenocortical
                      carcinoma, pediatric"
source               1..25
                     mol_type = genomic DNA
                     organism = Homo sapiens
SEQUENCE: 342
gggcgtgagc acttcgagat gttcc                                             25

SEQ ID NO: 343       moltype = DNA  length = 20
FEATURE              Location/Qualifiers
misc_feature         1..20
                     note = source = /note="target seq for Fumarase deficiency"
source               1..20
                     mol_type = genomic DNA
                     organism = Homo sapiens
SEQUENCE: 343
gattggacgt actcatactc                                                   20

SEQ ID NO: 344       moltype = DNA  length = 20
FEATURE              Location/Qualifiers
misc_feature         1..20
                     note = source = /note="target seq for Adenocarcinoma of
                      prostate"
source               1..20
                     mol_type = genomic DNA
                     organism = Homo sapiens
SEQUENCE: 344
gaacactgtc cattggcatg                                                   20

SEQ ID NO: 345       moltype = DNA  length = 20
FEATURE              Location/Qualifiers
misc_feature         1..20
                     note = source = /note="target seq for Familial hypertrophic
                      cardiomyopathy 1"
source               1..20
                     mol_type = genomic DNA
                     organism = Homo sapiens
SEQUENCE: 345
gcatcctcta cggggacttc                                                   20

SEQ ID NO: 346       moltype = DNA  length = 25
FEATURE              Location/Qualifiers
misc_feature         1..25
                     note = source = /note="target seq for Adult
                      hypophosphatasia"
source               1..25
```

```
                            mol_type = genomic DNA
                            organism = Homo sapiens
SEQUENCE: 346
gacaacgaga tgcccsctga ggcct                                          25

SEQ ID NO: 347          moltype = DNA  length = 25
FEATURE                 Location/Qualifiers
misc_feature            1..25
                        note = source = /note="target seq for Adult
                         hypophosphatasia"
source                  1..25
                        mol_type = genomic DNA
                        organism = Homo sapiens
SEQUENCE: 347
ggtactcaga caacaagatg ccccc                                          25

SEQ ID NO: 348          moltype = DNA  length = 25
FEATURE                 Location/Qualifiers
misc_feature            1..25
                        note = source = /note="target seq for Adult
                         hypophosphatasia"
source                  1..25
                        mol_type = genomic DNA
                        organism = Homo sapiens
SEQUENCE: 348
gacaacaaga tgcccsctga ggcct                                          25

SEQ ID NO: 349          moltype = DNA  length = 25
FEATURE                 Location/Qualifiers
misc_feature            1..25
                        note = source = /note="target seq for Inborn genetic
                         diseases"
source                  1..25
                        mol_type = genomic DNA
                        organism = Homo sapiens
SEQUENCE: 349
gccttcttgg acaacgtcac cacca                                          25

SEQ ID NO: 350          moltype = DNA  length = 25
FEATURE                 Location/Qualifiers
misc_feature            1..25
                        note = source = /note="target seq for Inborn genetic
                         diseases"
source                  1..25
                        mol_type = genomic DNA
                        organism = Homo sapiens
SEQUENCE: 350
ggtttgccat ccgaggggta gtgct                                          25

SEQ ID NO: 351          moltype = DNA  length = 20
FEATURE                 Location/Qualifiers
misc_feature            1..20
                        note = source = /note="target seq for Crouzon syndrome"
source                  1..20
                        mol_type = genomic DNA
                        organism = Homo sapiens
SEQUENCE: 351
gcaaatgcct ccacagtggt                                                20

SEQ ID NO: 352          moltype = DNA  length = 20
FEATURE                 Location/Qualifiers
misc_feature            1..20
                        note = source = /note="target seq for Propionyl-CoA
                         carboxylase deficiency"
source                  1..20
                        mol_type = genomic DNA
                        organism = Homo sapiens
SEQUENCE: 352
gacatcatag gcacctccat                                                20

SEQ ID NO: 353          moltype = DNA  length = 25
FEATURE                 Location/Qualifiers
misc_feature            1..25
                        note = source = /note="target seq for Cardiovascular
                         phenotype"
source                  1..25
                        mol_type = genomic DNA
                        organism = Homo sapiens
SEQUENCE: 353
```

```
ggtggaaggg atcggctacg acttc                                          25

SEQ ID NO: 354          moltype = DNA   length = 25
FEATURE                 Location/Qualifiers
misc_feature            1..25
                        note = source = /note="target seq for Dysostosis multiplex"
source                  1..25
                        mol_type = genomic DNA
                        organism = Homo sapiens
SEQUENCE: 354
ggagcagctc tgggccgaag tgtcg                                          25

SEQ ID NO: 355          moltype = DNA   length = 20
FEATURE                 Location/Qualifiers
misc_feature            1..20
                        note = source = /note="target seq for Multiple sulfatase
                         deficiency"
source                  1..20
                        mol_type = genomic DNA
                        organism = Homo sapiens
SEQUENCE: 355
ggcgactcct ttgtctttga                                                20

SEQ ID NO: 356          moltype = DNA   length = 20
FEATURE                 Location/Qualifiers
misc_feature            1..20
                        note = source = /note="target seq for Bifunctional
                         peroxisomal enzymedeficiency"
source                  1..20
                        mol_type = genomic DNA
                        organism = Homo sapiens
SEQUENCE: 356
ggtggtactg gtcaccggcg                                                20

SEQ ID NO: 357          moltype = DNA   length = 25
FEATURE                 Location/Qualifiers
misc_feature            1..25
                        note = source = /note="target seq for Bifunctional
                         peroxisomal enzymedeficiency"
source                  1..25
                        mol_type = genomic DNA
                        organism = Homo sapiens
SEQUENCE: 357
gtactggtca ccagcgcggg ggcag                                          25

SEQ ID NO: 358          moltype = DNA   length = 20
FEATURE                 Location/Qualifiers
misc_feature            1..20
                        note = source = /note="target seq for Hereditary
                         cancer-predisposingsyndrome"
source                  1..20
                        mol_type = genomic DNA
                        organism = Homo sapiens
SEQUENCE: 358
ggaaacttgt aagggcttcg                                                20

SEQ ID NO: 359          moltype = DNA   length = 25
FEATURE                 Location/Qualifiers
misc_feature            1..25
                        note = source = /note="target seq for Cardiovascular
                         phenotype"
source                  1..25
                        mol_type = genomic DNA
                        organism = Homo sapiens
SEQUENCE: 359
gtgcagacat tgacgaatgc cgcat                                          25

SEQ ID NO: 360          moltype = DNA   length = 25
FEATURE                 Location/Qualifiers
misc_feature            1..25
                        note = source = /note="target seq for Cardiovascular
                         phenotype"
source                  1..25
                        mol_type = genomic DNA
                        organism = Homo sapiens
SEQUENCE: 360
gacattgacg aatgccgcat atctc                                          25

SEQ ID NO: 361          moltype = DNA   length = 20
```

-continued

```
FEATURE                 Location/Qualifiers
misc_feature            1..20
                        note = source = /note="target seq for Limb-girdle muscular
                        dystrophy,type 2L"
source                  1..20
                        mol_type = genomic DNA
                        organism = Homo sapiens
SEQUENCE: 361
gcatagtagt aaactagacg                                                       20

SEQ ID NO: 362          moltype = DNA  length = 25
FEATURE                 Location/Qualifiers
misc_feature            1..25
                        note = source = /note="target seq for Familial
                        hypercholesterolemia"
source                  1..25
                        mol_type = genomic DNA
                        organism = Homo sapiens
SEQUENCE: 362
gcatcgatgt caacgagggc aaccg                                                 25

SEQ ID NO: 363          moltype = DNA  length = 20
FEATURE                 Location/Qualifiers
misc_feature            1..20
                        note = source = /note="target seq for Spastic Paraplegia,
                        Recessive"
source                  1..20
                        mol_type = genomic DNA
                        organism = Homo sapiens
SEQUENCE: 363
gcactgctgc tcggccccc                                                        20

SEQ ID NO: 364          moltype = DNA  length = 20
FEATURE                 Location/Qualifiers
misc_feature            1..20
                        note = source = /note="target seq for Isovaleryl-CoA
                        dehydrogenasedeficiency"
source                  1..20
                        mol_type = genomic DNA
                        organism = Homo sapiens
SEQUENCE: 364
ggagcagtgg ggctcagtta                                                       20

SEQ ID NO: 365          moltype = DNA  length = 20
FEATURE                 Location/Qualifiers
misc_feature            1..20
                        note = source = /note="target seq for Familial
                        hypercholesterolemia"
source                  1..20
                        mol_type = genomic DNA
                        organism = Homo sapiens
SEQUENCE: 365
gaggagctgc ctcacaggtg                                                       20

SEQ ID NO: 366          moltype = DNA  length = 20
FEATURE                 Location/Qualifiers
misc_feature            1..20
                        note = source = /note="target seq for Biotinidase
                        deficiency"
source                  1..20
                        mol_type = genomic DNA
                        organism = Homo sapiens
SEQUENCE: 366
gctccagcgc ctgagttgta                                                       20

SEQ ID NO: 367          moltype = DNA  length = 20
FEATURE                 Location/Qualifiers
misc_feature            1..20
                        note = source = /note="target seq for Biotinidase
                        deficiency"
source                  1..20
                        mol_type = genomic DNA
                        organism = Homo sapiens
SEQUENCE: 367
gcctgagttg tatggccatc                                                       20

SEQ ID NO: 368          moltype = DNA  length = 25
FEATURE                 Location/Qualifiers
misc_feature            1..25
```

```
                       note = source = /note="target seq for Leber congenital
                         amaurosis"
source                 1..25
                       mol_type = genomic DNA
                       organism = Homo sapiens
SEQUENCE: 368
gcataatttg tacagctcta agagt                                              25

SEQ ID NO: 369         moltype = DNA   length = 25
FEATURE                Location/Qualifiers
misc_feature           1..25
                       note = source = /note="target seq for Familial
                         hyperinsulinism"
source                 1..25
                       mol_type = genomic DNA
                       organism = Homo sapiens
SEQUENCE: 369
ggtggctgag cccagcccgg ccccc                                              25

SEQ ID NO: 370         moltype = DNA   length = 25
FEATURE                Location/Qualifiers
misc_feature           1..25
                       note = source = /note="target seq for Familial cancer of
                         breast"
source                 1..25
                       mol_type = genomic DNA
                       organism = Homo sapiens
SEQUENCE: 370
ggatgcttgg cagtgggaaa aactt                                              25

SEQ ID NO: 371         moltype = DNA   length = 20
FEATURE                Location/Qualifiers
misc_feature           1..20
                       note = source = /note="target seq for Cohen syndrome"
source                 1..20
                       mol_type = genomic DNA
                       organism = Homo sapiens
SEQUENCE: 371
ggaggtctac tacaggtctg                                                    20

SEQ ID NO: 372         moltype = DNA   length = 25
FEATURE                Location/Qualifiers
misc_feature           1..25
                       note = source = /note="target seq for Cardiovascular
                         phenotype"
source                 1..25
                       mol_type = genomic DNA
                       organism = Homo sapiens
SEQUENCE: 372
gctccctctg tactgtgcag gagtc                                              25

SEQ ID NO: 373         moltype = DNA   length = 20
FEATURE                Location/Qualifiers
misc_feature           1..20
                       note = source = /note="target seq for Wilson disease"
source                 1..20
                       mol_type = genomic DNA
                       organism = Homo sapiens
SEQUENCE: 373
ggcaatgaac acaaagagca                                                    20

SEQ ID NO: 374         moltype = DNA   length = 25
FEATURE                Location/Qualifiers
misc_feature           1..25
                       note = source = /note="target seq for Wilson disease"
source                 1..25
                       mol_type = genomic DNA
                       organism = Homo sapiens
SEQUENCE: 374
gccctggatg ggctcagcgg ccatg                                              25

SEQ ID NO: 375         moltype = DNA   length = 20
FEATURE                Location/Qualifiers
misc_feature           1..20
                       note = source = /note="target seq for Wilson disease"
source                 1..20
                       mol_type = genomic DNA
                       organism = Homo sapiens
SEQUENCE: 375
```

```
gcagccctgg atgggctcag                                              20

SEQ ID NO: 376          moltype = DNA    length = 20
FEATURE                 Location/Qualifiers
misc_feature            1..20
                        note = source = /note="target seq for Familial
                          hypercholesterolemia"
source                  1..20
                        mol_type = genomic DNA
                        organism = Homo sapiens
SEQUENCE: 376
gtggcccagc gaagatgcga                                              20

SEQ ID NO: 377          moltype = DNA    length = 20
FEATURE                 Location/Qualifiers
misc_feature            1..20
                        note = source = /note="target seq for Familial
                          hypercholesterolemia"
source                  1..20
                        mol_type = genomic DNA
                        organism = Homo sapiens
SEQUENCE: 377
gaagatgcga aggtgatttc                                              20

SEQ ID NO: 378          moltype = DNA    length = 20
FEATURE                 Location/Qualifiers
misc_feature            1..20
                        note = source = /note="target seq for Floating-Harbor
                          syndrome"
source                  1..20
                        mol_type = genomic DNA
                        organism = Homo sapiens
SEQUENCE: 378
gctgaagctg gagtgggtcg                                              20

SEQ ID NO: 379          moltype = DNA    length = 25
FEATURE                 Location/Qualifiers
misc_feature            1..25
                        note = source = /note="target seq for Congenital long QT
                          syndrome"
source                  1..25
                        mol_type = genomic DNA
                        organism = Homo sapiens
SEQUENCE: 379
gatgctacac gtcgaccgcc aggga                                        25

SEQ ID NO: 380          moltype = DNA    length = 20
FEATURE                 Location/Qualifiers
misc_feature            1..20
                        note = source = /note="target seq for Congenital long QT
                          syndrome"
source                  1..20
                        mol_type = genomic DNA
                        organism = Homo sapiens
SEQUENCE: 380
gatgctacac gtcgaccgcc                                              20

SEQ ID NO: 381          moltype = DNA    length = 25
FEATURE                 Location/Qualifiers
misc_feature            1..25
                        note = source = /note="target seq for Andersen Tawil
                          syndrome"
source                  1..25
                        mol_type = genomic DNA
                        organism = Homo sapiens
SEQUENCE: 381
gaggaagaga tcaaggtcct ttcca                                        25

SEQ ID NO: 382          moltype = DNA    length = 25
FEATURE                 Location/Qualifiers
misc_feature            1..25
                        note = source = /note="target seq for Cardiovascular
                          phenotype"
source                  1..25
                        mol_type = genomic DNA
                        organism = Homo sapiens
SEQUENCE: 382
gagctgataa ccaccctgta catcg                                        25
```

```
SEQ ID NO: 383            moltype = DNA   length = 20
FEATURE                   Location/Qualifiers
misc_feature              1..20
                          note = source = /note="target seq for Familial
                           hypercholesterolemia"
source                    1..20
                          mol_type = genomic DNA
                          organism = Homo sapiens
SEQUENCE: 383
ggaaaactgc ggtatgggcg                                                      20

SEQ ID NO: 384            moltype = DNA   length = 25
FEATURE                   Location/Qualifiers
misc_feature              1..25
                          note = source = /note="target seq for Cardiovascular
                           phenotype"
source                    1..25
                          mol_type = genomic DNA
                          organism = Homo sapiens
SEQUENCE: 384
gtatttgaag gtctcctccg gggtc                                                25

SEQ ID NO: 385            moltype = DNA   length = 20
FEATURE                   Location/Qualifiers
misc_feature              1..20
                          note = source = /note="target seq for Gastrointestinal
                           stroma tumor"
source                    1..20
                          mol_type = genomic DNA
                          organism = Homo sapiens
SEQUENCE: 385
gagggctaaa gtgggctcgg                                                      20

SEQ ID NO: 386            moltype = DNA   length = 20
FEATURE                   Location/Qualifiers
misc_feature              1..20
                          note = source = /note="target seq for Dyskeratosis
                           congenita"
source                    1..20
                          mol_type = genomic DNA
                          organism = Homo sapiens
SEQUENCE: 386
gctgccaagc ctgctggcaa                                                      20

SEQ ID NO: 387            moltype = DNA   length = 25
FEATURE                   Location/Qualifiers
misc_feature              1..25
                          note = source = /note="target seq for Dyskeratosis
                           congenita"
source                    1..25
                          mol_type = genomic DNA
                          organism = Homo sapiens
SEQUENCE: 387
gccctgcctg tgacttccag cactg                                                25

SEQ ID NO: 388            moltype = DNA   length = 25
FEATURE                   Location/Qualifiers
misc_feature              1..25
                          note = source = /note="target seq for Glycogen storage
                           disease IIIa"
source                    1..25
                          mol_type = genomic DNA
                          organism = Homo sapiens
SEQUENCE: 388
gatgagtaga acagaaaaat acaag                                                25

SEQ ID NO: 389            moltype = DNA   length = 25
FEATURE                   Location/Qualifiers
misc_feature              1..25
                          note = source = /note="target seq for Dilated
                           cardiomyopathy 1DD"
source                    1..25
                          mol_type = genomic DNA
                          organism = Homo sapiens
SEQUENCE: 389
gtctcgtagt ccggtgagcc ggtca                                                25

SEQ ID NO: 390            moltype = DNA   length = 20
FEATURE                   Location/Qualifiers
```

```
misc_feature        1..20
                    note = source = /note="target seq for Renal carnitine
                     transport defect"
source              1..20
                    mol_type = genomic DNA
                    organism = Homo sapiens
SEQUENCE: 390
gtggccatgg aatagcgccg                                                   20

SEQ ID NO: 391      moltype = DNA  length = 25
FEATURE             Location/Qualifiers
misc_feature        1..25
                    note = source = /note="target seq for Baraitser-Winter
                     syndrome 1"
source              1..25
                    mol_type = genomic DNA
                    organism = Homo sapiens
SEQUENCE: 391
gatcctcacc gagcgcggct acagc                                             25

SEQ ID NO: 392      moltype = DNA  length = 25
FEATURE             Location/Qualifiers
misc_feature        1..25
                    note = source = /note="target seq for Very long chain
                     acyl-CoAdehydrogenase deficiency"
source              1..25
                    mol_type = genomic DNA
                    organism = Homo sapiens
SEQUENCE: 392
gggcatgcat gaccttggcg tgggc                                             25

SEQ ID NO: 393      moltype = DNA  length = 20
FEATURE             Location/Qualifiers
misc_feature        1..20
                    note = source = /note="target seq for Familial
                     hypercholesterolemia"
source              1..20
                    mol_type = genomic DNA
                    organism = Homo sapiens
SEQUENCE: 393
gtcagatttg tccttgcagt                                                   20

SEQ ID NO: 394      moltype = DNA  length = 20
FEATURE             Location/Qualifiers
misc_feature        1..20
                    note = source = /note="target seq for Limb-girdle muscular
                     dystrophy,type 2A"
source              1..20
                    mol_type = genomic DNA
                    organism = Homo sapiens
SEQUENCE: 394
gtacggggtt gctctgccgg                                                   20

SEQ ID NO: 395      moltype = DNA  length = 25
FEATURE             Location/Qualifiers
misc_feature        1..25
                    note = source = /note="target seq for Familial
                     hypercholesterolemia"
source              1..25
                    mol_type = genomic DNA
                    organism = Homo sapiens
SEQUENCE: 395
gacagtagcc cctgctcggc cttcg                                             25

SEQ ID NO: 396      moltype = DNA  length = 20
FEATURE             Location/Qualifiers
misc_feature        1..20
                    note = source = /note="target seq for Aortic aneurysm,
                     familial thoracic 6"
source              1..20
                    mol_type = genomic DNA
                    organism = Homo sapiens
SEQUENCE: 396
gccccatgcc atcatgcgtc                                                   20

SEQ ID NO: 397      moltype = DNA  length = 25
FEATURE             Location/Qualifiers
misc_feature        1..25
                    note = source = /note="target seq for Acromicric dysplasia"
```

```
source                      1..25
                            mol_type = genomic DNA
                            organism = Homo sapiens
SEQUENCE: 397
gctttgtcat cgacatttat accgg                                               25

SEQ ID NO: 398              moltype = DNA   length = 25
FEATURE                     Location/Qualifiers
misc_feature                1..25
                            note = source = /note="target seq for Charcot-Marie-Tooth
                             disease type 2C"
source                      1..25
                            mol_type = genomic DNA
                            organism = Homo sapiens
SEQUENCE: 398
ggcggacatg cggcaccagg actcg                                               25

SEQ ID NO: 399              moltype = DNA   length = 25
FEATURE                     Location/Qualifiers
misc_feature                1..25
                            note = source = /note="target seq for Breast-ovarian
                             cancer, familial 2"
source                      1..25
                            mol_type = genomic DNA
                            organism = Homo sapiens
SEQUENCE: 399
gtgtaactgt atacgtatgg cgttt                                               25

SEQ ID NO: 400              moltype = DNA   length = 20
FEATURE                     Location/Qualifiers
misc_feature                1..20
                            note = source = /note="target seq for Breast-ovarian
                             cancer, familial 1"
source                      1..20
                            mol_type = genomic DNA
                            organism = Homo sapiens
SEQUENCE: 400
gatgcctgga cagaggacaa                                                     20

SEQ ID NO: 401              moltype = DNA   length = 25
FEATURE                     Location/Qualifiers
misc_feature                1..25
                            note = source = /note="target seq for Charcot-Marie-Tooth
                             disease type 2C"
source                      1..25
                            mol_type = genomic DNA
                            organism = Homo sapiens
SEQUENCE: 401
gcctaactga tgaggagttt cgagg                                               25

SEQ ID NO: 402              moltype = DNA   length = 25
FEATURE                     Location/Qualifiers
misc_feature                1..25
                            note = source = /note="target seq for Charcot-Marie-Tooth
                             disease type 2C"
source                      1..25
                            mol_type = genomic DNA
                            organism = Homo sapiens
SEQUENCE: 402
gcctaactga tgaggagttt caagg                                               25

SEQ ID NO: 403              moltype = DNA   length = 20
FEATURE                     Location/Qualifiers
misc_feature                1..20
                            note = source = /note="target seq for Hereditary
                             cancer-predisposingsyndrome"
source                      1..20
                            mol_type = genomic DNA
                            organism = Homo sapiens
SEQUENCE: 403
gagcgctgct cagatagcga                                                     20

SEQ ID NO: 404              moltype = DNA   length = 25
FEATURE                     Location/Qualifiers
misc_feature                1..25
                            note = source = /note="target seq for Early infantile
                             epilepticencephalopathy"
source                      1..25
                            mol_type = genomic DNA
```

```
                                 organism = Homo sapiens
SEQUENCE: 404
gatgatccgc atggaccggc gggga                                              25

SEQ ID NO: 405           moltype = DNA   length = 20
FEATURE                  Location/Qualifiers
misc_feature             1..20
                         note = source = /note="target seq for Early infantile
                          epilepticencephalopathy"
source                   1..20
                         mol_type = genomic DNA
                         organism = Homo sapiens
SEQUENCE: 405
ggatgatccg catggaccgg                                                    20

SEQ ID NO: 406           moltype = DNA   length = 25
FEATURE                  Location/Qualifiers
misc_feature             1..25
                         note = source = /note="target seq for Early infantile
                          epilepticencephalopathy"
source                   1..25
                         mol_type = genomic DNA
                         organism = Homo sapiens
SEQUENCE: 406
gcggatgatc cgcatggacc agcgg                                              25

SEQ ID NO: 407           moltype = DNA   length = 20
FEATURE                  Location/Qualifiers
misc_feature             1..20
                         note = source = /note="target seq for Acromicric dysplasia"
source                   1..20
                         mol_type = genomic DNA
                         organism = Homo sapiens
SEQUENCE: 407
gtacgtgatc catcctaggt                                                    20

SEQ ID NO: 408           moltype = DNA   length = 25
FEATURE                  Location/Qualifiers
misc_feature             1..25
                         note = source = /note="target seq for Hypertrophic
                          cardiomyopathy"
source                   1..25
                         mol_type = genomic DNA
                         organism = Homo sapiens
SEQUENCE: 408
gacaccacgg tctccctcaa gtggc                                              25

SEQ ID NO: 409           moltype = DNA   length = 25
FEATURE                  Location/Qualifiers
misc_feature             1..25
                         note = source = /note="target seq for Cardiovascular
                          phenotype"
source                   1..25
                         mol_type = genomic DNA
                         organism = Homo sapiens
SEQUENCE: 409
gctgtccggg gtagcccaa gatag                                               25

SEQ ID NO: 410           moltype = DNA   length = 25
FEATURE                  Location/Qualifiers
misc_feature             1..25
                         note = source = /note="target seq for Cardiovascular
                          phenotype"
source                   1..25
                         mol_type = genomic DNA
                         organism = Homo sapiens
SEQUENCE: 410
gtccacggtg aggggccct ggtgt                                               25

SEQ ID NO: 411           moltype = DNA   length = 25
FEATURE                  Location/Qualifiers
misc_feature             1..25
                         note = source = /note="target seq for Cardiovascular
                          phenotype"
source                   1..25
                         mol_type = genomic DNA
                         organism = Homo sapiens
SEQUENCE: 411
gcctagactg caggacacag ggact                                              25
```

```
SEQ ID NO: 412            moltype = DNA  length = 25
FEATURE                   Location/Qualifiers
misc_feature              1..25
                          note = source = /note="target seq for Familial
                          hypertrophiccardiomyopathy 1"
source                    1..25
                          mol_type = genomic DNA
                          organism = Homo sapiens
SEQUENCE: 412
gcatctgcag acatagagac ctgtg                                              25

SEQ ID NO: 413            moltype = DNA  length = 20
FEATURE                   Location/Qualifiers
misc_feature              1..20
                          note = source = /note="target seq for Benign
                          scapuloperoneal musculardystrophy with cardiomyopathy"
source                    1..20
                          mol_type = genomic DNA
                          organism = Homo sapiens
SEQUENCE: 413
gccctccaag agcttgcggt                                                    20

SEQ ID NO: 414            moltype = DNA  length = 25
FEATURE                   Location/Qualifiers
misc_feature              1..25
                          note = source = /note="target seq for Glycogen storage
                          disease, type II"
source                    1..25
                          mol_type = genomic DNA
                          organism = Homo sapiens
SEQUENCE: 414
ggccctcacc ctgcgctacg cactc                                              25

SEQ ID NO: 415            moltype = DNA  length = 25
FEATURE                   Location/Qualifiers
misc_feature              1..25
                          note = source = /note="target seq for Diffuse mesangial
                          sclerosis"
source                    1..25
                          mol_type = genomic DNA
                          organism = Homo sapiens
SEQUENCE: 415
gtttaggcac ttgttttacc tgtat                                              25

SEQ ID NO: 416            moltype = DNA  length = 20
FEATURE                   Location/Qualifiers
misc_feature              1..20
                          note = source = /note="target seq for Colobomatous
                          microphthalmia"
source                    1..20
                          mol_type = genomic DNA
                          organism = Homo sapiens
SEQUENCE: 416
gggtcgaggc ggacgccata                                                    20

SEQ ID NO: 417            moltype = DNA  length = 20
FEATURE                   Location/Qualifiers
misc_feature              1..20
                          note = source = /note="target seq for Ataxia-telangiectasia
                          syndrome"
source                    1..20
                          mol_type = genomic DNA
                          organism = Homo sapiens
SEQUENCE: 417
gtaaatacat atttactact                                                    20

SEQ ID NO: 418            moltype = DNA  length = 20
FEATURE                   Location/Qualifiers
misc_feature              1..20
                          note = source = /note="target seq for Familial cancer of
                          breast"
source                    1..20
                          mol_type = genomic DNA
                          organism = Homo sapiens
SEQUENCE: 418
ggctacagca cacagctcgt                                                    20

SEQ ID NO: 419            moltype = DNA  length = 25
```

```
FEATURE              Location/Qualifiers
misc_feature         1..25
                     note = source = /note="target seq for Limb-girdle muscular
                      dystrophy,type 2A"
source               1..25
                     mol_type = genomic DNA
                     organism = Homo sapiens
SEQUENCE: 419
gctacgagat gcaaaatgca gtcaa                                              25

SEQ ID NO: 420       moltype = DNA   length = 20
FEATURE              Location/Qualifiers
misc_feature         1..20
                     note = source = /note="target seq for Hereditary
                      cancer-predisposingsyndrome"
source               1..20
                     mol_type = genomic DNA
                     organism = Homo sapiens
SEQUENCE: 420
gccgcttacc aaaaggagta                                                    20

SEQ ID NO: 421       moltype = DNA   length = 25
FEATURE              Location/Qualifiers
misc_feature         1..25
                     note = source = /note="target seq for Asymmetric septal
                      hypertrophy"
source               1..25
                     mol_type = genomic DNA
                     organism = Homo sapiens
SEQUENCE: 421
gtgctgcagg ttgttggtgc atggc                                              25

SEQ ID NO: 422       moltype = DNA   length = 20
FEATURE              Location/Qualifiers
misc_feature         1..20
                     note = source = /note="target seq for Hereditary
                      cancer-predisposingsyndrome"
source               1..20
                     mol_type = genomic DNA
                     organism = Homo sapiens
SEQUENCE: 422
gtaattctat aactccttag                                                    20

SEQ ID NO: 423       moltype = DNA   length = 25
FEATURE              Location/Qualifiers
misc_feature         1..25
                     note = source = /note="target seq for Familial
                      hypertrophiccardiomyopathy 2"
source               1..25
                     mol_type = genomic DNA
                     organism = Homo sapiens
SEQUENCE: 423
gctaaagtca ccgggcgctg gaaat                                              25

SEQ ID NO: 424       moltype = DNA   length = 25
FEATURE              Location/Qualifiers
misc_feature         1..25
                     note = source = /note="target seq for Familial
                      hypertrophiccardiomyopathy 2"
source               1..25
                     mol_type = genomic DNA
                     organism = Homo sapiens
SEQUENCE: 424
ggctaaagtc accgggcgct agaaa                                              25

SEQ ID NO: 425       moltype = DNA   length = 25
FEATURE              Location/Qualifiers
misc_feature         1..25
                     note = source = /note="target seq for Familial
                      hypertrophiccardiomyopathy 2"
source               1..25
                     mol_type = genomic DNA
                     organism = Homo sapiens
SEQUENCE: 425
gctaaagtca ccgggcgcta gaaat                                              25

SEQ ID NO: 426       moltype = DNA   length = 25
FEATURE              Location/Qualifiers
misc_feature         1..25
```

```
                            note = source = /note="target seq for Erythrocytosis,
                              familial, 2"
source                      1..25
                            mol_type = genomic DNA
                            organism = Homo sapiens
SEQUENCE: 426
gaaagagcaa tgcctccagg ttgtc                                              25

SEQ ID NO: 427              moltype = DNA   length = 25
FEATURE                     Location/Qualifiers
misc_feature                1..25
                            note = source = /note="target seq for Death in infancy"
source                      1..25
                            mol_type = genomic DNA
                            organism = Homo sapiens
SEQUENCE: 427
gtattggaat ccggagcatc cacgt                                              25

SEQ ID NO: 428              moltype = DNA   length = 20
FEATURE                     Location/Qualifiers
misc_feature                1..20
                            note = source = /note="target seq for Muscular Diseases"
source                      1..20
                            mol_type = genomic DNA
                            organism = Homo sapiens
SEQUENCE: 428
gcatcttccg gatctttgag                                                    20

SEQ ID NO: 429              moltype = DNA   length = 25
FEATURE                     Location/Qualifiers
misc_feature                1..25
                            note = source = /note="target seq for Familial
                              hypercholesterolemia"
source                      1..25
                            mol_type = genomic DNA
                            organism = Homo sapiens
SEQUENCE: 429
gctgcgagca tggggccctg aggct                                              25

SEQ ID NO: 430              moltype = DNA   length = 20
FEATURE                     Location/Qualifiers
misc_feature                1..20
                            note = source = /note="target seq for Familial cancer of
                              breast"
source                      1..20
                            mol_type = genomic DNA
                            organism = Homo sapiens
SEQUENCE: 430
ggcagcgtta cccagtccga                                                    20

SEQ ID NO: 431              moltype = DNA   length = 25
FEATURE                     Location/Qualifiers
misc_feature                1..25
                            note = source = /note="target seq for Hereditary
                              cancer-predisposingsyndrome"
source                      1..25
                            mol_type = genomic DNA
                            organism = Homo sapiens
SEQUENCE: 431
gtgtaggcaa cttctatagc cacag                                              25

SEQ ID NO: 432              moltype = DNA   length = 25
FEATURE                     Location/Qualifiers
misc_feature                1..25
                            note = source = /note="target seq for Familial
                              hypercholesterolemia"
source                      1..25
                            mol_type = genomic DNA
                            organism = Homo sapiens
SEQUENCE: 432
ggaactcccg ccaagatcaa gaaag                                              25

SEQ ID NO: 433              moltype = DNA   length = 25
FEATURE                     Location/Qualifiers
misc_feature                1..25
                            note = source = /note="target seq for Familial
                              hypercholesterolemia"
source                      1..25
                            mol_type = genomic DNA
```

```
                                organism = Homo sapiens
SEQUENCE: 433
gcggctgcca gtatctgtgc ctccc                                             25

SEQ ID NO: 434          moltype = DNA   length = 25
FEATURE                 Location/Qualifiers
misc_feature            1..25
                        note = source = /note="target seq for Familial
                         hypercholesterolemia"
source                  1..25
                        mol_type = genomic DNA
                        organism = Homo sapiens
SEQUENCE: 434
gaatgatctg caggtgagcg tcgcc                                             25

SEQ ID NO: 435          moltype = DNA   length = 25
FEATURE                 Location/Qualifiers
misc_feature            1..25
                        note = source = /note="target seq for Inclusion body
                         myopathy 2"
source                  1..25
                        mol_type = genomic DNA
                        organism = Homo sapiens
SEQUENCE: 435
gtgctgtagt gcaccaatgt aatct                                             25

SEQ ID NO: 436          moltype = DNA   length = 20
FEATURE                 Location/Qualifiers
misc_feature            1..20
                        note = source = /note="target seq for Ataxia-telangiectasia
                         syndrome"
source                  1..20
                        mol_type = genomic DNA
                        organism = Homo sapiens
SEQUENCE: 436
gctttgatgt taacaatcgc                                                   20

SEQ ID NO: 437          moltype = DNA   length = 25
FEATURE                 Location/Qualifiers
misc_feature            1..25
                        note = source = /note="target seq for Benign
                         familialneonatal-infantile seizures"
source                  1..25
                        mol_type = genomic DNA
                        organism = Homo sapiens
SEQUENCE: 437
gtcagttctc cgatcattcc agctg                                             25

SEQ ID NO: 438          moltype = DNA   length = 20
FEATURE                 Location/Qualifiers
misc_feature            1..20
                        note = source = /note="target seq for Marfan
                         Syndrome/Loeys-DietzSyndrome/Familial Thoracic Aortic
                         Aneurysms andDissections"
source                  1..20
                        mol_type = genomic DNA
                        organism = Homo sapiens
SEQUENCE: 438
gtatctccat tgtctcctcg                                                   20

SEQ ID NO: 439          moltype = DNA   length = 25
FEATURE                 Location/Qualifiers
misc_feature            1..25
                        note = source = /note="target seq for Dilated
                         cardiomyopathy 1G"
source                  1..25
                        mol_type = genomic DNA
                        organism = Homo sapiens
SEQUENCE: 439
gtttcagatt ccctggccc acgtg                                              25

SEQ ID NO: 440          moltype = DNA   length = 20
FEATURE                 Location/Qualifiers
misc_feature            1..20
                        note = source = /note="target seq for Familial
                         hypercholesterolemia"
source                  1..20
                        mol_type = genomic DNA
                        organism = Homo sapiens
```

```
SEQUENCE: 440
gcggtgagtc tcggtgcagg                                                   20

SEQ ID NO: 441          moltype = DNA   length = 20
FEATURE                 Location/Qualifiers
misc_feature            1..20
                        note = source = /note="target seq for Breast-ovarian
                         cancer, familial 2"
source                  1..20
                        mol_type = genomic DNA
                        organism = Homo sapiens
SEQUENCE: 441
gatacagtat taattgactg                                                   20

SEQ ID NO: 442          moltype = DNA   length = 20
FEATURE                 Location/Qualifiers
misc_feature            1..20
                        note = source = /note="target seq for Familial
                         hypercholesterolemia"
source                  1..20
                        mol_type = genomic DNA
                        organism = Homo sapiens
SEQUENCE: 442
gcgagtgcat ccactccagc                                                   20

SEQ ID NO: 443          moltype = DNA   length = 25
FEATURE                 Location/Qualifiers
misc_feature            1..25
                        note = source = /note="target seq for Familial
                         hypercholesterolemia"
source                  1..25
                        mol_type = genomic DNA
                        organism = Homo sapiens
SEQUENCE: 443
ggctacaagt gccagtgtga ggaag                                             25

SEQ ID NO: 444          moltype = DNA   length = 25
FEATURE                 Location/Qualifiers
misc_feature            1..25
                        note = source = /note="target seq for Familial
                         hypercholesterolemia"
source                  1..25
                        mol_type = genomic DNA
                        organism = Homo sapiens
SEQUENCE: 444
gggtggctac aagtgccagc gtgag                                             25

SEQ ID NO: 445          moltype = DNA   length = 25
FEATURE                 Location/Qualifiers
misc_feature            1..25
                        note = source = /note="target seq for Familial
                         hypercholesterolemia"
source                  1..25
                        mol_type = genomic DNA
                        organism = Homo sapiens
SEQUENCE: 445
gtacaccagc ctcaccccca acctg                                             25

SEQ ID NO: 446          moltype = DNA   length = 25
FEATURE                 Location/Qualifiers
misc_feature            1..25
                        note = source = /note="target seq for Familial cancer of
                         breast"
source                  1..25
                        mol_type = genomic DNA
                        organism = Homo sapiens
SEQUENCE: 446
gcctgcccga tagacgagcc tcccg                                             25

SEQ ID NO: 447          moltype = DNA   length = 20
FEATURE                 Location/Qualifiers
misc_feature            1..20
                        note = source = /note="target seq for Hereditary
                         hemorrhagictelangiectasia type 2"
source                  1..20
                        mol_type = genomic DNA
                        organism = Homo sapiens
SEQUENCE: 447
gatccgcagc gcggtgagtc                                                   20
```

```
SEQ ID NO: 448          moltype =    length =
SEQUENCE: 448
000

SEQ ID NO: 449          moltype =    length =
SEQUENCE: 449
000

SEQ ID NO: 450          moltype = AA   length = 415
FEATURE                 Location/Qualifiers
REGION                  1..415
                        note = source = /note="Description of Artificial Sequence:
                         Syntheticpolypeptide"
REGION                  1..415
                        note = source = /note="ADAT"
source                  1..415
                        mol_type = protein
                        organism = synthetic construct
SEQUENCE: 450
MAKRPAATKK AGQAKKKKSE VEFSHEYWMR HALTLAKRAW DEREVPVGAV LVHNNRVIGE    60
GWNRPIGRHD PTAHAEIMAL RQGGLVMQNY RLIDATLYVT LEPCVMCAGA MIHSRIGRVV   120
FGARDAKTGA AGSLMDVLHH PGMNHRVEIT EGILADECAA LLSDFFRMRR QEIKAQKKAQ   180
SSTDSGGSSG GSSGSETPGT SESATPESSG GSSGGSSEVE FSHEYWMRHA LTLAKRARDE   240
REVPVGAVLV LNNRVIGEGW NRAIGLHDPT AHAEIMALRQ GGLVMQNYRL IDATLYVTFE   300
PCVMCAGAMI HSRIGRVVFG VRNAKTGAAG SLMDVLHYPG MNHRVEITEG ILADECAALL   360
CYFFRMPRQV FNAQKKAQSS TDSGGSSGGS SGSETPGTSE SATPESSGGS SGGSS        415

SEQ ID NO: 451          moltype = AA   length = 1494
FEATURE                 Location/Qualifiers
REGION                  1..1494
                        note = source = /note="Description of Artificial Sequence:
                         Syntheticpolypeptide"
REGION                  1..1494
                        note = source =
                         /note="Nuc-ADAT-Linker-dAPG08290.1-Linker-SV40"
source                  1..1494
                        mol_type = protein
                        organism = synthetic construct
SEQUENCE: 451
MAKRPAATKK AGQAKKKKSE VEFSHEYWMR HALTLAKRAW DEREVPVGAV LVHNNRVIGE    60
GWNRPIGRHD PTAHAEIMAL RQGGLVMQNY RLIDATLYVT LEPCVMCAGA MIHSRIGRVV   120
FGARDAKTGA AGSLMDVLHH PGMNHRVEIT EGILADECAA LLSDFFRMRR QEIKAQKKAQ   180
SSTDSGGSSG GSSGSETPGT SESATPESSG GSSGGSSEVE FSHEYWMRHA LTLAKRARDE   240
REVPVGAVLV LNNRVIGEGW NRAIGLHDPT AHAEIMALRQ GGLVMQNYRL IDATLYVTFE   300
PCVMCAGAMI HSRIGRVVFG VRNAKTGAAG SLMDVLHYPG MNHRVEITEG ILADECAALL   360
CYFFRMPRQV FNAQKKAQSS TDSGGSSGGS SGSETPGTSE SATPESSGGS SGGSSMSELD   420
YRIGLAIGTN SIGWGVIELF WNKDRERYEK VRIVDKGVRM FDKAEIPNKG ASLAEPRRIA   480
RSSRRRLNRK SQRKKEIRNL LVQHGMITQE ELDLLYPLSK KSIDIWDIRL DGLDRLLNHL   540
EWARLLIHLA QRRGFKSNRK SELKDAETGK VLSSIQVNEK RLFLYRTVGE MWIKDAEFSK   600
YDRRRNSPNE YVFSVSRADL EKEIVTLFEA QRKFQSSYAS KNLQETYLQI WAHQLPFASG   660
NAILNKVGYC SLLKGKERRI PKATYTFQYF SALDQVNRTR LGPDFQPFTQ EQKEIILDKM   720
FQRTDYYKKK TIPEVSYYDI RKWLELDETI QFKGLNYDPN EELKKIEKKP FINLKAFYEI   780
KKVVANYAER TNEAFSTLDY DAIAYALTVY KTDKDIRSYL KKSNNLSKRC YDDQLIEELF   840
TLSYTKFGHL SFKAINHVLP IMQEGRTYQE AIHQLGRTYL NLKKENRSMF LPLIPDEITN   900
PIVKRAITQA RKVVNAIIRR YGSPNSVHIA LARELSKSHD ERKKIMTAHD ENYKKNKGAI   960
SILIENGILN PTGYDIVRYK LWKEQGERCA YSLKEIPPDT FFNELKKERN GSPILEVDHI  1020
LPYSQSFIDS YHNKVLVYSD ENRNKGNRIP YTYFLETNKD WEAFERYVRS NKLFSKKKRE  1080
YLLKKTYLPR ESELIKERHL NDTRYASTFL KNFIEQNLQF KEVEVNLRKK RVQTVNGVIT  1140
AHLRKRWGLE KNRQETYLHH AMDAIIVACT DHHMVTRITE YYQIKESNKS VKKPYFPMPW  1200
EGFRDELLSH LASQPIAKKI SEELKAGYQS SDYIFVSRMP KRSVTGAAHD QTIRRKGGID  1260
KKGKTIIIKR VRLKDIKFDE NGDFKMVGKE QDLATYEAIK QRYLEHRKNS KKAFETPLYK  1320
PSKKGTGNLI KRVKIEGQTK AFVREVNGGV AQNSDLVRVD LFEKDDKYYM VPIYVPDTVC  1380
SELPKKVVKS GKGYEQWLTL DNSFTFKSSL YPYDLVRLVK GNEDRFYFG TLDIDSDRLN   1440
FKDVNKPSKQ NEYRYSLKTI ENLEKYEVGV LGDLRLVKQE TRRIFNRPKK KRKV        1494

SEQ ID NO: 452          moltype = AA   length = 1494
FEATURE                 Location/Qualifiers
REGION                  1..1494
                        note = source = /note="Description of Artificial Sequence:
                         Syntheticpolypeptide"
REGION                  1..1494
                        note = source =
                         /note="Nuc-ADAT-Linker-nAPG08290.1-Linker-SV40"
source                  1..1494
                        mol_type = protein
                        organism = synthetic construct
SEQUENCE: 452
MAKRPAATKK AGQAKKKKSE VEFSHEYWMR HALTLAKRAW DEREVPVGAV LVHNNRVIGE    60
```

```
GWNRPIGRHD  PTAHAEIMAL  RQGGLVMQNY  RLIDATLYVT  LEPCVMCAGA  MIHSRIGRVV   120
FGARDAKTGA  AGSLMDVLHH  PGMNHRVEIT  EGILADECAA  LLSDFFRMRR  QEIKAQKKAQ   180
SSTDSGGSSG  GSSGSETPGT  SESATPESSG  GSSGGSSEVE  FSHEYWMRHA  LTLAKRARDE   240
REVPVGAVLV  LNNRVIGEGW  NRAIGLHDPT  AHAEIMALRQ  GGLVMQNYRL  IDATLYVTFE   300
PCVMCAGAMI  HSRIGRVVFG  VRNAKTGAAG  SLMDVLHPG   MNHRVEITEG  ILADECAALL   360
CYFFRMPRQV  FNAQKKAQSS  TDSGGSSGGS  SGSETPGTSE  SATPESSGGS  SGGSSMSELD   420
YRIGLAIGTN  SIGWGVIELF  WNKDRERYEK  VRIVDKGVRM  FDKAEIPNKG  ASLAEPRRIA   480
RSSRRRLNRK  SQRKKEIRNL  LVQHGMITQE  ELDLLYPLSK  KSIDIWDIRL  DGLDRLLNHL   540
EWARLLIHLA  QRRGFKSNRK  SELKDAETGK  VLSSIQVNEK  RLFLYRTVGE  MWIKDAEFSK   600
YDRRRNSPNE  YVFSVSRADL  EKEIVTLFEA  QRKFQSSYAS  KNLQETYLQI  WAHQLPFASG   660
NAILNKVGYC  SLLKGKERRI  PKATYTFQYF  SALDQVNRTR  LGPDFQPFTQ  EQKEIILDKM   720
FQRTDYYKKK  TIPEVSYYDI  RKWLELDETI  QFKGLNYDPN  EELKKIEKKP  FINLKAFYEI   780
KKVVANYAER  TNEAFSTLDY  DAIAYALTVY  KTDKDIRSYL  KKSNNLSKRC  YDDQLIEELF   840
TLSYTKFGHL  SFKAINHVLP  IMQEGRTYQE  AIHQLGYDTT  NLKKENRSMF  LPLIPDEITN   900
PIVKRAITQA  RKVVNAIIRR  YGSPNSVHIE  LARELSKSHD  ERKKIMTAHD  ENYKKNKGAI   960
SILIENGILN  PTGYDIVRYK  LWKEQGERCA  YSLKEIPPDT  FFNELKKERN  GSPILEVDHI  1020
LPYSQSFIDS  YHNKVLVYSD  ENRNKGNRIP  YTYFLETNKD  WEAFERYVRS  NKLFSKKKRE  1080
YLLKKTYLPR  ESELIKERHL  NDTRYASTFL  KNFIEQNLQF  KEVEVNLRKK  RVQTVNGVIT  1140
AHLRKRWGLE  KNRQETYLHH  AMDAIIVACT  DHHMVTRITE  YYQIKESNKS  VKKPYFPMPW  1200
EGFRDELLSH  LASQPIAKKI  SEELKAGYQS  SDYIFVSRMP  KRSVTGAAHD  QTIRRKGGID  1260
KKGKTIIIKR  VRLKDIKFDE  NGDFKMVGKE  QDLATYEAIK  QRYLEHRKNS  KKAFETPLYK  1320
PSKKGTGNLI  KRVKIEGQTK  AFVREVNGGV  AQNSDLVRQL  LFEKDDKYYM  VPIYVPDTVC  1380
SELPKKVVKS  GKGYEQWLTL  DNSFTFKSSL  YPYDLVRLVK  GNEDRFLYFG  TLDIDSDRLN  1440
FKDVNKPSKQ  NEYRYSLKTI  ENLEKYEVGV  LGDLRLVKQE  TRRIFNRPKK  KRKV        1494

SEQ ID NO: 453          moltype = DNA  length = 25
FEATURE                 Location/Qualifiers
misc_feature            1..25
                        note = source = /note="Hurler target 1"
source                  1..25
                        mol_type = genomic DNA
                        organism = Homo sapiens
SEQUENCE: 453
ggagcagctc taggccgaag tgtcg                                              25

SEQ ID NO: 454          moltype = DNA  length = 25
FEATURE                 Location/Qualifiers
misc_feature            1..25
                        note = source = /note="Hurler target 2"
source                  1..25
                        mol_type = genomic DNA
                        organism = Homo sapiens
SEQUENCE: 454
taggccgaag tgtcgcaggc cggga                                              25

SEQ ID NO: 455          moltype = DNA  length = 25
FEATURE                 Location/Qualifiers
misc_feature            1..25
                        note = source = /note="Hurler target 3"
source                  1..25
                        mol_type = genomic DNA
                        organism = Homo sapiens
SEQUENCE: 455
gctctaggcc gaagtgtcgc aggcc                                              25

SEQ ID NO: 456          moltype = DNA  length = 135
FEATURE                 Location/Qualifiers
misc_feature            1..135
                        note = source = /note="Description of Artificial Sequence:
                         Syntheticpolynucleotide"
misc_feature            1..135
                        note = source = /note="sgRNA Hurler target 1"
source                  1..135
                        mol_type = other DNA
                        organism = synthetic construct
SEQUENCE: 456
ggagcagctc taggccgaag tgtcggtcat agttccatga aagccaaaag tggctttgat        60
gtttctatga taagggtttc ggcccgtggc gtcgggatc  gcctgccat  tccgatgggc      120
ttctccccat ttatt                                                        135

SEQ ID NO: 457          moltype = DNA  length = 135
FEATURE                 Location/Qualifiers
misc_feature            1..135
                        note = source = /note="Description of Artificial Sequence:
                         Syntheticpolynucleotide"
misc_feature            1..135
                        note = source = /note="sgRNA Hurler target 2"
source                  1..135
                        mol_type = other DNA
```

-continued

```
                            organism = synthetic construct
SEQUENCE: 457
taggccgaag tgtcgcaggc cgggagtcat agttccatga aagccaaaag tggctttgat   60
gtttctatga taagggtttc ggcccgtggc gtcggggatc gcctgcccat tccgatgggc  120
ttctccccat ttatt                                                   135

SEQ ID NO: 458          moltype = DNA   length = 135
FEATURE                 Location/Qualifiers
misc_feature            1..135
                        note = source = /note="Description of Artificial Sequence:
                           Syntheticpolynucleotide"
misc_feature            1..135
                        note = source = /note="sgRNA Hurler target 3"
source                  1..135
                        mol_type = other DNA
                        organism = synthetic construct
SEQUENCE: 458
ggcctgcgac acttcggcct agagcgtcat agttccatga aagccaaaag tggctttgat   60
gtttctatga taagggtttc ggcccgtggc gtcggggatc gcctgcccat tccgatgggc  120
ttctccccat ttatt                                                   135

SEQ ID NO: 459          moltype = DNA   length = 15
FEATURE                 Location/Qualifiers
misc_feature            1..15
                        note = source = /note="Description of Artificial Sequence:
                           Syntheticoligonucleotide"
misc_feature            1..15
                        note = source = /note="Hurler Forward Amplification Primer"
source                  1..15
                        mol_type = other DNA
                        organism = synthetic construct
SEQUENCE: 459
gactccttca ccaag                                                    15

SEQ ID NO: 460          moltype = DNA   length = 14
FEATURE                 Location/Qualifiers
misc_feature            1..14
                        note = source = /note="Description of Artificial Sequence:
                           Syntheticoligonucleotide"
misc_feature            1..14
                        note = source = /note="Hurler Reverse Amplification Primer"
source                  1..14
                        mol_type = other DNA
                        organism = synthetic construct
SEQUENCE: 460
gtagatcagc accg                                                     14

SEQ ID NO: 461          moltype = DNA   length = 14
FEATURE                 Location/Qualifiers
misc_feature            1..14
                        note = source = /note="Description of Artificial Sequence:
                           Syntheticoligonucleotide"
misc_feature            1..14
                        note = source = /note="Hurler Wild Type Probe"
source                  1..14
                        mol_type = other DNA
                        organism = synthetic construct
SEQUENCE: 461
ctctgggccg aagt                                                     14

SEQ ID NO: 462          moltype = DNA   length = 14
FEATURE                 Location/Qualifiers
misc_feature            1..14
                        note = source = /note="Description of Artificial Sequence:
                           Syntheticoligonucleotide"
misc_feature            1..14
                        note = source = /note="Hurler W402X Probe-beta"
source                  1..14
                        mol_type = other DNA
                        organism = synthetic construct
SEQUENCE: 462
ctctaggccg aagt                                                     14

SEQ ID NO: 463          moltype = DNA   length = 13
FEATURE                 Location/Qualifiers
misc_feature            1..13
                        note = source = /note="Description of Artificial Sequence:
                           Syntheticoligonucleotide"
misc_feature            1..13
```

```
                        note = source = /note="Hurler NGS forward"
source                  1..13
                        mol_type = other DNA
                        organism = synthetic construct
SEQUENCE: 463
acttcctcca gcc                                                          13

SEQ ID NO: 464          moltype = DNA  length = 13
FEATURE                 Location/Qualifiers
misc_feature            1..13
                        note = source = /note="Description of Artificial Sequence:
                         Syntheticoligonucleotide"
misc_feature            1..13
                        note = source = /note="Hurler NGS Reverse"
source                  1..13
                        mol_type = other DNA
                        organism = synthetic construct
SEQUENCE: 464
gaacccggc tta                                                           13

SEQ ID NO: 465          moltype = DNA  length = 31
FEATURE                 Location/Qualifiers
misc_feature            1..31
                        note = source = /note="Human W402X"
source                  1..31
                        mol_type = genomic DNA
                        organism = Homo sapiens
SEQUENCE: 465
ggagcagctc taggccgaag tgtcgcaggc c                                      31

SEQ ID NO: 466          moltype = DNA  length = 31
FEATURE                 Location/Qualifiers
misc_feature            1..31
                        note = source = /note="Mouse W392X"
source                  1..31
                        mol_type = genomic DNA
                        organism = Mus musculus
SEQUENCE: 466
agaacaactc taggcagagg tctcaaaggc t                                      31

SEQ ID NO: 467          moltype = DNA  length = 31
FEATURE                 Location/Qualifiers
misc_feature            1..31
                        note = source = /note="Description of Artificial Sequence:
                         Syntheticoligonucleotide"
misc_feature            1..31
                        note = source = /note="humanized mouse"
source                  1..31
                        mol_type = other DNA
                        organism = synthetic construct
SEQUENCE: 467
ggagcagctc taggccgaag tgtcgcaggc c                                      31

SEQ ID NO: 468          moltype = DNA  length = 25
FEATURE                 Location/Qualifiers
misc_feature            1..25
                        note = source = /note="FRDA target 1"
source                  1..25
                        mol_type = genomic DNA
                        organism = Homo sapiens
SEQUENCE: 468
atcacctgag gtccggagtt caaga                                             25

SEQ ID NO: 469          moltype = DNA  length = 25
FEATURE                 Location/Qualifiers
misc_feature            1..25
                        note = source = /note="FRDA target 2"
source                  1..25
                        mol_type = genomic DNA
                        organism = Homo sapiens
SEQUENCE: 469
gtcttgaact ccggacctca ggtga                                             25

SEQ ID NO: 470          moltype = DNA  length = 25
FEATURE                 Location/Qualifiers
misc_feature            1..25
                        note = source = /note="FRDA target 3"
source                  1..25
                        mol_type = genomic DNA
```

```
                              -continued
                        organism = Homo sapiens
SEQUENCE: 470
tgaactccgg acctcaggtg atcca                                          25

SEQ ID NO: 471          moltype = DNA  length = 25
FEATURE                 Location/Qualifiers
misc_feature            1..25
                        note = source = /note="FRDA target 4"
source                  1..25
                        mol_type = genomic DNA
                        organism = Homo sapiens
SEQUENCE: 471
gaaaagttag ccgggcgtgg tgtcg                                          25

SEQ ID NO: 472          moltype = DNA  length = 500
FEATURE                 Location/Qualifiers
misc_feature            1..500
                        note = source = /note="Description of Artificial Sequence:
                         Syntheticpolynucleotide"
misc_feature            1..500
                        note = source = /note="BCL11A enhancer region"
source                  1..500
                        mol_type = other DNA
                        organism = synthetic construct
SEQUENCE: 472
aaaaatggac aattatgagg aggggagagt gcagacaggg gaagcttcac ctcctttaca    60
attttgggag tccacacggc atggcataca aattatttca ttcccattga gaaataaaat   120
ccaattctcc atcaccaaga gagccttccg aaagaggccc ccctgggcaa acggccaccg   180
atggagaggt ctgccagtcc tcttctaccc cacccacgcc cccaccctaa tcagaggcca   240
aacccttcct ggagcctgtg ataaaagcaa ctgttagctt gcactagact agcttcaaag   300
ttgtattgac cctggtgtgt tatgtctaag agtagatgcc atatctcttt tctggcctat   360
gttattacct gtatggactt tgcactggaa tcagctatct gctcttactt atgcacacct   420
ggggcataga gccagccctg tatcgctttt cagccatctc actacagata actcccaagt   480
cctgtctagc tgccttcctt                                               500

SEQ ID NO: 473          moltype = DNA  length = 26
FEATURE                 Location/Qualifiers
misc_feature            1..26
                        note = source = /note="SCD target seq 1"
source                  1..26
                        mol_type = genomic DNA
                        organism = Homo sapiens
SEQUENCE: 473
gcactagact agcttcaaag ttgtag                                         26

SEQ ID NO: 474          moltype = DNA  length = 26
FEATURE                 Location/Qualifiers
misc_feature            1..26
                        note = source = /note="SCD target seq 2"
source                  1..26
                        mol_type = genomic DNA
                        organism = Homo sapiens
SEQUENCE: 474
cctaatcaga ggccaaaccc ttcctg                                         26

SEQ ID NO: 475          moltype = DNA  length = 26
FEATURE                 Location/Qualifiers
misc_feature            1..26
                        note = source = /note="SCD target seq 3"
source                  1..26
                        mol_type = genomic DNA
                        organism = Homo sapiens
SEQUENCE: 475
caagctaaca gttgctttta tcacag                                         26

SEQ ID NO: 476          moltype = DNA  length = 26
FEATURE                 Location/Qualifiers
misc_feature            1..26
                        note = source = /note="SCD target seq 4"
source                  1..26
                        mol_type = genomic DNA
                        organism = Homo sapiens
SEQUENCE: 476
gcactagact agcttcaaag ttgtag                                         26

SEQ ID NO: 477          moltype = DNA  length = 26
FEATURE                 Location/Qualifiers
misc_feature            1..26
                        note = source = /note="SCD target seq 5"
```

```
source                  1..26
                        mol_type = genomic DNA
                        organism = Homo sapiens
SEQUENCE: 477
cctaatcaga ggccaaaccc ttcctg                                              26

SEQ ID NO: 478          moltype = DNA  length = 26
FEATURE                 Location/Qualifiers
misc_feature            1..26
                        note = source = /note="SCD target seq 6"
source                  1..26
                        mol_type = genomic DNA
                        organism = Homo sapiens
SEQUENCE: 478
caagctaaca gttgctttta tcacag                                              26

SEQ ID NO: 479          moltype = DNA  length = 22
FEATURE                 Location/Qualifiers
misc_feature            1..22
                        note = source = /note="Description of Artificial Sequence:
                        Syntheticoligonucleotide"
misc_feature            1..22
                        note = source = /note="RelA FWD"
source                  1..22
                        mol_type = other DNA
                        organism = synthetic construct
SEQUENCE: 479
cttagtttca ccgcaggttc ta                                                  22

SEQ ID NO: 480          moltype = DNA  length = 22
FEATURE                 Location/Qualifiers
misc_feature            1..22
                        note = source = /note="Description of Artificial Sequence:
                        Syntheticoligonucleotide"
misc_feature            1..22
                        note = source = /note="RelA REV"
source                  1..22
                        mol_type = other DNA
                        organism = synthetic construct
SEQUENCE: 480
ctgtgcactc aacactgatc ta                                                  22

SEQ ID NO: 481          moltype = DNA  length = 21
FEATURE                 Location/Qualifiers
misc_feature            1..21
                        note = source = /note="Description of Artificial Sequence:
                        Syntheticoligonucleotide"
misc_feature            1..21
                        note = source = /note="AurkB FWD"
source                  1..21
                        mol_type = other DNA
                        organism = synthetic construct
SEQUENCE: 481
cccagcccta ggttgtttat t                                                   21

SEQ ID NO: 482          moltype = DNA  length = 23
FEATURE                 Location/Qualifiers
misc_feature            1..23
                        note = source = /note="Description of Artificial Sequence:
                        Syntheticoligonucleotide"
misc_feature            1..23
                        note = source = /note="AurkB REV"
source                  1..23
                        mol_type = other DNA
                        organism = synthetic construct
SEQUENCE: 482
ctggctacat cttccttgac tac                                                 23

SEQ ID NO: 483          moltype = DNA  length = 20
FEATURE                 Location/Qualifiers
misc_feature            1..20
                        note = source = /note="Description of Artificial Sequence:
                        Syntheticoligonucleotide"
misc_feature            1..20
                        note = source = /note="HPRT1 FWD"
source                  1..20
                        mol_type = other DNA
                        organism = synthetic construct
SEQUENCE: 483
```

```
gtggcagaag cagtgagtaa                                                   20

SEQ ID NO: 484          moltype = DNA  length = 22
FEATURE                 Location/Qualifiers
misc_feature            1..22
                        note = source = /note="Description of Artificial Sequence:
                          Syntheticoligonucleotide"
misc_feature            1..22
                        note = source = /note="HPRT1 REV"
source                  1..22
                        mol_type = other DNA
                        organism = synthetic construct
SEQUENCE: 484
tcccatctag gcactaggta aa                                                22

SEQ ID NO: 485          moltype = DNA  length = 54
FEATURE                 Location/Qualifiers
misc_feature            1..54
                        note = source = /note="Description of Artificial Sequence:
                          Syntheticoligonucleotide"
misc_feature            1..54
                        note = source = /note="FWD_Guide 134, Guide 135, Guide 136,
                          Guide 137"
source                  1..54
                        mol_type = other DNA
                        organism = synthetic construct
SEQUENCE: 485
gtctcgtggg ctcggagatg tgtataagag acagacaatt ctcctgcctc agcc            54

SEQ ID NO: 486          moltype = DNA  length = 53
FEATURE                 Location/Qualifiers
misc_feature            1..53
                        note = source = /note="Description of Artificial Sequence:
                          Syntheticoligonucleotide"
misc_feature            1..53
                        note = source = /note="REV_Guide 134, Guide 135, Guide 136,
                          Guide 137"
source                  1..53
                        mol_type = other DNA
                        organism = synthetic construct
SEQUENCE: 486
tcgtcggcag cgtcagatgt gtataagaga cagactgcca tgggaagaag gtg             53

SEQ ID NO: 487          moltype = DNA  length = 54
FEATURE                 Location/Qualifiers
misc_feature            1..54
                        note = source = /note="Description of Artificial Sequence:
                          Syntheticoligonucleotide"
misc_feature            1..54
                        note = source = /note="FWD_Guide 138, Guide 139, Guide 140,
                          Guide 141"
source                  1..54
                        mol_type = other DNA
                        organism = synthetic construct
SEQUENCE: 487
gtctcgtggg ctcggagatg tgtataagag acagacaatt ctcctgcctc agcc            54

SEQ ID NO: 488          moltype = DNA  length = 53
FEATURE                 Location/Qualifiers
misc_feature            1..53
                        note = source = /note="Description of Artificial Sequence:
                          Syntheticoligonucleotide"
misc_feature            1..53
                        note = source = /note="REV_Guide 138, Guide 139, Guide 140,
                          Guide 141"
source                  1..53
                        mol_type = other DNA
                        organism = synthetic construct
SEQUENCE: 488
tcgtcggcag cgtcagatgt gtataagaga cagactgcca tgggaagaag gtg             53

SEQ ID NO: 489          moltype = DNA  length = 53
FEATURE                 Location/Qualifiers
misc_feature            1..53
                        note = source = /note="Description of Artificial Sequence:
                          Syntheticoligonucleotide"
misc_feature            1..53
                        note = source = /note="REV_Guide 142, Guide 143, Guide 144,
                          Guide 145"
```

```
source                    1..53
                          mol_type = other DNA
                          organism = synthetic construct
SEQUENCE: 489
tcgtcggcag cgtcagatgt gtataagaga caggagctgc acatttgacg agc              53

SEQ ID NO: 490            moltype = DNA   length = 54
FEATURE                   Location/Qualifiers
misc_feature              1..54
                          note = source = /note="Description of Artificial Sequence:
                            Syntheticoligonucleotide"
misc_feature              1..54
                          note = source = /note="FWD_Guide 142, Guide 143, Guide 144,
                            Guide 145"
source                    1..54
                          mol_type = other DNA
                          organism = synthetic construct
SEQUENCE: 490
gtctcgtggg ctcggagatg tgtataagag acagattaca ggtgtgagcc acgg             54

SEQ ID NO: 491            moltype = DNA   length = 53
FEATURE                   Location/Qualifiers
misc_feature              1..53
                          note = source = /note="Description of Artificial Sequence:
                            Syntheticoligonucleotide"
misc_feature              1..53
                          note = source = /note="REV_Guide 164, Guide 165, Guide 166,
                            Guide 167"
source                    1..53
                          mol_type = other DNA
                          organism = synthetic construct
SEQUENCE: 491
tcgtcggcag cgtcagatgt gtataagaga cagctgacct caggtgatac gcc              53

SEQ ID NO: 492            moltype = DNA   length = 54
FEATURE                   Location/Qualifiers
misc_feature              1..54
                          note = source = /note="Description of Artificial Sequence:
                            Syntheticoligonucleotide"
misc_feature              1..54
                          note = source = /note="FWD_Guide 164, Guide 165, Guide 166,
                            Guide 167"
source                    1..54
                          mol_type = other DNA
                          organism = synthetic construct
SEQUENCE: 492
gtctcgtggg ctcggagatg tgtataagag acagctttgg gaggctgaga cagg             54

SEQ ID NO: 493            moltype = DNA   length = 53
FEATURE                   Location/Qualifiers
misc_feature              1..53
                          note = source = /note="Description of Artificial Sequence:
                            Syntheticoligonucleotide"
misc_feature              1..53
                          note = source = /note="REV_Guide 168, Guide 169, Guide 170,
                            Guide 171"
source                    1..53
                          mol_type = other DNA
                          organism = synthetic construct
SEQUENCE: 493
tcgtcggcag cgtcagatgt gtataagaga cagtgctcta ttgtccaggc tgg              53

SEQ ID NO: 494            moltype = DNA   length = 54
FEATURE                   Location/Qualifiers
misc_feature              1..54
                          note = source = /note="Description of Artificial Sequence:
                            Syntheticoligonucleotide"
misc_feature              1..54
                          note = source = /note="FWD_Guide 168, Guide 169, Guide 170,
                            Guide 171"
source                    1..54
                          mol_type = other DNA
                          organism = synthetic construct
SEQUENCE: 494
gtctcgtggg ctcggagatg tgtataagag acagtccagc aggtcagcaa agaa             54

SEQ ID NO: 495            moltype = DNA   length = 53
FEATURE                   Location/Qualifiers
misc_feature              1..53
```

```
                           note = source = /note="Description of Artificial Sequence:
                             Syntheticoligonucleotide"
misc_feature               1..53
                           note = source = /note="REV_Guide 172, Guide 173, Guide 174,
                             Guide 175"
source                     1..53
                           mol_type = other DNA
                           organism = synthetic construct
SEQUENCE: 495
tcgtcggcag cgtcagatgt gtataagaga caggcagtat aactggccag cct         53

SEQ ID NO: 496             moltype = DNA   length = 56
FEATURE                    Location/Qualifiers
misc_feature               1..56
                           note = source = /note="Description of Artificial Sequence:
                             Syntheticoligonucleotide"
misc_feature               1..56
                           note = source = /note="FWD_Guide 172, Guide 173, Guide 174,
                             Guide 175"
source                     1..56
                           mol_type = other DNA
                           organism = synthetic construct
SEQUENCE: 496
gtctcgtggg ctcggagatg tgtataagag acagtcagtt gaggagttca gcttaa      56

SEQ ID NO: 497             moltype = DNA   length = 53
FEATURE                    Location/Qualifiers
misc_feature               1..53
                           note = source = /note="Description of Artificial Sequence:
                             Syntheticoligonucleotide"
misc_feature               1..53
                           note = source = /note="REV_Guide 185, Guide 186, Guide 187,
                             Guide 188"
source                     1..53
                           mol_type = other DNA
                           organism = synthetic construct
SEQUENCE: 497
tcgtcggcag cgtcagatgt gtataagaga cagtggcccc tatgtggaga tca         53

SEQ ID NO: 498             moltype = DNA   length = 54
FEATURE                    Location/Qualifiers
misc_feature               1..54
                           note = source = /note="Description of Artificial Sequence:
                             Syntheticoligonucleotide"
misc_feature               1..54
                           note = source = /note="FWD_Guide 185, Guide 186, Guide 187,
                             Guide 188"
source                     1..54
                           mol_type = other DNA
                           organism = synthetic construct
SEQUENCE: 498
gtctcgtggg ctcggagatg tgtataagag acagggcaga gctcagcctc atag        54

SEQ ID NO: 499             moltype = DNA   length = 53
FEATURE                    Location/Qualifiers
misc_feature               1..53
                           note = source = /note="Description of Artificial Sequence:
                             Syntheticoligonucleotide"
misc_feature               1..53
                           note = source = /note="REV_Guide 189, Guide 190, Guide 191,
                             Guide 192"
source                     1..53
                           mol_type = other DNA
                           organism = synthetic construct
SEQUENCE: 499
tcgtcggcag cgtcagatgt gtataagaga cagatatccc cacttcccct gct         53

SEQ ID NO: 500             moltype = DNA   length = 54
FEATURE                    Location/Qualifiers
misc_feature               1..54
                           note = source = /note="Description of Artificial Sequence:
                             Syntheticoligonucleotide"
misc_feature               1..54
                           note = source = /note="FWD_Guide 189, Guide 190, Guide 191,
                             Guide 192"
source                     1..54
                           mol_type = other DNA
                           organism = synthetic construct
SEQUENCE: 500
```

```
gtctcgtggg ctcggagatg tgtataagag acagcacctc aaggacagct ctgg        54

SEQ ID NO: 501          moltype = DNA   length = 53
FEATURE                 Location/Qualifiers
misc_feature            1..53
                        note = source = /note="Description of Artificial Sequence:
                          Syntheticoligonucleotide"
misc_feature            1..53
                        note = source = /note="REV_Guide 193, Guide 194, Guide 195,
                          Guide 196"
source                  1..53
                        mol_type = other DNA
                        organism = synthetic construct
SEQUENCE: 501
tcgtcggcag cgtcagatgt gtataagaga cagatatccc cacttcccct gct        53

SEQ ID NO: 502          moltype = DNA   length = 54
FEATURE                 Location/Qualifiers
misc_feature            1..54
                        note = source = /note="Description of Artificial Sequence:
                          Syntheticoligonucleotide"
misc_feature            1..54
                        note = source = /note="FWD_Guide 193, Guide 194, Guide 195,
                          Guide 196"
source                  1..54
                        mol_type = other DNA
                        organism = synthetic construct
SEQUENCE: 502
gtctcgtggg ctcggagatg tgtataagag acagcacctc aaggacagct ctgg        54

SEQ ID NO: 503          moltype = DNA   length = 54
FEATURE                 Location/Qualifiers
misc_feature            1..54
                        note = source = /note="Description of Artificial Sequence:
                          Syntheticoligonucleotide"
misc_feature            1..54
                        note = source = /note="FWD_Guide 146"
source                  1..54
                        mol_type = other DNA
                        organism = synthetic construct
SEQUENCE: 503
gtctcgtggg ctcggagatg tgtataagag acagacaatt ctcctgcctc agcc        54

SEQ ID NO: 504          moltype = DNA   length = 53
FEATURE                 Location/Qualifiers
misc_feature            1..53
                        note = source = /note="Description of Artificial Sequence:
                          Syntheticoligonucleotide"
misc_feature            1..53
                        note = source = /note="REV_Guide 146"
source                  1..53
                        mol_type = other DNA
                        organism = synthetic construct
SEQUENCE: 504
tcgtcggcag cgtcagatgt gtataagaga cagactgcca tgggaagaag gtg        53

SEQ ID NO: 505          moltype = DNA   length = 54
FEATURE                 Location/Qualifiers
misc_feature            1..54
                        note = source = /note="Description of Artificial Sequence:
                          Syntheticoligonucleotide"
misc_feature            1..54
                        note = source = /note="FWD_Guide 147"
source                  1..54
                        mol_type = other DNA
                        organism = synthetic construct
SEQUENCE: 505
gtctcgtggg ctcggagatg tgtataagag acagacaatt ctcctgcctc agcc        54

SEQ ID NO: 506          moltype = DNA   length = 53
FEATURE                 Location/Qualifiers
misc_feature            1..53
                        note = source = /note="Description of Artificial Sequence:
                          Syntheticoligonucleotide"
misc_feature            1..53
                        note = source = /note="REV_Guide 147"
source                  1..53
                        mol_type = other DNA
                        organism = synthetic construct
```

```
SEQUENCE: 506
tcgtcggcag cgtcagatgt gtataagaga cagactgcca tgggaagaag gtg             53

SEQ ID NO: 507          moltype = DNA   length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 148"
source                  1..53
                        mol_type = other DNA
                        organism = synthetic construct
SEQUENCE: 507
tcgtcggcag cgtcagatgt gtataagaga cagactgcca tgggaagaag gtg             53

SEQ ID NO: 508          moltype = DNA   length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 148"
source                  1..54
                        mol_type = other DNA
                        organism = synthetic construct
SEQUENCE: 508
gtctcgtggg ctcggagatg tgtataagag acagacaatt ctcctgcctc agcc            54

SEQ ID NO: 509          moltype = DNA   length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 176"
source                  1..53
                        mol_type = other DNA
                        organism = synthetic construct
SEQUENCE: 509
tcgtcggcag cgtcagatgt gtataagaga caggtagctc actgcagcct caa             53

SEQ ID NO: 510          moltype = DNA   length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 176"
source                  1..54
                        mol_type = other DNA
                        organism = synthetic construct
SEQUENCE: 510
gtctcgtggg ctcggagatg tgtataagag acagtgggtg atgaacatac gggt            54

SEQ ID NO: 511          moltype = DNA   length = 57
FEATURE                 Location/Qualifiers
misc_feature            1..57
                        note = source = /note="Description of Artificial Sequence:
                        Syntheticoligonucleotide"
misc_feature            1..57
                        note = source = /note="REV_Guide 177"
source                  1..57
                        mol_type = other DNA
                        organism = synthetic construct
SEQUENCE: 511
tcgtcggcag cgtcagatgt gtataagaga cagtcagact gaagagctat tgtgtga        57

SEQ ID NO: 512          moltype = DNA   length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 177"
source                  1..54
                        mol_type = other DNA
                        organism = synthetic construct
SEQUENCE: 512
```

```
gtctcgtggg ctcggagatg tgtataagag acagccccac aaaccgatgt agct          54

SEQ ID NO: 513          moltype = DNA   length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 209"
source                  1..53
                        mol_type = other DNA
                        organism = synthetic construct
SEQUENCE: 513
tcgtcggcag cgtcagatgt gtataagaga cagtggagtg cagtggtgtg atc           53

SEQ ID NO: 514          moltype = DNA   length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 209"
source                  1..54
                        mol_type = other DNA
                        organism = synthetic construct
SEQUENCE: 514
gtctcgtggg ctcggagatg tgtataagag acagttgagg ctgcagtgag ctac          54

SEQ ID NO: 515          moltype = DNA   length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 197"
source                  1..53
                        mol_type = other DNA
                        organism = synthetic construct
SEQUENCE: 515
tcgtcggcag cgtcagatgt gtataagaga cagtggcccc tatgtggaga tca           53

SEQ ID NO: 516          moltype = DNA   length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 197"
source                  1..54
                        mol_type = other DNA
                        organism = synthetic construct
SEQUENCE: 516
gtctcgtggg ctcggagatg tgtataagag acagggcaga gctcagcctc atag          54

SEQ ID NO: 517          moltype = DNA   length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 198"
source                  1..53
                        mol_type = other DNA
                        organism = synthetic construct
SEQUENCE: 517
tcgtcggcag cgtcagatgt gtataagaga cagccaagcc gaccaaacaa gtg           53

SEQ ID NO: 518          moltype = DNA   length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 198"
source                  1..54
                        mol_type = other DNA
                        organism = synthetic construct
SEQUENCE: 518
gtctcgtggg ctcggagatg tgtataagag acaggatgcg ctgactgata gcct          54
```

```
SEQ ID NO: 519          moltype = DNA   length = 53
FEATURE                 Location/Qualifiers
misc_feature            1..53
                        note = source = /note="Description of Artificial Sequence:
                          Syntheticoligonucleotide"
misc_feature            1..53
                        note = source = /note="REV_Guide 199"
source                  1..53
                        mol_type = other DNA
                        organism = synthetic construct
SEQUENCE: 519
tcgtcggcag cgtcagatgt gtataagaga cagtggcccc tatgtggaga tca            53

SEQ ID NO: 520          moltype = DNA   length = 54
FEATURE                 Location/Qualifiers
misc_feature            1..54
                        note = source = /note="Description of Artificial Sequence:
                          Syntheticoligonucleotide"
misc_feature            1..54
                        note = source = /note="FWD_Guide 199"
source                  1..54
                        mol_type = other DNA
                        organism = synthetic construct
SEQUENCE: 520
gtctcgtggg ctcggagatg tgtataagag acagggcaga gctcagcctc atag           54

SEQ ID NO: 521          moltype = DNA   length = 54
FEATURE                 Location/Qualifiers
misc_feature            1..54
                        note = source = /note="Description of Artificial Sequence:
                          Syntheticoligonucleotide"
misc_feature            1..54
                        note = source = /note="FWD_Guide 149"
source                  1..54
                        mol_type = other DNA
                        organism = synthetic construct
SEQUENCE: 521
gtctcgtggg ctcggagatg tgtataagag acagggtaag gggaaactgg aggc           54

SEQ ID NO: 522          moltype = DNA   length = 53
FEATURE                 Location/Qualifiers
misc_feature            1..53
                        note = source = /note="Description of Artificial Sequence:
                          Syntheticoligonucleotide"
misc_feature            1..53
                        note = source = /note="REV_Guide 149"
source                  1..53
                        mol_type = other DNA
                        organism = synthetic construct
SEQUENCE: 522
tcgtcggcag cgtcagatgt gtataagaga cagtccactt tctaagcagg cgg            53

SEQ ID NO: 523          moltype = DNA   length = 54
FEATURE                 Location/Qualifiers
misc_feature            1..54
                        note = source = /note="Description of Artificial Sequence:
                          Syntheticoligonucleotide"
misc_feature            1..54
                        note = source = /note="FWD_Guide 150"
source                  1..54
                        mol_type = other DNA
                        organism = synthetic construct
SEQUENCE: 523
gtctcgtggg ctcggagatg tgtataagag acaggtgggc ctggatttcg atct           54

SEQ ID NO: 524          moltype = DNA   length = 53
FEATURE                 Location/Qualifiers
misc_feature            1..53
                        note = source = /note="Description of Artificial Sequence:
                          Syntheticoligonucleotide"
misc_feature            1..53
                        note = source = /note="REV_Guide 150"
source                  1..53
                        mol_type = other DNA
                        organism = synthetic construct
SEQUENCE: 524
tcgtcggcag cgtcagatgt gtataagaga cagatgaaca ggcaggaagt cgg            53
```

```
SEQ ID NO: 525            moltype = DNA  length = 53
FEATURE                   Location/Qualifiers
misc_feature              1..53
                          note = source = /note="Description of Artificial Sequence:
                          Syntheticoligonucleotide"
misc_feature              1..53
                          note = source = /note="REV_Guide 151"
source                    1..53
                          mol_type = other DNA
                          organism = synthetic construct
SEQUENCE: 525
tcgtcggcag cgtcagatgt gtataagaga cagcggttct gagttgcctt cct           53

SEQ ID NO: 526            moltype = DNA  length = 54
FEATURE                   Location/Qualifiers
misc_feature              1..54
                          note = source = /note="Description of Artificial Sequence:
                          Syntheticoligonucleotide"
misc_feature              1..54
                          note = source = /note="FWD_Guide 151"
source                    1..54
                          mol_type = other DNA
                          organism = synthetic construct
SEQUENCE: 526
gtctcgtggg ctcggagatg tgtataagag acagggtaag gggaaactgg aggc          54

SEQ ID NO: 527            moltype = DNA  length = 53
FEATURE                   Location/Qualifiers
misc_feature              1..53
                          note = source = /note="Description of Artificial Sequence:
                          Syntheticoligonucleotide"
misc_feature              1..53
                          note = source = /note="REV_Guide 179"
source                    1..53
                          mol_type = other DNA
                          organism = synthetic construct
SEQUENCE: 527
tcgtcggcag cgtcagatgt gtataagaga cagtcagtgg tccacatgca agt           53

SEQ ID NO: 528            moltype = DNA  length = 54
FEATURE                   Location/Qualifiers
misc_feature              1..54
                          note = source = /note="Description of Artificial Sequence:
                          Syntheticoligonucleotide"
misc_feature              1..54
                          note = source = /note="FWD_Guide 179"
source                    1..54
                          mol_type = other DNA
                          organism = synthetic construct
SEQUENCE: 528
gtctcgtggg ctcggagatg tgtataagag acagaaggca agttgatcgc tcga          54

SEQ ID NO: 529            moltype = DNA  length = 53
FEATURE                   Location/Qualifiers
misc_feature              1..53
                          note = source = /note="Description of Artificial Sequence:
                          Syntheticoligonucleotide"
misc_feature              1..53
                          note = source = /note="REV_Guide 180"
source                    1..53
                          mol_type = other DNA
                          organism = synthetic construct
SEQUENCE: 529
tcgtcggcag cgtcagatgt gtataagaga cagagtggtt ctgttgcaca cgt           53

SEQ ID NO: 530            moltype = DNA  length = 54
FEATURE                   Location/Qualifiers
misc_feature              1..54
                          note = source = /note="Description of Artificial Sequence:
                          Syntheticoligonucleotide"
misc_feature              1..54
                          note = source = /note="FWD_Guide 180"
source                    1..54
                          mol_type = other DNA
                          organism = synthetic construct
SEQUENCE: 530
gtctcgtggg ctcggagatg tgtataagag acagtcgctt aagcccagga gttc          54

SEQ ID NO: 531            moltype = DNA  length = 55
```

```
FEATURE                 Location/Qualifiers
misc_feature            1..55
                        note = source = /note="Description of Artificial Sequence:
                        Syntheticoligonucleotide"
misc_feature            1..55
                        note = source = /note="REV_Guide 181"
source                  1..55
                        mol_type = other DNA
                        organism = synthetic construct
SEQUENCE: 531
tcgtcggcag cgtcagatgt gtataagaga cagtctggct gatccgtact aatcc       55

SEQ ID NO: 532          moltype = DNA  length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 181"
source                  1..54
                        mol_type = other DNA
                        organism = synthetic construct
SEQUENCE: 532
gtctcgtggg ctcggagatg tgtataagag acagtaggct caagggatgc tcct        54

SEQ ID NO: 533          moltype = DNA  length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 200"
source                  1..53
                        mol_type = other DNA
                        organism = synthetic construct
SEQUENCE: 533
tcgtcggcag cgtcagatgt gtataagaga cagccagagc tgtccttgag gtg         53

SEQ ID NO: 534          moltype = DNA  length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 200"
source                  1..54
                        mol_type = other DNA
                        organism = synthetic construct
SEQUENCE: 534
gtctcgtggg ctcggagatg tgtataagag acaggtccat acccaccttg gcaa        54

SEQ ID NO: 535          moltype = DNA  length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 201"
source                  1..53
                        mol_type = other DNA
                        organism = synthetic construct
SEQUENCE: 535
tcgtcggcag cgtcagatgt gtataagaga cagccaagcc gaccaaacaa gtg         53

SEQ ID NO: 536          moltype = DNA  length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 201"
source                  1..54
                        mol_type = other DNA
                        organism = synthetic construct
SEQUENCE: 536
gtctcgtggg ctcggagatg tgtataagag acaggatgcg ctgactgata gcct        54

SEQ ID NO: 537          moltype = DNA  length = 53
FEATURE                 Location/Qualifiers
```

```
misc_feature            1..53
                        note = source = /note="Description of Artificial Sequence:
                        Syntheticoligonucleotide"
misc_feature            1..53
                        note = source = /note="REV_Guide 202"
source                  1..53
                        mol_type = other DNA
                        organism = synthetic construct
SEQUENCE: 537
tcgtcggcag cgtcagatgt gtataagaga cagaggctat cagtcagcgc atc          53

SEQ ID NO: 538          moltype = DNA  length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 202"
source                  1..54
                        mol_type = other DNA
                        organism = synthetic construct
SEQUENCE: 538
gtctcgtggg ctcggagatg tgtataagag acagagcagg ggaagtgggg atat         54

SEQ ID NO: 539          moltype = DNA  length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 152"
source                  1..54
                        mol_type = other DNA
                        organism = synthetic construct
SEQUENCE: 539
gtctcgtggg ctcggagatg tgtataagag acagattaca ggtgtgagcc acgg         54

SEQ ID NO: 540          moltype = DNA  length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 152"
source                  1..53
                        mol_type = other DNA
                        organism = synthetic construct
SEQUENCE: 540
tcgtcggcag cgtcagatgt gtataagaga caggagctgc acatttgacg agc          53

SEQ ID NO: 541          moltype = DNA  length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 153"
source                  1..54
                        mol_type = other DNA
                        organism = synthetic construct
SEQUENCE: 541
gtctcgtggg ctcggagatg tgtataagag acagacaatt ctcctgcctc agcc         54

SEQ ID NO: 542          moltype = DNA  length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 153"
source                  1..53
                        mol_type = other DNA
                        organism = synthetic construct
SEQUENCE: 542
tcgtcggcag cgtcagatgt gtataagaga cagactgcca tgggaagaag gtg          53

SEQ ID NO: 543          moltype = DNA  length = 54
FEATURE                 Location/Qualifiers
misc_feature            1..54
```

```
                        note = source = /note="Description of Artificial Sequence:
                           Syntheticoligonucleotide"
misc_feature            1..54
                        note = source = /note="FWD_Guide 154"
source                  1..54
                        mol_type = other DNA
                        organism = synthetic construct
SEQUENCE: 543
gtctcgtggg ctcggagatg tgtataagag acagattaca ggtgtgagcc acgg            54

SEQ ID NO: 544          moltype = DNA   length = 53
FEATURE                 Location/Qualifiers
misc_feature            1..53
                        note = source = /note="Description of Artificial Sequence:
                           Syntheticoligonucleotide"
misc_feature            1..53
                        note = source = /note="REV_Guide 154"
source                  1..53
                        mol_type = other DNA
                        organism = synthetic construct
SEQUENCE: 544
tcgtcggcag cgtcagatgt gtataagaga caggagctgc acatttgacg agc             53

SEQ ID NO: 545          moltype = DNA   length = 54
FEATURE                 Location/Qualifiers
misc_feature            1..54
                        note = source = /note="Description of Artificial Sequence:
                           Syntheticoligonucleotide"
misc_feature            1..54
                        note = source = /note="FWD_Guide 182"
source                  1..54
                        mol_type = other DNA
                        organism = synthetic construct
SEQUENCE: 545
gtctcgtggg ctcggagatg tgtataagag acagtgggtg atgaacatac gggt            54

SEQ ID NO: 546          moltype = DNA   length = 53
FEATURE                 Location/Qualifiers
misc_feature            1..53
                        note = source = /note="Description of Artificial Sequence:
                           Syntheticoligonucleotide"
misc_feature            1..53
                        note = source = /note="REV_Guide 182"
source                  1..53
                        mol_type = other DNA
                        organism = synthetic construct
SEQUENCE: 546
tcgtcggcag cgtcagatgt gtataagaga caggtagctc actgcagcct caa             53

SEQ ID NO: 547          moltype = DNA   length = 54
FEATURE                 Location/Qualifiers
misc_feature            1..54
                        note = source = /note="Description of Artificial Sequence:
                           Syntheticoligonucleotide"
misc_feature            1..54
                        note = source = /note="FWD_Guide 183"
source                  1..54
                        mol_type = other DNA
                        organism = synthetic construct
SEQUENCE: 547
gtctcgtggg ctcggagatg tgtataagag acagtgcctg tagtcccagc tact            54

SEQ ID NO: 548          moltype = DNA   length = 53
FEATURE                 Location/Qualifiers
misc_feature            1..53
                        note = source = /note="Description of Artificial Sequence:
                           Syntheticoligonucleotide"
misc_feature            1..53
                        note = source = /note="REV_Guide 183"
source                  1..53
                        mol_type = other DNA
                        organism = synthetic construct
SEQUENCE: 548
tcgtcggcag cgtcagatgt gtataagaga cagtcagctc agtgcaacct ctg             53

SEQ ID NO: 549          moltype = DNA   length = 54
FEATURE                 Location/Qualifiers
misc_feature            1..54
                        note = source = /note="Description of Artificial Sequence:
```

```
                        Syntheticoligonucleotide"
misc_feature            1..54
                        note = source = /note="FWD_Guide 184"
source                  1..54
                        mol_type = other DNA
                        organism = synthetic construct
SEQUENCE: 549
gtctcgtggg ctcggagatg tgtataagag acagctttgg gaggctgaga cagg          54

SEQ ID NO: 550          moltype = DNA  length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 184"
source                  1..53
                        mol_type = other DNA
                        organism = synthetic construct
SEQUENCE: 550
tcgtcggcag cgtcagatgt gtataagaga cagctgacct caggtgatac gcc           53

SEQ ID NO: 551          moltype = DNA  length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 203"
source                  1..54
                        mol_type = other DNA
                        organism = synthetic construct
SEQUENCE: 551
gtctcgtggg ctcggagatg tgtataagag acaggatgcg ctgactgata gcct          54

SEQ ID NO: 552          moltype = DNA  length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 203"
source                  1..53
                        mol_type = other DNA
                        organism = synthetic construct
SEQUENCE: 552
tcgtcggcag cgtcagatgt gtataagaga cagccaagcc gaccaaacaa gtg           53

SEQ ID NO: 553          moltype = DNA  length = 54
FEATURE                 Location/Qualifiers
misc_feature            1..54
                        note = source = /note="Description of Artificial Sequence:
                        Syntheticoligonucleotide"
misc_feature            1..54
                        note = source = /note="FWD_Guide 204"
source                  1..54
                        mol_type = other DNA
                        organism = synthetic construct
SEQUENCE: 553
gtctcgtggg ctcggagatg tgtataagag acagcacctc aaggacagct ctgg          54

SEQ ID NO: 554          moltype = DNA  length = 53
FEATURE                 Location/Qualifiers
misc_feature            1..53
                        note = source = /note="Description of Artificial Sequence:
                        Syntheticoligonucleotide"
misc_feature            1..53
                        note = source = /note="REV_Guide 204"
source                  1..53
                        mol_type = other DNA
                        organism = synthetic construct
SEQUENCE: 554
tcgtcggcag cgtcagatgt gtataagaga cagatatccc cacttcccct gct           53

SEQ ID NO: 555          moltype = DNA  length = 54
FEATURE                 Location/Qualifiers
misc_feature            1..54
                        note = source = /note="Description of Artificial Sequence:
                        Syntheticoligonucleotide"
```

```
misc_feature                   1..54
                               note = source = /note="FWD_Guide 205"
source                         1..54
                               mol_type = other DNA
                               organism = synthetic construct
SEQUENCE: 555
gtctcgtggg ctcggagatg tgtataagag acagggcaga gctcagcctc atag          54

SEQ ID NO: 556                 moltype = DNA  length = 53
FEATURE                        Location/Qualifiers
misc_feature                   1..53
                               note = source = /note="Description of Artificial Sequence:
                                 Syntheticoligonucleotide"
misc_feature                   1..53
                               note = source = /note="REV_Guide 205"
source                         1..53
                               mol_type = other DNA
                               organism = synthetic construct
SEQUENCE: 556
tcgtcggcag cgtcagatgt gtataagaga cagtggcccc tatgtggaga tca           53

SEQ ID NO: 557                 moltype =   length =
SEQUENCE: 557
000

SEQ ID NO: 558                 moltype =   length =
SEQUENCE: 558
000

SEQ ID NO: 559                 moltype = DNA  length = 30
FEATURE                        Location/Qualifiers
misc_feature                   1..30
                               note = source = /note="Description of Artificial Sequence:
                                 Syntheticoligonucleotide"
misc_feature                   1..30
                               note = source = /note="sequence 2 for cleavage site assay"
source                         1..30
                               mol_type = other DNA
                               organism = synthetic construct
SEQUENCE: 559
ccatgatata gacgttgtgg ctgttgtagt                                     30

SEQ ID NO: 560                 moltype = AA  length = 6
FEATURE                        Location/Qualifiers
REGION                         1..6
                               note = source = /note="Description of Artificial Sequence:
                                 Synthetic6xHis tag"
source                         1..6
                               mol_type = protein
                               organism = synthetic construct
SEQUENCE: 560
HHHHHH                                                               6

SEQ ID NO: 561                 moltype = AA  length = 10
FEATURE                        Location/Qualifiers
REGION                         1..10
                               note = source = /note="Description of Artificial Sequence:
                                 Synthetic10xHis tag"
source                         1..10
                               mol_type = protein
                               organism = synthetic construct
SEQUENCE: 561
HHHHHHHHHH                                                           10

SEQ ID NO: 562                 moltype = DNA  length = 34
FEATURE                        Location/Qualifiers
misc_feature                   1..34
                               note = source = /note="Description of Artificial Sequence:
                                 Syntheticoligonucleotide"
source                         1..34
                               mol_type = other DNA
                               organism = synthetic construct
SEQUENCE: 562
cctgggtgtg aggctgggcc attaaaacct ctcc                                34

SEQ ID NO: 563                 moltype = DNA  length = 15
FEATURE                        Location/Qualifiers
misc_feature                   1..15
                               note = source = /note="Description of Artificial Sequence:
```

```
                            -continued
                            Syntheticoligonucleotide"
source                      1..15
                            mol_type = other DNA
                            organism = synthetic construct
SEQUENCE: 563
cctgaaaacc tctcc                                                            15

SEQ ID NO: 564              moltype = DNA   length = 33
FEATURE                     Location/Qualifiers
misc_feature                1..33
                            note = source = /note="Description of Artificial Sequence:
                            Syntheticoligonucleotide"
source                      1..33
                            mol_type = other DNA
                            organism = synthetic construct
SEQUENCE: 564
cctgggtgtg agctgggcca ttaaaacctc tcc                                        33

SEQ ID NO: 565              moltype = DNA   length = 22
FEATURE                     Location/Qualifiers
misc_feature                1..22
                            note = source = /note="Description of Artificial Sequence:
                            Syntheticoligonucleotide"
source                      1..22
                            mol_type = other DNA
                            organism = synthetic construct
SEQUENCE: 565
cctgggccat taaaacctct cc                                                    22

SEQ ID NO: 566              moltype = DNA   length = 11
FEATURE                     Location/Qualifiers
misc_feature                1..11
                            note = source = /note="Description of Artificial Sequence:
                            Syntheticoligonucleotide"
source                      1..11
                            mol_type = other DNA
                            organism = synthetic construct
SEQUENCE: 566
cctggctctc c                                                                11

SEQ ID NO: 567              moltype = DNA   length = 20
FEATURE                     Location/Qualifiers
misc_feature                1..20
                            note = source = /note="Description of Artificial Sequence:
                            Syntheticoligonucleotide"
source                      1..20
                            mol_type = other DNA
                            organism = synthetic construct
SEQUENCE: 567
cgggccatta aaacctctcc                                                       20

SEQ ID NO: 568              moltype = DNA   length = 40
FEATURE                     Location/Qualifiers
misc_feature                1..40
                            note = source = /note="Description of Artificial Sequence:
                            Syntheticoligonucleotide"
source                      1..40
                            mol_type = other DNA
                            organism = synthetic construct
SEQUENCE: 568
cctgggtgtg aggccagacc tgggccatta aaacctctcc                                 40

SEQ ID NO: 569              moltype = DNA   length = 79
FEATURE                     Location/Qualifiers
misc_feature                1..79
                            note = source = /note="Description of Artificial Sequence:
                            Syntheticoligonucleotide"
source                      1..79
                            mol_type = other DNA
                            organism = synthetic construct
SEQUENCE: 569
cctgggtgtg aggggaagct gacgtccttt ccatggctgc tcgcctgtgt tgccaccgct           60
gggccattaa aacctctcc                                                        79

SEQ ID NO: 570              moltype = DNA   length = 33
FEATURE                     Location/Qualifiers
misc_feature                1..33
                            note = source = /note="Description of Artificial Sequence:
                            Syntheticoligonucleotide"
```

```
source                  1..33
                        mol_type = other DNA
                        organism = synthetic construct
SEQUENCE: 570
cctgggtgtg acctgggcca ttaaaacctc tcc                                    33

SEQ ID NO: 571          moltype = DNA   length = 35
FEATURE                 Location/Qualifiers
misc_feature            1..35
                        note = source = /note="Description of Artificial Sequence:
                        Syntheticoligonucleotide"
source                  1..35
                        mol_type = other DNA
                        organism = synthetic construct
SEQUENCE: 571
cctgggtgtg aggactgggc cattaaaacc tctcc                                  35

SEQ ID NO: 572          moltype = DNA   length = 34
FEATURE                 Location/Qualifiers
misc_feature            1..34
                        note = source = /note="Description of Artificial Sequence:
                        Syntheticoligonucleotide"
source                  1..34
                        mol_type = other DNA
                        organism = synthetic construct
SEQUENCE: 572
agttggcaga tgctctaatg tactgccatg ggaa                                   34

SEQ ID NO: 573          moltype = DNA   length = 31
FEATURE                 Location/Qualifiers
misc_feature            1..31
                        note = source = /note="Description of Artificial Sequence:
                        Syntheticoligonucleotide"
source                  1..31
                        mol_type = other DNA
                        organism = synthetic construct
SEQUENCE: 573
agttggcaga tgcaatgtac tgccatggga a                                      31

SEQ ID NO: 574          moltype = DNA   length = 30
FEATURE                 Location/Qualifiers
misc_feature            1..30
                        note = source = /note="Description of Artificial Sequence:
                        Syntheticoligonucleotide"
source                  1..30
                        mol_type = other DNA
                        organism = synthetic construct
SEQUENCE: 574
agttggcaga tgcatgtact gccatgggaa                                        30

SEQ ID NO: 575          moltype = DNA   length = 31
FEATURE                 Location/Qualifiers
misc_feature            1..31
                        note = source = /note="Description of Artificial Sequence:
                        Syntheticoligonucleotide"
source                  1..31
                        mol_type = other DNA
                        organism = synthetic construct
SEQUENCE: 575
agttggcaga tgctatgtac tgccatggga a                                      31

SEQ ID NO: 576          moltype = DNA   length = 32
FEATURE                 Location/Qualifiers
misc_feature            1..32
                        note = source = /note="Description of Artificial Sequence:
                        Syntheticoligonucleotide"
source                  1..32
                        mol_type = other DNA
                        organism = synthetic construct
SEQUENCE: 576
agttggcaga tgctaatgta ctgccatggg aa                                     32

SEQ ID NO: 577          moltype = DNA   length = 31
FEATURE                 Location/Qualifiers
misc_feature            1..31
                        note = source = /note="Description of Artificial Sequence:
                        Syntheticoligonucleotide"
source                  1..31
                        mol_type = other DNA
```

```
                            organism = synthetic construct
SEQUENCE: 577
agttggcaga tgctatgtaa tgccatggga a                                  31

SEQ ID NO: 578          moltype = DNA  length = 33
FEATURE                 Location/Qualifiers
misc_feature            1..33
                        note = source = /note="Description of Artificial Sequence:
                            Syntheticoligonucleotide"
source                  1..33
                        mol_type = other DNA
                        organism = synthetic construct
SEQUENCE: 578
agttggcaga tgctctatgt actgccatgg gaa                                33

SEQ ID NO: 579          moltype = DNA  length = 39
FEATURE                 Location/Qualifiers
misc_feature            1..39
                        note = source = /note="Description of Artificial Sequence:
                            Syntheticoligonucleotide"
source                  1..39
                        mol_type = other DNA
                        organism = synthetic construct
SEQUENCE: 579
cgacctgaat gctgtgcggc gctctggctt cattcaatc                          39

SEQ ID NO: 580          moltype = DNA  length = 35
FEATURE                 Location/Qualifiers
misc_feature            1..35
                        note = source = /note="Description of Artificial Sequence:
                            Syntheticoligonucleotide"
source                  1..35
                        mol_type = other DNA
                        organism = synthetic construct
SEQUENCE: 580
cgacctgaat gctgtgcggc tctgcttcca ggtga                              35

SEQ ID NO: 581          moltype = DNA  length = 36
FEATURE                 Location/Qualifiers
misc_feature            1..36
                        note = source = /note="Description of Artificial Sequence:
                            Syntheticoligonucleotide"
source                  1..36
                        mol_type = other DNA
                        organism = synthetic construct
SEQUENCE: 581
cgacctgaat gctgtgcggc atctgcttcc aggtga                             36

SEQ ID NO: 582          moltype = DNA  length = 25
FEATURE                 Location/Qualifiers
misc_feature            1..25
                        note = source = /note="Description of Artificial Sequence:
                            Syntheticoligonucleotide"
source                  1..25
                        mol_type = other DNA
                        organism = synthetic construct
SEQUENCE: 582
cgacctgaat gctgcttcca ggtga                                         25

SEQ ID NO: 583          moltype = DNA  length = 28
FEATURE                 Location/Qualifiers
misc_feature            1..28
                        note = source = /note="Description of Artificial Sequence:
                            Syntheticoligonucleotide"
source                  1..28
                        mol_type = other DNA
                        organism = synthetic construct
SEQUENCE: 583
cgacctgaat gcttctgctt ccaggtga                                      28

SEQ ID NO: 584          moltype = DNA  length = 22
FEATURE                 Location/Qualifiers
misc_feature            1..22
                        note = source = /note="Description of Artificial Sequence:
                            Syntheticoligonucleotide"
source                  1..22
                        mol_type = other DNA
                        organism = synthetic construct
SEQUENCE: 584
```

```
cgacctgaat gcttccaggt ga                                              22

SEQ ID NO: 585         moltype = DNA   length = 35
FEATURE                Location/Qualifiers
misc_feature           1..35
                       note = source = /note="Description of Artificial Sequence:
                       Syntheticoligonucleotide"
source                 1..35
                       mol_type = other DNA
                       organism = synthetic construct
SEQUENCE: 585
gcgtggggac tacgacctga atgctgtgcg gctct                                35

SEQ ID NO: 586         moltype = DNA   length = 24
FEATURE                Location/Qualifiers
misc_feature           1..24
                       note = source = /note="Description of Artificial Sequence:
                       Syntheticoligonucleotide"
source                 1..24
                       mol_type = other DNA
                       organism = synthetic construct
SEQUENCE: 586
gcgacctgaa tgctgtgcgg ctct                                            24

SEQ ID NO: 587         moltype = DNA   length = 28
FEATURE                Location/Qualifiers
misc_feature           1..28
                       note = source = /note="Description of Artificial Sequence:
                       Syntheticoligonucleotide"
source                 1..28
                       mol_type = other DNA
                       organism = synthetic construct
SEQUENCE: 587
gcgtggggac tacgagctgt gcggctct                                        28

SEQ ID NO: 588         moltype = DNA   length = 28
FEATURE                Location/Qualifiers
misc_feature           1..28
                       note = source = /note="Description of Artificial Sequence:
                       Syntheticoligonucleotide"
source                 1..28
                       mol_type = other DNA
                       organism = synthetic construct
SEQUENCE: 588
gcgtggggac tgaatgctgt gcggctct                                        28

SEQ ID NO: 589         moltype = DNA   length = 31
FEATURE                Location/Qualifiers
misc_feature           1..31
                       note = source = /note="Description of Artificial Sequence:
                       Syntheticoligonucleotide"
source                 1..31
                       mol_type = other DNA
                       organism = synthetic construct
SEQUENCE: 589
gcgtggggac tcctgaatgc tgtgcggctc t                                    31

SEQ ID NO: 590         moltype = DNA   length = 36
FEATURE                Location/Qualifiers
misc_feature           1..36
                       note = source = /note="Description of Artificial Sequence:
                       Syntheticoligonucleotide"
source                 1..36
                       mol_type = other DNA
                       organism = synthetic construct
SEQUENCE: 590
gcgtggggac tacgaacctg aatgctgtgc ggctct                               36

SEQ ID NO: 591         moltype = DNA   length = 30
FEATURE                Location/Qualifiers
misc_feature           1..30
                       note = source = /note="Description of Artificial Sequence:
                       Syntheticoligonucleotide"
source                 1..30
                       mol_type = other DNA
                       organism = synthetic construct
SEQUENCE: 591
gcgtggggac tacgaatgct gtgcggctct                                      30
```

```
SEQ ID NO: 592          moltype = DNA  length = 32
FEATURE                 Location/Qualifiers
misc_feature            1..32
                        note = source = /note="Description of Artificial Sequence:
                        Syntheticoligonucleotide"
source                  1..32
                        mol_type = other DNA
                        organism = synthetic construct
SEQUENCE: 592
gcgtggggac tacctgaatg ctgtgcggct ct                                    32

SEQ ID NO: 593          moltype = DNA  length = 21
FEATURE                 Location/Qualifiers
misc_feature            1..21
                        note = source = /note="Description of Artificial Sequence:
                        Syntheticoligonucleotide"
source                  1..21
                        mol_type = other DNA
                        organism = synthetic construct
SEQUENCE: 593
gcgtgaatgc tgtgcggctc t                                                21

SEQ ID NO: 594          moltype = DNA  length = 24
FEATURE                 Location/Qualifiers
misc_feature            1..24
                        note = source = /note="Description of Artificial Sequence:
                        Syntheticoligonucleotide"
source                  1..24
                        mol_type = other DNA
                        organism = synthetic construct
SEQUENCE: 594
gcgacctgac tgctgtgcgg ctct                                             24

SEQ ID NO: 595          moltype = DNA  length = 34
FEATURE                 Location/Qualifiers
misc_feature            1..34
                        note = source = /note="Description of Artificial Sequence:
                        Syntheticoligonucleotide"
source                  1..34
                        mol_type = other DNA
                        organism = synthetic construct
SEQUENCE: 595
gcgtggggac tacgcctgaa tgctgtgcgg ctct                                  34

SEQ ID NO: 596          moltype = DNA  length = 42
FEATURE                 Location/Qualifiers
misc_feature            1..42
                        note = source = /note="Description of Artificial Sequence:
                        Syntheticoligonucleotide"
source                  1..42
                        mol_type = other DNA
                        organism = synthetic construct
SEQUENCE: 596
atggaggagt tggcagatgc tctaatgtac tgccatggga ag                         42

SEQ ID NO: 597          moltype = DNA  length = 40
FEATURE                 Location/Qualifiers
misc_feature            1..40
                        note = source = /note="Description of Artificial Sequence:
                        Syntheticoligonucleotide"
source                  1..40
                        mol_type = other DNA
                        organism = synthetic construct
SEQUENCE: 597
atggaggagt tggcagatgc taatgtactg ccatgggaag                            40

SEQ ID NO: 598          moltype = DNA  length = 34
FEATURE                 Location/Qualifiers
misc_feature            1..34
                        note = source = /note="Description of Artificial Sequence:
                        Syntheticoligonucleotide"
source                  1..34
                        mol_type = other DNA
                        organism = synthetic construct
SEQUENCE: 598
atggaggagt tggcagatgt actgccatgg gaag                                  34

SEQ ID NO: 599          moltype = DNA  length = 18
FEATURE                 Location/Qualifiers
```

```
misc_feature          1..18
                      note = source = /note="Description of Artificial Sequence:
                         Syntheticoligonucleotide"
source                1..18
                      mol_type = other DNA
                      organism = synthetic construct
SEQUENCE: 599
atgtactgcc atgggaag                                                        18

SEQ ID NO: 600        moltype = DNA  length = 30
FEATURE               Location/Qualifiers
misc_feature          1..30
                      note = source = /note="Description of Artificial Sequence:
                         Syntheticoligonucleotide"
source                1..30
                      mol_type = other DNA
                      organism = synthetic construct
SEQUENCE: 600
atggaggagt tggtgtactg ccatgggaag                                           30

SEQ ID NO: 601        moltype = DNA  length = 43
FEATURE               Location/Qualifiers
misc_feature          1..43
                      note = source = /note="Description of Artificial Sequence:
                         Syntheticoligonucleotide"
source                1..43
                      mol_type = other DNA
                      organism = synthetic construct
SEQUENCE: 601
atggaggagt tggcagatgc tctaaatgta ctgccatggg aag                            43

SEQ ID NO: 602        moltype = DNA  length = 45
FEATURE               Location/Qualifiers
misc_feature          1..45
                      note = source = /note="Description of Artificial Sequence:
                         Syntheticoligonucleotide"
source                1..45
                      mol_type = other DNA
                      organism = synthetic construct
SEQUENCE: 602
atggaggagt tggcagatgc tcttctaatg tactgccatg ggaag                          45

SEQ ID NO: 603        moltype = DNA  length = 44
FEATURE               Location/Qualifiers
misc_feature          1..44
                      note = source = /note="Description of Artificial Sequence:
                         Syntheticoligonucleotide"
source                1..44
                      mol_type = other DNA
                      organism = synthetic construct
SEQUENCE: 603
atggaggagt tggcagatgc cctctaatgt actgccatgg gaag                           44

SEQ ID NO: 604        moltype = DNA  length = 40
FEATURE               Location/Qualifiers
misc_feature          1..40
                      note = source = /note="Description of Artificial Sequence:
                         Syntheticoligonucleotide"
source                1..40
                      mol_type = other DNA
                      organism = synthetic construct
SEQUENCE: 604
atggaggagt tggcagataa tgtactgcca tgggaagaag                                40

SEQ ID NO: 605        moltype = DNA  length = 24
FEATURE               Location/Qualifiers
misc_feature          1..24
                      note = source = /note="Description of Artificial Sequence:
                         Syntheticoligonucleotide"
source                1..24
                      mol_type = other DNA
                      organism = synthetic construct
SEQUENCE: 605
atggcgtact gccatgggaa gaag                                                 24

SEQ ID NO: 606        moltype = DNA  length = 46
FEATURE               Location/Qualifiers
misc_feature          1..46
                      note = source = /note="Description of Artificial Sequence:
```

```
                        Syntheticoligonucleotide"
source                  1..46
                        mol_type = other DNA
                        organism = synthetic construct
SEQUENCE: 606
atggaggagt tggcagatgc ttctaatgta ctgccatggg aagaag         46

SEQ ID NO: 607          moltype = DNA  length = 32
FEATURE                 Location/Qualifiers
misc_feature            1..32
                        note = source = /note="Description of Artificial Sequence:
                        Syntheticoligonucleotide"
source                  1..32
                        mol_type = other DNA
                        organism = synthetic construct
SEQUENCE: 607
atggaggagt tggcatctgc catgggaaga ag                        32

SEQ ID NO: 608          moltype = DNA  length = 42
FEATURE                 Location/Qualifiers
misc_feature            1..42
                        note = source = /note="Description of Artificial Sequence:
                        Syntheticoligonucleotide"
source                  1..42
                        mol_type = other DNA
                        organism = synthetic construct
SEQUENCE: 608
atggaggagt tggcagatgc aatgtactgc catgggaaga ag             42

SEQ ID NO: 609          moltype = DNA  length = 124
FEATURE                 Location/Qualifiers
misc_feature            1..124
                        note = source = /note="Description of Artificial Sequence:
                        Syntheticpolynucleotide"
source                  1..124
                        mol_type = other DNA
                        organism = synthetic construct
SEQUENCE: 609
atggaggagt tggcagatgc caaactgaaa aacaaatcaa agcactctta ttgagtgctg  60
gcgatccccg acgccacggg ccgaaaccct tatcatgaaa actctaatgt actgccatgg 120
gaag                                                             124

SEQ ID NO: 610          moltype = DNA  length = 84
FEATURE                 Location/Qualifiers
misc_feature            1..84
                        note = source = /note="Description of Artificial Sequence:
                        Syntheticoligonucleotide"
source                  1..84
                        mol_type = other DNA
                        organism = synthetic construct
SEQUENCE: 610
atggaggagt tggcagatgc tgcttatata gacctcccac cgtacacgcc taccgcccat  60
tttctaatgt actgccatgg gaag                                        84

SEQ ID NO: 611          moltype = DNA  length = 34
FEATURE                 Location/Qualifiers
misc_feature            1..34
                        note = source = /note="Description of Artificial Sequence:
                        Syntheticoligonucleotide"
source                  1..34
                        mol_type = other DNA
                        organism = synthetic construct
SEQUENCE: 611
atggaggagt tgtctaatgt actgccatgg gaag                      34

SEQ ID NO: 612          moltype = DNA  length = 16
FEATURE                 Location/Qualifiers
misc_feature            1..16
                        note = source = /note="Description of Artificial Sequence:
                        Syntheticoligonucleotide"
source                  1..16
                        mol_type = other DNA
                        organism = synthetic construct
SEQUENCE: 612
ctgccatggg aagaag                                          16

SEQ ID NO: 613          moltype = DNA  length = 90
FEATURE                 Location/Qualifiers
misc_feature            1..90
```

```
                        note = source = /note="Description of Artificial Sequence:
                            Syntheticoligonucleotide"
source                  1..90
                        mol_type = other DNA
                        organism = synthetic construct
SEQUENCE: 613
atggaggagt tggcagatgc gcggctgttc ctgtacagaa ccgtgggcga gatgtggatc    60
aaggatgctc taatgtactg ccatgggaag                                     90

SEQ ID NO: 614          moltype = DNA  length = 41
FEATURE                 Location/Qualifiers
misc_feature            1..41
                        note = source = /note="Description of Artificial Sequence:
                            Syntheticoligonucleotide"
source                  1..41
                        mol_type = other DNA
                        organism = synthetic construct
SEQUENCE: 614
atggaggagt tggcagatgc ctaatgtact gccatgggaa g                        41

SEQ ID NO: 615          moltype = DNA  length = 97
FEATURE                 Location/Qualifiers
misc_feature            1..97
                        note = source = /note="Description of Artificial Sequence:
                            Syntheticoligonucleotide"
source                  1..97
                        mol_type = other DNA
                        organism = synthetic construct
SEQUENCE: 615
atggaggagt tggcagatgc tgtcatgatc tttttccgct cgtcgtggga cttgctcagt    60
tctctggcca gctcgtctaa tgtactgcca tgggaag                             97

SEQ ID NO: 616          moltype = DNA  length = 41
FEATURE                 Location/Qualifiers
misc_feature            1..41
                        note = source = /note="Description of Artificial Sequence:
                            Syntheticoligonucleotide"
source                  1..41
                        mol_type = other DNA
                        organism = synthetic construct
SEQUENCE: 616
atggaggagt tggcagatgc tctatgtact gccatgggaa g                        41

SEQ ID NO: 617          moltype = DNA  length = 32
FEATURE                 Location/Qualifiers
misc_feature            1..32
                        note = source = /note="Description of Artificial Sequence:
                            Syntheticoligonucleotide"
source                  1..32
                        mol_type = other DNA
                        organism = synthetic construct
SEQUENCE: 617
cagggacagt gcgcatctcc ctggtcacca ag                                  32

SEQ ID NO: 618          moltype = DNA  length = 17
FEATURE                 Location/Qualifiers
misc_feature            1..17
                        note = source = /note="Description of Artificial Sequence:
                            Syntheticoligonucleotide"
source                  1..17
                        mol_type = other DNA
                        organism = synthetic construct
SEQUENCE: 618
cagggacagt caccaag                                                   17

SEQ ID NO: 619          moltype = DNA  length = 31
FEATURE                 Location/Qualifiers
misc_feature            1..31
                        note = source = /note="Description of Artificial Sequence:
                            Syntheticoligonucleotide"
source                  1..31
                        mol_type = other DNA
                        organism = synthetic construct
SEQUENCE: 619
cagggacagt gcgcatctcc tggtcaccaa g                                   31

SEQ ID NO: 620          moltype = DNA  length = 30
FEATURE                 Location/Qualifiers
misc_feature            1..30
```

```
                        note = source = /note="Description of Artificial Sequence:
                                Syntheticoligonucleotide"
source                  1..30
                        mol_type = other DNA
                        organism = synthetic construct
SEQUENCE: 620
cagggacagt gcgcatctct ggtcaccaag                                          30

SEQ ID NO: 621          moltype = DNA  length = 33
FEATURE                 Location/Qualifiers
misc_feature            1..33
                        note = source = /note="Description of Artificial Sequence:
                                Syntheticoligonucleotide"
source                  1..33
                        mol_type = other DNA
                        organism = synthetic construct
SEQUENCE: 621
cagggacagt gcgcatctcc tctggtcacc aag                                      33

SEQ ID NO: 622          moltype = DNA  length = 29
FEATURE                 Location/Qualifiers
misc_feature            1..29
                        note = source = /note="Description of Artificial Sequence:
                                Syntheticoligonucleotide"
source                  1..29
                        mol_type = other DNA
                        organism = synthetic construct
SEQUENCE: 622
cagggacagt gcgcatcctg gtcaccaag                                           29

SEQ ID NO: 623          moltype = DNA  length = 17
FEATURE                 Location/Qualifiers
misc_feature            1..17
                        note = source = /note="Description of Artificial Sequence:
                                Syntheticoligonucleotide"
source                  1..17
                        mol_type = other DNA
                        organism = synthetic construct
SEQUENCE: 623
cagggacggt caccaag                                                        17

SEQ ID NO: 624          moltype = DNA  length = 31
FEATURE                 Location/Qualifiers
misc_feature            1..31
                        note = source = /note="Description of Artificial Sequence:
                                Syntheticoligonucleotide"
source                  1..31
                        mol_type = other DNA
                        organism = synthetic construct
SEQUENCE: 624
cggggacagg gcgcatctcc tggtcaccaa g                                        31

SEQ ID NO: 625          moltype = DNA  length = 32
FEATURE                 Location/Qualifiers
misc_feature            1..32
                        note = source = /note="Description of Artificial Sequence:
                                Syntheticoligonucleotide"
source                  1..32
                        mol_type = other DNA
                        organism = synthetic construct
SEQUENCE: 625
cgacctgaat gctgtgcggc tctgcttcca gg                                       32

SEQ ID NO: 626          moltype = DNA  length = 33
FEATURE                 Location/Qualifiers
misc_feature            1..33
                        note = source = /note="Description of Artificial Sequence:
                                Syntheticoligonucleotide"
source                  1..33
                        mol_type = other DNA
                        organism = synthetic construct
SEQUENCE: 626
cgacctgaat gctgtgcggc atctgcttcc agg                                      33

SEQ ID NO: 627          moltype = DNA  length = 33
FEATURE                 Location/Qualifiers
misc_feature            1..33
                        note = source = /note="Description of Artificial Sequence:
                                Syntheticoligonucleotide"
```

```
source                  1..33
                        mol_type = other DNA
                        organism = synthetic construct
SEQUENCE: 627
cgacctgaat gctgtgcggc ttctgcttcc agg                          33

SEQ ID NO: 628          moltype = DNA   length = 28
FEATURE                 Location/Qualifiers
misc_feature            1..28
                        note = source = /note="Description of Artificial Sequence:
                        Syntheticoligonucleotide"
source                  1..28
                        mol_type = other DNA
                        organism = synthetic construct
SEQUENCE: 628
cgacctgaat gctgtgtctg cttccagg                                28

SEQ ID NO: 629          moltype = DNA   length = 33
FEATURE                 Location/Qualifiers
misc_feature            1..33
                        note = source = /note="Description of Artificial Sequence:
                        Syntheticoligonucleotide"
source                  1..33
                        mol_type = other DNA
                        organism = synthetic construct
SEQUENCE: 629
cgacctgcat gctgtgcggc atctgcttcc agg                          33

SEQ ID NO: 630          moltype = DNA   length = 33
FEATURE                 Location/Qualifiers
misc_feature            1..33
                        note = source = /note="Description of Artificial Sequence:
                        Syntheticoligonucleotide"
source                  1..33
                        mol_type = other DNA
                        organism = synthetic construct
SEQUENCE: 630
cgacctgcat gctgtgcggc ttctgcttcc agg                          33

SEQ ID NO: 631          moltype = DNA   length = 28
FEATURE                 Location/Qualifiers
misc_feature            1..28
                        note = source = /note="Description of Artificial Sequence:
                        Syntheticoligonucleotide"
source                  1..28
                        mol_type = other DNA
                        organism = synthetic construct
SEQUENCE: 631
cgacctgcat gctgtgtctg cttccagg                                28

SEQ ID NO: 632          moltype = DNA   length = 33
FEATURE                 Location/Qualifiers
misc_feature            1..33
                        note = source = /note="Description of Artificial Sequence:
                        Syntheticoligonucleotide"
source                  1..33
                        mol_type = other DNA
                        organism = synthetic construct
SEQUENCE: 632
cgacctgaat gctgtgcgac atctgcttcc agg                          33

SEQ ID NO: 633          moltype = DNA   length = 32
FEATURE                 Location/Qualifiers
misc_feature            1..32
                        note = source = /note="Description of Artificial Sequence:
                        Syntheticoligonucleotide"
source                  1..32
                        mol_type = other DNA
                        organism = synthetic construct
SEQUENCE: 633
tggggactac gacctgaatg ctgtgcggct ct                           32

SEQ ID NO: 634          moltype = DNA   length = 27
FEATURE                 Location/Qualifiers
misc_feature            1..27
                        note = source = /note="Description of Artificial Sequence:
                        Syntheticoligonucleotide"
source                  1..27
                        mol_type = other DNA
```

```
                        organism = synthetic construct
SEQUENCE: 634
tggggactac gaatgctgtg cggctct                                              27

SEQ ID NO: 635          moltype = DNA  length = 66
FEATURE                 Location/Qualifiers
misc_feature            1..66
                        note = source = /note="Description of Artificial Sequence:
                        Syntheticoligonucleotide"
source                  1..66
                        mol_type = other DNA
                        organism = synthetic construct
SEQUENCE: 635
tggggactac gagcaggcag aagtatgcaa agcatgcatc tcaattcctg aatgctgtgc          60
ggctct                                                                    66

SEQ ID NO: 636          moltype = DNA  length = 72
FEATURE                 Location/Qualifiers
misc_feature            1..72
                        note = source = /note="Description of Artificial Sequence:
                        Syntheticoligonucleotide"
source                  1..72
                        mol_type = other DNA
                        organism = synthetic construct
SEQUENCE: 636
tggggactac gaagaaggcg atagaaggcc atgcgctgcg aatcgggagc ggcctgaatg          60
ctgtgcggct ct                                                             72

SEQ ID NO: 637          moltype = DNA  length = 99
FEATURE                 Location/Qualifiers
misc_feature            1..99
                        note = source = /note="Description of Artificial Sequence:
                        Syntheticoligonucleotide"
source                  1..99
                        mol_type = other DNA
                        organism = synthetic construct
SEQUENCE: 637
tggggactac gatgactcgc tgcgctcggt cgttcggctg cggcgagcgg tatcagctca          60
ctcaaaggcg gtaatacggc ctgaatgctg tgcggctct                                99

SEQ ID NO: 638          moltype = DNA  length = 14
FEATURE                 Location/Qualifiers
misc_feature            1..14
                        note = source = /note="Description of Artificial Sequence:
                        Syntheticoligonucleotide"
source                  1..14
                        mol_type = other DNA
                        organism = synthetic construct
SEQUENCE: 638
tggggtgcgg ctct                                                           14

SEQ ID NO: 639          moltype = DNA  length = 27
FEATURE                 Location/Qualifiers
misc_feature            1..27
                        note = source = /note="Description of Artificial Sequence:
                        Syntheticoligonucleotide"
source                  1..27
                        mol_type = other DNA
                        organism = synthetic construct
SEQUENCE: 639
tggggactac gactgctgtg cggctct                                              27

SEQ ID NO: 640          moltype = DNA  length = 39
FEATURE                 Location/Qualifiers
misc_feature            1..39
                        note = source = /note="Description of Artificial Sequence:
                        Syntheticoligonucleotide"
source                  1..39
                        mol_type = other DNA
                        organism = synthetic construct
SEQUENCE: 640
cgacctgaat gctgtgcggc gctctggctt cattcaatc                                39

SEQ ID NO: 641          moltype = DNA  length = 35
FEATURE                 Location/Qualifiers
misc_feature            1..35
                        note = source = /note="Description of Artificial Sequence:
                        Syntheticoligonucleotide"
source                  1..35
```

```
                        mol_type = other DNA
                        organism = synthetic construct
SEQUENCE: 641
cgacctgaat gctgtgcggc tctgcttcca ggtga                              35

SEQ ID NO: 642          moltype = DNA  length = 36
FEATURE                 Location/Qualifiers
misc_feature            1..36
                        note = source = /note="Description of Artificial Sequence:
                         Syntheticoligonucleotide"
source                  1..36
                        mol_type = other DNA
                        organism = synthetic construct
SEQUENCE: 642
cgacctgaat gctgtgcggc atctgcttcc aggtga                             36

SEQ ID NO: 643          moltype = DNA  length = 25
FEATURE                 Location/Qualifiers
misc_feature            1..25
                        note = source = /note="Description of Artificial Sequence:
                         Syntheticoligonucleotide"
source                  1..25
                        mol_type = other DNA
                        organism = synthetic construct
SEQUENCE: 643
cgacctgaat gctgcttcca ggtga                                         25

SEQ ID NO: 644          moltype = DNA  length = 28
FEATURE                 Location/Qualifiers
misc_feature            1..28
                        note = source = /note="Description of Artificial Sequence:
                         Syntheticoligonucleotide"
source                  1..28
                        mol_type = other DNA
                        organism = synthetic construct
SEQUENCE: 644
cgacctgaat gcttctgctt ccaggtga                                      28

SEQ ID NO: 645          moltype = DNA  length = 22
FEATURE                 Location/Qualifiers
misc_feature            1..22
                        note = source = /note="Description of Artificial Sequence:
                         Syntheticoligonucleotide"
source                  1..22
                        mol_type = other DNA
                        organism = synthetic construct
SEQUENCE: 645
cgacctgaat gcttccaggt ga                                            22

SEQ ID NO: 646          moltype = AA  length = 4
FEATURE                 Location/Qualifiers
source                  1..4
                        mol_type = protein
                        organism = Homo sapiens
SEQUENCE: 646
EEQL                                                                 4

SEQ ID NO: 647          moltype = AA  length = 6
FEATURE                 Location/Qualifiers
source                  1..6
                        mol_type = protein
                        organism = Homo sapiens
SEQUENCE: 647
AEVSQA                                                               6

SEQ ID NO: 648          moltype = AA  length = 4
FEATURE                 Location/Qualifiers
source                  1..4
                        mol_type = protein
                        organism = Mus musculus
SEQUENCE: 648
GEQL                                                                 4

SEQ ID NO: 649          moltype = AA  length = 6
FEATURE                 Location/Qualifiers
source                  1..6
                        mol_type = protein
                        organism = Mus musculus
SEQUENCE: 649
```

```
AEVSKA                                                                      6

SEQ ID NO: 650         moltype = AA  length = 4
FEATURE                Location/Qualifiers
REGION                 1..4
                       note = source = /note="Description of Artificial Sequence:
                        Syntheticpeptide"
source                 1..4
                       mol_type = protein
                       organism = synthetic construct
SEQUENCE: 650
GEQL                                                                        4

SEQ ID NO: 651         moltype = AA  length = 6
FEATURE                Location/Qualifiers
REGION                 1..6
                       note = source = /note="Description of Artificial Sequence:
                        Syntheticpeptide"
source                 1..6
                       mol_type = protein
                       organism = synthetic construct
SEQUENCE: 651
AEVSQA                                                                      6
```

That which is claimed:

1. A fusion polypeptide comprising:
 (A) an RNA-guided nuclease (RGN) polypeptide comprising an amino acid sequence:
  (i) having at least 95% sequence identity to any one of SEQ ID NOs: 11, 27, 45, or 54;
  (ii) having at least 98% sequence identity to SEQ ID NOs: 1 or 19; or
  (iii) set forth as SEQ ID NO: 36; and
 (B) a heterologous polypeptide.

2. The fusion polypeptide of claim 1, wherein the heterologous polypeptide comprises a cell penetrating domain or an effector domain.

3. The fusion polypeptide of claim 2, wherein the effector domain comprises a cleavage domain, a deaminase domain, or an expression modulator domain.

4. The fusion polypeptide of claim 1, wherein the RGN polypeptide of (i) or (ii) is nuclease dead or functions as a nickase.

5. The fusion polypeptide of claim 1, wherein the heterologous polypeptide comprises a base-editing polypeptide.

6. The fusion polypeptide of claim 5, wherein the base-editing polypeptide is a deaminase.

7. The fusion polypeptide of claim 1, wherein the fusion polypeptide further comprises one or more nuclear localization signals.

8. A cell comprising the fusion polypeptide of claim 1.

9. The cell of claim 8, wherein the cell is a eukaryotic cell.

10. A nucleic acid molecule comprising a polynucleotide encoding the fusion polypeptide of claim 1.

11. A vector comprising the nucleic acid molecule of claim 10.

12. An RNA polynucleotide comprising a nucleotide sequence encoding the fusion polypeptide of claim 1.

13. The RNA polynucleotide of claim 12, wherein the heterologous polypeptide comprises a base-editing polypeptide.

14. The RNA polynucleotide of claim 12, wherein the RNA polynucleotide is an mRNA.

15. An RNA polynucleotide comprising:
 (A) a nucleotide sequence encoding an RNA-guided nuclease (RGN) polypeptide comprising an amino acid sequence:
  (i) having at least 95% sequence identity to any one of SEQ ID NOs: 11, 27, 45, or 54;
  (ii) having at least 98% sequence identify to SEQ ID NOs: 1 or 19; or
  (iii) set forth as SEQ ID NO: 36;
 and
 (B) a heterologous 5' or 3' regulatory sequence.

16. A method for making an RGN polypeptide comprising:
 introducing into a cell a heterologous nucleic acid molecule comprising a nucleotide sequence encoding an RNA-guided nuclease (RGN) polypeptide comprising an amino acid sequence:
  (i) having at least 95% sequence identity to any one of SEQ ID NOs: 11, 27, 45, or 54;
  (ii) having at least 98% sequence identify to SEQ ID NOs: 1 or 19; or
  (iii) set forth as SEQ ID NO: 36;
 and
 culturing the cell under conditions in which the RGN polypeptide is expressed.

17. A method for binding a target DNA sequence comprising delivering an RGN polypeptide comprising an amino acid sequence:
 (i) having at least 95% sequence identity to any one of SEQ ID NOs: 11, 27, 45, or 54;
 (ii) having at least 98% sequence identity to SEQ ID NOs: 1 or 19; or
 (iii) set forth as SEQ ID NO: 36;
to the target DNA sequence or a cell comprising the target DNA sequence, wherein said RGN polypeptide is capable of forming a RGN ribonucleotide complex with one or more guide RNAs capable of hybridizing to the target DNA sequence.

18. A method for producing a genetically modified cell with a correction in a causal mutation for a genetically inherited disease, the method comprising introducing into a cell:
 a) an RNA-guided nuclease (RGN) polypeptide, wherein the RGN polypeptide comprises an amino acid sequence:
  (i) having at least 95% sequence identity to any one of SEQ ID NOs: 11, 27, 45, or 54;

(ii) having at least 98% sequence identity to SEQ ID NOs: 1 or 19; or (iii) set forth as SEQ ID NO: 36;

or a polynucleotide encoding the RGN polypeptide operably linked to a promoter; and b) a guide RNA (gRNA), wherein the gRNA comprises a CRISPR repeat comprising a nucleotide sequence having at least 95% sequence identity to SEQ ID NOs: 2, 12, 20, 28, 37, 46, or 55, or a polynucleotide encoding the gRNA operably linked to a promoter, wherein the RGN polypeptide and the gRNA target to and modify a genomic sequence in the cell comprising the causal mutation, thereby producing a genetically modified cell with a correction in a causal mutation for a genetically inherited disease.

19. A method for producing a genetically modified cell with a deletion in a disease-causing genomic region of instability, the method comprising introducing into a cell:

a) an RNA-guided nuclease (RGN) polypeptide, wherein the RGN polypeptide comprises an amino acid sequence:

(i) having at least 95% sequence identity to any one of SEQ ID NOs: 11, 27, 45, or 54;

(ii) having at least 98% sequence identity to SEQ ID NOs: 1 or 19; or (iii) set forth as SEQ ID NO: 36;

or a polynucleotide encoding the RGN polypeptide operably linked to a promoter; and b) a first guide RNA (gRNA), wherein the first gRNA comprises a CRISPR repeat comprising a nucleotide sequence having at least 95% sequence identity to SEQ ID NOs: 2, 12, 20, 28, 37, 46, or 55, or a polynucleotide encoding the first gRNA operably linked to a promoter, and further wherein the first gRNA comprises a spacer that targets the 5' flank of the genomic region of instability; and c) a second gRNA, wherein the second gRNA comprises a CRISPR repeat comprising a nucleotide sequence having at least 95% sequence identity to SEQ ID NOs: 2, 12, 20, 28, 37, 46, or 55, or a polynucleotide encoding the second gRNA operably linked to a promoter, and further wherein the second gRNA comprises a spacer that targets the 3' flank of the genomic region of instability;

wherein the RGN polypeptide and the first and second gRNAs target to and remove at least a portion of the genomic region of instability in the cell, thereby producing a genetically modified cell with a deletion in a disease-causing genomic region of instability.

* * * * *